US012227586B2

(12) United States Patent
Tenda et al.

(10) Patent No.: US 12,227,586 B2
(45) Date of Patent: Feb. 18, 2025

(54) ANTI-CLDN4/ANTI-CD137 BISPECIFIC ANTIBODY

(71) Applicants: Astellas Pharma Inc., Tokyo (JP); National Cancer Center, Tokyo (JP)

(72) Inventors: Yoshiyuki Tenda, Tokyo (JP); Masatoshi Yuri, Tokyo (JP); Shigenori Yagi, Tokyo (JP); Yoshiki Satake, Tokyo (JP); Kazunori Hirayama, Tokyo (JP); Hiroki Shirai, Tokyo (JP); Hiroki Sasaki, Tokyo (JP); Fumiko Chiwaki, Tokyo (JP); Masayuki Komatsu, Tokyo (JP)

(73) Assignees: Astellas Pharma Inc., Tokyo (JP); National Cancer Center, Tokyo (JP)

( * ) Notice: Subject to any disclaimer, the term of this patent is extended or adjusted under 35 U.S.C. 154(b) by 0 days.

(21) Appl. No.: 18/556,606

(22) PCT Filed: Apr. 21, 2022

(86) PCT No.: PCT/JP2022/018350
§ 371 (c)(1),
(2) Date: Oct. 20, 2023

(87) PCT Pub. No.: WO2022/224997
PCT Pub. Date: Oct. 27, 2022

(65) Prior Publication Data
US 2024/0209108 A1 Jun. 27, 2024

(30) Foreign Application Priority Data
Apr. 22, 2021 (JP) ................. 2021-072429

(51) Int. Cl.
*C07K 16/28* (2006.01)
*A61K 39/00* (2006.01)
*A61P 35/00* (2006.01)

(52) U.S. Cl.
CPC ......... *C07K 16/2878* (2013.01); *A61P 35/00* (2018.01); *C07K 16/28* (2013.01); *A61K 2039/505* (2013.01); *C07K 2317/31* (2013.01); *C07K 2317/622* (2013.01)

(58) Field of Classification Search
None
See application file for complete search history.

(56) References Cited

U.S. PATENT DOCUMENTS

| 2009/0202556 A1 | 8/2009 | Ohta et al. |
| 2017/0022287 A1 | 1/2017 | Igawa et al. |
| 2020/0199221 A1 | 6/2020 | Mitnacht-Kraus et al. |
| 2021/0054076 A1 | 2/2021 | Kimura |

FOREIGN PATENT DOCUMENTS

| JP | 2020-532572 A | 11/2020 |
| JP | 2021-510064 A | 4/2021 |
| WO | WO-2008/114733 A1 | 9/2008 |
| WO | WO-2014/132647 A1 | 9/2014 |
| WO | WO-2015/156268 A1 | 10/2015 |
| WO | WO-2016/177802 A1 | 11/2016 |
| WO | WO-2019/178356 A1 | 9/2019 |
| WO | WO-2020/011966 A1 | 1/2020 |

OTHER PUBLICATIONS

Brinkmann, et al., "The making of bispecific antibodies," mAbs, 2017, 9(2):182-212.
Fisher et al., "Targeting of 4-1BB by monoclonal antibody PF-05082566 enhances T-cell function and promotes anti-tumor activity," Cancer Immunology Immunotherapy, Mar. 11, 2012, 61(5):1721-1733.
Fujiwara-Tani et al., "Anti-claudin-4 extracellular domain antibody enhances the antitumoral effects of chemotherapeutic and antibody drugs in colorectal cancer," Oncotarget, Dec. 21, 2018, 9(100):37367-37378.
Hinner et al., "Tumor-Localized Costimulatory T-Cell Engagement by the 4-1BB/HER2 Bispecific Antibody-Anticalin Fusion PRS-343," Clinical Cancer Research, Oct. 1, 2019, 25(19):5878-5889.
International Search Report dated Jun. 7, 2022 in PCT/JP2022/018350.
Lakins et al., "FS222, a CD137/PD-L1 Tetravalent Bispecific Antibody, Exhibits Low Toxicity and Antitumor Activity in Colorectal Cancer Models," Clinical Cancer Research, Aug. 1, 2020, 26(15):4154-4167.
Li et al., "Development of an Anti-Claudin-3 and-4 Bispecific Monoclonal Antibody for Cancer Diagnosis and Therapy," J. Pharmacol. Exp. Ther., Oct. 2014, 351(1):206-213.
Rajendran et al., "Development of a Bispecific Antibody Targeting CD30 and CD137 on Hodgkin and Reed-Sternberg Cells," Frontiers in Oncology, Sep. 24, 2019, 9:945, 1-9.
Segal et al., "Results from an Integrated Safety Analysis of Urelumab, an Agonist Anti-CD137 Monoclonal Antibody," Clinical Cancer Research, Apr. 15, 2017, 23(8):1929-1936.
Suzuki et al., "Therapeutic antitumor efficacy of monoclonal antibody against Claudin-4 for pancreatic and ovarian cancers," Cancer Science, Jun. 25, 2009, 100(9):1623-1630.
Trueb et al., "Fibroblast activation protein-targeted-4-1BB ligand agonist amplifies effector functions of intratumoral T cells in human cancer," Journal for Immunotherapy of Cancer, 2020, 8(2):e000238, 1-14.
Ye et al., "CD137, an attractive candidate for the immunotherapy of lung cancer," Cancer Science, 2020, 111(5):1461-1467.

*Primary Examiner* — Ruixiang Li
(74) *Attorney, Agent, or Firm* — Foley & Lardner LLP

(57) ABSTRACT

An object of the present invention is to provide an anti-CLDN4/anti-CD137 bispecific antibody usable in treatment of cancer.
An anti-CLDN4/anti-CD137 bispecific antibody produced using an anti-CLDN4 antibody binding to CLDN4 and an anti-CD137 antibody binding to CD137 had agonistic activity for CD137, promoted production of interferon γ by a T cell, and exhibited cytotoxic activity against a cancer cell expressing CLDN4 on a cell surface thereof. Besides, it was shown that the anti-CLDN4/anti-CD137 bispecific antibody can be safely administered to monkeys. Therefore, the anti-CLDN4/anti-CD137 bispecific antibody is usable in treatment of human cancer.

25 Claims, 8 Drawing Sheets
Specification includes a Sequence Listing.

ANTI-CLDN4/ANTI-CD137 BISPECIFIC ANTIBODY

CROSS-REFERENCE TO RELATED APPLICATIONS

This application is the U.S. National Stage of PCT/JP2022/018350, filed Apr. 21, 2022, which claims priority to JP2021-072429, filed Apr. 22, 2021.

SEQUENCE LISTING

The instant application contains a Sequence Listing which has been submitted electronically in ASCII format and is hereby incorporated by reference in its entirety. Said ASCII copy, created on Oct. 30, 2023, is named 050499-0114_SL.txt and is 120,982 bytes in size.

TECHNICAL FIELD

The present invention relates to an anti-CLDN4/anti-CD137 bispecific antibody expected to be useful as an active ingredient of a pharmaceutical composition for use in treatment of cancer.

BACKGROUND ART

Claudin-4 (CLDN4) is a tetraspan membrane protein belonging to the claudin family. It is expressed in an epithelial cell and an endothelial cell, and plays a significant role as a main molecule contained in a tight junction. CLDN4 is highly expressed in a cancer tissue of colorectal cancer, bladder cancer, ovarian cancer and the like, and it has been suggested that an anti-CLDN4 antibody is possibly applicable to treatment or diagnosis of cancer (PTL 1 and NPL 1). Besides, it has been described that use of both an anti-CLDN4 antibody and an anti-epidermal growth factor receptor (EGFR) antibody has an antitumor effect in an animal model (NPL 2).

Cluster of differentiation 137 (CD137, another name 4-1BB) is a molecule belonging to the tumor necrosis factor receptor superfamily (TNFRSF), and has been reported to express on a cell surface of an immune cell such as a T cell, a B cell, a natural killer (NK) cell, a dendritic cell, an eosinophil, or a mast cell. In particular, CD137 on a T cell binds to a CD137 ligand on an antigen presenting cell and is known to be involved in activation and survival of the T cell as a costimulatory molecule (NPL 3). An anti-CD137 agonist antibody presents an antitumor effect through activation of an immune cell in a tumor microenvironment in an animal model (NPL 4). Urelumab, that is, an anti-CD137 agonist antibody, presented a therapeutic effect in a clinical trial, but is reported to cause an adverse reaction of liver disorder (NPL 5).

As an innovative method by which cancer cell-selective cytotoxic activity can be obtained at a low antibody concentration, a bispecific T cell recruiting antibody with various antibody formats has been reported. A bispecific T cell recruiting antibody is a bispecific antibody containing an antibody against a tumor-associated antigen (TAA) expressing on a cancer cell surface, and an antibody binding to a T cell, and is started to be examined for an effect of these antibodies in T cell-mediated immunotherapy (NPL 6). As an antibody binding to a T cell, an anti-CD3 antibody is often used, and bispecific T cell recruiting antibodies to various TAAs are now being studied and developed.

Furthermore, bispecific T cell recruiting antibodies against CD137 and TAA are being earnestly studied in recent years. Studies are being made on an anti-GPC3/anti-CD137 bispecific antibody, an anti-HER2/anti-CD137 bispecific antibody, an anti-PDL1/anti-CD137 bispecific antibody, an anti-FAP/anti-CD137 bispecific antibody and the like recognizing TAAs of glypican 3 (GPC3), human epidermal growth factor receptor type 2 (HER2), programmed cell-death ligand 1 (PD-L1), and fibroblast activation protein (FAP) (PTLs 2 and 3, and NPLs 7 to 9).

There is, until now, however, no report on an anti-CLDN4/anti-CD137 bispecific antibody.

CITATION LIST

Patent Literature

PTL 1: WO2008/114733
PTL 2: WO2015/156268
PTL 3: WO2016/177802

Non Patent Literature

NPL 1: Cancer Science, 2009: 100(9): pp. 1623-1630
NPL 2: Oncotarget, 2018: 9(100): p. 37367-37378
NPL 3: Cancer Science, 2020: 111(5): p. 1461-1467
NPL 4: Cancer Immunology Immunotherapy, 2012: 61(5): p. 1721-1733
NPL 5: Clinical Cancer Research, 2017: 23(8): p. 1929-1936
NPL 6: mAbs, 2017: 9(2): p. 182-212
NPL 7: Clinical Cancer Research, 2019: 25(19): p. 5878-5889
NPL 8: Clinical Cancer Research, 2020: 26(15): p. 4154-4167
NPL 9: Journal for Immunotherapy of Cancer, 2020; 8(2): e000238

SUMMARY OF INVENTION

Technical Problem

An object of the present invention is to provide an anti-CLDN4/anti-CD137 bispecific antibody usable in treatment of cancer.

Solution to Problem

The present inventors searched for antibodies selectively bind to an antigen expressed in a peritoneal metastatic cancer cell to obtain 3D11 that is an anti-CLDN4 antibody (Examples 1 and 2). A bispecific T cell recruiting antibody using 3D11 and an anti-CD3 antibody was found to be unusable for treating a cancer patient (Reference Example). Therefore, 3D11 and an antibody KM3900, which is a known anti-CLDN4 antibody, were used to try to obtain the bispecific T cell recruiting antibody with the anti-CD137 antibody (Examples 3 and 4). The thus obtained anti-CLDN4/anti-CD137 bispecific antibody bound to CLDN4 and CD137 (Example 5), promoted production of interferon γ of a T cell in vitro, and exhibited cytotoxic activity to a cancer cell expressing CLDN4 on a cell surface thereof (Example 6). Besides, it was confirmed that the obtained anti-CLDN4/anti-CD137 bispecific antibody exerted antitumor activity in an in vivo mouse model (Example 7-1) and could be used safely in a cynomolgus monkey (Examples 7-2). It has been suggested that the anti-CLDN4/anti-CD137 bispecific antibody of the present invention is useful for the treatment of cancer.

Specifically, the present invention relates to the following [1] to [32].

[1] An anti-CLDN4/anti-CD137 bispecific antibody comprising a heavy chain variable region and a light chain variable region of an anti-CLDN4 antibody, and a heavy chain variable region and a light chain variable region of an anti-CD137 antibody, wherein the heavy chain variable region and the light chain variable region of the anti-CLDN4 antibody are either of the following (a) or (b):
  (a) a heavy chain variable region containing a CDR1 consisting of an amino acid sequence at amino acid positions 31-35 of SEQ ID NO: 2, a CDR2 consisting of an amino acid sequence at amino acid positions 50-66 of SEQ ID NO: 2, and a CDR3 consisting of an amino acid sequence at amino acid positions 99-114 of SEQ ID NO: 2, and a light chain variable region containing a CDR1 consisting of an amino acid sequence at amino acid positions 24-35 of SEQ ID NO: 4, a CDR2 consisting of an amino acid sequence at amino acid positions 51-57 of SEQ ID NO: 4, and a CDR3 consisting of an amino acid sequence at amino acid positions 90-98 of SEQ ID NO: 4; or
  (b) a heavy chain variable region containing a CDR1 consisting of an amino acid sequence at amino acid positions 31-35 of SEQ ID NO: 6, a CDR2 consisting of an amino acid sequence at amino acid positions 50-66 of SEQ ID NO: 6, and a CDR3 consisting of an amino acid sequence at amino acid positions 99-112 of SEQ ID NO: 6, and a light chain variable region containing a CDR1 consisting of an amino acid sequence at amino acid positions 24-35 of SEQ ID NO: 8, a CDR2 consisting of an amino acid sequence at amino acid positions 51-57 of SEQ ID NO: 8, and a CDR3 consisting of an amino acid sequence at amino acid positions 90-98 of SEQ ID NO: 8.

[2] The bispecific antibody according to [1], wherein the heavy chain variable region and the light chain variable region of the anti-CLDN4 antibody are either of the following (a) or (b):
  (a) a heavy chain variable region consisting of an amino acid sequence at amino acid positions 1-125 of SEQ ID NO: 2 and a light chain variable region consisting of an amino acid sequence at amino acid positions 1-109 of SEQ ID NO: 4; or
  (b) a heavy chain variable region consisting of an amino acid sequence at amino acid positions 1-123 of SEQ ID NO: 6 and a light chain variable region consisting of an amino acid sequence at amino acid positions 1-109 of SEQ ID NO: 8.

[3] The bispecific antibody according to any of [1] and [2], comprising an IgG antibody (anti-CLDN4 IgG antibody) consisting of a heavy chain containing the heavy chain variable region and a light chain containing the light chain variable region of the anti-CLDN4 antibody.

[4] The bispecific antibody according to [3], comprising LALA mutation (L234A and L235A, wherein a position of the mutation is an amino acid position in human Igγ1 constant region according to EU index) in a Fc region of the anti-CLDN4 IgG antibody.

[5] The anti-CLDN4/anti-CD137 bispecific antibody according to [3], comprising P331G mutation in a Fc region of the anti-CLDN4 IgG antibody (wherein a position of the mutation is an amino acid position in human Igγ1 constant region according to EU index).

[6] The bispecific antibody according to [3], comprising LALA mutation and P331G mutation in a Fc region of the anti-CLDN4 IgG antibody.

[7] The bispecific antibody according to any one of [1] to [6], wherein the heavy chain variable region and the light chain variable region of the anti-CD137 antibody are any of the following (a) to (d):
  (a) a heavy chain variable region containing a CDR1 consisting of an amino acid sequence at amino acid positions 31-35 of SEQ ID NO: 10, a CDR2 consisting of an amino acid sequence at amino acid positions 50-66 of SEQ ID NO: 10, and a CDR3 consisting of an amino acid sequence at amino acid positions 99-107 of SEQ ID NO: 10, and a light chain variable region containing a CDR1 consisting of an amino acid sequence at amino acid positions 24-34 of SEQ ID NO: 12, a CDR2 consisting of an amino acid sequence at amino acid positions 50-56 of SEQ ID NO: 12, and a CDR3 consisting of an amino acid sequence at amino acid positions 89-98 of SEQ ID NO: 12;
  (b) a heavy chain variable region containing a CDR1 consisting of an amino acid sequence at amino acid positions 31-35 of SEQ ID NO: 14, a CDR2 consisting of an amino acid sequence at amino acid positions 50-65 of SEQ ID NO: 14, and a CDR3 consisting of an amino acid sequence at amino acid positions 98-107 of SEQ ID NO: 14, and a light chain variable region containing a CDR1 consisting of an amino acid sequence at amino acid positions 23-35 of SEQ ID NO: 16, a CDR2 consisting of an amino acid sequence at amino acid positions 51-57 of SEQ ID NO: 16, and a CDR3 consisting of an amino acid sequence at amino acid positions 90-100 of SEQ ID NO: 16;
  (c) a heavy chain variable region containing a CDR1 consisting of an amino acid sequence at amino acid positions 31-35 of SEQ ID NO: 18, a CDR2 consisting of an amino acid sequence at amino acid positions 50-65 of SEQ ID NO: 18, and a CDR3 consisting of an amino acid sequence at amino acid positions 98-107 of SEQ ID NO: 18, and a light chain variable region containing a CDR1 consisting of an amino acid sequence at amino acid positions 23-35 of SEQ ID NO: 20, a CDR2 consisting of an amino acid sequence at amino acid positions 51-57 of SEQ ID NO: 20, and a CDR3 consisting of an amino acid sequence at amino acid positions 90-100 of SEQ ID NO: 20; or
  (d) a heavy chain variable region containing a CDR1 consisting of an amino acid sequence at amino acid positions 31-35 of SEQ ID NO: 22, a CDR2 consisting of an amino acid sequence at amino acid positions 50-65 of SEQ ID NO: 22, and a CDR3 consisting of an amino acid sequence at amino acid positions 98-110 of SEQ ID NO: 22, and a light chain variable region containing a CDR1 consisting of an amino acid sequence at amino acid positions 23-35 of SEQ ID NO: 24, a CDR2 consisting of an amino acid sequence at amino acid positions 51-57 of SEQ ID NO: 24, and a CDR3 consisting of an amino acid sequence at amino acid positions 90-100 of SEQ ID NO: 24.

[8] The bispecific antibody according to any of [1] to [7], wherein the heavy chain variable region and the light chain variable region of the anti-CD137 antibody are any of the following (a) to (i):
  (a) a heavy chain variable region consisting of an amino acid sequence at amino acid positions 1-118 of SEQ ID NO: 10 and a light chain variable region consisting of an amino acid sequence at amino acid positions 1-109 of SEQ ID NO: 12;
(b) a heavy chain variable region consisting of an amino acid sequence at amino acid positions 1-118 of SEQ ID NO: 14 and a light chain variable region consisting of an amino acid sequence at amino acid positions 1-111 of SEQ ID NO: 16;
(c) a heavy chain variable region consisting of an amino acid sequence at amino acid positions 1-118 of SEQ ID NO: 18 and a light chain variable region consisting of an amino acid sequence at amino acid positions 1-111 of SEQ ID NO: 20;
(d) a heavy chain variable region consisting of an amino acid sequence at amino acid positions 1-121 of SEQ ID NO: 22 and a light chain variable region consisting of an amino acid sequence at amino acid positions 1-111 of SEQ ID NO: 24;
(e) a heavy chain variable region consisting of an amino acid sequence at amino acid positions 1-118 of SEQ ID NO: 26 and a light chain variable region consisting of an amino acid sequence at amino acid positions 134-242 of SEQ ID NO: 26;
(f) a heavy chain variable region consisting of an amino acid sequence at amino acid positions 1-118 of SEQ ID NO: 28 and a light chain variable region consisting of an amino acid sequence at amino acid positions 134-244 of SEQ ID NO: 28;
(g) a light chain variable region consisting of an amino acid sequence at amino acid positions 1-111 of SEQ ID NO: 30 and a heavy chain variable region consisting of an amino acid sequence at amino acid positions 132-249 of SEQ ID NO: 30;
(h) a heavy chain variable region consisting of an amino acid sequence at amino acid positions 1-118 of SEQ ID NO: 32 and a light chain variable region consisting of an amino acid sequence at amino acid positions 134-244 of SEQ ID NO: 32; or
(i) a heavy chain variable region consisting of an amino acid sequence at amino acid positions 1-121 of SEQ ID NO: 34 and a light chain variable region consisting of an amino acid sequence at amino acid positions 137-247 of SEQ ID NO: 34.

[9] The bispecific antibody according to any of [7] and [8], comprising an anti-CD137 single chain variable fragment (anti-CD137 scFv) containing the heavy chain variable region and the light chain variable region of the anti-CD137 antibody.

[10] The bispecific antibody according to [9], wherein the anti-CD137 scFv is any of the following (a) to (e):
(a) an anti-CD137 scFv consisting of an amino acid sequence at amino acid positions 1-242 of SEQ ID NO: 26;
(b) an anti-CD137 scFv consisting of an amino acid sequence at amino acid positions 1-244 of SEQ ID NO: 28;
(c) an anti-CD137 scFv consisting of an amino acid sequence at amino acid positions 1-249 of SEQ ID NO: 30;
(d) an anti-CD137 scFv consisting of an amino acid sequence at amino acid positions 1-244 of SEQ ID NO: 32; or
(e) an anti-CD137 scFv consisting of an amino acid sequence at amino acid positions 1-247 of SEQ ID NO: 34.

[11] The bispecific antibody according to any of [9] and [10], comprising an anti-CLDN4 IgG antibody and the anti-CD137 scFv, wherein an amino terminal of the anti-CD137 scFv is linked to a heavy chain or light chain carboxy terminal of the anti-CLDN4 IgG antibody via a linker.

[12] An anti-CLDN4/anti-CD137 bispecific antibody described in any of the following (a) to (j):
(a) a bispecific antibody comprising a heavy chain of an anti-CLDN4 antibody containing a heavy chain variable region consisting of an amino acid sequence at amino acid positions 1-125 of SEQ ID NO: 2 and a light chain of an anti-CLDN4 antibody containing a light chain variable region consisting of an amino acid sequence at amino acid positions 1-109 of SEQ ID NO: 4, and an anti-CD137 scFv containing a heavy chain variable region consisting of an amino acid sequence at amino acid positions 1-118 of SEQ ID NO: 26 and a light chain variable region consisting of an amino acid sequence at amino acid positions 134-242 of SEQ ID NO: 26, wherein an amino terminal of the anti-CD137 scFv is linked to a heavy chain carboxy terminal of the anti-CLDN4 antibody via a linker;
(b) a bispecific antibody comprising a heavy chain of an anti-CLDN4 antibody containing a heavy chain variable region consisting of an amino acid sequence at amino acid positions 1-125 of SEQ ID NO: 2 and a light chain of an anti-CLDN4 antibody containing a light chain variable region consisting of an amino acid sequence at amino acid positions 1-109 of SEQ ID NO: 4, and an anti-CD137 scFv containing a heavy chain variable region consisting of an amino acid sequence at amino acid positions 1-118 of SEQ ID NO: 28 and a light chain variable region consisting of an amino acid sequence at amino acid positions 134-244 of SEQ ID NO: 28, wherein an amino terminal of the anti-CD137 scFv is linked to a heavy chain carboxy terminal of the anti-CLDN4 antibody via a linker;
(c) a bispecific antibody comprising a heavy chain of an anti-CLDN4 antibody containing a heavy chain variable region consisting of an amino acid sequence at amino acid positions 1-125 of SEQ ID NO: 2 and a light chain of an anti-CLDN4 antibody containing a light chain variable region consisting of an amino acid sequence at amino acid positions 1-109 of SEQ ID NO: 4, and an anti-CD137 scFv containing a light chain variable region consisting of an amino acid sequence at amino acid positions 1-111 of SEQ ID NO: 30 and a heavy chain variable region consisting of an amino acid sequence at amino acid positions 132-249 of SEQ ID NO: 30, wherein an amino terminal of the anti-CD137 scFv is linked to a heavy chain carboxy terminal of the anti-CLDN4 antibody via a linker;
(d) a bispecific antibody comprising a heavy chain of an anti-CLDN4 antibody containing a heavy chain variable region consisting of an amino acid sequence at amino acid positions 1-125 of SEQ ID NO: 2 and a light chain of an anti-CLDN4 antibody containing a light chain variable region consisting of an amino acid sequence at amino acid positions 1-109 of SEQ ID NO: 4, and an anti-CD137 scFv containing a heavy chain variable region consisting of an amino acid sequence at amino acid positions 1-118 of SEQ ID NO: 32 and a light chain variable region consisting of an amino acid sequence at amino acid positions 134-244 of SEQ ID NO: 32, wherein an amino terminal of the anti-CD137 scFv is linked to a heavy chain carboxy terminal of the anti-CLDN4 antibody via a linker;
(e) a bispecific antibody comprising a heavy chain of an anti-CLDN4 antibody containing a heavy chain variable region consisting of an amino acid sequence at amino acid positions 1-125 of SEQ ID NO: 2 and a light chain of an anti-CLDN4 antibody containing a light chain variable region consisting of an amino acid sequence at amino acid positions 1-109 of SEQ ID NO: 4, and an anti-CD137 scFv containing a heavy chain variable region consisting of an amino acid sequence at amino acid positions 1-121 of SEQ ID NO: 34 and a light chain variable region consisting of an amino acid sequence at amino acid positions 137-247 of SEQ ID NO: 34, wherein an amino terminal of the anti-CD137 scFv is linked to a heavy chain carboxy terminal of the anti-CLDN4 antibody via a linker;

(f) a bispecific antibody comprising a heavy chain of an anti-CLDN4 antibody containing a heavy chain variable region consisting of an amino acid sequence at amino acid positions 1-123 of SEQ ID NO: 6 and a light chain of an anti-CLDN4 antibody containing a light chain variable region consisting of an amino acid sequence at amino acid positions 1-109 of SEQ ID NO: 8, and an anti-CD137 scFv containing a heavy chain variable region consisting of an amino acid sequence at amino acid positions 1-118 of SEQ ID NO: 26 and a light chain variable region consisting of an amino acid sequence at amino acid positions 134-242 of SEQ ID NO: 26, wherein an amino terminal of the anti-CD137 scFv is linked to a heavy chain carboxy terminal of the anti-CLDN4 antibody via a linker;

(g) a bispecific antibody comprising a heavy chain of an anti-CLDN4 antibody containing a heavy chain variable region consisting of an amino acid sequence at amino acid positions 1-123 of SEQ ID NO: 6 and a light chain of an anti-CLDN4 antibody containing a light chain variable region consisting of an amino acid sequence at amino acid positions 1-109 of SEQ ID NO: 8, and an anti-CD137 scFv containing a heavy chain variable region consisting of an amino acid sequence at amino acid positions 1-118 of SEQ ID NO: 28 and a light chain variable region consisting of an amino acid sequence at amino acid positions 134-244 of SEQ ID NO: 28, wherein an amino terminal of the anti-CD137 scFv is linked to a heavy chain carboxy terminal of the anti-CLDN4 antibody via a linker;

(h) a bispecific antibody comprising a heavy chain of an anti-CLDN4 antibody containing a heavy chain variable region consisting of an amino acid sequence at amino acid positions 1-123 of SEQ ID NO: 6 and a light chain of an anti-CLDN4 antibody containing a light chain variable region consisting of an amino acid sequence at amino acid positions 1-109 of SEQ ID NO: 8, and an anti-CD137 scFv containing a light chain variable region consisting of an amino acid sequence at amino acid positions 1-111 of SEQ ID NO: 30 and a heavy chain variable region consisting of an amino acid sequence at amino acid positions 132-249 of SEQ ID NO: 30, wherein an amino terminal of the anti-CD137 scFv is linked to a heavy chain carboxy terminal of the anti-CLDN4 antibody via a linker;

(i) a bispecific antibody comprising a heavy chain of an anti-CLDN4 antibody containing a heavy chain variable region consisting of an amino acid sequence at amino acid positions 1-123 of SEQ ID NO: 6 and a light chain of an anti-CLDN4 antibody containing a light chain variable region consisting of an amino acid sequence at amino acid positions 1-109 of SEQ ID NO: 8, and an anti-CD137 scFv containing a heavy chain variable region consisting of an amino acid sequence at amino acid positions 1-118 of SEQ ID NO: 32 and a light chain variable region consisting of an amino acid sequence at amino acid positions 134-244 of SEQ ID NO: 32, wherein an amino terminal of the anti-CD137 scFv is linked to a heavy chain carboxy terminal of the anti-CLDN4 antibody via a linker; or (j) a bispecific antibody comprising a heavy chain of an anti-CLDN4 antibody containing a heavy chain variable region consisting of an amino acid sequence at amino acid positions 1-123 of SEQ ID NO: 6 and a light chain of an anti-CLDN4 antibody containing a light chain variable region consisting of an amino acid sequence at amino acid positions 1-109 of SEQ ID NO: 8, and an anti-CD137 scFv containing a heavy chain variable region consisting of an amino acid sequence at amino acid positions 1-121 of SEQ ID NO: 34 and a light chain variable region consisting of an amino acid sequence at amino acid positions 137-247 of SEQ ID NO: 34, wherein an amino terminal of the anti-CD137 scFv is linked to a heavy chain carboxy terminal of the anti-CLDN4 antibody via a linker.

[13] The anti-CLDN4/anti-CD137 bispecific antibody according to any of and [12], wherein the linker is a GS linker.

[14] The anti-CLDN4/anti-CD137 bispecific antibody according to [13], wherein the GS linker is a linker consisting of an amino acid sequence of SEQ ID NO: 54.

[15] An anti-CLDN4/anti-CD137 bispecific antibody described in either of the following (a) or (b):

(a) a bispecific antibody comprising a polypeptide consisting of an amino acid sequence at amino acid positions 1-705 of SEQ ID NO: 36 containing a heavy chain of an anti-CLDN4 antibody and an anti-CD137 scFv, and a light chain of an anti-CLDN4 antibody consisting of an amino acid sequence at amino acid positions 1-215 of SEQ ID NO: 40; or (b) a bispecific antibody comprising a polypeptide consisting of an amino acid sequence at amino acid positions 1-712 of SEQ ID NO: 38 containing a heavy chain of an anti-CLDN4 antibody and an anti-CD137 scFv, and a light chain of an anti-CLDN4 antibody consisting of an amino acid sequence at amino acid positions 1-215 of SEQ ID NO: 40.

[16] The anti-CLDN4/anti-CD137 bispecific antibody according to any of [1] to [15], which is post-translationally modified.

[17] The anti-CLDN4/anti-CD137 bispecific antibody according to [16], wherein the post-translational modification is pyroglutamylation at an N-terminal of a heavy chain variable region and/or lysine deletion at a heavy chain C-terminal.

[18] A polynucleotide having a nucleotide sequence encoding a heavy chain variable region or light chain variable region of an anti-CLDN4 antibody, which is selected from the group consisting of the following (a) to (d):

(a) a polynucleotide having a nucleotide sequence encoding a heavy chain variable region of an anti-CLDN4 antibody consisting of an amino acid sequence at amino acid positions 1-125 of SEQ ID NO: 2;

(b) a polynucleotide having a nucleotide sequence encoding a light chain variable region of an anti-CLDN4 antibody consisting of an amino acid sequence at amino acid positions 1-109 of SEQ ID NO: 4;

(c) a polynucleotide having a nucleotide sequence encoding a heavy chain variable region of an anti-CLDN4 antibody consisting of an amino acid sequence at amino acid positions 1-123 of SEQ ID NO: 6; or (d) a polynucleotide having a nucleotide sequence encoding a light chain variable region of an anti-CLDN4 antibody consisting of an amino acid sequence at amino acid positions 1-109 of SEQ ID NO: 8.

[19] A polynucleotide having a nucleotide sequence encoding a heavy chain variable region or light chain variable region of an anti-CD137 antibody, which is selected from the group consisting of the following (a) to (r):

(a) a polynucleotide having a nucleotide sequence encoding a heavy chain variable region of an anti-CD137 antibody consisting of an amino acid sequence at amino acid positions 1-118 of SEQ ID NO: 10;

(b) a polynucleotide having a nucleotide sequence encoding a light chain variable region of an anti-CD137 antibody consisting of an amino acid sequence at amino acid positions 1-109 of SEQ ID NO: 12;

(c) a polynucleotide having a nucleotide sequence encoding a heavy chain variable region of an anti-CD137 antibody consisting of an amino acid sequence at amino acid positions 1-118 of SEQ ID NO: 14;

(d) a polynucleotide having a nucleotide sequence encoding a light chain variable region of an anti-CD137 antibody consisting of an amino acid sequence at amino acid positions 1-111 of SEQ ID NO: 16;

(e) a polynucleotide having a nucleotide sequence encoding a heavy chain variable region of an anti-CD137 antibody consisting of an amino acid sequence at amino acid positions 1-118 of SEQ ID NO: 18;

(f) a polynucleotide having a nucleotide sequence encoding a light chain variable region of an anti-CD137 antibody consisting of an amino acid sequence at amino acid positions 1-111 of SEQ ID NO: 20;

(g) a polynucleotide having a nucleotide sequence encoding a heavy chain variable region of an anti-CD137 antibody consisting of an amino acid sequence at amino acid positions 1-121 of SEQ ID NO: 22;

(h) a polynucleotide having a nucleotide sequence encoding a light chain variable region of an anti-CD137 antibody consisting of an amino acid sequence at amino acid positions 1-111 of SEQ ID NO: 24;

(i) a polynucleotide having a nucleotide sequence encoding a heavy chain variable region of an anti-CD137 antibody consisting of an amino acid sequence at amino acid positions 1-118 of SEQ ID NO: 26;

(j) a polynucleotide having a nucleotide sequence encoding a light chain variable region of an anti-CD137 antibody consisting of an amino acid sequence at amino acid positions 134-242 of SEQ ID NO: 26;

(k) a polynucleotide having a nucleotide sequence encoding a heavy chain variable region of an anti-CD137 antibody consisting of an amino acid sequence at amino acid positions 1-118 of SEQ ID NO: 28;

(l) a polynucleotide having a nucleotide sequence encoding a light chain variable region of an anti-CD137 antibody consisting of an amino acid sequence at amino acid positions 134-244 of SEQ ID NO: 28;

(m) a polynucleotide having a nucleotide sequence encoding a light chain variable region of an anti-CD137 antibody consisting of an amino acid sequence at amino acid positions 1-111 of SEQ ID NO: 30;

(n) a polynucleotide having a nucleotide sequence encoding a heavy chain variable region of an anti-CD137 antibody consisting of an amino acid sequence at amino acid positions 132-249 of SEQ ID NO: 30;

(o) a polynucleotide having a nucleotide sequence encoding a heavy chain variable region of an anti-CD137 antibody consisting of an amino acid sequence at amino acid positions 1-118 of SEQ ID NO: 32;

(p) a polynucleotide having a nucleotide sequence encoding a light chain variable region of an anti-CD137 antibody consisting of an amino acid sequence at amino acid positions 134-244 of SEQ ID NO: 32;

(q) a polynucleotide having a nucleotide sequence encoding a heavy chain variable region of an anti-CD137 antibody consisting of an amino acid sequence at amino acid positions 1-121 of SEQ ID NO: 34; or (r) a polynucleotide having a nucleotide sequence encoding a light chain variable region of an anti-CD137 antibody consisting of an amino acid sequence at amino acid positions 137-247 of SEQ ID NO: 34.

[20] A polynucleotide having a nucleotide sequence encoding an anti-CD137 scFv, which is selected from the group consisting of the following (a) to (e):

(a) a polynucleotide having a nucleotide sequence encoding an anti-CD137 scFv consisting of an amino acid sequence at amino acid positions 1-242 of SEQ ID NO: 26;

(b) a polynucleotide having a nucleotide sequence encoding an anti-CD137 scFv consisting of an amino acid sequence at amino acid positions 1-244 of SEQ ID NO: 28;

(c) a polynucleotide having a nucleotide sequence encoding an anti-CD137 scFv consisting of an amino acid sequence at amino acid positions 1-249 of SEQ ID NO: 30;

(d) a polynucleotide having a nucleotide sequence encoding of an anti-CD137 scFv consisting of an amino acid sequence at amino acid positions 1-244 of SEQ ID NO: 32; or (e) a polynucleotide having a nucleotide sequence encoding an anti-CD137 scFv consisting of an amino acid sequence at amino acid positions 1-247 of SEQ ID NO: 34.

[21] A polynucleotide for use in production of the anti-CLDN4/anti-CD137 bispecific antibody according to [15], which is selected from the group consisting of the following (a) to (e):

(a) a polynucleotide having a nucleotide sequence encoding a polypeptide consisting of an amino acid sequence at amino acid positions 1-705 of SEQ ID NO: 36 containing a heavy chain of an anti-CLDN4 antibody and an anti-CD137 scFv;

(b) a polynucleotide having a nucleotide sequence encoding a polypeptide consisting of an amino acid sequence at amino acid positions 1-712 of SEQ ID NO: 38 containing a heavy chain of an anti-CLDN4 antibody and an anti-CD137 scFv;

(c) a polynucleotide having a nucleotide sequence encoding a light chain of an anti-CLDN4 antibody consisting of an amino acid sequence at amino acid positions 1-215 of SEQ ID NO: 40;

(d) a polynucleotide having a nucleotide sequence encoding a polypeptide consisting of an amino acid sequence at amino acid positions 1-705 of SEQ ID NO: 36 containing a heavy chain of an anti-CLDN4 antibody and an anti-CD137 scFv, and a polynucleotide having a nucleotide sequence encoding a light chain of an anti-CLDN4 antibody consisting of an amino acid sequence at amino acid positions 1-215 of SEQ ID NO: 40; or (e) a polynucleotide having a nucleotide sequence encoding a polypeptide consisting of an amino acid sequence at amino acid positions 1-712 of SEQ ID NO: 38 containing a heavy chain of an anti-CLDN4 antibody and an anti-CD137 scFv, and a polynucleotide having a nucleotide sequence encoding a light chain of an anti-CLDN4 antibody consisting of an amino acid sequence at amino acid positions 1-215 of SEQ ID NO: 40.

[22] An expression vector, comprising the polynucleotide according to any of [18] to [21].

[23] A host cell transformed with the expression vector according to [22].

[24] A host cell comprising a polynucleotide selected from the group consisting of the following (a) to (dd):
- (a) a polynucleotide having a nucleotide sequence encoding a heavy chain variable region of an anti-CLDN4 antibody consisting of an amino acid sequence at amino acid positions 1-125 of SEQ ID NO: 2;
- (b) a polynucleotide having a nucleotide sequence encoding a light chain variable region of an anti-CLDN4 antibody consisting of an amino acid sequence at amino acid positions 1-109 of SEQ ID NO: 4;
- (c) a polynucleotide having a nucleotide sequence encoding a heavy chain variable region of an anti-CLDN4 antibody consisting of an amino acid sequence at amino acid positions 1-123 of SEQ ID NO: 6;
- (d) a polynucleotide having a nucleotide sequence encoding a light chain variable region of an anti-CLDN4 antibody consisting of an amino acid sequence at amino acid positions 1-109 of SEQ ID NO: 8;
- (e) a polynucleotide having a nucleotide sequence encoding a heavy chain variable region of an anti-CD137 antibody consisting of an amino acid sequence at amino acid positions 1-118 of SEQ ID NO: 10;
- (f) a polynucleotide having a nucleotide sequence encoding a light chain variable region of an anti-CD137 antibody consisting of an amino acid sequence at amino acid positions 1-109 of SEQ ID NO: 12;
- (g) a polynucleotide having a nucleotide sequence encoding a heavy chain variable region of an anti-CD137 antibody consisting of an amino acid sequence at amino acid positions 1-118 of SEQ ID NO: 14;
- (h) a polynucleotide having a nucleotide sequence encoding a light chain variable region of an anti-CD137 antibody consisting of an amino acid sequence at amino acid positions 1-111 of SEQ ID NO: 16;
- (i) a polynucleotide having a nucleotide sequence encoding a heavy chain variable region of an anti-CD137 antibody consisting of an amino acid sequence at amino acid positions 1-118 of SEQ ID NO: 18;
- (j) a polynucleotide having a nucleotide sequence encoding a light chain variable region of an anti-CD137 antibody consisting of an amino acid sequence at amino acid positions 1-111 of SEQ ID NO: 20;
- (k) a polynucleotide having a nucleotide sequence encoding a heavy chain variable region of an anti-CD137 antibody consisting of an amino acid sequence at amino acid positions 1-121 of SEQ ID NO: 22;
- (l) a polynucleotide having a nucleotide sequence encoding a light chain variable region of an anti-CD137 antibody consisting of an amino acid sequence at amino acid positions 1-111 of SEQ ID NO: 24;
- (m) a polynucleotide having a nucleotide sequence encoding a heavy chain variable region of an anti-CD137 antibody consisting of an amino acid sequence at amino acid positions 1-118 of SEQ ID NO: 26;
- (n) a polynucleotide having a nucleotide sequence encoding a light chain variable region of an anti-CD137 antibody consisting of an amino acid sequence at amino acid positions 134-242 of SEQ ID NO: 26;
- (o) a polynucleotide having a nucleotide sequence encoding a heavy chain variable region of an anti-CD137 antibody consisting of an amino acid sequence at amino acid positions 1-118 of SEQ ID NO: 28;
- (p) a polynucleotide having a nucleotide sequence encoding a light chain variable region of an anti-CD137 antibody consisting of an amino acid sequence at amino acid positions 134-244 of SEQ ID NO: 28;
- (q) a polynucleotide having a nucleotide sequence encoding a light chain variable region of an anti-CD137 antibody consisting of an amino acid sequence at amino acid positions 1-111 of SEQ ID NO: 30;
- (r) a polynucleotide having a nucleotide sequence encoding a heavy chain variable region of an anti-CD137 antibody consisting of an amino acid sequence at amino acid positions 132-249 of SEQ ID NO: 30;
- (s) a polynucleotide having a nucleotide sequence encoding a heavy chain variable region of an anti-CD137 antibody consisting of an amino acid sequence at amino acid positions 1-118 of SEQ ID NO: 32;
- (t) a polynucleotide having a nucleotide sequence encoding a light chain variable region of an anti-CD137 antibody consisting of an amino acid sequence at amino acid positions 134-244 of SEQ ID NO: 32;
- (u) a polynucleotide having a nucleotide sequence encoding a heavy chain variable region of an anti-CD137 antibody consisting of an amino acid sequence at amino acid positions 1-121 of SEQ ID NO: 34;
- (v) a polynucleotide having a nucleotide sequence encoding a light chain variable region of an anti-CD137 antibody consisting of an amino acid sequence at amino acid positions 137-247 of SEQ ID NO: 34;
- (w) a polynucleotide having a nucleotide sequence encoding an anti-CD137 scFv consisting of an amino acid sequence at amino acid positions 1-242 of SEQ ID NO: 26;
- (x) a polynucleotide having a nucleotide sequence encoding an anti-CD137 scFv consisting of an amino acid sequence at amino acid positions 1-244 of SEQ ID NO: 28;
- (y) a polynucleotide having a nucleotide sequence encoding an anti-CD137 scFv consisting of an amino acid sequence at amino acid positions 1-249 of SEQ ID NO: 30;
- (z) a polynucleotide having a nucleotide sequence encoding an anti-CD137 scFv consisting of an amino acid sequence at amino acid positions 1-244 of SEQ ID NO: 32;
- (aa) a polynucleotide having a nucleotide sequence encoding an anti-CD137 scFv consisting of an amino acid sequence at amino acid positions 1-247 of SEQ ID NO: 34;
- (bb) a polynucleotide having a nucleotide sequence encoding a polypeptide consisting of an amino acid sequence at amino acid positions 1-705 of SEQ ID NO: 36 containing a heavy chain of an anti-CLDN4 antibody and an anti-CD137 scFv;
- (cc) a polynucleotide having a nucleotide sequence encoding a polypeptide consisting of an amino acid sequence at amino acid positions 1-712 of SEQ ID NO: 38 containing a heavy chain of an anti-CLDN4 antibody and an anti-CD137 scFv; or (dd) a polynucleotide having a nucleotide sequence encoding a light chain of an anti-CLDN4 antibody consisting of an amino acid sequence at amino acid positions 1-215 of SEQ ID NO: 40.

[25] A host cell comprising a polynucleotide of either of the following (a) or (b):
  (a) a polynucleotide having a nucleotide sequence encoding a polypeptide consisting of an amino acid sequence at amino acid positions 1-705 of SEQ ID NO: 36 containing a heavy chain of an anti-CLDN4 antibody and an anti-CD137 scFv, and a polynucleotide having a nucleotide sequence encoding a light chain of an anti-CLDN4 antibody consisting of an amino acid sequence at amino acid positions 1-215 of SEQ ID NO: 40; or
  (b) a polynucleotide having a nucleotide sequence encoding a polypeptide consisting of an amino acid sequence at amino acid positions 1-712 of SEQ ID NO: 38 containing a heavy chain of an anti-CLDN4 antibody and an anti-CD137 scFv, and a polynucleotide having a nucleotide sequence encoding a light chain of an anti-CLDN4 antibody consisting of an amino acid sequence at amino acid positions 1-215 of SEQ ID NO: 40.

[26] A method for producing an anti-CLDN4/anti-CD137 bispecific antibody, comprising a step of culturing the host cell according to any of [23] to [25].

[27] A pharmaceutical composition comprising the anti-CLDN4/anti-CD137 bispecific antibody according to any of [1] to [17], and a pharmaceutically acceptable excipient.

[28] The anti-CLDN4/anti-CD137 bispecific antibody according to any of [1] to [17] for use in treatment of cancer.

[29] The pharmaceutical composition according to for use in treatment of cancer.

[30] A method for treating cancer, comprising a step of administering a therapeutically effective amount of the anti-CLDN4/anti-CD137 bispecific antibody according to any of [1] to [17] to a subject.

[31] Use of the anti-CLDN4/anti-CD137 bispecific antibody according to any of [1] to [17] in production of a pharmaceutical composition for use in treatment of cancer.

Advantageous Effects of Invention

An anti-CLDN4/anti-CD137 bispecific antibody of the present invention binds both to CLDN4 that is a cancer antigen and CD137 expressing on a cell surface of an immune cell such as a T cell to activate immune cells present around a cancer cell, and thus enhances killing activity on the cancer cell. The anti-CLDN4/anti-CD137 bispecific antibody of the present invention or a pharmaceutical composition containing the antibody can be used for treatment of various cancers.

BRIEF DESCRIPTION OF DRAWINGS

FIG. 1-2 illustrates binding activity to CD137 of test antibodies measured and evaluated by ELISA. The ordinate of the drawings indicates a value obtained by subtracting an absorbance at 570 nm from an absorbance at 450 nm, and the abscissa indicates a concentration of the test antibody. Each of symbols indicates an average of the absorbance obtained in adding each of test antibodies.

FIG. 1-3 illustrates binding activity to CD137 of test antibodies measured and evaluated by ELISA. The ordinate of the drawings indicates a value obtained by subtracting an absorbance at 570 nm from an absorbance at 450 nm, and the abscissa indicates a concentration of the test antibody. Each of symbols indicates an average of the absorbance obtained in adding each of test antibodies.

FIG. 1-4 illustrates binding activity to CD137 of test antibodies measured and evaluated by ELISA. The ordinate of the drawings indicates a value obtained by subtracting an absorbance at 570 nm from an absorbance at 450 nm, and the abscissa indicates a concentration of the test antibody. Each of symbols indicates an average of the absorbance obtained in adding each of test antibodies.

FIG. 2-1 illustrates CD137 agonistic activity of test antibodies obtained in a coculture test of CLDN4 expressing cancer cells (NCI-H322 cell) and 4-1BB Effector Cells. The ordinate of the drawings indicates a relative amount of luminescence, and the abscissa indicates a concentration of the test antibody. Each of symbols indicates an average of the relative amount of luminescence obtained in adding each of test antibodies, and an error bar indicates the standard deviation.

FIG. 2-2 illustrates CD137 agonistic activity of test antibodies obtained in a coculture test of CLDN4 expressing cancer cells (NCI-H322 cell) and 4-1BB Effector Cells. The ordinate of the drawing indicates a relative amount of luminescence, and the abscissa indicates a concentration of the test antibody. Each of symbols indicates an average of the relative amount of luminescence obtained in adding each of test antibodies.

FIG. 2-3 illustrates CD137 agonistic activity of test antibodies obtained in a coculture test of CLDN4 expressing cancer cells (NCI-H322 cell) and 4-1BB Effector Cells. The ordinate of the drawings indicates a relative amount of luminescence, and the abscissa indicates a concentration of the test antibody. Each of symbols indicates an average of the relative amount of luminescence obtained in adding each of test antibodies, and an error bar indicates the standard deviation.

FIG. 2-4 illustrates CD137 agonistic activity of test antibodies obtained in a monoculture test of 4-1BB Effector Cells. The ordinate of the drawings indicates a relative amount of luminescence, and the abscissa indicates a concentration of the test antibody. Each of symbols indicates an average of the relative amount of luminescence obtained in adding each of test antibodies, and an error bar indicates the standard deviation.

FIG. 2-5 illustrates CD137 agonistic activity of test antibodies obtained in a monoculture test of 4-1BB Effector Cells. The ordinate of the drawing indicates a relative amount of luminescence, and the abscissa indicates a concentration of the test antibody. Each of symbols indicates an average of the relative amount of luminescence obtained in adding each of test antibodies.

FIG. 2-6 illustrates CD137 agonistic activity of test antibodies obtained in a monoculture test of 4-1BB Effector Cells. The ordinate of the drawings indicates a relative amount of luminescence, and the abscissa indicates a concentration of the test antibody. Each of symbols indicates an average of the relative amount of luminescence obtained in adding each of test antibodies, and an error bar indicates the standard deviation.

FIG. 3-1 illustrates interferon-γ production promoting function obtained in adding each test antibody to a coculture system of 60As6-Luc/GFP cells and expanded pan T cells. The ordinate indicates a production amount (pg/mL) of interferon γ obtained 6 days after the antibody addition, and the abscissa indicates a concentration of the antibody. Each of symbols indicates an average of the production amount of interferon γ at each concentration of the antibody.

FIG. 3-2 illustrates interferon-γ production promoting function obtained in adding each test antibody to a coculture system of 60As6-Luc/GFP cells and expanded pan T cells. The ordinate of the drawing indicates a production amount (pg/mL) of interferon γ obtained 4 days after the antibody addition, and the abscissa indicates a concentration of the antibody. Each of symbols indicates an average of the production amount of interferon γ at each concentration of the antibody, and an error bar indicates the standard deviation.

FIG. 3-3 illustrates a production amount of interferon γ obtained in adding each test antibody to a monoculture system of expanded pan T cells. The ordinate of the drawing indicates a production amount (pg/mL) of interferon γ obtained 6 days after the antibody addition, and the abscissa indicates a concentration of the antibody. Each of symbols indicates an average of the production amount of interferon γ at each concentration of the antibody.

FIG. 3-4 illustrates a production amount of interferon γ obtained in adding each test antibody to a monoculture system of expanded pan T cells. The ordinate of the drawing indicates a production amount (pg/mL) of interferon γ obtained 5 days after the antibody addition, and the abscissa indicates a concentration of the antibody. Each of symbols indicates an average of the production amount of interferon γ at each concentration of the antibody, and an error bar indicates the standard deviation.

FIG. 4 illustrates cancer cytotoxic activity (cancer cell growth inhibitory activity) by each test antibody in a coculture system of 60As6-Luc/GFP cells and expanded pan T cells. The ordinate of the drawing indicates a cell growth rate obtained assuming that, in a fluorescence area increased from 0 hours to 168 hours after the start of measurement, a well where the test antibody was not added corresponds to 100%. The abscissa indicates a concentration of the antibody. Each of symbols indicates an average of the cancer cell growth rate in each antibody.

FIG. 5 illustrates cancer cell cytotoxic activity obtained in adding each test antibody to a coculture system of 60As6-Luc/GFP cells and expanded pan T cells. The ordinate of the drawing indicates a cancer cell death rate (%) obtained assuming that, in measured values of chemiluminescence of the 60As6-Luc/GFP cells measured 6 days after the antibody addition, an average obtained without adding the antibody corresponds to a death rate of 0%, and an average obtained with Triton-X100 added corresponds to a death rate of 100%. The abscissa indicates a concentration of the antibody. Each of symbols indicates an average of the cancer cell death rate at each concentration of the antibody, and an error bar indicates the standard deviation.

FIG. 6 illustrates a tumor volume change in a PBMC-transferred mouse subcutaneously bearing cancer of an NCI-H322 cell. The abscissa of the drawing indicates days after the first administration, the ordinate indicates an average of the tumor volume, and an error bar indicates the standard deviation.

DESCRIPTION OF EMBODIMENTS

Figure 1:
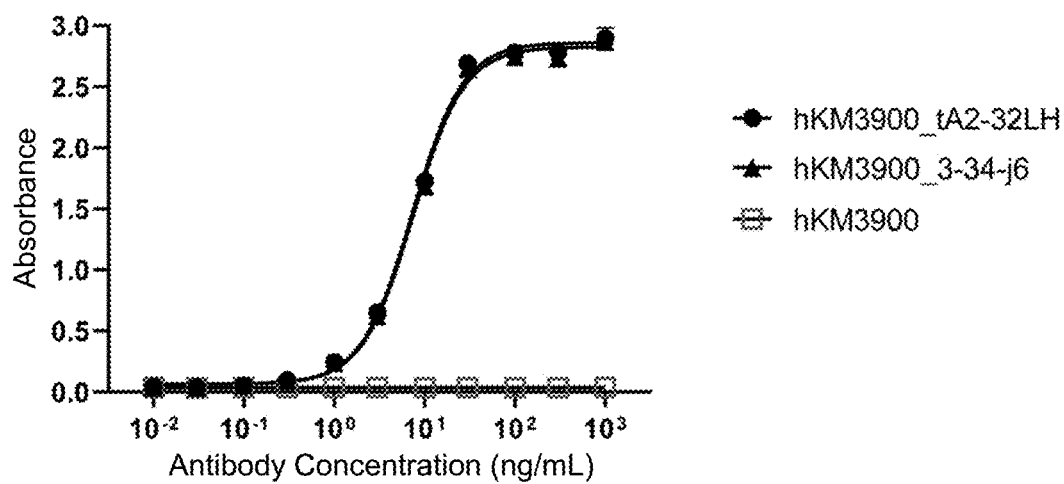
FIG. 1-1 illustrates binding activity to CD137 of test antibodies measured and evaluated by ELISA. The ordinate of the drawing indicates a value obtained by subtracting an absorbance at 570 nm from an absorbance at 450 nm, and the abscissa indicates a concentration of the test antibody. Each symbol indicates an average of the absorbance obtained in adding each of test antibodies, and an error bar indicates the standard deviation.

The present invention will now be described in detail.
<Definitions>

Terms used herein are used to have meanings generally used in this technical field by those skilled in the art unless especially defined in the following.

An antibody (or immunoglobulin) is a glycoprotein whose basic structure is a four-chain structure of a bilaterally symmetrical Y-shape including two heavy chains having a single sequence and two light chains having a single sequence. There are five classes of antibody, that is, IgG, IgM, IgA, IgD and IgE. A basic structure of an antibody molecule is common among these classes, and two heavy chains having a molecular weight of 50,000 to 70,000 and two light chains having a molecular weight of 20,000 to 30,000 are bound via a disulfide bond and a noncovalent bond to form an antibody molecule having a Y-shaped four chain structure with a molecular weight of 150,000 to 190,000. The heavy chain is a polypeptide chain usually containing about 440 amino acids, and has a structure peculiar to each class, and is designated respectively as Igγ, Igμ, Igα, Igδ, and Igε correspondingly to IgG, IgM, IgA, IgD, or IgE. IgG has subclasses of IgG1, IgG2, IgG3 and IgG4, and heavy chains respectively corresponding to these subclasses are designated as Igγ1, Igγ2, Igγ3, and Igγ4. The light chain is a polypeptide chain usually containing about 220 amino acids, and it is known to have two types, λ type and κ type, which are respectively designated as Igλ and Igκ. Each of the two types of the light chains can be paired with any type of the heavy chain.

In an antibody molecule, the heavy chain has four intra-chain disulfide bonds (five in Igμ and Igε), the light chain has two intrachain disulfide bonds, and thus, one loop is formed every 100 to 110 amino acid residues. The three-dimensional structures of these are similar among the loops, and are designated as a structural unit or a domain. In both the heavy chain and the light chain, a domain positioned at the N-terminal is designated as a variable region, and has an amino acid sequence varied even among antibodies produced from the same class (or subclass) of the same species of animal, and is known to be involved in antibody-antigen bond specific binding. A domain disposed on the downstream side from the variable region on the C-terminal side has an amino acid sequence substantially constant in each class or subclass, and is designated as a constant region. The heavy chain has, in a direction from the N-terminal to the C-terminal, a heavy chain variable region (VH) and a heavy chain constant region (CH). The CH is further divided, from the N-terminal side, into three domains of a CH1 domain, a CH2 domain and a CH3 domain. The light chain has, in a direction from the N-terminal to the C-terminal, a light chain variable region (VL) and a light chain constant region (CL).

An amino acid sequence of three complementarity determining regions (CDRs) present in the VH and VL is largely varied, and contributes to variability of the variable regions. Each CDR is a region consisting of 5 to 10 amino acid residues, which is present in the order of CDR1, CDR2 and CDR3 in the N-terminal of each of the heavy chain and the light chain, and comes into contact with an antigen to form an antibody binding site. It is known that the CDRs of the heavy chain make a larger contribution to antigen binding than the CDRs of the light chain, and that the CDR3 makes a largest contribution among the CDR1 to CDR3. On the other hand, a portion excluding the CDRs of the variable region is designated as a framework region (FR), consists of FR1 to FR4, and is comparatively little varied in the amino acid sequence.

When an antibody is treated with papain, that is, a protease, three antibody fragments are obtained. Two fragments disposed on the N-terminal side are designated as a Fab (antigen binding fragment, Fragment, antigen binding) region. The Fab region refers to a region consisting of the VH of the heavy chain, a part of the CH1 domain and a hinge region, and the light chain (VL and CL), and binds to an antigen at the VH and VL (antigen binding site) included in the Fab region. Besides, a fragment disposed on the C-terminal side is designated as a Fc (crystallizable fragment, Fragment, crystallizable) region.

Herein, an "IgG antibody" refers to an antibody having a Y-shaped structure including two Fab regions and a Fc region. In one embodiment, the two Fab regions of the IgG antibody contain the same Fab region sequences. In one embodiment, the two Fab regions of the IgG antibody contain different Fab region sequences.

Herein, an "antigen binding fragment" and a "fragment antibody" can be interchangeably used, and refer to a molecule that contains at least one polypeptide chain containing a heavy chain variable region and a light chain variable region of an immunoglobulin molecule, and having antigen binding activity. Representative examples of the antigen binding fragment include a single chain variable fragment (scFv), a Fab fragment, a Fab' fragment, and a F(ab')2 fragment. Herein, a "scFv" refers to a monovalent antigen binding fragment containing a VH and a VL linked via a linker. A Fab fragment is a monovalent antigen binding fragment containing a fragment consisting of a light chain, a VH and a CH1 domain of a heavy chain, and a part of a hinge region. A Fab' fragment is a monovalent antigen binding fragment containing a fragment consisting of a light chain, a VH and a CH1 domain of a heavy chain, and a part of a hinge region, and this part of the hinge region contains a cysteine residue contained in the disulfide bond between the heavy chains. A F(ab')$_2$ fragment is a bivalent antigen binding fragment containing Fab' fragments bounded via a disulfide bond. The term "monovalent" means that one antigen binding site is contained, and the term "bivalent" means that two antigen binding sites are contained.

Herein, a "bispecific antibody" refers to an antibody molecule containing two antibodies or antigen binding fragments specifically binding to different antigens, and having binding activity to the respective antigens. As bispecific antibodies, bispecific antibodies having various structures are known to those skilled in the art (NPL 6). The term "antibody" used herein encompasses full length antibodies (various immunoglobulins, especially an IgG antibody), an antigen binding fragment, and bispecific antibodies having any structure unless particularly limited contextually.

Herein, an IgG type anti-CLDN4 antibody is designated as an "anti-CLDN4 IgG antibody."

Herein, a "human antibody" refers to an antibody having a human immunoglobulin amino acid sequence. Herein, a "humanized antibody" refers to an antibody in which a part of, most of, or all of amino acid residues excluding the CDRs are substituted with amino acid residues derived from a human immunoglobulin molecule. A humanization method is not especially limited, and for example, U.S. Pat. Nos. 5,225,539, 6,180,370 and the like can be referred to for producing a humanized antibody.

An amino acid residue number of an antibody used herein can be prescribed by specifying the Kabat numbering or EU index (Kabat et al., Sequences of Proteins of Immunological Interest, 5th Ed., 1991, NIH Publication No. 91-3242) in accordance with the numbering system.

Herein, the term "link" or "linked" means that a plurality of components (such as a Fab region and a Fc region) are connected directly or via an intermediary (such as a peptide linker). Herein, the term "peptide linker" means at least one amino acid sequence that can be introduced by a genetic engineering method used for linking a plurality of components. The length of a peptide linker used in the present invention is not especially limited, and can be appropriately selected by those skilled in the art depending on purpose.

Herein, the term "identity" means a value of identity obtained using EMBOSS Needle (Nucleic Acids Res., 2015, Vol. 43, p. W580-W584) with parameters prepared as default. The parameters are as follows:
Gap Open Penalty=10
Gap Extend Penalty=0.5
Matrix=EBLOSUM62
End Gap Penalty=false <Anti-CLDN4/Anti-CD137 Bispecific Antibody of Invention>

The present invention provides a bispecific antibody binding to CLDN4 and CD137 (also referred to as the "anti-CLDN4/anti-CD137 bispecific antibody"). The anti-CLDN4/anti-CD137 bispecific antibody of the present invention contains a heavy chain variable region and a light chain variable region of an anti-CLDN4 antibody, and a heavy chain variable region and a light chain variable region of an anti-CD137 antibody. The anti-CLDN4/anti-CD137 bispecific antibody of the present invention contains a bispecific antibody containing an anti-CLDN4 IgG antibody and a scFv of an anti-CD137 antibody (also referred to as the "anti-CD137 scFv"). In one embodiment, the anti-CLDN4/anti-CD137 bispecific antibody of the present invention is a bispecific antibody containing the anti-CLDN4 IgG antibody and the anti-CD137 scFv.

Herein, the "anti-CLDN4 antibody" is an antibody capable of binding to human CLDN4, and the "anti-CD137 antibody" is an antibody capable of binding to human CD137. It can be checked by employing a known binding activity measurement method whether or not an antibody binds to human CLDN4 or human CD137. Examples of a method for measuring binding activity include a method such as enzyme-linked immunosorbent assay (ELISA) or flow cytometry. ELISA or flow cytometry can be carried out by a method usually employed by those skilled in the art, and a method described in, for example, Example 3 or 5 can be employed.

The anti-CLDN4/anti-CD137 bispecific antibody of the present invention may have any structure as long as it binds to CLDN4 and CD137, and examples thereof include a bispecific antibody having a structure described in NPL 6. In one embodiment, the anti-CLDN4/anti-CD137 bispecific antibody of the present invention may be a conjugate in which a Fab region of an anti-CLDN4 antibody and a Fab region of an anti-CD137 antibody are linked to each other, a conjugate of an anti-CLDN4 IgG antibody and an IgG type anti-CD137 antibody (also referred to as the "anti-CD137 IgG antibody"), a conjugate of an anti-CLDN4 IgG antibody and an antigen binding fragment of an anti-CD137 antibody, a conjugate of an antigen binding fragment of an anti-CLDN4 antibody and an anti-CD137 IgG antibody, or a conjugate of an antigen binding fragment of an anti-CLDN4 antibody and an antigen binding fragment of an anti-CD137 antibody.

In one embodiment, the anti-CLDN4/anti-CD137 bispecific antibody of the present invention contains a full length anti-CLDN4 antibody and a full length anti-CD137 antibody. In one embodiment, the anti-CLDN4/anti-CD137 bispecific antibody of the present invention contains an anti-CLDN4 IgG antibody and an anti-CD137 IgG antibody. Two antibodies may be linked to each other via a linker. In one embodiment, the anti-CLDN4/anti-CD137 bispecific antibody of the present invention contains a full length anti-CLDN4 antibody and an antigen binding fragment of an anti-CD137 antibody. A linkage site of the two antibodies is not especially limited, and they are linked directly or via a linker. In one embodiment, the anti-CLDN4/anti-CD137 bispecific antibody of the present invention contains an anti-CLDN4 IgG antibody and a scFv of an anti-CD137 antibody (herein referred to as the "anti-CD137 scFv"). In one embodiment, the anti-CLDN4/anti-CD137 bispecific antibody of the present invention contains an anti-CLDN4 IgG antibody and an anti-CD137 scFv, in which the amino terminal of the anti-CD137 scFv is linked to the heavy chain carboxy terminal of the anti-CLDN4 antibody. In one embodiment, the anti-CLDN4/anti-CD137 bispecific antibody of the present invention contains an anti-CLDN4 IgG antibody and an anti-CD137 scFv, in which the amino terminal of the anti-CD137 scFv is linked to the light chain carboxy terminal of the anti-CLDN4 antibody. In one embodiment, the anti-CLDN4/anti-CD137 bispecific antibody of the present invention contains an anti-CLDN4 IgG antibody and an anti-CD137 scFv, in which the carboxy terminal of the anti-CD137 scFv is linked to the amino terminal of a heavy chain of the anti-CLDN4 antibody. In one embodiment, the anti-CLDN4/anti-CD137 bispecific antibody of the present invention contains an anti-CLDN4 IgG antibody and an anti-CD137 scFv, in which the carboxy terminal of the anti-CD137 scFv is linked to the amino terminal of a light chain of the anti-CLDN4 antibody. In one embodiment, the anti-CLDN4/anti-CD137 bispecific antibody of the present invention contains an antigen binding fragment of an anti-CLDN4 antibody and an antigen binding fragment of anti-CD137. In one embodiment, the anti-CLDN4/anti-CD137 bispecific antibody of the present invention contains a scFv of an anti-CLDN4 antibody and a scFv of anti-CD137. In one embodiment, the anti-CLDN4/anti-CD137 bispecific antibody of the present invention contains an anti-CD137 scFv.

In the anti-CLDN4/anti-CD137 bispecific antibody of the present invention, the heavy chain variable regions and the light chain variable regions of the anti-CLDN4 antibody and the anti-CD137 antibody may be those derived from a human antibody, or derived from a humanized antibody, or a combination of these. In one embodiment, the anti-CLDN4/anti-CD137 bispecific antibody of the present invention is an antibody containing a human antibody, a humanized antibody, or a combination of these.

The anti-CLDN4/anti-CD137 bispecific antibody of the present invention is an anti-CLDN4/anti-CD137 bispecific antibody containing a heavy chain variable region and a light chain variable region of an anti-CLDN4 antibody, and a heavy chain variable region and a light chain variable region of an anti-CD137 antibody, wherein the heavy chain variable region and the light chain variable region of the anti-CLDN4 antibody are either of the following (a) or (b):

(a) a heavy chain variable region containing a CDR1 consisting of an amino acid sequence at amino acid positions 31-35 of SEQ ID NO: 2, a CDR2 consisting of an amino acid sequence at amino acid positions 50-66 of SEQ ID NO: 2, and a CDR3 consisting of an amino acid sequence at amino acid positions 99-114 of SEQ ID NO: 2, and a light chain variable region containing a CDR1 consisting of an amino acid sequence at amino acid positions 24-35 of SEQ ID NO: 4, a CDR2 consisting of an amino acid sequence at amino acid positions 51-57 of SEQ ID NO: 4, and a CDR3 consisting of an amino acid sequence at amino acid positions 90-98 of SEQ ID NO: 4; or (b) a heavy chain variable region containing a CDR1 consisting of an amino acid sequence at amino acid positions 31-35 of SEQ ID NO: 6, a CDR2 consisting of an amino acid sequence at amino acid positions 50-66 of SEQ ID NO: 6, and a CDR3 consisting of an amino acid sequence at amino acid positions 99-112 of SEQ ID NO: 6, and a light chain variable region containing a CDR1 consisting of an amino acid sequence at amino acid positions 24-35 of SEQ ID NO: 8, a CDR2 consisting of an amino acid sequence at amino acid positions 51-57 of SEQ ID NO: 8, and a CDR3 consisting of an amino acid sequence at amino acid positions 90-98 of SEQ ID NO: 8.

In one embodiment, the anti-CLDN4/anti-CD137 bispecific antibody of the present invention contains a heavy chain variable region and a light chain variable region of an anti-CLDN4 antibody described in the following (a) or (b):

(a) a heavy chain variable region consisting of an amino acid sequence at amino acid positions 1-125 of SEQ ID NO: 2 and a light chain variable region consisting of an amino acid sequence at amino acid positions 1-109 of SEQ ID NO: 4; or (b) a heavy chain variable region consisting of an amino acid sequence at amino acid positions 1-123 of SEQ ID NO: 6 and a light chain variable region consisting of an amino acid sequence at amino acid positions 1-109 of SEQ ID NO: 8.

The anti-CLDN4/anti-CD137 bispecific antibody of the present invention may contain, as an anti-CLDN4 antibody, a full length antibody such as an IgG antibody, or may contain an antigen binding fragment such as a Fab fragment, a Fab' fragment, a F(ab')2 fragment, or a scFv.

As the heavy chain constant region contained in the anti-CLDN4 antibody contained in the anti-CLDN4/anti-CD137 bispecific antibody of the present invention, any of the constant regions Igγ, Igμ, Igα, Igδ and Igε can be selected. Igγ can be selected from, for example, Igγ1, Igγ2, Igγ3 and Igγ4. As the light chain constant region contained in the anti-CLDN4 antibody contained in the anti-CLDN4/anti-CD137 bispecific antibody of the present invention, either of the constant regions Igλ and Igκ can be selected. When the anti-CLDN4 antibody contained in the anti-CLDN4/anti-CD137 bispecific antibody of the present invention is an IgG antibody, the heavy chain and the light chain of the anti-CLDN4 antibody are respectively human Igγ1 and Igκ in one embodiment. In one embodiment, the anti-CLDN4/anti-CD137 bispecific antibody of the present invention contains a full length anti-CLDN4 antibody. In one embodiment, the anti-CLDN4 antibody contained in the anti-CLDN4/anti-CD137 bispecific antibody of the present invention is an IgG antibody containing a heavy chain variable region and a light chain variable region of an anti-CLDN4 antibody (anti-CLDN4 IgG antibody).

When the anti-CLDN4/anti-CD137 bispecific antibody of the present invention contains a Fc region, the Fc region of the bispecific antibody may contain mutation that deteriorates antibody-dependent cellular cytotoxicity (ADCC) or complement-dependent cytotoxicity (CDC). L234A is replacement of leucine with alanine at amino acid position 234 in human Igγ1 constant region. L235A is replacement of leucine with alanine at amino acid position 235 in human Igγ1 constant region. The amino acid mutation L234A and L235A of human Igγ1 constant region is designated as "LALA mutation." Here, the positions 234 and 235 are amino acid positions in human Igγ1 constant region according to EU index. This mutation is known to deteriorate ADCC and CDC of an antibody (Mol. Immunol., 1992, Vol. 29, p. 633-639; and J. Immunol., 2000, Vol. 164, p. 4178-4184). P331G or P331S is replacement of proline with glycine or serine at amino acid position 331 in human Igγ1 constant region. Here, the position 331 is an amino acid position in human Igγ1 constant region according to EU index. This mutation is known to deteriorate CDC of an antibody (J. Immunol., 2000, Vol. 164(8), p. 4178-4184).

In one embodiment, the anti-CLDN4 IgG antibody contained in the anti-CLDN4/anti-CD137 bispecific antibody of the present invention contains a Fc region containing amino acid mutation L234A and L235A (LALA mutation). In one embodiment, the anti-CLDN4 IgG antibody contains a Fc region containing either P331G or P331S mutation. In one embodiment, the anti-CLDN4 IgG antibody contains a Fc region containing mutations of LALA mutation and either P331G or P331S mutation.

The present inventors created a novel anti-CD137 antibody or its binding fragment (scFv) in the process of creating the anti-CLDN4/anti-CD137 bispecific antibody of the present invention. The present inventors identified an anti-CLDN4/anti-CD137 bispecific antibody that does not transduce a CD137 signal when binding only to CD137, but transduces the CD137 signal only when binding simultaneously to CD137 and CLDN4. The antibody does not exhibit agonistic activity when not binding to CLDN4. On the other hand, binding of the anti-CLDN4/anti-CD137 bispecific antibody to CLDN4 and CD137 leads to CD137 signal transduction and activation of a T cell. This activity is expected to alleviate hepatotoxicity or the like observed in a clinical trial of Urelumab, and therefore is expected to be a preferable profile as an anti-CD137 antibody used in the bispecific antibody.

In one embodiment, the anti-CLDN4/anti-CD137 bispecific antibody of the present invention contains a heavy chain variable region and a light chain variable region of an anti-CD137 antibody described in any of the following (a) to (d):

(a) a heavy chain variable region containing a CDR1 consisting of an amino acid sequence at amino acid positions 31-35 of SEQ ID NO: 10, a CDR2 consisting of an amino acid sequence at amino acid positions 50-66 of SEQ ID NO: 10, and a CDR3 consisting of an amino acid sequence at amino acid positions 99-107 of SEQ ID NO: 10, and a light chain variable region containing a CDR1 consisting of an amino acid sequence at amino acid positions 24-34 of SEQ ID NO: 12, a CDR2 consisting of an amino acid sequence at amino acid positions 50-56 of SEQ ID NO: 12, and a CDR3 consisting of an amino acid sequence at amino acid positions 89-98 of SEQ ID NO: 12;

(b) a heavy chain variable region containing a CDR1 consisting of an amino acid sequence at amino acid positions 31-35 of SEQ ID NO: 14, a CDR2 consisting of an amino acid sequence at amino acid positions 50-65 of SEQ ID NO: 14, and a CDR3 consisting of an amino acid sequence at amino acid positions 98-107 of SEQ ID NO: 14, and a light chain variable region containing a CDR1 consisting of an amino acid sequence at amino acid positions 23-35 of SEQ ID NO: 16, a CDR2 consisting of an amino acid sequence at amino acid positions 51-57 of SEQ ID NO: 16, and a CDR3 consisting of an amino acid sequence at amino acid positions 90-100 of SEQ ID NO: 16;

(c) a heavy chain variable region containing a CDR1 consisting of an amino acid sequence at amino acid positions 31-35 of SEQ ID NO: 18, a CDR2 consisting of an amino acid sequence at amino acid positions 50-65 of SEQ ID NO: 18, and a CDR3 consisting of an amino acid sequence at amino acid positions 98-107 of SEQ ID NO: 18, and a light chain variable region containing a CDR1 consisting of an amino acid sequence at amino acid positions 23-35 of SEQ ID NO: 20, a CDR2 consisting of an amino acid sequence at amino acid positions 51-57 of SEQ ID NO: 20, and a CDR3 consisting of an amino acid sequence at amino acid positions 90-100 of SEQ ID NO: 20; or (d) a heavy chain variable region containing a CDR1 consisting of an amino acid sequence at amino acid positions 31-35 of SEQ ID NO: 22, a CDR2 consisting of an amino acid sequence at amino acid positions 50-65 of SEQ ID NO: 22, and a CDR3 consisting of an amino acid sequence at amino acid positions 98-110 of SEQ ID NO: 22, and a light chain variable region containing a CDR1 consisting of an amino acid sequence at amino acid positions 23-35 of SEQ ID NO: 24, a CDR2 consisting of an amino acid sequence at amino acid positions 51-57 of SEQ ID NO: 24, and a CDR3 consisting of an amino acid sequence at amino acid positions 90-100 of SEQ ID NO: 24.

In one embodiment, the anti-CLDN4/anti-CD137 bispecific antibody of the present invention contains a heavy chain variable region and a light chain variable region of an anti-CD137 antibody described in any of the following (a) to (i):

(a) a heavy chain variable region consisting of an amino acid sequence at amino acid positions 1-118 of SEQ ID NO: 10 and a light chain variable region consisting of an amino acid sequence at amino acid positions 1-109 of SEQ ID NO: 12;

(b) a heavy chain variable region consisting of an amino acid sequence at amino acid positions 1-118 of SEQ ID NO: 14 and a light chain variable region consisting of an amino acid sequence at amino acid positions 1-111 of SEQ ID NO: 16;

(c) a heavy chain variable region consisting of an amino acid sequence at amino acid positions 1-118 of SEQ ID NO: 18 and a light chain variable region consisting of an amino acid sequence at amino acid positions 1-111 of SEQ ID NO: 20;

(d) a heavy chain variable region consisting of an amino acid sequence at amino acid positions 1-121 of SEQ ID NO: 22 and a light chain variable region consisting of an amino acid sequence at amino acid positions 1-111 of SEQ ID NO: 24;

(e) a heavy chain variable region consisting of an amino acid sequence at amino acid positions 1-118 of SEQ ID NO: 26 and a light chain variable region consisting of an amino acid sequence at amino acid positions 134-242 of SEQ ID NO: 26;

(f) a heavy chain variable region consisting of an amino acid sequence at amino acid positions 1-118 of SEQ ID NO: 28 and a light chain variable region consisting of an amino acid sequence at amino acid positions 134-244 of SEQ ID NO: 28;

(g) a light chain variable region consisting of an amino acid sequence at amino acid positions 1-111 of SEQ ID NO: 30 and a heavy chain variable region consisting of an amino acid sequence at amino acid positions 132-249 of SEQ ID NO: 30;

(h) a heavy chain variable region consisting of an amino acid sequence at amino acid positions 1-118 of SEQ ID NO: 32 and a light chain variable region consisting of an amino acid sequence at amino acid positions 134-244 of SEQ ID NO: 32; or (i) a heavy chain variable region consisting of an amino acid sequence at amino acid positions 1-121 of SEQ ID NO: 34 and a light chain variable region consisting of an amino acid sequence at amino acid positions 137-247 of SEQ ID NO: 34.

The anti-CLDN4/anti-CD137 bispecific antibody of the present invention may contain, as an anti-CD137 antibody, a full length antibody such as an IgG antibody, or may contain an antigen binding fragment such as a Fab fragment, a Fab' fragment, a F(ab')2 fragment, or a scFv. In one embodiment, the anti-CD137 antibody contained in the anti-CLDN4/anti-CD137 bispecific antibody is an antigen binding fragment of an anti-CD137 antibody. In one embodiment, the antigen binding fragment of the anti-CD137 antibody contained in the anti-CLDN4/anti-CD137 bispecific antibody is an anti-CD137 scFv.

In one embodiment, the anti-CLDN4/anti-CD137 bispecific antibody of the present invention contains an anti-CD137 scFv containing a heavy chain variable region and a light chain variable region of an anti-CD137 antibody described in the following (a) to (m):

(a) a heavy chain variable region containing a CDR1 consisting of an amino acid sequence at amino acid positions 31-35 of SEQ ID NO: 10, a CDR2 consisting of an amino acid sequence at amino acid positions 50-66 of SEQ ID NO: 10, and a CDR3 consisting of an amino acid sequence at amino acid positions 99-107 of SEQ ID NO: 10, and a light chain variable region containing a CDR1 consisting of an amino acid sequence at amino acid positions 24-34 of SEQ ID NO: 12, a CDR2 consisting of an amino acid sequence at amino acid positions 50-56 of SEQ ID NO: 12, and a CDR3 consisting of an amino acid sequence at amino acid positions 89-98 of SEQ ID NO: 12;

(b) a heavy chain variable region containing a CDR1 consisting of an amino acid sequence at amino acid positions 31-35 of SEQ ID NO: 14, a CDR2 consisting of an amino acid sequence at amino acid positions 50-65 of SEQ ID NO: 14, and a CDR3 consisting of an amino acid sequence at amino acid positions 98-107 of SEQ ID NO: 14, and a light chain variable region containing a CDR1 consisting of an amino acid sequence at amino acid positions 23-35 of SEQ ID NO: 16, a CDR2 consisting of an amino acid sequence at amino acid positions 51-57 of SEQ ID NO: 16, and a CDR3 consisting of an amino acid sequence at amino acid positions 90-100 of SEQ ID NO: 16;

(c) a heavy chain variable region containing a CDR1 consisting of an amino acid sequence at amino acid positions 31-35 of SEQ ID NO: 18, a CDR2 consisting of an amino acid sequence at amino acid positions 50-65 of SEQ ID NO: 18, and a CDR3 consisting of an amino acid sequence at amino acid positions 98-107 of SEQ ID NO: 18, and a light chain variable region containing a CDR1 consisting of an amino acid sequence at amino acid positions 23-35 of SEQ ID NO: 20, a CDR2 consisting of an amino acid sequence at amino acid positions 51-57 of SEQ ID NO: 20, and a CDR3 consisting of an amino acid sequence at amino acid positions 90-100 of SEQ ID NO: 20;

(d) a heavy chain variable region containing a CDR1 consisting of an amino acid sequence at amino acid positions 31-35 of SEQ ID NO: 22, a CDR2 consisting of an amino acid sequence at amino acid positions 50-65 of SEQ ID NO: 22, and a CDR3 consisting of an amino acid sequence at amino acid positions 98-110 of SEQ ID NO: 22, and a light chain variable region containing a CDR1 consisting of an amino acid sequence at amino acid positions 23-35 of SEQ ID NO: 24, a CDR2 consisting of an amino acid sequence at amino acid positions 51-57 of SEQ ID NO: 24, and a CDR3 consisting of an amino acid sequence at amino acid positions 90-100 of SEQ ID NO: 24;

(e) a heavy chain variable region consisting of an amino acid sequence at amino acid positions 1-118 of SEQ ID NO: 10 and a light chain variable region consisting of an amino acid sequence at amino acid positions 1-109 of SEQ ID NO: 12;

(f) a heavy chain variable region consisting of an amino acid sequence at amino acid positions 1-118 of SEQ ID NO: 14 and a light chain variable region consisting of an amino acid sequence at amino acid positions 1-111 of SEQ ID NO: 16;

(g) a heavy chain variable region consisting of an amino acid sequence at amino acid positions 1-118 of SEQ ID NO: 18 and a light chain variable region consisting of an amino acid sequence at amino acid positions 1-111 of SEQ ID NO: 20;

(h) a heavy chain variable region consisting of an amino acid sequence at amino acid positions 1-121 of SEQ ID NO: 22 and a light chain variable region consisting of an amino acid sequence at amino acid positions 1-111 of SEQ ID NO: 24;

(i) a heavy chain variable region consisting of an amino acid sequence at amino acid positions 1-118 of SEQ ID NO: 26 and a light chain variable region consisting of an amino acid sequence at amino acid positions 134-242 of SEQ ID NO: 26;

(j) a heavy chain variable region consisting of an amino acid sequence at amino acid positions 1-118 of SEQ ID NO: 28 and a light chain variable region consisting of an amino acid sequence at amino acid positions 134-244 of SEQ ID NO: 28;

(k) a light chain variable region consisting of an amino acid sequence at amino acid positions 1-111 of SEQ ID NO: 30 and a heavy chain variable region consisting of an amino acid sequence at amino acid positions 132-249 of SEQ ID NO: 30;

(l) a heavy chain variable region consisting of an amino acid sequence at amino acid positions 1-118 of SEQ ID NO: 32 and a light chain variable region consisting of an amino acid sequence at amino acid positions 134-244 of SEQ ID NO: 32; or (m) a heavy chain variable region consisting of an amino acid sequence at amino acid positions 1-121 of SEQ ID NO: 34 and a light chain variable region consisting of an amino acid sequence at amino acid positions 137-247 of SEQ ID NO: 34.

The type and the length of a linker used for linking the heavy chain variable region and the light chain variable region of the anti-CD137 antibody in the anti-CD137 scFv are not especially limited, and can be appropriately selected by those skilled in the art. As the linker, a peptide linker may be used. A preferable length is 5 or more amino acids (with an upper limit being not especially limited, but being usually 30 or less amino acids, and preferably 20 or less amino acids), and is particularly preferably 15 amino acids. As the linker, for example, a glycine-serine linker (GS linker), or a glycine-lysine-proline-glycine-serine linker (GKPGS linker) (SEQ ID NO: 55) can be used. Examples of such linkers include the following:

```
Ser

Gly-Ser

Gly-Gly-Ser

Ser-Gly-Gly (SEQ ID No. 46)
Gly-Gly-Gly-Ser (SEQ ID No. 47)
Ser-Gly-Gly-Gly (SEQ ID No. 48)
Gly-Gly-Gly-Gly-Ser (SEQ ID No. 49)
Ser-Gly-Gly-Gly-Gly (SEQ ID No. 50)
Gly-Gly-Gly-Gly-Gly-Ser (SEQ ID No. 51)
Ser-Gly-Gly-Gly-Gly-Gly (SEQ ID No. 52)
Gly-Gly-Gly-Gly-Gly-Gly-Ser (SEQ ID No. 53)
Ser-Gly-Gly-Gly-Gly-Gly-Gly (SEQ ID No. 54)
Gly-Gly-Gly-Gly-Ser-Gly-Gly-Gly-Gly-Ser (SEQ ID NO: 56)
(Gly-Gly-Gly-Gly-Ser)n (SEQ ID NO: 57)
(Ser-Gly-Gly-Gly-Gly)n (SEQ ID No. 55)
Gly-Lys-Pro-Gly-Ser (SEQ ID NO: 58)
(Gly-Lys-Pro-Gly-Ser)n
```

In the above-described examples, n represents an integer of 1 or more. In one aspect, n is 1 to 10, 2 to 8, or 2 to 6. The length and the sequence of the linker can be appropriately selected depending on purpose by those skilled in the art. In one embodiment, the linker used in the anti-CD137 scFv is a GS linker. In one embodiment, the linker used in the anti-CD137 scFv is a GS linker of (Gly-Gly-Gly-Gly-Ser)n, and n is either 3 (SEQ ID NO: 59) or 4 (SEQ ID NO: 60).

In one embodiment, the anti-CLDN4/anti-CD137 bispecific antibody of the present invention contains an anti-CD137 scFv described in any of the following (a) to (e):
  (a) an anti-CD137 scFv consisting of an amino acid sequence at amino acid positions 1-242 of SEQ ID NO: 26;
  (b) an anti-CD137 scFv consisting of an amino acid sequence at amino acid positions 1-244 of SEQ ID NO: 28;
  (c) an anti-CD137 scFv consisting of an amino acid sequence at amino acid positions 1-249 of SEQ ID NO: 30;
  (d) an anti-CD137 scFv consisting of an amino acid sequence at amino acid positions 1-244 of SEQ ID NO: 32; or
  (e) an anti-CD137 scFv consisting of an amino acid sequence at amino acid positions 1-247 of SEQ ID NO: 34.

In the anti-CLDN4/anti-CD137 bispecific antibody of the present invention, the anti-CLDN4 antibody or its antigen binding fragment may be linked to the anti-CD137 antibody or its antigen binding fragment via a linker. The type and the length of the linker for linking the anti-CLDN4 antibody or its antigen binding fragment to the anti-CD137 antibody or its antigen binding fragment are not especially limited, and can be appropriately selected by those skilled in the art. As the linker, a peptide linker may be used. A preferable length is 5 or more amino acids (with an upper limit being not especially limited, but being usually 30 or less amino acids, and preferably 20 or less amino acids), and is particularly preferably 10 amino acids. As the peptide linker, for example, a glycine-serine linker (GS linker), or a glycine-lysine-proline-glycine-serine linker (GKPGS linker) (SEQ ID NO: 55) can be used. Examples of such linkers include the following:

```
Ser

Gly-Ser

Gly-Gly-Ser

Ser-Gly-Gly (SEQ ID No. 46)
Gly-Gly-Gly-Ser (SEQ ID No. 47)
Ser-Gly-Gly-Gly (SEQ ID No. 48)
Gly-Gly-Gly-Gly-Ser (SEQ ID NO. 49)
Ser-Gly-Gly-Gly-Gly (SEQ ID No. 50)
Gly-Gly-Gly-Gly-Gly-Ser (SEQ ID No. 51)
Ser-Gly-Gly-Gly-Gly-Gly (SEQ ID No. 52)
Gly-Gly-Gly-Gly-Gly-Gly-Ser (SEQ ID No. 53)
Ser-Gly-Gly-Gly-Gly-Gly-Gly (SEQ ID No. 54)
Gly-Gly-Gly-Gly-Ser-Gly-Gly-Gly-Gly-Ser (SEQ ID NO: 56)
(Gly-Gly-Gly-Gly-Ser)n (SEQ ID NO: 57)
(Ser-Gly-Gly-Gly-Gly)n (SEQ ID No. 55)
Gly-Lys-Pro-Gly-Ser (SEQ ID NO: 58)
(Gly-Lys-Pro-Gly-Ser)n
```

In the above-described examples, n represents an integer of 1 or more. In one aspect, n is 1 to 10, 2 to 8, or 2 to 6. The length and the sequence of the peptide linker can be appropriately selected depending on purpose by those skilled in the art. In one embodiment, a linker used as the linker for linking the anti-CLDN4 antibody or its antigen binding fragment to the anti-CD137 antibody or its antigen binding fragment is a GS linker or a GKPGS linker (SEQ ID NO: 55), and in another embodiment, is a linker having an amino acid sequence of SEQ ID NO: 54.

In one embodiment, the anti-CLDN4/anti-CD137 bispecific antibody of the present invention contains an anti-CLDN4 IgG antibody and an anti-CD137 scFv, and has a structure in which the anti-CLDN4 IgG antibody is linked to the anti-CD137 scFv via a linker. The linkage site between the anti-CLDN4 IgG antibody and the anti-CD137 scFv is not especially limited, and for example, the anti-CLDN4/anti-CD137 bispecific antibody of the present invention can take various structures, such as the heavy chain amino terminal of the anti-CLDN4 IgG antibody linked to the carboxy terminal of the anti-CD137 scFv, the light chain amino terminal of the anti-CLDN4 IgG antibody linked to the carboxy terminal of the anti-CD137 scFv, the amino terminal of the anti-CD137 scFv linked to the heavy chain carboxy terminal of the anti-CLDN4 IgG antibody, and the amino terminal of the anti-CD137 scFv linked to the light chain carboxy terminal of the anti-CLDN4 IgG antibody. In one embodiment, the anti-CLDN4/anti-CD137 bispecific antibody of the present invention comprises the amino terminal of the anti-CD137 scFv linked to the heavy chain carboxy terminal of the anti-CLDN4 IgG antibody, or the amino terminal of the anti-CD137 scFv linked to the light chain carboxy terminal of the anti-CLDN4 IgG antibody. In one embodiment, the anti-CLDN4/anti-CD137 bispecific antibody of the present invention comprises the amino terminal of the anti-CD137 scFv linked to the heavy chain carboxy terminal of the anti-CLDN4 IgG antibody.

In one embodiment, the anti-CLDN4/anti-CD137 bispecific antibody of the present invention is an anti-CLDN4/anti-CD137 bispecific antibody containing an anti-CLDN4 IgG antibody and an anti-CD137 scFv, in which the amino terminal of the anti-CD137 scFv is linked to a heavy chain or light chain carboxy terminal of the anti-CLDN4 IgG antibody via a linker, and a heavy chain variable region and a light chain variable region of the anti-CD137 scFv are described in any of the following (a) to (m):

(a) a heavy chain variable region containing a CDR1 consisting of an amino acid sequence at amino acid positions 31-35 of SEQ ID NO: 10, a CDR2 consisting of an amino acid sequence at amino acid positions 50-66 of SEQ ID NO: 10, and a CDR3 consisting of an amino acid sequence at amino acid positions 99-107 of SEQ ID NO: 10, and a light chain variable region containing a CDR1 consisting of an amino acid sequence at amino acid positions 24-34 of SEQ ID NO: 12, a CDR2 consisting of an amino acid sequence at amino acid positions 50-56 of SEQ ID NO: 12, and a CDR3 consisting of an amino acid sequence at amino acid positions 89-98 of SEQ ID NO: 12;

(b) a heavy chain variable region containing a CDR1 consisting of an amino acid sequence at amino acid positions 31-35 of SEQ ID NO: 14, a CDR2 consisting of an amino acid sequence at amino acid positions 50-65 of SEQ ID NO: 14, and a CDR3 consisting of an amino acid sequence at amino acid positions 98-107 of SEQ ID NO: 14, and a light chain variable region containing a CDR1 consisting of an amino acid sequence at amino acid positions 23-35 of SEQ ID NO: 16, a CDR2 consisting of an amino acid sequence at amino acid positions 51-57 of SEQ ID NO: 16, and a CDR3 consisting of an amino acid sequence at amino acid positions 90-100 of SEQ ID NO: 16;

(c) a heavy chain variable region containing a CDR1 consisting of an amino acid sequence at amino acid positions 31-35 of SEQ ID NO: 18, a CDR2 consisting of an amino acid sequence at amino acid positions 50-65 of SEQ ID NO: 18, and a CDR3 consisting of an amino acid sequence at amino acid positions 98-107 of SEQ ID NO: 18, and a light chain variable region containing a CDR1 consisting of an amino acid sequence at amino acid positions 23-35 of SEQ ID NO: 20, a CDR2 consisting of an amino acid sequence at amino acid positions 51-57 of SEQ ID NO: 20, and a CDR3 consisting of an amino acid sequence at amino acid positions 90-100 of SEQ ID NO: 20;

(d) a heavy chain variable region containing a CDR1 consisting of an amino acid sequence at amino acid positions 31-35 of SEQ ID NO: 22, a CDR2 consisting of an amino acid sequence at amino acid positions 50-65 of SEQ ID NO: 22, and a CDR3 consisting of an amino acid sequence at amino acid positions 98-110 of SEQ ID NO: 22, and a light chain variable region containing a CDR1 consisting of an amino acid sequence at amino acid positions 23-35 of SEQ ID NO: 24, a CDR2 consisting of an amino acid sequence at amino acid positions 51-57 of SEQ ID NO: 24, and a CDR3 consisting of an amino acid sequence at amino acid positions 90-100 of SEQ ID NO: 24;

(e) a heavy chain variable region consisting of an amino acid sequence at amino acid positions 1-118 of SEQ ID NO: 10 and a light chain variable region consisting of an amino acid sequence at amino acid positions 1-109 of SEQ ID NO: 12;

(f) a heavy chain variable region consisting of an amino acid sequence at amino acid positions 1-118 of SEQ ID NO: 14 and a light chain variable region consisting of an amino acid sequence at amino acid positions 1-111 of SEQ ID NO: 16;

(g) a heavy chain variable region consisting of an amino acid sequence at amino acid positions 1-118 of SEQ ID NO: 18 and a light chain variable region consisting of an amino acid sequence at amino acid positions 1-111 of SEQ ID NO: 20;

(h) a heavy chain variable region consisting of an amino acid sequence at amino acid positions 1-121 of SEQ ID NO: 22 and a light chain variable region consisting of an amino acid sequence at amino acid positions 1-111 of SEQ ID NO: 24;

(i) a heavy chain variable region consisting of an amino acid sequence at amino acid positions 1-118 of SEQ ID NO: 26 and a light chain variable region consisting of an amino acid sequence at amino acid positions 134-242 of SEQ ID NO: 26;

(j) a heavy chain variable region consisting of an amino acid sequence at amino acid positions 1-118 of SEQ ID NO: 28 and a light chain variable region consisting of an amino acid sequence at amino acid positions 134-244 of SEQ ID NO: 28;

(k) a light chain variable region consisting of an amino acid sequence at amino acid positions 1-111 of SEQ ID NO: 30 and a heavy chain variable region consisting of an amino acid sequence at amino acid positions 132-249 of SEQ ID NO: 30;

(l) a heavy chain variable region consisting of an amino acid sequence at amino acid positions 1-118 of SEQ ID NO: 32 and a light chain variable region consisting of an amino acid sequence at amino acid positions 134-244 of SEQ ID NO: 32; or (m) a heavy chain variable region consisting of an amino acid sequence at amino acid positions 1-121 of SEQ ID NO: 34 and a light chain variable region consisting of an amino acid sequence at amino acid positions 137-247 of SEQ ID NO: 34.

In one embodiment, the anti-CLDN4/anti-CD137 bispecific antibody of the present invention is an anti-CLDN4/anti-CD137 bispecific antibody containing an anti-CLDN4 IgG antibody and an anti-CD137 scFv, in which the amino terminal of the anti-CD137 scFv is linked to a heavy chain or light chain carboxy terminal of the anti-CLDN4 IgG antibody via a linker, and the anti-CD137 scFv is described in any of the following (a) to (e):

(a) an anti-CD137 scFv consisting of an amino acid sequence at amino acid positions 1-242 of SEQ ID NO: 26;

(b) an anti-CD137 scFv consisting of an amino acid sequence at amino acid positions 1-244 of SEQ ID NO: 28;

(c) an anti-CD137 scFv consisting of an amino acid sequence at amino acid positions 1-249 of SEQ ID NO: 30;

(d) an anti-CD137 scFv consisting of an amino acid sequence at amino acid positions 1-244 of SEQ ID NO: 32; or (e) an anti-CD137 scFv consisting of an amino acid sequence at amino acid positions 1-247 of SEQ ID NO: 34.

In one embodiment, the anti-CLDN4/anti-CD137 bispecific antibody of the present invention is an anti-CLDN4/anti-CD137 scFv bispecific antibody described in any of the following (a) to (h):

(a) a bispecific antibody containing: a heavy chain of an anti-CLDN4 antibody containing a heavy chain variable region containing a CDR1 consisting of an amino acid sequence at amino acid positions 31-35 of SEQ ID NO: 2, a CDR2 consisting of an amino acid sequence at amino acid positions 50-66 of SEQ ID NO: 2, and a CDR3 consisting of an amino acid sequence at amino acid positions 99-114 of SEQ ID NO: 2, and a light chain of an anti-CLDN4 antibody containing a light chain variable region containing a CDR1 consisting of an amino acid sequence at amino acid positions 24-35 of SEQ ID NO: 4, a CDR2 consisting of an amino acid sequence at amino acid positions 51-57 of SEQ ID NO: 4, and a CDR3 consisting of an amino acid sequence at amino acid positions 90-98 of SEQ ID NO: 4; and an anti-CD137 scFv containing a heavy chain variable region containing a CDR1 consisting of an amino acid sequence at amino acid positions 31-35 of SEQ ID NO: 10, a CDR2 consisting of an amino acid sequence at amino acid positions 50-66 of SEQ ID NO: 10, and a CDR3 consisting of an amino acid sequence at amino acid positions 99-107 of SEQ ID NO: 10, and a light chain variable region containing a CDR1 consisting of an amino acid sequence at amino acid positions 24-34 of SEQ ID NO: 12, a CDR2 consisting of an amino acid sequence at amino acid positions 50-56 of SEQ ID NO: 12, and a CDR3 consisting of an amino acid sequence at amino acid positions 89-98 of SEQ ID NO: 12, in which the amino terminal of the anti-CD137 scFv is linked to the heavy chain carboxy terminal of the anti-CLDN4 antibody via a linker;

(b) a bispecific antibody containing: a heavy chain of an anti-CLDN4 antibody containing a heavy chain variable region containing a CDR1 consisting of an amino acid sequence at amino acid positions 31-35 of SEQ ID NO: 2, a CDR2 consisting of an amino acid sequence at amino acid positions 50-66 of SEQ ID NO: 2, and a CDR3 consisting of an amino acid sequence at amino acid positions 99-114 of SEQ ID NO: 2, and a light chain of an anti-CLDN4 antibody containing a light chain variable region containing a CDR1 consisting of an amino acid sequence at amino acid positions 24-35 of SEQ ID NO: 4, a CDR2 consisting of an amino acid sequence at amino acid positions 51-57 of SEQ ID NO: 4, and a CDR3 consisting of an amino acid sequence at amino acid positions 90-98 of SEQ ID NO: 4; and an anti-CD137 scFv containing a heavy chain variable region containing a CDR1 consisting of an amino acid sequence at amino acid positions 31-35 of SEQ ID NO: 14, a CDR2 consisting of an amino acid sequence at amino acid positions 50-65 of SEQ ID NO: 14, and a CDR3 consisting of an amino acid sequence at amino acid positions 98-107 of SEQ ID NO: 14, and a light chain variable region containing a CDR1 consisting of an amino acid sequence at amino acid positions 23-35 of SEQ ID NO: 16, a CDR2 consisting of an amino acid sequence at amino acid positions 51-57 of SEQ ID NO: 16, and a CDR3 consisting of an amino acid sequence at amino acid positions 90-100 of SEQ ID NO: 16, in which the amino terminal of the anti-CD137 scFv is linked to the heavy chain carboxy terminal of the anti-CLDN4 antibody via a linker;

(c) a bispecific antibody containing: a heavy chain of an anti-CLDN4 antibody containing a heavy chain variable region containing a CDR1 consisting of an amino acid sequence at amino acid positions 31-35 of SEQ ID NO: 2, a CDR2 consisting of an amino acid sequence at amino acid positions 50-66 of SEQ ID NO: 2, and a CDR3 consisting of an amino acid sequence at amino acid positions 99-114 of SEQ ID NO: 2, and a light chain of an anti-CLDN4 antibody containing a light chain variable region containing a CDR1 consisting of an amino acid sequence at amino acid positions 24-35 of SEQ ID NO: 4, a CDR2 consisting of an amino acid sequence at amino acid positions 51-57 of SEQ ID NO: 4, and a CDR3 consisting of an amino acid sequence at amino acid positions 90-98 of SEQ ID NO: 4; and an anti-CD137 scFv containing a heavy chain variable region containing a CDR1 consisting of an amino acid sequence at amino acid positions 31-35 of SEQ ID NO: 18, a CDR2 consisting of an amino acid sequence at amino acid positions 50-65 of SEQ ID NO: 18, and a CDR3 consisting of an amino acid sequence at amino acid positions 98-107 of SEQ ID NO: 18, and a light chain variable region containing a CDR1 consisting of an amino acid sequence at amino acid positions 23-35 of SEQ ID NO: 20, a CDR2 consisting of an amino acid sequence at amino acid positions 51-57 of SEQ ID NO: 20, and a CDR3 consisting of an amino acid sequence at amino acid positions 90-100 of SEQ ID NO: 20, in which the amino terminal of the anti-CD137 scFv is linked to the heavy chain carboxy terminal of the anti-CLDN4 antibody via a linker;

(d) a bispecific antibody containing: a heavy chain of an anti-CLDN4 antibody containing a heavy chain variable region containing a CDR1 consisting of an amino acid sequence at amino acid positions 31-35 of SEQ ID NO: 2, a CDR2 consisting of an amino acid sequence at amino acid positions 50-66 of SEQ ID NO: 2, and a CDR3 consisting of an amino acid sequence at amino acid positions 99-114 of SEQ ID NO: 2, and a light chain of an anti-CLDN4 antibody containing a light chain variable region containing a CDR1 consisting of an amino acid sequence at amino acid positions 24-35 of SEQ ID NO: 4, a CDR2 consisting of an amino acid sequence at amino acid positions 51-57 of SEQ ID NO: 4, and a CDR3 consisting of an amino acid sequence at amino acid positions 90-98 of SEQ ID NO: 4; and an anti-CD137 scFv containing a heavy chain variable region containing a CDR1 consisting of an amino acid sequence at amino acid positions 31-35 of SEQ ID NO: 22, a CDR2 consisting of an amino acid sequence at amino acid positions 50-65 of SEQ ID NO: 22, and a CDR3 consisting of an amino acid sequence at amino acid positions 98-110 of SEQ ID NO: 22, and a light chain variable region containing a CDR1 consisting of an amino acid sequence at amino acid positions 23-35 of SEQ ID NO: 24, a CDR2 consisting of an amino acid sequence at amino acid positions 51-57 of SEQ ID NO: 24, and a CDR3 consisting of an amino acid sequence at amino acid positions 90-100 of SEQ ID NO: 24, in which the amino terminal of the anti-CD137 scFv is linked to the heavy chain carboxy terminal of the anti-CLDN4 antibody via a linker;

(e) a bispecific antibody containing: a heavy chain of an anti-CLDN4 antibody containing a heavy chain variable region containing a CDR1 consisting of an amino acid sequence at amino acid positions 31-35 of SEQ ID NO: 6, a CDR2 consisting of an amino acid sequence at amino acid positions 50-66 of SEQ ID NO: 6, and a CDR3 consisting of an amino acid sequence at amino acid positions 99-112 of SEQ ID NO: 6, and a light chain of an anti-CLDN4 antibody containing a light chain variable region containing a CDR1 consisting of an amino acid sequence at amino acid positions 24-35 of SEQ ID NO: 8, a CDR2 consisting of an amino acid sequence at amino acid positions 51-57 of SEQ ID NO: 8, and a CDR3 consisting of an amino acid sequence at amino acid positions 90-98 of SEQ ID NO: 8; and an anti-CD137 scFv containing a heavy chain variable region containing a CDR1 consisting of an amino acid sequence at amino acid positions 31-35 of SEQ ID NO: 10, a CDR2 consisting of an amino acid sequence at amino acid positions 50-66 of SEQ ID NO: 10, and a CDR3 consisting of an amino acid sequence at amino acid positions 99-107 of SEQ ID NO: 10, and a light chain variable region containing a CDR1 consisting of an amino acid sequence at amino acid positions 24-34 of SEQ ID NO: 12, a CDR2 consisting of an amino acid sequence at amino acid positions 50-56 of SEQ ID NO: 12, and a CDR3 consisting of an amino acid sequence at amino acid positions 89-98 of SEQ ID NO: 12, in which the amino terminal of the anti-CD137 scFv is linked to the heavy chain carboxy terminal of the anti-CLDN4 antibody via a linker;

(f) a bispecific antibody containing: a heavy chain of an anti-CLDN4 antibody containing a heavy chain variable region containing a CDR1 consisting of an amino acid sequence at amino acid positions 31-35 of SEQ ID NO: 6, a CDR2 consisting of an amino acid sequence at amino acid positions 50-66 of SEQ ID NO: 6, and a CDR3 consisting of an amino acid sequence at amino acid positions 99-112 of SEQ ID NO: 6, and a light chain of an anti-CLDN4 antibody containing a light chain variable region containing a CDR1 consisting of an amino acid sequence at amino acid positions 24-35 of SEQ ID NO: 8, a CDR2 consisting of an amino acid sequence at amino acid positions 51-57 of SEQ ID NO: 8, and a CDR3 consisting of an amino acid sequence at amino acid positions 90-98 of SEQ ID NO: 8; and an anti-CD137 scFv containing a heavy chain variable region containing a CDR1 consisting of an amino acid sequence at amino acid positions 31-35 of SEQ ID NO: 14, a CDR2 consisting of an amino acid sequence at amino acid positions 50-65 of SEQ ID NO: 14, and a CDR3 consisting of an amino acid sequence at amino acid positions 98-107 of SEQ ID NO: 14, and a light chain variable region containing a CDR1 consisting of an amino acid sequence at amino acid positions 23-35 of SEQ ID NO: 16, a CDR2 consisting of an amino acid sequence at amino acid positions 51-57 of SEQ ID NO: 16, and a CDR3 consisting of an amino acid sequence at amino acid positions 90-100 of SEQ ID NO: 16, in which the amino terminal of the anti-CD137 scFv is linked to the heavy chain carboxy terminal of the anti-CLDN4 antibody via a linker;

(g) a bispecific antibody containing: a heavy chain of an anti-CLDN4 antibody containing a heavy chain variable region containing a CDR1 consisting of an amino acid sequence at amino acid positions 31-35 of SEQ ID NO: 6, a CDR2 consisting of an amino acid sequence at amino acid positions 50-66 of SEQ ID NO: 6, and a CDR3 consisting of an amino acid sequence at amino acid positions 99-112 of SEQ ID NO: 6, and a light chain of an anti-CLDN4 antibody containing a light chain variable region containing a CDR1 consisting of an amino acid sequence at amino acid positions 24-35 of SEQ ID NO: 8, a CDR2 consisting of an amino acid sequence at amino acid positions 51-57 of SEQ ID NO: 8, and a CDR3 consisting of an amino acid sequence at amino acid positions 90-98 of SEQ ID NO: 8; and an anti-CD137 scFv containing a heavy chain variable region containing a CDR1 consisting of an amino acid sequence at amino acid positions 31-35 of SEQ ID NO: 18, a CDR2 consisting of an amino acid sequence at amino acid positions 50-65 of SEQ ID NO: 18, and a CDR3 consisting of an amino acid sequence at amino acid positions 98-107 of SEQ ID NO: 18, and a light chain variable region containing a CDR1 consisting of an amino acid sequence at amino acid positions 23-35 of SEQ ID NO: 20, a CDR2 consisting of an amino acid sequence at amino acid positions 51-57 of SEQ ID NO: 20, and a CDR3 consisting of an amino acid sequence at amino acid positions 90-100 of SEQ ID NO: 20, in which the amino terminal of the anti-CD137 scFv is linked to the heavy chain carboxy terminal of the anti-CLDN4 antibody via a linker; or (h) a bispecific antibody containing: a heavy chain of an anti-CLDN4 antibody containing a heavy chain variable region containing a CDR1 consisting of an amino acid sequence at amino acid positions 31-35 of SEQ ID NO: 6, a CDR2 consisting of an amino acid sequence at amino acid positions 50-66 of SEQ ID NO: 6, and a CDR3 consisting of an amino acid sequence at amino acid positions 99-112 of SEQ ID NO: 6, and a light chain of an anti-CLDN4 antibody containing a light chain variable region containing a CDR1 consisting of an amino acid sequence at amino acid positions 24-35 of SEQ ID NO: 8, a CDR2 consisting of an amino acid sequence at amino acid positions 51-57 of SEQ ID NO: 8, and a CDR3 consisting of an amino acid sequence at amino acid positions 90-98 of SEQ ID NO: 8; and an anti-CD137 scFv containing a heavy chain variable region containing a CDR1 consisting of an amino acid sequence at amino acid positions 31-35 of SEQ ID NO: 22, a CDR2 consisting of an amino acid sequence at amino acid positions 50-65 of SEQ ID NO: 22, and a CDR3 consisting of an amino acid sequence at amino acid positions 98-110 of SEQ ID NO: 22, and a light chain variable region containing a CDR1 consisting of an amino acid sequence at amino acid positions 23-35 of SEQ ID NO: 24, a CDR2 consisting of an amino acid sequence at amino acid positions 51-57 of SEQ ID NO: 24, and a CDR3 consisting of an amino acid sequence at amino acid positions 90-100 of SEQ ID NO: 24, in which the amino terminal of the anti-CD137 scFv is linked to the heavy chain carboxy terminal of the anti-CLDN4 antibody via a linker.

In one embodiment, the anti-CLDN4/anti-CD137 bispecific antibody of the present invention is an anti-CLDN4/anti-CD137 scFv bispecific antibody described in any of the following (a) to (j):

(a) a bispecific antibody comprising a heavy chain of an anti-CLDN4 antibody containing a heavy chain variable region consisting of an amino acid sequence at amino acid positions 1-125 of SEQ ID NO: 2 and a light chain of an anti-CLDN4 antibody containing a light chain variable region consisting of an amino acid sequence at amino acid positions 1-109 of SEQ ID NO: 4, and an anti-CD137 scFv containing a heavy chain variable region consisting of an amino acid sequence at amino acid positions 1-118 of SEQ ID NO: 26 and a light chain variable region consisting of an amino acid sequence at amino acid positions 134-242 of SEQ ID NO: 26, wherein an amino terminal of the anti-CD137 scFv is linked to a heavy chain carboxy terminal of the anti-CLDN4 antibody via a linker;

(b) a bispecific antibody comprising a heavy chain of an anti-CLDN4 antibody containing a heavy chain variable region consisting of an amino acid sequence at amino acid positions 1-125 of SEQ ID NO: 2 and a light chain of an anti-CLDN4 antibody containing a light chain variable region consisting of an amino acid sequence at amino acid positions 1-109 of SEQ ID NO: 4, and an anti-CD137 scFv containing a heavy chain variable region consisting of an amino acid sequence at amino acid positions 1-118 of SEQ ID NO: 28 and a light chain variable region consisting of an amino acid sequence at amino acid positions 134-244 of SEQ ID NO: 28, wherein an amino terminal of the anti-CD137 scFv is linked to a heavy chain carboxy terminal of the anti-CLDN4 antibody via a linker;

(c) a bispecific antibody comprising a heavy chain of an anti-CLDN4 antibody containing a heavy chain variable region consisting of an amino acid sequence at amino acid positions 1-125 of SEQ ID NO: 2 and a light chain of an anti-CLDN4 antibody containing a light chain variable region consisting of an amino acid sequence at amino acid positions 1-109 of SEQ ID NO: 4, and an anti-CD137 scFv containing a light chain variable region consisting of an amino acid sequence at amino acid positions 1-111 of SEQ ID NO: 30 and a heavy chain variable region consisting of an amino acid sequence at amino acid positions 132-249 of SEQ ID NO: 30, wherein an amino terminal of the anti-CD137 scFv is linked to a heavy chain carboxy terminal of the anti-CLDN4 antibody via a linker;

(d) a bispecific antibody comprising a heavy chain of an anti-CLDN4 antibody containing a heavy chain variable region consisting of an amino acid sequence at amino acid positions 1-125 of SEQ ID NO: 2 and a light chain of an anti-CLDN4 antibody containing a light chain variable region consisting of an amino acid sequence at amino acid positions 1-109 of SEQ ID NO: 4, and an anti-CD137 scFv containing a heavy chain variable region consisting of an amino acid sequence at amino acid positions 1-118 of SEQ ID NO: 32 and a light chain variable region consisting of an amino acid sequence at amino acid positions 134-244 of SEQ ID NO: 32, wherein an amino terminal of the anti-CD137 scFv is linked to a heavy chain carboxy terminal of the anti-CLDN4 antibody via a linker;

(e) a bispecific antibody comprising a heavy chain of an anti-CLDN4 antibody containing a heavy chain variable region consisting of an amino acid sequence at amino acid positions 1-125 of SEQ ID NO: 2 and a light chain of an anti-CLDN4 antibody containing a light chain variable region consisting of an amino acid sequence at amino acid positions 1-109 of SEQ ID NO: 4, and an anti-CD137 scFv containing a heavy chain variable region consisting of an amino acid sequence at amino acid positions 1-121 of SEQ ID NO: 34 and a light chain variable region consisting of an amino acid sequence at amino acid positions 137-247 of SEQ ID NO: 34, wherein an amino terminal of the anti-CD137 scFv is linked to a heavy chain carboxy terminal of the anti-CLDN4 antibody via a linker;

(f) a bispecific antibody comprising a heavy chain of an anti-CLDN4 antibody containing a heavy chain variable region consisting of an amino acid sequence at amino acid positions 1-123 of SEQ ID NO: 6 and a light chain of an anti-CLDN4 antibody containing a light chain variable region consisting of an amino acid sequence at amino acid positions 1-109 of SEQ ID NO: 8, and an anti-CD137 scFv containing a heavy chain variable region consisting of an amino acid sequence at amino acid positions 1-118 of SEQ ID NO: 26 and a light chain variable region consisting of an amino acid sequence at amino acid positions 134-242 of SEQ ID NO: 26, wherein an amino terminal of the anti-CD137 scFv is linked to a heavy chain carboxy terminal of the anti-CLDN4 antibody via a linker;

(g) a bispecific antibody comprising a heavy chain of an anti-CLDN4 antibody containing a heavy chain variable region consisting of an amino acid sequence at amino acid positions 1-123 of SEQ ID NO: 6 and a light chain of an anti-CLDN4 antibody containing a light chain variable region consisting of an amino acid sequence at amino acid positions 1-109 of SEQ ID NO: 8, and an anti-CD137 scFv containing a heavy chain variable region consisting of an amino acid sequence at amino acid positions 1-118 of SEQ ID NO: 28 and a light chain variable region consisting of an amino acid sequence at amino acid positions 134-244 of SEQ ID NO: 28, wherein an amino terminal of the anti-CD137 scFv is linked to a heavy chain carboxy terminal of the anti-CLDN4 antibody via a linker;

(h) a bispecific antibody comprising a heavy chain of an anti-CLDN4 antibody containing a heavy chain variable region consisting of an amino acid sequence at amino acid positions 1-123 of SEQ ID NO: 6 and a light chain of an anti-CLDN4 antibody containing a light chain variable region consisting of an amino acid sequence at amino acid positions 1-109 of SEQ ID NO: 8, and an anti-CD137 scFv containing a light chain variable region consisting of an amino acid sequence at amino acid positions 1-111 of SEQ ID NO: 30 and a heavy chain variable region consisting of an amino acid sequence at amino acid positions 132-249 of SEQ ID NO: 30, wherein an amino terminal of the anti-CD137 scFv is linked to a heavy chain carboxy terminal of the anti-CLDN4 antibody via a linker;

(i) a bispecific antibody comprising a heavy chain of an anti-CLDN4 antibody containing a heavy chain variable region consisting of an amino acid sequence at amino acid positions 1-123 of SEQ ID NO: 6 and a light chain of an anti-CLDN4 antibody containing a light chain variable region consisting of an amino acid sequence at amino acid positions 1-109 of SEQ ID NO: 8, and an anti-CD137 scFv containing a heavy chain variable region consisting of an amino acid sequence at amino acid positions 1-118 of SEQ ID NO: 32 and a light chain variable region consisting of an amino acid sequence at amino acid positions 134-244 of SEQ ID NO: 32, wherein an amino terminal of the anti-CD137 scFv is linked to a heavy chain carboxy terminal of the anti-CLDN4 antibody via a linker;

(j) a bispecific antibody comprising a heavy chain of an anti-CLDN4 antibody containing a heavy chain variable region consisting of an amino acid sequence at amino acid positions 1-123 of SEQ ID NO: 6 and a light chain of an anti-CLDN4 antibody containing a light chain variable region consisting of an amino acid sequence at amino acid positions 1-109 of SEQ ID NO: 8, and an anti-CD137 scFv containing a heavy chain variable region consisting of an amino acid sequence at amino acid positions 1-121 of SEQ ID NO: 34 and a light chain variable region consisting of an amino acid sequence at amino acid positions 137-247 of SEQ ID NO: 34, wherein an amino terminal of the anti-CD137 scFv is linked to a heavy chain carboxy terminal of the anti-CLDN4 antibody via a linker;

(k) a bispecific antibody comprising a heavy chain of an anti-CLDN4 antibody containing a heavy chain variable region consisting of an amino acid sequence at amino acid positions 1-125 of SEQ ID NO: 2 and a light chain of an anti-CLDN4 antibody containing a light chain variable region consisting of an amino acid sequence at amino acid positions 1-109 of SEQ ID NO: 4, and an anti-CD137 scFv containing a heavy chain variable region consisting of an amino acid sequence at amino acid positions 1-118 of SEQ ID NO: 26 and a light chain variable region consisting of an amino acid sequence at amino acid positions 134-242 of SEQ ID NO: 26, wherein an amino terminal of the anti-CD137 scFv is linked to a light chain carboxy terminal of the anti-CLDN4 antibody via a linker;

(l) a bispecific antibody comprising a heavy chain of an anti-CLDN4 antibody containing a heavy chain variable region consisting of an amino acid sequence at amino acid positions 1-125 of SEQ ID NO: 2 and a light chain of an anti-CLDN4 antibody containing a light chain variable region consisting of an amino acid sequence at amino acid positions 1-109 of SEQ ID NO: 4, and an anti-CD137 scFv containing a heavy chain variable region consisting of an amino acid sequence at amino acid positions 1-118 of SEQ ID NO: 28 and a light chain variable region consisting of an amino acid sequence at amino acid positions 134-244 of SEQ ID NO: 28, wherein an amino terminal of the anti-CD137 scFv is linked to a light chain carboxy terminal of the anti-CLDN4 antibody via a linker;

(m) a bispecific antibody comprising a heavy chain of an anti-CLDN4 antibody containing a heavy chain variable region consisting of an amino acid sequence at amino acid positions 1-125 of SEQ ID NO: 2 and a light chain of an anti-CLDN4 antibody containing a light chain variable region consisting of an amino acid sequence at amino acid positions 1-109 of SEQ ID NO: 4, and an anti-CD137 scFv containing a light chain variable region consisting of an amino acid sequence at amino acid positions 1-111 of SEQ ID NO: 30 and a heavy chain variable region consisting of an amino acid sequence at amino acid positions 132-249 of SEQ ID NO: 30, wherein an amino terminal of the anti-CD137 scFv is linked to a light chain carboxy terminal of the anti-CLDN4 antibody via a linker;

(n) a bispecific antibody comprising a heavy chain of an anti-CLDN4 antibody containing a heavy chain variable region consisting of an amino acid sequence at amino acid positions 1-125 of SEQ ID NO: 2 and a light chain of an anti-CLDN4 antibody containing a light chain variable region consisting of an amino acid sequence at amino acid positions 1-109 of SEQ ID NO: 4, and an anti-CD137 scFv containing a heavy chain variable region consisting of an amino acid sequence at amino acid positions 1-118 of SEQ ID NO: 32 and a light chain variable region consisting of an amino acid sequence at amino acid positions 134-244 of SEQ ID NO: 32, wherein an amino terminal of the anti-CD137 scFv is linked to a light chain carboxy terminal of the anti-CLDN4 antibody via a linker;

(o) a bispecific antibody comprising a heavy chain of an anti-CLDN4 antibody containing a heavy chain variable region consisting of an amino acid sequence at amino acid positions 1-125 of SEQ ID NO: 2 and a light chain of an anti-CLDN4 antibody containing a light chain variable region consisting of an amino acid sequence at amino acid positions 1-109 of SEQ ID NO: 4, and an anti-CD137 scFv containing a heavy chain variable region consisting of an amino acid sequence at amino acid positions 1-121 of SEQ ID NO: 34 and a light chain variable region consisting of an amino acid sequence at amino acid positions 137-247 of SEQ ID NO: 34, wherein an amino terminal of the anti-CD137 scFv is linked to a light chain carboxy terminal of the anti-CLDN4 antibody via a linker;

(p) a bispecific antibody comprising a heavy chain of an anti-CLDN4 antibody containing a heavy chain variable region consisting of an amino acid sequence at amino acid positions 1-123 of SEQ ID NO: 6 and a light chain of an anti-CLDN4 antibody containing a light chain variable region consisting of an amino acid sequence at amino acid positions 1-109 of SEQ ID NO: 8, and an anti-CD137 scFv containing a heavy chain variable region consisting of an amino acid sequence at amino acid positions 1-118 of SEQ ID NO: 26 and a light chain variable region consisting of an amino acid sequence at amino acid positions 134-242 of SEQ ID NO: 26, wherein an amino terminal of the anti-CD137 scFv is linked to a light chain carboxy terminal of the anti-CLDN4 antibody via a linker;

(q) a bispecific antibody comprising a heavy chain of an anti-CLDN4 antibody containing a heavy chain variable region consisting of an amino acid sequence at amino acid positions 1-123 of SEQ ID NO: 6 and a light chain of an anti-CLDN4 antibody containing a light chain variable region consisting of an amino acid sequence at amino acid positions 1-109 of SEQ ID NO: 8, and an anti-CD137 scFv containing a heavy chain variable region consisting of an amino acid sequence at amino acid positions 1-118 of SEQ ID NO: 28 and a light chain variable region consisting of an amino acid sequence at amino acid positions 134-244 of SEQ ID NO: 28, wherein an amino terminal of the anti-CD137 scFv is linked to a light chain carboxy terminal of the anti-CLDN4 antibody via a linker;

(r) a bispecific antibody comprising a heavy chain of an anti-CLDN4 antibody containing a heavy chain variable region consisting of an amino acid sequence at amino acid positions 1-123 of SEQ ID NO: 6 and a light chain of an anti-CLDN4 antibody containing a light chain variable region consisting of an amino acid sequence at amino acid positions 1-109 of SEQ ID NO: 8, and an anti-CD137 scFv containing a light chain variable region consisting of an amino acid sequence at amino acid positions 1-111 of SEQ ID NO: 30 and a heavy chain variable region consisting of an amino acid sequence at amino acid positions 132-249 of SEQ ID NO: 30, wherein an amino terminal of the anti-CD137 scFv is linked to a light chain carboxy terminal of the anti-CLDN4 antibody via a linker;

(s) a bispecific antibody comprising a heavy chain of an anti-CLDN4 antibody containing a heavy chain variable region consisting of an amino acid sequence at amino acid positions 1-123 of SEQ ID NO: 6 and a light chain of an anti-CLDN4 antibody containing a light chain variable region consisting of an amino acid sequence at amino acid positions 1-109 of SEQ ID NO: 8, and an anti-CD137 scFv containing a heavy chain variable region consisting of an amino acid sequence at amino acid positions 1-118 of SEQ ID NO: 32 and a light chain variable region consisting of an amino acid sequence at amino acid positions 134-244 of SEQ ID NO: 32, wherein an amino terminal of the anti-CD137 scFv is linked to a light chain carboxy terminal of the anti-CLDN4 antibody via a linker; or (t) a bispecific antibody containing a heavy chain of an anti-CLDN4 antibody containing a heavy chain variable region consisting of an amino acid sequence at amino acid positions 1-123 of SEQ ID NO: 6 and a light chain of an anti-CLDN4 antibody containing a light chain variable region consisting of an amino acid sequence at amino acid positions 1-109 of SEQ ID NO: 8, and an anti-CD137 scFv containing a heavy chain variable region consisting of an amino acid sequence at amino acid positions 1-121 of SEQ ID NO: 34 and a light chain variable region consisting of an amino acid sequence at amino acid positions 137-247 of SEQ ID NO: 34, in which the amino terminal of the anti-CD137 scFv is linked to the light chain carboxy terminal of the anti-CLDN4 antibody via a linker.

In one embodiment, the anti-CLDN4/anti-CD137 bispecific antibody of the present invention is an anti-CLDN4/anti-CD137 scFv bispecific antibody described in the following (a) or (b):

(a) a bispecific antibody containing a polypeptide consisting of an amino acid sequence at amino acid positions 1-705 of SEQ ID NO: 36 containing a heavy chain of an anti-CLDN4 antibody and an anti-CD137 scFv, and a polypeptide containing a light chain of an anti-CLDN4 antibody consisting of an amino acid sequence at amino acid positions 1-215 of SEQ ID NO: 40; or (b) a bispecific antibody containing a polypeptide consisting of an amino acid sequence at amino acid positions 1-712 of SEQ ID NO: 38 containing a heavy chain of an anti-CLDN4 antibody and an anti-CD137 scFv, and a light chain of an anti-CLDN4 antibody consisting of an amino acid sequence at amino acid positions 1-215 of SEQ ID NO: 40.

Herein, the term "post-translational modification" refers to that an antibody expressed in a cell is modified after translation. Examples of the post-translational modification include modification such as pyroglutamylation, glycosylation, oxidation, deamidation or glycation of glutamine or glutamic acid at the heavy chain N-terminal, and lysine deletion by cutting lysine at the heavy chain C-terminal with carboxypeptidase. It is known that such post-translational modification is caused in various antibodies (J. Pharm. Sci., 2008, Vol. 97, p. 2426-2447).

In one embodiment, the anti-CLDN4/anti-CD137 bispecific antibody of the present invention may be post-translationally modified. In one embodiment, the post-translational modification is pyroglutamylation at the N-terminal of the heavy chain variable region and/or lysine deletion at the heavy chain C-terminal. It is known in this field that the post-translational modification by pyroglutamylation at the N-terminal or lysine deletion at the C-terminal does not affect the activity of the antibody (Analytical Biochemistry, 2006, Vol. 348, p. 24-39).

The anti-CLDN4/anti-CD137 bispecific antibody of the present invention binds to human CLDN4 and human CD137. It can be checked by employing a known binding activity measurement method whether or not the antibody binds to human CLDN4 and human CD137. Examples of a method for measuring binding activity include a method such as ELISA and flow cytometry. ELISA or flow cytometry can be carried out by a method usually employed by those skilled in the art, and a method described in, for example, Example 3 or 5 can be employed.

The anti-CLDN4/anti-CD137 bispecific antibody of the present invention can be easily produced by those skilled in the art with human CLDN4 and human CD137 used as antigens by employing an antibody production technique known in this field, or can be easily produced by those skilled in the art based on sequence information and the like of the heavy chain variable regions and the light chain variable regions of the anti-CLDN4 antibody and the anti-CD137 antibody disclosed herein by employing a method known in this field.

The anti-CLDN4/anti-CD137 bispecific antibody of the present invention can be produced in accordance with, for example, a method described in <Method for Producing Bispecific Antibody of Invention> described below, although not especially limited thereto.

<Polynucleotide of Bispecific Antibody of Invention>

The present invention also provides a polynucleotide usable in production of the anti-CLDN4/anti-CD137 bispecific antibody of the present invention (also referred to as the "polynucleotide of the bispecific antibody of the present invention").

In one embodiment, the polynucleotide of the bispecific antibody of the present invention is a polynucleotide having a nucleotide sequence encoding a heavy chain variable region or light chain variable region of an anti-CLDN4 antibody, which is selected from the group consisting of the following (a) to (d):

(a) a polynucleotide having a nucleotide sequence encoding a heavy chain variable region of an anti-CLDN4 antibody consisting of an amino acid sequence at amino acid positions 1-125 of SEQ ID NO: 2;

(b) a polynucleotide having a nucleotide sequence encoding a light chain variable region of an anti-CLDN4 antibody consisting of an amino acid sequence at amino acid positions 1-109 of SEQ ID NO: 4;
(c) a polynucleotide having a nucleotide sequence encoding a heavy chain variable region of an anti-CLDN4 antibody consisting of an amino acid sequence at amino acid positions 1-123 of SEQ ID NO: 6; or
(d) a polynucleotide having a nucleotide sequence encoding a light chain variable region of an anti-CLDN4 antibody consisting of an amino acid sequence at amino acid positions 1-109 of SEQ ID NO: 8.

In one embodiment, the polynucleotide of the bispecific antibody of the present invention is a polynucleotide having a nucleotide sequence encoding a heavy chain variable region and a light chain variable region of an anti-CLDN4 antibody, which is selected from the following (a) or (b):

(a) a polynucleotide having a nucleotide sequence encoding a heavy chain variable region of an anti-CLDN4 antibody consisting of an amino acid sequence at amino acid positions 1-125 of SEQ ID NO: 2, and a polynucleotide having a nucleotide sequence encoding a light chain variable region of an anti-CLDN4 antibody consisting of an amino acid sequence at amino acid positions 1-109 of SEQ ID NO: 4; or
(b) a polynucleotide having a nucleotide sequence encoding a heavy chain variable region of an anti-CLDN4 antibody consisting of an amino acid sequence at amino acid positions 1-123 of SEQ ID NO: 6, and a polynucleotide having a nucleotide sequence encoding a light chain variable region of an anti-CLDN4 antibody consisting of an amino acid sequence at amino acid positions 1-109 of SEQ ID NO: 8.

In one embodiment, the polynucleotide of the bispecific antibody of the present invention is a polynucleotide having a nucleotide sequence encoding a heavy chain variable region or light chain variable region of an anti-CD137 antibody, which is selected from the group consisting of the following (a) to (r):

(a) a polynucleotide having a nucleotide sequence encoding a heavy chain variable region of an anti-CD137 antibody consisting of an amino acid sequence at amino acid positions 1-118 of SEQ ID NO: 10;
(b) a polynucleotide having a nucleotide sequence encoding a light chain variable region of an anti-CD137 antibody consisting of an amino acid sequence at amino acid positions 1-109 of SEQ ID NO: 12;
(c) a polynucleotide having a nucleotide sequence encoding a heavy chain variable region of an anti-CD137 antibody consisting of an amino acid sequence at amino acid positions 1-118 of SEQ ID NO: 14;
(d) a polynucleotide having a nucleotide sequence encoding a light chain variable region of an anti-CD137 antibody consisting of an amino acid sequence at amino acid positions 1-111 of SEQ ID NO: 16;
(e) a polynucleotide having a nucleotide sequence encoding a heavy chain variable region of an anti-CD137 antibody consisting of an amino acid sequence at amino acid positions 1-118 of SEQ ID NO: 18;
(f) a polynucleotide having a nucleotide sequence encoding a light chain variable region of an anti-CD137 antibody consisting of an amino acid sequence at amino acid positions 1-111 of SEQ ID NO: 20;
(g) a polynucleotide having a nucleotide sequence encoding a heavy chain variable region of an anti-CD137 antibody consisting of an amino acid sequence at amino acid positions 1-121 of SEQ ID NO: 22;
(h) a polynucleotide having a nucleotide sequence encoding a light chain variable region of an anti-CD137 antibody consisting of an amino acid sequence at amino acid positions 1-111 of SEQ ID NO: 24;
(i) a polynucleotide having a nucleotide sequence encoding a heavy chain variable region of an anti-CD137 antibody consisting of an amino acid sequence at amino acid positions 1-118 of SEQ ID NO: 26;
(j) a polynucleotide having a nucleotide sequence encoding a light chain variable region of an anti-CD137 antibody consisting of an amino acid sequence at amino acid positions 134-242 of SEQ ID NO: 26;
(k) a polynucleotide having a nucleotide sequence encoding a heavy chain variable region of an anti-CD137 antibody consisting of an amino acid sequence at amino acid positions 1-118 of SEQ ID NO: 28;
(l) a polynucleotide having a nucleotide sequence encoding a light chain variable region of an anti-CD137 antibody consisting of an amino acid sequence at amino acid positions 134-244 of SEQ ID NO: 28;
(m) a polynucleotide having a nucleotide sequence encoding a light chain variable region of an anti-CD137 antibody consisting of an amino acid sequence at amino acid positions 1-111 of SEQ ID NO: 30;
(n) a polynucleotide having a nucleotide sequence encoding a heavy chain variable region of an anti-CD137 antibody consisting of an amino acid sequence at amino acid positions 132-249 of SEQ ID NO: 30;
(o) a polynucleotide having a nucleotide sequence encoding a heavy chain variable region of an anti-CD137 antibody consisting of an amino acid sequence at amino acid positions 1-118 of SEQ ID NO: 32;
(p) a polynucleotide having a nucleotide sequence encoding a light chain variable region of an anti-CD137 antibody consisting of an amino acid sequence at amino acid positions 134-244 of SEQ ID NO: 32;
(q) a polynucleotide having a nucleotide sequence encoding a heavy chain variable region of an anti-CD137 antibody consisting of an amino acid sequence at amino acid positions 1-121 of SEQ ID NO: 34; or
(r) a polynucleotide having a nucleotide sequence encoding a light chain variable region of an anti-CD137 antibody consisting of an amino acid sequence at amino acid positions 137-247 of SEQ ID NO: 34.

In one embodiment, the polynucleotide of the bispecific antibody of the present invention is a polynucleotide having a nucleotide sequence encoding a heavy chain variable region and a light chain variable region of an anti-CD137 antibody, which is selected from the group consisting of the following (a) to (i):

(a) a polynucleotide having a nucleotide sequence encoding a heavy chain variable region of an anti-CD137 antibody consisting of an amino acid sequence at amino acid positions 1-118 of SEQ ID NO: 10, and a polynucleotide having a nucleotide sequence encoding a light chain variable region of an anti-CD137 antibody consisting of an amino acid sequence at amino acid positions 1-109 of SEQ ID NO: 12;
(b) a polynucleotide having a nucleotide sequence encoding a heavy chain variable region of an anti-CD137 antibody consisting of an amino acid sequence at amino acid positions 1-118 of SEQ ID NO: 14, and a polynucleotide having a nucleotide sequence encoding a light chain variable region of an anti-CD137 antibody consisting of an amino acid sequence at amino acid positions 1-111 of SEQ ID NO: 16;
(c) a polynucleotide having a nucleotide sequence encoding a heavy chain variable region of an anti-CD137 antibody consisting of an amino acid sequence at amino acid positions 1-118 of SEQ ID NO: 18, and a polynucleotide having a nucleotide sequence encoding a light chain variable region of an anti-CD137 antibody consisting of an amino acid sequence at amino acid positions 1-111 of SEQ ID NO: 20;
(d) a polynucleotide having a nucleotide sequence encoding a heavy chain variable region of an anti-CD137 antibody consisting of an amino acid sequence at amino acid positions 1-121 of SEQ ID NO: 22, and a polynucleotide having a nucleotide sequence encoding a light chain variable region of an anti-CD137 antibody consisting of an amino acid sequence at amino acid positions 1-111 of SEQ ID NO: 24;
(e) a polynucleotide having a nucleotide sequence encoding a heavy chain variable region of an anti-CD137 antibody consisting of an amino acid sequence at amino acid positions 1-118 of SEQ ID NO: 26, and a polynucleotide having a nucleotide sequence encoding a light chain variable region of an anti-CD137 antibody consisting of an amino acid sequence at amino acid positions 134-242 of SEQ ID NO: 26;
(f) a polynucleotide having a nucleotide sequence encoding a heavy chain variable region of an anti-CD137 antibody consisting of an amino acid sequence at amino acid positions 1-118 of SEQ ID NO: 28, and a polynucleotide having a nucleotide sequence encoding a light chain variable region of an anti-CD137 antibody consisting of an amino acid sequence at amino acid positions 134-244 of SEQ ID NO: 28;
(g) a polynucleotide having a nucleotide sequence encoding a light chain variable region of an anti-CD137 antibody consisting of an amino acid sequence at amino acid positions 1-111 of SEQ ID NO: 30, and a polynucleotide having a nucleotide sequence encoding a heavy chain variable region of an anti-CD137 antibody consisting of an amino acid sequence at amino acid positions 132-249 of SEQ ID NO: 30;
(h) a polynucleotide having a nucleotide sequence encoding a heavy chain variable region of an anti-CD137 antibody consisting of an amino acid sequence at amino acid positions 1-118 of SEQ ID NO: 32, and a polynucleotide having a nucleotide sequence encoding a light chain variable region of an anti-CD137 antibody consisting of an amino acid sequence at amino acid positions 134-244 of SEQ ID NO: 32; or
(i) a polynucleotide having a nucleotide sequence encoding a heavy chain variable region of an anti-CD137 antibody consisting of an amino acid sequence at amino acid positions 1-121 of SEQ ID NO: 34, and a polynucleotide having a nucleotide sequence encoding a light chain variable region of an anti-CD137 antibody consisting of an amino acid sequence at amino acid positions 137-247 of SEQ ID NO: 34.

In one embodiment, the polynucleotide of the bispecific antibody of the present invention is a polynucleotide having a nucleotide sequence encoding an anti-CD137 scFv, which is selected from the group consisting of the following (a) to (e):
(a) a polynucleotide having a nucleotide sequence encoding an anti-CD137 scFv consisting of an amino acid sequence at amino acid positions 1-242 of SEQ ID NO: 26;
(b) a polynucleotide having a nucleotide sequence encoding an anti-CD137 scFv consisting of an amino acid sequence at amino acid positions 1-244 of SEQ ID NO: 28;
(c) a polynucleotide having a nucleotide sequence encoding an anti-CD137 scFv consisting of an amino acid sequence at amino acid positions 1-249 of SEQ ID NO: 30;
(d) a polynucleotide having a nucleotide sequence encoding an anti-CD137 scFv consisting of an amino acid sequence at amino acid positions 1-244 of SEQ ID NO: 32; or
(e) a polynucleotide having a nucleotide sequence encoding an anti-CD137 scFv consisting of an amino acid sequence at amino acid positions 1-247 of SEQ ID NO: 34.

In one embodiment, the polynucleotide of the bispecific antibody of the present invention is a polynucleotide selected from the group consisting of the following (a) to (e):
(a) a polynucleotide having a nucleotide sequence encoding a polypeptide consisting of an amino acid sequence at amino acid positions 1-705 of SEQ ID NO: 36 containing a heavy chain of an anti-CLDN4 antibody and an anti-CD137 scFv;
(b) a polynucleotide having a nucleotide sequence encoding a polypeptide consisting of an amino acid sequence at amino acid positions 1-712 of SEQ ID NO: 38 containing a heavy chain of an anti-CLDN4 antibody and an anti-CD137 scFv;
(c) a polynucleotide having a nucleotide sequence encoding a light chain of an anti-CLDN4 antibody consisting of an amino acid sequence at amino acid positions 1-215 of SEQ ID NO: 40;
(d) a polynucleotide having a nucleotide sequence encoding a polypeptide consisting of an amino acid sequence at amino acid positions 1-705 of SEQ ID NO: 36 containing a heavy chain of an anti-CLDN4 antibody and an anti-CD137 scFv, and a polynucleotide having a nucleotide sequence encoding a light chain of an anti-CLDN4 antibody consisting of an amino acid sequence at amino acid positions 1-215 of SEQ ID NO: 40; or
(e) a polynucleotide having a nucleotide sequence encoding a polypeptide consisting of an amino acid sequence at amino acid positions 1-712 of SEQ ID NO: 38 containing a heavy chain of an anti-CLDN4 antibody and an anti-CD137 scFv, and a polynucleotide having a nucleotide sequence encoding a light chain of an anti-CLDN4 antibody consisting of an amino acid sequence at amino acid positions 1-215 of SEQ ID NO: 40.

The polynucleotide of the bispecific antibody of the present invention can be easily produced by those skilled in the art based on the nucleotide sequence by employing a method known in this field. For example, the polynucleotide of the bispecific antibody of the present invention can be synthesized by utilizing a gene synthesis method known in this field. As such a gene synthesis method, various methods known to those skilled in the art such as a synthesis method for an antibody gene described in WO90/07861 can be employed.

<Expression Vector for Bispecific Antibody of Invention>

The present invention also provides an expression vector containing a polynucleotide of the bispecific antibody of the present invention (also referred to as the "expression vector for the bispecific antibody of the present invention"). These polynucleotides may be contained respectively in different vectors, or a plurality of the polynucleotides may be contained in one vector.

In one embodiment, the expression vector for the bispecific antibody of the present invention contains a polynucleotide selected from the group consisting of the following (a) to (aa):

(a) a polynucleotide having a nucleotide sequence encoding a heavy chain variable region of an anti-CLDN4 antibody consisting of an amino acid sequence at amino acid positions 1-125 of SEQ ID NO: 2;

(b) a polynucleotide having a nucleotide sequence encoding a light chain variable region of an anti-CLDN4 antibody consisting of an amino acid sequence at amino acid positions 1-109 of SEQ ID NO: 4;

(c) a polynucleotide having a nucleotide sequence encoding a heavy chain variable region of an anti-CLDN4 antibody consisting of an amino acid sequence at amino acid positions 1-123 of SEQ ID NO: 6;

(d) a polynucleotide having a nucleotide sequence encoding a light chain variable region of an anti-CLDN4 antibody consisting of an amino acid sequence at amino acid positions 1-109 of SEQ ID NO: 8;

(e) a polynucleotide having a nucleotide sequence encoding a heavy chain variable region of an anti-CD137 antibody consisting of an amino acid sequence at amino acid positions 1-118 of SEQ ID NO: 10;

(f) a polynucleotide having a nucleotide sequence encoding a light chain variable region of an anti-CD137 antibody consisting of an amino acid sequence at amino acid positions 1-109 of SEQ ID NO: 12;

(g) a polynucleotide having a nucleotide sequence encoding a heavy chain variable region of an anti-CD137 antibody consisting of an amino acid sequence at amino acid positions 1-118 of SEQ ID NO: 14;

(h) a polynucleotide having a nucleotide sequence encoding a light chain variable region of an anti-CD137 antibody consisting of an amino acid sequence at amino acid positions 1-111 of SEQ ID NO: 16;

(i) a polynucleotide having a nucleotide sequence encoding a heavy chain variable region of an anti-CD137 antibody consisting of an amino acid sequence at amino acid positions 1-118 of SEQ ID NO: 18;

(j) a polynucleotide having a nucleotide sequence encoding a light chain variable region of an anti-CD137 antibody consisting of an amino acid sequence at amino acid positions 1-111 of SEQ ID NO: 20;

(k) a polynucleotide having a nucleotide sequence encoding a heavy chain variable region of an anti-CD137 antibody consisting of an amino acid sequence at amino acid positions 1-121 of SEQ ID NO: 22;

(l) a polynucleotide having a nucleotide sequence encoding a light chain variable region of an anti-CD137 antibody consisting of an amino acid sequence at amino acid positions 1-111 of SEQ ID NO: 24;

(m) a polynucleotide having a nucleotide sequence encoding a heavy chain variable region of an anti-CD137 antibody consisting of an amino acid sequence at amino acid positions 1-118 of SEQ ID NO: 26;

(n) a polynucleotide having a nucleotide sequence encoding a light chain variable region of an anti-CD137 antibody consisting of an amino acid sequence at amino acid positions 134-242 of SEQ ID NO: 26;

(o) a polynucleotide having a nucleotide sequence encoding a heavy chain variable region of an anti-CD137 antibody consisting of an amino acid sequence at amino acid positions 1-118 of SEQ ID NO: 28;

(p) a polynucleotide having a nucleotide sequence encoding a light chain variable region of an anti-CD137 antibody consisting of an amino acid sequence at amino acid positions 134-244 of SEQ ID NO: 28;

(q) a polynucleotide having a nucleotide sequence encoding a light chain variable region of an anti-CD137 antibody consisting of an amino acid sequence at amino acid positions 1-111 of SEQ ID NO: 30;

(r) a polynucleotide having a nucleotide sequence encoding a heavy chain variable region of an anti-CD137 antibody consisting of an amino acid sequence at amino acid positions 132-249 of SEQ ID NO: 30;

(s) a polynucleotide having a nucleotide sequence encoding a heavy chain variable region of an anti-CD137 antibody consisting of an amino acid sequence at amino acid positions 1-118 of SEQ ID NO: 32;

(t) a polynucleotide having a nucleotide sequence encoding a light chain variable region of an anti-CD137 antibody consisting of an amino acid sequence at amino acid positions 134-244 of SEQ ID NO: 32;

(u) a polynucleotide having a nucleotide sequence encoding a heavy chain variable region of an anti-CD137 antibody consisting of an amino acid sequence at amino acid positions 1-121 of SEQ ID NO: 34;

(v) a polynucleotide having a nucleotide sequence encoding a light chain variable region of an anti-CD137 antibody consisting of an amino acid sequence at amino acid positions 137-247 of SEQ ID NO: 34;

(w) a polynucleotide having a nucleotide sequence encoding an anti-CD137 scFv consisting of an amino acid sequence at amino acid positions 1-242 of SEQ ID NO: 26;

(x) a polynucleotide having a nucleotide sequence encoding an anti-CD137 scFv consisting of an amino acid sequence at amino acid positions 1-244 of SEQ ID NO: 28;

(y) a polynucleotide having a nucleotide sequence encoding an anti-CD137 scFv consisting of an amino acid sequence at amino acid positions 1-249 of SEQ ID NO: 30;

(z) a polynucleotide having a nucleotide sequence encoding an anti-CD137 scFv consisting of an amino acid sequence at amino acid positions 1-244 of SEQ ID NO: 32; or (aa) a polynucleotide having a nucleotide sequence encoding an anti-CD137 scFv consisting of an amino acid sequence at amino acid positions 1-247 of SEQ ID NO: 34.

In one embodiment, the expression vector for the bispecific antibody of the present invention contains a polynucleotide selected from the group consisting of the following (a) to (k):

(a) a polynucleotide having a nucleotide sequence encoding a heavy chain variable region of an anti-CLDN4 antibody consisting of an amino acid sequence at amino acid positions 1-125 of SEQ ID NO: 2, and a polynucleotide having a nucleotide sequence encoding a light chain variable region of an anti-CLDN4 antibody consisting of an amino acid sequence at amino acid positions 1-109 of SEQ ID NO: 4;

(b) a polynucleotide having a nucleotide sequence encoding a heavy chain variable region of an anti-CLDN4 antibody consisting of an amino acid sequence at amino acid positions 1-123 of SEQ ID NO: 6, and a polynucleotide having a nucleotide sequence encoding a light chain variable region of an anti-CLDN4 antibody consisting of an amino acid sequence at amino acid positions 1-109 of SEQ ID NO: 8;

(c) a polynucleotide having a nucleotide sequence encoding a heavy chain variable region of an anti-CD137 antibody consisting of an amino acid sequence at amino acid positions 1-118 of SEQ ID NO: 10, and a polynucleotide having a nucleotide sequence encoding a light chain variable region of an anti-CD137 antibody consisting of an amino acid sequence at amino acid positions 1-109 of SEQ ID NO: 12;

(d) a polynucleotide having a nucleotide sequence encoding a heavy chain variable region of an anti-CD137 antibody consisting of an amino acid sequence at amino acid positions 1-118 of SEQ ID NO: 14, and a polynucleotide having a nucleotide sequence encoding a light chain variable region of an anti-CD137 antibody consisting of an amino acid sequence at amino acid positions 1-111 of SEQ ID NO: 16;

(e) a polynucleotide having a nucleotide sequence encoding a heavy chain variable region of an anti-CD137 antibody consisting of an amino acid sequence at amino acid positions 1-118 of SEQ ID NO: 18, and a polynucleotide having a nucleotide sequence encoding a light chain variable region of an anti-CD137 antibody consisting of an amino acid sequence at amino acid positions 1-111 of SEQ ID NO: 20;

(f) a polynucleotide having a nucleotide sequence encoding a heavy chain variable region of an anti-CD137 antibody consisting of an amino acid sequence at amino acid positions 1-121 of SEQ ID NO: 22, and a polynucleotide having a nucleotide sequence encoding a light chain variable region of an anti-CD137 antibody consisting of an amino acid sequence at amino acid positions 1-111 of SEQ ID NO: 24;

(g) a polynucleotide having a nucleotide sequence encoding a heavy chain variable region of an anti-CD137 antibody consisting of an amino acid sequence at amino acid positions 1-118 of SEQ ID NO: 26, and a polynucleotide having a nucleotide sequence encoding a light chain variable region of an anti-CD137 antibody consisting of an amino acid sequence at amino acid positions 134-242 of SEQ ID NO: 26;

(h) a polynucleotide having a nucleotide sequence encoding a heavy chain variable region of an anti-CD137 antibody consisting of an amino acid sequence at amino acid positions 1-118 of SEQ ID NO: 28, and a polynucleotide having a nucleotide sequence encoding a light chain variable region of an anti-CD137 antibody consisting of an amino acid sequence at amino acid positions 134-244 of SEQ ID NO: 28;

(i) a polynucleotide having a nucleotide sequence encoding a light chain variable region of an anti-CD137 antibody consisting of an amino acid sequence at amino acid positions 1-111 of SEQ ID NO: 30, and a polynucleotide having a nucleotide sequence encoding a heavy chain variable region of an anti-CD137 antibody consisting of an amino acid sequence at amino acid positions 132-249 of SEQ ID NO: 30;

(j) a polynucleotide having a nucleotide sequence encoding a heavy chain variable region of an anti-CD137 antibody consisting of an amino acid sequence at amino acid positions 1-118 of SEQ ID NO: 32, and a polynucleotide having a nucleotide sequence encoding a light chain variable region of an anti-CD137 antibody consisting of an amino acid sequence at amino acid positions 134-244 of SEQ ID NO: 32; or (k) a polynucleotide having a nucleotide sequence encoding a heavy chain variable region of an anti-CD137 antibody consisting of an amino acid sequence at amino acid positions 1-121 of SEQ ID NO: 34, and a polynucleotide having a nucleotide sequence encoding a light chain variable region of an anti-CD137 antibody consisting of an amino acid sequence at amino acid positions 137-247 of SEQ ID NO: 34.

In one embodiment, the expression vector for the bispecific antibody of the present invention contains a polynucleotide selected from the group consisting of the following (a) to (c):

(a) a polynucleotide having a nucleotide sequence encoding a polypeptide consisting of an amino acid sequence at amino acid positions 1-705 of SEQ ID NO: 36 containing a heavy chain of an anti-CLDN4 antibody and an anti-CD137 scFv;

(b) a polynucleotide having a nucleotide sequence encoding a polypeptide consisting of an amino acid sequence at amino acid positions 1-712 of SEQ ID NO: 38 containing a heavy chain of an anti-CLDN4 antibody and an anti-CD137 scFv; or (c) a polynucleotide having a nucleotide sequence encoding a light chain of an anti-CLDN4 antibody consisting of an amino acid sequence at amino acid positions 1-215 of SEQ ID NO: 40.

In one embodiment, the expression vector for the bispecific antibody of the present invention contains a polynucleotide selected from the following (a) or (b):

(a) a polynucleotide having a nucleotide sequence encoding a polypeptide consisting of an amino acid sequence at amino acid positions 1-705 of SEQ ID NO: 36 containing a heavy chain of an anti-CLDN4 antibody and an anti-CD137 scFv, and a polynucleotide having a nucleotide sequence encoding a light chain of an anti-CLDN4 antibody consisting of an amino acid sequence at amino acid positions 1-215 of SEQ ID NO: 40; or (b) a polynucleotide having a nucleotide sequence encoding a polypeptide consisting of an amino acid sequence at amino acid positions 1-712 of SEQ ID NO: 38 containing a heavy chain of an anti-CLDN4 antibody and an anti-CD137 scFv, and a polynucleotide having a nucleotide sequence encoding a light chain of an anti-CLDN4 antibody consisting of an amino acid sequence at amino acid positions 1-215 of SEQ ID NO: 40.

The expression vector for the bispecific antibody of the present invention is not especially limited as long as it can produce the polynucleotide of the present invention in various host cells such as a eukaryotic cell (such as an animal cell, an insect cell, a plant cell or a yeast) and/or a prokaryotic cell (such as *E. coli*). Examples of such an expression vector include a plasmid vector and a viral vector. As the plasmid vector, for example, pcDNA series (Thermo Fisher Scientific), pALTER®-MAX (Promega Corporation), pHEK293 Ultra Expression Vector (Takara Bio Inc.), pEE 6.4 or pEE 12.4 (Lonza Biologics) or the like can be used. As the viral vector, for example, a lentivirus, an adenovirus, a retrovirus, or an adeno-associated virus can be used. For example, when a lentivirus is used for introducing the polynucleotide of the present invention into a cell, pLVSIN-CMV/EF1α vector (Takara Bio Inc.), pLenti vector (Thermo Fisher Scientific) or the like can be used as the lentivirus. In one embodiment, a vector used in the expression vector for the bispecific antibody of the present invention is pcDNA 3.4-TOPO® (Thermo Fisher Scientific) or pcDNA 3.1 (Thermo Fisher Scientific).

The expression vector for the bispecific antibody of the present invention can contain a promoter operably linked to the polynucleotide of the bispecific antibody of the present invention. Examples of the promoter for expressing the polynucleotide of the bispecific antibody of the present invention in an animal cell include virus-derived promoters such as CMV, RSV and SV40, an actin promoter, an EF (elongation factor) 1α promoter, and a heat shock promoter. Examples of the promoter for expressing the polynucleotide of the bispecific antibody of the present invention in a bacterium (such as one belonging to the genus *Escherichia*) include a trp promoter, a lac promoter, a APL promoter, and a tac promoter. Examples of the promoter for expressing the polynucleotide of the bispecific antibody of the present invention in a yeast include a GAL1 promoter, a GAL10 promoter, a PH05 promoter, a PGK promoter, a GAP promoter, and an ADH promoter.

When an animal cell, an insect cell or a yeast is used as the host cell, the expression vector for the bispecific antibody of the present invention can contain a start codon and a stop codon. In this case, an enhancer sequence, the 5'-side and 3'-side untranslated regions of a gene encoding the antibody of the present invention, or the heavy chain or light chain thereof, a secretory signal sequence, a splice joint, a polyadenylation site, a replicable unit or the like may be contained. When *E. coli* is used as the host cell, the expression vector of the present invention can contain a start codon, a stop codon, a terminator region, and a replicable unit. The expression vector of the present invention may contain a drug selection marker gene usually used depending on purpose (such as a tetracycline resistance gene, an ampicillin resistance gene, a kanamycin resistance gene, a neomycin resistance gene, or a dihydrofolate reductase gene).

<Host Cell of Invention>

The present invention also provides a host cell transformed by the polynucleotide of the bispecific antibody of the present invention or the expression vector for the bispecific antibody of the present invention (also referred to as the "polynucleotide or the like of the present invention") (also referred to as the "host cell of the present invention"). The host cell of the present invention contains the polynucleotide or the like of the present invention in the cell. The introduced polynucleotide or the like of the present invention may be or may not be integrated into the genomic DNA of the host cell. A cell used as the host cell may be either a cell capable of being cultured in vitro or an in vivo cell. When the host cell is a cell capable of being cultured in vitro, the host cell of the present invention can be produced by introducing the polynucleotide or the like of the present invention into the cell in vitro. A method for transforming the host cell is not especially limited, and for example, a method generally employed by those skilled in the art such as the calcium phosphate method, the electroporation method or the lipofection method can be employed. When the host cell is an in vivo cell, a method for introducing the polynucleotide or the like of the present invention into the host cell is not especially limited, and a nucleic acid delivery carrier (cationic carrier or non-cationic carrier (for example, including, but not limited to, a liposome and a lipid nanoparticle (LNP)) and the like) can be used.

The cell capable of being cultured in vitro is not especially limited as long as it can be transformed by the expression vector to be used or a method such as electroporation to express an antibody or a polypeptide. Examples of the cell capable of being cultured in vitro include various cells including conventional cells usually used in this technical field and artificially established cells (for example, animal cells (such as a CHO-K1 cell, an ExpiCHO-S® cell, a CHOK1SV cell, a CHO-DG44 cell, a HEK293 cell, an Expi293F cell, and a NS0 cell), insect cells (such as Sf9), bacteria (such as those belonging to the genus *Escherichia*), and yeasts (such as those belonging to the genus *Saccharomyces* and the genus *Pichia*)). In one embodiment, the host cell of the present invention is an Expi293F cell, a CHO-K1 cell or an ExpiCHO-S cell.

Selection of a transformed host cell in vitro can be performed by a method generally employed by those skilled in the art. As the selection method, for example, a drug selection method using a drug selection marker gene and a drug such as tetracycline, ampicillin, neomycin or hygromycin, or a cell isolation method such as a limiting dilution method, a single cell sorting method, or a colony pick-up method can be employed.

In one embodiment of the host cell of the present invention, the host cell contains a polynucleotide selected from the group consisting of the following (a) to (aa):

(a) a polynucleotide having a nucleotide sequence encoding a heavy chain variable region of an anti-CLDN4 antibody consisting of an amino acid sequence at amino acid positions 1-125 of SEQ ID NO: 2;

(b) a polynucleotide having a nucleotide sequence encoding a light chain variable region of an anti-CLDN4 antibody consisting of an amino acid sequence at amino acid positions 1-109 of SEQ ID NO: 4;

(c) a polynucleotide having a nucleotide sequence encoding a heavy chain variable region of an anti-CLDN4 antibody consisting of an amino acid sequence at amino acid positions 1-123 of SEQ ID NO: 6;

(d) a polynucleotide having a nucleotide sequence encoding a light chain variable region of an anti-CLDN4 antibody consisting of an amino acid sequence at amino acid positions 1-109 of SEQ ID NO: 8;

(e) a polynucleotide having a nucleotide sequence encoding a heavy chain variable region of an anti-CD137 antibody consisting of an amino acid sequence at amino acid positions 1-118 of SEQ ID NO: 10;

(f) a polynucleotide having a nucleotide sequence encoding a light chain variable region of an anti-CD137 antibody consisting of an amino acid sequence at amino acid positions 1-109 of SEQ ID NO: 12;

(g) a polynucleotide having a nucleotide sequence encoding a heavy chain variable region of an anti-CD137 antibody consisting of an amino acid sequence at amino acid positions 1-118 of SEQ ID NO: 14;

(h) a polynucleotide having a nucleotide sequence encoding a light chain variable region of an anti-CD137 antibody consisting of an amino acid sequence at amino acid positions 1-111 of SEQ ID NO: 16;

(i) a polynucleotide having a nucleotide sequence encoding a heavy chain variable region of an anti-CD137 antibody consisting of an amino acid sequence at amino acid positions 1-118 of SEQ ID NO: 18;

(j) a polynucleotide having a nucleotide sequence encoding a light chain variable region of an anti-CD137 antibody consisting of an amino acid sequence at amino acid positions 1-111 of SEQ ID NO: 20;

(k) a polynucleotide having a nucleotide sequence encoding a heavy chain variable region of an anti-CD137 antibody consisting of an amino acid sequence at amino acid positions 1-121 of SEQ ID NO: 22;

(l) a polynucleotide having a nucleotide sequence encoding a light chain variable region of an anti-CD137 antibody consisting of an amino acid sequence at amino acid positions 1-111 of SEQ ID NO: 24;

(m) a polynucleotide having a nucleotide sequence encoding a heavy chain variable region of an anti-CD137 antibody consisting of an amino acid sequence at amino acid positions 1-118 of SEQ ID NO: 26;

(n) a polynucleotide having a nucleotide sequence encoding a light chain variable region of an anti-CD137 antibody consisting of an amino acid sequence at amino acid positions 134-242 of SEQ ID NO: 26;

(o) a polynucleotide having a nucleotide sequence encoding a heavy chain variable region of an anti-CD137 antibody consisting of an amino acid sequence at amino acid positions 1-118 of SEQ ID NO: 28;

(p) a polynucleotide having a nucleotide sequence encoding a light chain variable region of an anti-CD137 antibody consisting of an amino acid sequence at amino acid positions 134-244 of SEQ ID NO: 28;

(q) a polynucleotide having a nucleotide sequence encoding a light chain variable region of an anti-CD137 antibody consisting of an amino acid sequence at amino acid positions 1-111 of SEQ ID NO: 30;

(r) a polynucleotide having a nucleotide sequence encoding a heavy chain variable region of an anti-CD137 antibody consisting of an amino acid sequence at amino acid positions 132-249 of SEQ ID NO: 30;

(s) a polynucleotide having a nucleotide sequence encoding a heavy chain variable region of an anti-CD137 antibody consisting of an amino acid sequence at amino acid positions 1-118 of SEQ ID NO: 32;

(t) a polynucleotide having a nucleotide sequence encoding a light chain variable region of an anti-CD137 antibody consisting of an amino acid sequence at amino acid positions 134-244 of SEQ ID NO: 32;

(u) a polynucleotide having a nucleotide sequence encoding a heavy chain variable region of an anti-CD137 antibody consisting of an amino acid sequence at amino acid positions 1-121 of SEQ ID NO: 34;

(v) a polynucleotide having a nucleotide sequence encoding a light chain variable region of an anti-CD137 antibody consisting of an amino acid sequence at amino acid positions 137-247 of SEQ ID NO: 34;

(w) a polynucleotide having a nucleotide sequence encoding an anti-CD137 scFv consisting of an amino acid sequence at amino acid positions 1-242 of SEQ ID NO: 26; (x) a polynucleotide having a nucleotide sequence encoding an anti-CD137 scFv consisting of an amino acid sequence at amino acid positions 1-244 of SEQ ID NO: 28;

(y) a polynucleotide having a nucleotide sequence encoding an anti-CD137 scFv consisting of an amino acid sequence at amino acid positions 1-249 of SEQ ID NO: 30;

(z) a polynucleotide having a nucleotide sequence encoding an anti-CD137 scFv consisting of an amino acid sequence at amino acid positions 1-244 of SEQ ID NO: 32; or (aa) a polynucleotide having a nucleotide sequence encoding an anti-CD137 scFv consisting of an amino acid sequence at amino acid positions 1-247 of SEQ ID NO: 34.

In one embodiment, the host cell contains a polynucleotide selected from the group consisting of the following (a) or (k):

(a) a polynucleotide having a nucleotide sequence encoding a heavy chain variable region of an anti-CLDN4 antibody consisting of an amino acid sequence at amino acid positions 1-125 of SEQ ID NO: 2, and a polynucleotide having a nucleotide sequence encoding a light chain variable region of an anti-CLDN4 antibody consisting of an amino acid sequence at amino acid positions 1-109 of SEQ ID NO: 4;

(b) a polynucleotide having a nucleotide sequence encoding a heavy chain variable region of an anti-CLDN4 antibody consisting of an amino acid sequence at amino acid positions 1-123 of SEQ ID NO: 6, and a polynucleotide having a nucleotide sequence encoding a light chain variable region of an anti-CLDN4 antibody consisting of an amino acid sequence at amino acid positions 1-109 of SEQ ID NO: 8;

(c) a polynucleotide having a nucleotide sequence encoding a heavy chain variable region of an anti-CD137 antibody consisting of an amino acid sequence at amino acid positions 1-118 of SEQ ID NO: 10, and a polynucleotide having a nucleotide sequence encoding a light chain variable region of an anti-CD137 antibody consisting of an amino acid sequence at amino acid positions 1-109 of SEQ ID NO: 12;

(d) a polynucleotide having a nucleotide sequence encoding a heavy chain variable region of an anti-CD137 antibody consisting of an amino acid sequence at amino acid positions 1-118 of SEQ ID NO: 14, and a polynucleotide having a nucleotide sequence encoding a light chain variable region of an anti-CD137 antibody consisting of an amino acid sequence at amino acid positions 1-111 of SEQ ID NO: 16;

(e) a polynucleotide having a nucleotide sequence encoding a heavy chain variable region of an anti-CD137 antibody consisting of an amino acid sequence at amino acid positions 1-118 of SEQ ID NO: 18, and a polynucleotide having a nucleotide sequence encoding a light chain variable region of an anti-CD137 antibody consisting of an amino acid sequence at amino acid positions 1-111 of SEQ ID NO: 20;

(f) a polynucleotide having a nucleotide sequence encoding a heavy chain variable region of an anti-CD137 antibody consisting of an amino acid sequence at amino acid positions 1-121 of SEQ ID NO: 22, and a polynucleotide having a nucleotide sequence encoding a light chain variable region of an anti-CD137 antibody consisting of an amino acid sequence at amino acid positions 1-111 of SEQ ID NO: 24;

(g) a polynucleotide having a nucleotide sequence encoding a heavy chain variable region of an anti-CD137 antibody consisting of an amino acid sequence at amino acid positions 1-118 of SEQ ID NO: 26, and a polynucleotide having a nucleotide sequence encoding a light chain variable region of an anti-CD137 antibody consisting of an amino acid sequence at amino acid positions 134-242 of SEQ ID NO: 26;

(h) a polynucleotide having a nucleotide sequence encoding a heavy chain variable region of an anti-CD137 antibody consisting of an amino acid sequence at amino acid positions 1-118 of SEQ ID NO: 28, and a polynucleotide having a nucleotide sequence encoding a light chain variable region of an anti-CD137 antibody consisting of an amino acid sequence at amino acid positions 134-244 of SEQ ID NO: 28;

(i) a polynucleotide having a nucleotide sequence encoding a light chain variable region of an anti-CD137 antibody consisting of an amino acid sequence at amino acid positions 1-111 of SEQ ID NO: 30, and a polynucleotide having a nucleotide sequence encoding a heavy chain variable region of an anti-CD137 antibody consisting of an amino acid sequence at amino acid positions 132-249 of SEQ ID NO: 30;

(j) a polynucleotide having a nucleotide sequence encoding a heavy chain variable region of an anti-CD137 antibody consisting of an amino acid sequence at amino acid positions 1-118 of SEQ ID NO: 32, and a polynucleotide having a nucleotide sequence encoding a light chain variable region of an anti-CD137 antibody consisting of an amino acid sequence at amino acid positions 134-244 of SEQ ID NO: 32; or (k) a polynucleotide having a nucleotide sequence encoding a heavy chain variable region of an anti-CD137 antibody consisting of an amino acid sequence at amino acid positions 1-121 of SEQ ID NO: 34, and a polynucleotide having a nucleotide sequence encoding a light chain variable region of an anti-CD137 antibody consisting of an amino acid sequence at amino acid positions 137-247 of SEQ ID NO: 34.

In one embodiment of the host cell of the present invention, the host cell contains a polynucleotide selected from the group consisting of the following (a) to (c):

(a) a polynucleotide having a nucleotide sequence encoding a polypeptide consisting of an amino acid sequence at amino acid positions 1-705 of SEQ ID NO: 36 containing a heavy chain of an anti-CLDN4 antibody and an anti-CD137 scFv;

(b) a polynucleotide having a nucleotide sequence encoding a polypeptide consisting of an amino acid sequence at amino acid positions 1-712 of SEQ ID NO: 38 containing a heavy chain of an anti-CLDN4 antibody and an anti-CD137 scFv; or (c) a polynucleotide having a nucleotide sequence encoding a light chain of an anti-CLDN4 antibody consisting of an amino acid sequence at amino acid positions 1-215 of SEQ ID NO: 40.

In one embodiment, the host cell contains a polynucleotide selected from the following (a) or (b):

(a) a polynucleotide having a nucleotide sequence encoding a polypeptide consisting of an amino acid sequence at amino acid positions 1-705 of SEQ ID NO: 36 containing a heavy chain of an anti-CLDN4 antibody and an anti-CD137 scFv, and a polynucleotide having a nucleotide sequence encoding a light chain of an anti-CLDN4 antibody consisting of an amino acid sequence at amino acid positions 1-215 of SEQ ID NO: 40; or (b) a polynucleotide having a nucleotide sequence encoding a polypeptide consisting of an amino acid sequence at amino acid positions 1-712 of SEQ ID NO: 38 containing a heavy chain of an anti-CLDN4 antibody and an anti-CD137 scFv, and a polynucleotide having a nucleotide sequence encoding a light chain of an anti-CLDN4 antibody consisting of an amino acid sequence at amino acid positions 1-215 of SEQ ID NO: 40.

In one embodiment of the host cell of the present invention, the host cell contains polypeptides described in the following (a) to (j):

(a) a polynucleotide having a nucleotide sequence encoding a polypeptide containing a heavy chain of an anti-CLDN4 antibody containing a heavy chain variable region consisting of an amino acid sequence at amino acid positions 1-125 of SEQ ID NO: 2, and an anti-CD137 scFv containing a heavy chain variable region of an anti-CD137 antibody consisting of an amino acid sequence at amino acid positions 1-118 of SEQ ID NO: 26 and a light chain variable region of an anti-CD137 antibody consisting of an amino acid sequence at amino acid positions 134-242 of SEQ ID NO: 26, in which the amino terminal of the anti-CD137 scFv is linked to the heavy chain carboxy terminal of the anti-CLDN4 antibody via a linker; and a polynucleotide having a nucleotide sequence encoding a light chain of an anti-CLDN4 antibody containing a light chain variable region consisting of an amino acid sequence at amino acid positions 1-109 of SEQ ID NO: 4;

(b) a polynucleotide having a nucleotide sequence encoding a polypeptide containing a heavy chain of an anti-CLDN4 antibody containing a heavy chain variable region consisting of an amino acid sequence at amino acid positions 1-125 of SEQ ID NO: 2, and an anti-CD137 scFv containing a heavy chain variable region of an anti-CD137 antibody consisting of an amino acid sequence at amino acid positions 1-118 of SEQ ID NO: 28 and a light chain variable region of an anti-CD137 antibody consisting of an amino acid sequence at amino acid positions 134-244 of SEQ ID NO: 28, in which the amino terminal of the anti-CD137 scFv is linked to the heavy chain carboxy terminal of the anti-CLDN4 antibody via a linker; and a polynucleotide having a nucleotide sequence encoding a light chain of an anti-CLDN4 antibody containing a light chain variable region consisting of an amino acid sequence at amino acid positions 1-109 of SEQ ID NO: 4;

(c) a polynucleotide having a nucleotide sequence encoding a polypeptide containing a heavy chain of an anti-CLDN4 antibody containing a heavy chain variable region consisting of an amino acid sequence at amino acid positions 1-125 of SEQ ID NO: 2, and an anti-CD137 scFv containing a light chain variable region of an anti-CD137 antibody consisting of an amino acid sequence at amino acid positions 1-111 of SEQ ID NO: 30 and a heavy chain variable region of an anti-CD137 antibody consisting of an amino acid sequence at amino acid positions 132-249 of SEQ ID NO: 30, in which the amino terminal of the anti-CD137 scFv is linked to the heavy chain carboxy terminal of the anti-CLDN4 antibody via a linker; and a polynucleotide having a nucleotide sequence encoding a light chain of an anti-CLDN4 antibody containing a light chain variable region consisting of an amino acid sequence at amino acid positions 1-109 of SEQ ID NO: 4;

(d) a polynucleotide having a nucleotide sequence encoding a polypeptide containing a heavy chain of an anti-CLDN4 antibody containing a heavy chain variable region consisting of an amino acid sequence at amino acid positions 1-125 of SEQ ID NO: 2, and an anti-CD137 scFv containing a heavy chain variable region of an anti-CD137 antibody consisting of an amino acid sequence at amino acid positions 1-118 of SEQ ID NO: 32 and a light chain variable region of an anti-CD137 antibody consisting of an amino acid sequence at amino acid positions 134-244 of SEQ ID NO: 32, in which the amino terminal of the anti-CD137 scFv is linked to the heavy chain carboxy terminal of the anti-CLDN4 antibody via a linker; and a polynucleotide having a nucleotide sequence encoding a light chain of an anti-CLDN4 antibody containing a light chain variable region consisting of an amino acid sequence at amino acid positions 1-109 of SEQ ID NO: 4;

(e) a polynucleotide having a nucleotide sequence encoding a polypeptide, which contains a heavy chain of an anti-CLDN4 antibody containing a heavy chain variable region consisting of an amino acid sequence at amino acid positions 1-125 of SEQ ID NO: 2, and an anti-CD137 scFv containing a heavy chain variable region of an anti-CD137 antibody consisting of an amino acid sequence at amino acid positions 1-121 of SEQ ID NO: 34 and a light chain variable region of an anti-CD137 antibody consisting of an amino acid sequence at amino acid positions 137-247 of SEQ ID NO: 34, wherein the amino terminal of the anti-CD137 scFv is linked to the heavy chain carboxy terminal of the anti-CLDN4 antibody via a linker; and a polynucleotide having a nucleotide sequence encoding a light chain of an anti-CLDN4 antibody containing a light chain variable region consisting of an amino acid sequence at amino acid positions 1-109 of SEQ ID NO: 4;

(f) a polynucleotide having a nucleotide sequence encoding a polypeptide containing a heavy chain of an anti-CLDN4 antibody containing a heavy chain variable region consisting of an amino acid sequence at amino acid positions 1-123 of SEQ ID NO: 6, and an anti-CD137 scFv containing a heavy chain variable region of an anti-CD137 antibody consisting of an amino acid sequence at amino acid positions 1-118 of SEQ ID NO: 26 and a light chain variable region of an anti-CD137 antibody consisting of an amino acid sequence at amino acid positions 134-242 of SEQ ID NO: 26, in which the amino terminal of the anti-CD137 scFv is linked to the heavy chain carboxy terminal of the anti-CLDN4 antibody via a linker; and a polynucleotide having a nucleotide sequence encoding a light chain of an anti-CLDN4 antibody containing a light chain variable region consisting of an amino acid sequence at amino acid positions 1-109 of SEQ ID NO: 8;

(g) a polynucleotide having a nucleotide sequence encoding a polypeptide containing a heavy chain of an anti-CLDN4 antibody containing a heavy chain variable region consisting of an amino acid sequence at amino acid positions 1-123 of SEQ ID NO: 6, and an anti-CD137 scFv containing a heavy chain variable region of an anti-CD137 antibody consisting of an amino acid sequence at amino acid positions 1-118 of SEQ ID NO: 28 and a light chain variable region of an anti-CD137 antibody consisting of an amino acid sequence at amino acid positions 134-244 of SEQ ID NO: 28, in which the amino terminal of the anti-CD137 scFv is linked to the heavy chain carboxy terminal of the anti-CLDN4 antibody via a linker; and a polynucleotide having a nucleotide sequence encoding a light chain of an anti-CLDN4 antibody containing a light chain variable region consisting of an amino acid sequence at amino acid positions 1-109 of SEQ ID NO: 8;

(h) a polynucleotide having a nucleotide sequence encoding a polypeptide containing a heavy chain of an anti-CLDN4 antibody containing a heavy chain variable region consisting of an amino acid sequence at amino acid positions 1-123 of SEQ ID NO: 6, and an anti-CD137 scFv containing a light chain variable region of an anti-CD137 antibody consisting of an amino acid sequence at amino acid positions 1-111 of SEQ ID NO: 30 and a heavy chain variable region of an anti-CD137 antibody consisting of an amino acid sequence at amino acid positions 132-249 of SEQ ID NO: 30, in which the amino terminal of the anti-CD137 scFv is linked to the heavy chain carboxy terminal of the anti-CLDN4 antibody via a linker; and a polynucleotide having a nucleotide sequence encoding a light chain of an anti-CLDN4 antibody containing a light chain variable region consisting of an amino acid sequence at amino acid positions 1-109 of SEQ ID NO: 8;

(i) a polynucleotide having a nucleotide sequence encoding a polypeptide containing a heavy chain of an anti-CLDN4 antibody containing a heavy chain variable region consisting of an amino acid sequence at amino acid positions 1-123 of SEQ ID NO: 6, and an anti-CD137 scFv containing a heavy chain variable region of an anti-CD137 antibody consisting of an amino acid sequence at amino acid positions 1-118 of SEQ ID NO: 32 and a light chain variable region of an anti-CD137 antibody consisting of an amino acid sequence at amino acid positions 134-244 of SEQ ID NO: 32, in which the amino terminal of the anti-CD137 scFv is linked to the heavy chain carboxy terminal of the anti-CLDN4 antibody via a linker; and a polynucleotide having a nucleotide sequence encoding a light chain of an anti-CLDN4 antibody containing a light chain variable region consisting of an amino acid sequence at amino acid positions 1-109 of SEQ ID NO: 8; or (j) a polynucleotide having a nucleotide sequence encoding a polypeptide containing a heavy chain of an anti-CLDN4 antibody containing a heavy chain variable region consisting of an amino acid sequence at amino acid positions 1-123 of SEQ ID NO: 6, and an anti-CD137 scFv containing a heavy chain variable region of an anti-CD137 antibody consisting of an amino acid sequence at amino acid positions 1-121 of SEQ ID NO: 34 and a light chain variable region of an anti-CD137 antibody consisting of an amino acid sequence at amino acid positions 137-247 of SEQ ID NO: 34, in which the amino terminal of the anti-CD137 scFv is linked to the heavy chain carboxy terminal of the anti-CLDN4 antibody via a linker; and a polynucleotide having a nucleotide sequence encoding a light chain of an anti-CLDN4 antibody containing a light chain variable region consisting of an amino acid sequence at amino acid positions 1-109 of SEQ ID NO: 8.

In one embodiment of the host cell of the present invention, the host cell is a host cell described in the following (a) or (b):

(a) a host cell containing a polynucleotide having a nucleotide sequence encoding a polypeptide consisting of an amino acid sequence at amino acid positions 1-705 of SEQ ID NO: 36 containing a heavy chain of an anti-CLDN4 antibody and an anti-CD137 scFv, and a polynucleotide having a nucleotide sequence encoding a light chain of an anti-CLDN4 antibody consisting of an amino acid sequence at amino acid positions 1-215 of SEQ ID NO: 40; or (b) a host cell containing a polynucleotide having a nucleotide sequence encoding a polypeptide consisting of an amino acid sequence at amino acid positions 1-712 of SEQ ID NO: 38 containing a heavy chain of an anti-CLDN4 antibody and an anti-CD137 scFv, and a polynucleotide having a nucleotide sequence encoding a light chain of an anti-CLDN4 antibody consisting of an amino acid sequence at amino acid positions 1-215 of SEQ ID NO: 40.

In one embodiment of the host cell of the present invention, the host cell is a host cell containing a polynucleotide having a nucleotide sequence encoding a polypeptide consisting of an amino acid sequence at amino acid positions 1-712 of SEQ ID NO: 38 containing a heavy chain of an anti-CLDN4 antibody and an anti-CD137 scFv, and a polynucleotide having a nucleotide sequence encoding a light chain of an anti-CLDN4 antibody consisting of an amino acid sequence at amino acid positions 1-215 of SEQ ID NO: 40.

<Method for Producing Bispecific Antibody of Invention>

The present invention also provides a method for producing the anti-CLDN4/anti-CD137 bispecific antibody of the present invention (also referred to as the "production method of the present invention"). The production method of the present invention can include a method for producing the polynucleotide of the bispecific antibody of the present invention, a method for producing the expression vector for the bispecific antibody of the present invention, and a method for producing the host cell of the present invention, described above. Besides, the production method of the present invention can include a step of culturing the host cell described above in <Host Cell of Invention> to express the antibody in the cell or the culture supernatant, a method for collecting, isolating and purifying the antibody, and the like. The production method of the present invention is, however, not limited to these methods as long as the anti-CLDN4/anti-CD137 bispecific antibody of the present invention is produced.

In one embodiment, the production method of the present invention includes a step of culturing a host cell described in the following (a) to (j):

(a) a host cell containing: a polynucleotide having a nucleotide sequence encoding a polypeptide, which contains a heavy chain of an anti-CLDN4 antibody containing a heavy chain variable region consisting of an amino acid sequence at amino acid positions 1-125 of SEQ ID NO: 2, and an anti-CD137 scFv containing a heavy chain variable region of an anti-CD137 antibody consisting of an amino acid sequence at amino acid positions 1-118 of SEQ ID NO: 26 and a light chain variable region of an anti-CD137 antibody consisting of an amino acid sequence at amino acid positions 134-242 of SEQ ID NO: 26, wherein the amino terminal of the anti-CD137 scFv is linked to the heavy chain carboxy terminal of the anti-CLDN4 antibody via a linker; and a polynucleotide having a nucleotide sequence encoding a light chain of an anti-CLDN4 antibody containing a light chain variable region consisting of an amino acid sequence at amino acid positions 1-109 of SEQ ID NO: 4;

(b) a host cell containing: a polynucleotide having a nucleotide sequence encoding a polypeptide, which contains a heavy chain of an anti-CLDN4 antibody containing a heavy chain variable region consisting of an amino acid sequence at amino acid positions 1-125 of SEQ ID NO: 2, and an anti-CD137 scFv containing a heavy chain variable region of an anti-CD137 antibody consisting of an amino acid sequence at amino acid positions 1-118 of SEQ ID NO: 28 and a light chain variable region of an anti-CD137 antibody consisting of an amino acid sequence at amino acid positions 134-244 of SEQ ID NO: 28, wherein the amino terminal of the anti-CD137 scFv is linked to the heavy chain carboxy terminal of the anti-CLDN4 antibody via a linker; and a polynucleotide having a nucleotide sequence encoding a light chain of an anti-CLDN4 antibody containing a light chain variable region consisting of an amino acid sequence at amino acid positions 1-109 of SEQ ID NO: 4;

(c) a host cell containing: a polynucleotide having a nucleotide sequence encoding a polypeptide, which contains a heavy chain of an anti-CLDN4 antibody containing a heavy chain variable region consisting of an amino acid sequence at amino acid positions 1-125 of SEQ ID NO: 2, and an anti-CD137 scFv containing a light chain variable region of an anti-CD137 antibody consisting of an amino acid sequence at amino acid positions 1-111 of SEQ ID NO: 30 and a heavy chain variable region of an anti-CD137 antibody consisting of an amino acid sequence at amino acid positions 132-249 of SEQ ID NO: 30, wherein the amino terminal of the anti-CD137 scFv is linked to the heavy chain carboxy terminal of the anti-CLDN4 antibody via a linker; and a polynucleotide having a nucleotide sequence encoding a light chain of an anti-CLDN4 antibody containing a light chain variable region consisting of an amino acid sequence at amino acid positions 1-109 of SEQ ID NO: 4;

(d) a host cell containing: a polynucleotide having a nucleotide sequence encoding a polypeptide, which contains a heavy chain of an anti-CLDN4 antibody containing a heavy chain variable region consisting of an amino acid sequence at amino acid positions 1-125 of SEQ ID NO: 2, and an anti-CD137 scFv containing a heavy chain variable region of an anti-CD137 antibody consisting of an amino acid sequence at amino acid positions 1-118 of SEQ ID NO: 32 and a light chain variable region of an anti-CD137 antibody consisting of an amino acid sequence at amino acid positions 134-244 of SEQ ID NO: 32, wherein the amino terminal of the anti-CD137 scFv is linked to the heavy chain carboxy terminal of the anti-CLDN4 antibody via a linker; and a polynucleotide having a nucleotide sequence encoding a light chain of an anti-CLDN4 antibody containing a light chain variable region consisting of an amino acid sequence at amino acid positions 1-109 of SEQ ID NO: 4;

(e) a host cell containing: a polynucleotide having a nucleotide sequence encoding a polypeptide, which contains a heavy chain of an anti-CLDN4 antibody containing a heavy chain variable region consisting of an amino acid sequence at amino acid positions 1-125 of SEQ ID NO: 2, and an anti-CD137 scFv containing a heavy chain variable region of an anti-CD137 antibody consisting of an amino acid sequence at amino acid positions 1-121 of SEQ ID NO: 34 and a light chain variable region of an anti-CD137 antibody consisting of an amino acid sequence at amino acid positions 137-247 of SEQ ID NO: 34, wherein the amino terminal of the anti-CD137 scFv is linked to the heavy chain carboxy terminal of the anti-CLDN4 antibody via a linker; and a polynucleotide having a nucleotide sequence encoding a light chain of an anti-CLDN4 antibody containing a light chain variable region consisting of an amino acid sequence at amino acid positions 1-109 of SEQ ID NO: 4;

(f) a host cell containing: a polynucleotide having a nucleotide sequence encoding a polypeptide, which contains a heavy chain of an anti-CLDN4 antibody containing a heavy chain variable region consisting of an amino acid sequence at amino acid positions 1-123 of SEQ ID NO: 6, and an anti-CD137 scFv containing a heavy chain variable region of an anti-CD137 antibody consisting of an amino acid sequence at amino acid positions 1-118 of SEQ ID NO: 26 and a light chain variable region of an anti-CD137 antibody consisting of an amino acid sequence at amino acid positions 134-242 of SEQ ID NO: 26, wherein the amino terminal of the anti-CD137 scFv is linked to the heavy chain carboxy terminal of the anti-CLDN4 antibody via a linker; and a polynucleotide having a nucleotide sequence encoding a light chain of an anti-CLDN4 antibody containing a light chain variable region consisting of an amino acid sequence at amino acid positions 1-109 of SEQ ID NO: 8;

(g) a host cell containing: a polynucleotide having a nucleotide sequence encoding a polypeptide, which contains a heavy chain of an anti-CLDN4 antibody containing a heavy chain variable region consisting of an amino acid sequence at amino acid positions 1-123 of SEQ ID NO: 6, and an anti-CD137 scFv containing a heavy chain variable region of an anti-CD137 antibody consisting of an amino acid sequence at amino acid positions 1-118 of SEQ ID NO: 28 and a light chain variable region of an anti-CD137 antibody consisting of an amino acid sequence at amino acid positions 134-244 of SEQ ID NO: 28, wherein the amino terminal of the anti-CD137 scFv is linked to the heavy chain carboxy terminal of the anti-CLDN4 antibody via a linker; and a polynucleotide having a nucleotide sequence encoding a light chain of an anti-CLDN4 antibody containing a light chain variable region consisting of an amino acid sequence at amino acid positions 1-109 of SEQ ID NO: 8;

(h) a host cell containing: a polynucleotide having a nucleotide sequence encoding a polypeptide, which contains a heavy chain of an anti-CLDN4 antibody containing a heavy chain variable region consisting of an amino acid sequence at amino acid positions 1-123 of SEQ ID NO: 6, and an anti-CD137 scFv containing a light chain variable region of an anti-CD137 antibody consisting of an amino acid sequence at amino acid positions 1-111 of SEQ ID NO: 30 and a heavy chain variable region of an anti-CD137 antibody consisting of an amino acid sequence at amino acid positions 132-249 of SEQ ID NO: 30, wherein the amino terminal of the anti-CD137 scFv is linked to the heavy chain carboxy terminal of the anti-CLDN4 antibody via a linker; and a polynucleotide having a nucleotide sequence encoding a light chain of an anti-CLDN4 antibody containing a light chain variable region consisting of an amino acid sequence at amino acid positions 1-109 of SEQ ID NO: 8;

(i) a host cell containing: a polynucleotide having a nucleotide sequence encoding a polypeptide, which contains a heavy chain of an anti-CLDN4 antibody containing a heavy chain variable region consisting of an amino acid sequence at amino acid positions 1-123 of SEQ ID NO: 6, and an anti-CD137 scFv containing a heavy chain variable region of an anti-CD137 antibody consisting of an amino acid sequence at amino acid positions 1-118 of SEQ ID NO: 32 and a light chain variable region of an anti-CD137 antibody consisting of an amino acid sequence at amino acid positions 134-244 of SEQ ID NO: 32, wherein the amino terminal of the anti-CD137 scFv is linked to the heavy chain carboxy terminal of the anti-CLDN4 antibody via a linker; and a polynucleotide having a nucleotide sequence encoding a light chain of an anti-CLDN4 antibody containing a light chain variable region consisting of an amino acid sequence at amino acid positions 1-109 of SEQ ID NO: 8; or (j) a host cell containing: a polynucleotide having a nucleotide sequence encoding a polypeptide, which contains a heavy chain of an anti-CLDN4 antibody containing a heavy chain variable region consisting of an amino acid sequence at amino acid positions 1-123 of SEQ ID NO: 6, and an anti-CD137 scFv containing a heavy chain variable region of an anti-CD137 antibody consisting of an amino acid sequence at amino acid positions 1-121 of SEQ ID NO: 34 and a light chain variable region of an anti-CD137 antibody consisting of an amino acid sequence at amino acid positions 137-247 of SEQ ID NO: 34, wherein the amino terminal of the anti-CD137 scFv is linked to the heavy chain carboxy terminal of the anti-CLDN4 antibody via a linker; and a polynucleotide having a nucleotide sequence encoding a light chain of an anti-CLDN4 antibody containing a light chain variable region consisting of an amino acid sequence at amino acid positions 1-109 of SEQ ID NO: 8.

In one embodiment, the production method of the present invention includes a step of culturing a host cell described in the following (a) or (b):

(a) a host cell containing a polynucleotide having a nucleotide sequence encoding a polypeptide consisting of an amino acid sequence at amino acid positions 1-705 of SEQ ID NO: 36 containing a heavy chain of an anti-CLDN4 antibody and an anti-CD137 scFv, and a polynucleotide having a nucleotide sequence encoding a light chain of an anti-CLDN4 antibody consisting of an amino acid sequence at amino acid positions 1-215 of SEQ ID NO: 40; or (b) a host cell containing a polynucleotide having a nucleotide sequence encoding a polypeptide consisting of an amino acid sequence at amino acid positions 1-712 of SEQ ID NO: 38 containing a heavy chain of an anti-CLDN4 antibody and an anti-CD137 scFv, and a polynucleotide having a nucleotide sequence encoding a light chain of an anti-CLDN4 antibody consisting of an amino acid sequence at amino acid positions 1-215 of SEQ ID NO: 40.

The host cell of the present invention can be cultured by a known method. Culture conditions such as a temperature, pH of a medium and a culture time can be appropriately selected by those skilled in the art. When the host cell is an animal cell, for example, MEM medium (Science, 1959, Vol. 130, p. 432-437) containing about 5 to 20% of fetal bovine serum, D-MEM medium (Virol., 1959, Vol. 8, p. 396), RPMI-1640 medium (J. Am. Med. Assoc., 1967, Vol. 199, p. 519), 199 medium (Exp. Biol. Med., 1950, Vol. 73, p. 1-8) or the like can be used as the medium. The pH of the medium is, for example, about 6 to 8, and the culture is performed usually at about 30 to 40° C. for about 15 to 336 hours with aeration or stirring if necessary. When the host cell is an insect cell, for example, Grace's medium (Proc. Natl. Acad. Sci. USA., 1985, Vol. 82, p. 8404) containing fetal bovine serum or the like can be used as the medium. The pH of the medium is, for example, about 5 to 8, and the culture is performed usually at about 20 to 40° C. for about 15 to 100 hours with aeration or stirring if necessary. When the host cell is *E. coli* or a yeast, for example, a liquid medium containing a nutrition source is suitably used as the medium. A nutrient medium contains, for example, a carbon source, an inorganic nitrogen source, or an organic nitrogen source necessary for growth of the transformed host cell. Examples of the carbon source include glucose, dextran, soluble starch, and sucrose, examples of the inorganic nitrogen source or organic nitrogen source include ammonium salts, nitric acid salts, amino acids, a corn steep liquor, peptone, casein, a meat extract, a soybean cake, and a potato extract. Other nutrients (for example, inorganic salts (such as calcium chloride, sodium dihydrogen phosphate, and magnesium chloride) or vitamins), an antibiotic (such as tetracycline, neomycin, ampicillin, or kanamycin), or the like may be contained if desired. The pH of the medium is, for example, about 5 to 8. When the host cell is E. coli, for example, LB medium, M9 medium (Molecular Cloning, Cold Spring Harbor Laboratory, Vol. 3, A2.2) or the like can be used as the medium. The culture is performed usually at about 14 to 43° C. for about 3 to 24 hours with aeration or stirring if necessary. When the host cell is a yeast, for example, Burkholder minimum medium (Proc. Natl. Acad. Sci. USA., 1980, Vol. 77, p. 4505) or the like can be used as the medium. The culture is performed usually at about 20 to 35° C. for about 14 to 144 hours with aeration or stirring if necessary. Through such culture, the anti-CLDN4/anti-CD137 bispecific antibody of the present invention can be expressed.

The production method of the present invention can include, in addition to the step of culturing the host cell of the present invention to express the anti-CLDN4/anti-CD137 bispecific antibody, a step of collecting, isolating or purifying the anti-CLDN4/anti-CD137 bispecific antibody from the host cell. Examples of an isolating or purifying method include a method utilizing solubility such as salting-out or a solvent precipitation method, a method utilizing a difference in a molecular weight such as dialysis, ultrafiltration and gel filtration, a method utilizing charge such as ion exchange chromatography or hydroxyapatite chromatography, a method utilizing specific affinity such as affinity chromatography, a method utilizing a difference in hydrophobicity such as reverse phase high performance liquid chromatography, and a method utilizing a difference in an isoelectric point such as isoelectric focusing. In one embodiment, the antibody secreted into a culture supernatant can be purified by various chromatographies such as column chromatography using a protein A column or a protein G column.

The anti-CLDN4/anti-CD137 bispecific antibody of the present invention embraces an anti-CLDN4/anti-CD137 bispecific antibody and an anti-CLDN4/anti-CD137 scFv bispecific antibody produced by the production method of the present invention.

<Pharmaceutical Composition or the Like of Invention>

The present invention also provides a pharmaceutical composition or the like containing the anti-CLDN4/anti-CD137 bispecific antibody of the present invention (also referred to as a "pharmaceutical composition of the present invention"). The pharmaceutical composition of the present invention embraces a pharmaceutical composition containing the anti-CLDN4/anti-CD137 bispecific antibody of the present invention and a pharmaceutically acceptable excipient. The pharmaceutical composition of the present invention can be prepared by a usually employed method with an excipient usually used in this field, namely, a pharmaceutical excipient, a pharmaceutical carrier or the like. Examples of a dosage form of such a pharmaceutical composition include parenteral agents such as an injection and a drop, and administration can be performed by an appropriate method such as intravenous administration, subcutaneous administration, intraperitoneal administration, or intratumoral administration. In formulation, an excipient, a carrier, an additive or the like suitable to the dosage form can be used in a pharmaceutically acceptable range.

The pharmaceutical composition of the present invention can contain a post-translationally modified product of the anti-CLDN4/anti-CD137 bispecific antibody of the present invention. For example, a pharmaceutical composition containing an antibody or the like containing both of or one of lysine deletion in the C-terminal and pyroglutamylation in the N-terminal can be embraced in the present invention.

In one embodiment, the pharmaceutical composition of the present invention is a pharmaceutical composition containing the anti-CLDN4/anti-CD137 bispecific antibody of the present invention and/or a post-translationally modified product of the antibody described in any of the following (a) to (j):

(a) an anti-CLDN4/anti-CD137 bispecific antibody and/or a post-translationally modified product of the antibody containing a heavy chain of an anti-CLDN4 antibody containing a heavy chain variable region consisting of an amino acid sequence at amino acid positions 1-125 of SEQ ID NO: 2 and a light chain of an anti-CLDN4 antibody containing a light chain variable region consisting of an amino acid sequence at amino acid positions 1-109 of SEQ ID NO: 4, and an anti-CD137 scFv containing a heavy chain variable region consisting of an amino acid sequence at amino acid positions 1-118 of SEQ ID NO: 26 and a light chain variable region consisting of an amino acid sequence at amino acid positions 134-242 of SEQ ID NO: 26, in which the amino terminal of the anti-CD137 scFv is linked to the heavy chain carboxy terminal of the anti-CLDN4 antibody via a linker;

(b) an anti-CLDN4/anti-CD137 bispecific antibody and/or a post-translationally modified product of the antibody containing a heavy chain of an anti-CLDN4 antibody containing a heavy chain variable region consisting of an amino acid sequence at amino acid positions 1-125 of SEQ ID NO: 2 and a light chain of an anti-CLDN4 antibody containing a light chain variable region consisting of an amino acid sequence at amino acid positions 1-109 of SEQ ID NO: 4, and an anti-CD137 scFv containing a heavy chain variable region consisting of an amino acid sequence at amino acid positions 1-118 of SEQ ID NO: 28 and a light chain variable region consisting of an amino acid sequence at amino acid positions 134-244 of SEQ ID NO: 28, in which the amino terminal of the anti-CD137 scFv is linked to the heavy chain carboxy terminal of the anti-CLDN4 antibody via a linker;

(c) an anti-CLDN4/anti-CD137 bispecific antibody and/or a post-translationally modified product of the antibody containing a heavy chain of an anti-CLDN4 antibody containing a heavy chain variable region consisting of an amino acid sequence at amino acid positions 1-125 of SEQ ID NO: 2 and a light chain of an anti-CLDN4 antibody containing a light chain variable region consisting of an amino acid sequence at amino acid positions 1-109 of SEQ ID NO: 4, and an anti-CD137 scFv containing a light chain variable region consisting of an amino acid sequence at amino acid positions 1-111 of SEQ ID NO: 30 and a heavy chain variable region consisting of an amino acid sequence at amino acid positions 132-249 of SEQ ID NO: 30, in which the amino terminal of the anti-CD137 scFv is linked to the heavy chain carboxy terminal of the anti-CLDN4 antibody via a linker;

(d) an anti-CLDN4/anti-CD137 bispecific antibody and/or a post-translationally modified product of the antibody containing a heavy chain of an anti-CLDN4 antibody containing a heavy chain variable region consisting of an amino acid sequence at amino acid positions 1-125 of SEQ ID NO: 2 and a light chain of an anti-CLDN4 antibody containing a light chain variable region consisting of an amino acid sequence at amino acid positions 1-109 of SEQ ID NO: 4, and an anti-CD137 scFv containing a heavy chain variable region consisting of an amino acid sequence at amino acid positions 1-118 of SEQ ID NO: 32 and a light chain variable region consisting of an amino acid sequence at amino acid positions 134-244 of SEQ ID NO: 32, in which the amino terminal of the anti-CD137 scFv is linked to the heavy chain carboxy terminal of the anti-CLDN4 antibody via a linker;

(e) an anti-CLDN4/anti-CD137 bispecific antibody and/or a post-translationally modified product of the antibody containing a heavy chain of an anti-CLDN4 antibody containing a heavy chain variable region consisting of an amino acid sequence at amino acid positions 1-125 of SEQ ID NO: 2 and a light chain of an anti-CLDN4 antibody containing a light chain variable region consisting of an amino acid sequence at amino acid positions 1-109 of SEQ ID NO: 4, and an anti-CD137 scFv containing a heavy chain variable region consisting of an amino acid sequence at amino acid positions 1-121 of SEQ ID NO: 34 and a light chain variable region consisting of an amino acid sequence at amino acid positions 137-247 of SEQ ID NO: 34, in which the amino terminal of the anti-CD137 scFv is linked to the heavy chain carboxy terminal of the anti-CLDN4 antibody via a linker;

(f) an anti-CLDN4/anti-CD137 bispecific antibody and/or a post-translationally modified product of the antibody containing a heavy chain of an anti-CLDN4 antibody containing a heavy chain variable region consisting of an amino acid sequence at amino acid positions 1-123 of SEQ ID NO: 6 and a light chain of an anti-CLDN4 antibody containing a light chain variable region consisting of an amino acid sequence at amino acid positions 1-109 of SEQ ID NO: 8, and an anti-CD137 scFv containing a heavy chain variable region consisting of an amino acid sequence at amino acid positions 1-118 of SEQ ID NO: 26 and a light chain variable region consisting of an amino acid sequence at amino acid positions 134-242 of SEQ ID NO: 26, in which the amino terminal of the anti-CD137 scFv is linked to the heavy chain carboxy terminal of the anti-CLDN4 antibody via a linker;

(g) an anti-CLDN4/anti-CD137 bispecific antibody and/or a post-translationally modified product of the antibody containing a heavy chain of an anti-CLDN4 antibody containing a heavy chain variable region consisting of an amino acid sequence at amino acid positions 1-123 of SEQ ID NO: 6 and a light chain of an anti-CLDN4 antibody containing a light chain variable region consisting of an amino acid sequence at amino acid positions 1-109 of SEQ ID NO: 8, and an anti-CD137 scFv containing a heavy chain variable region consisting of an amino acid sequence at amino acid positions 1-118 of SEQ ID NO: 28 and a light chain variable region consisting of an amino acid sequence at amino acid positions 134-244 of SEQ ID NO: 28, in which the amino terminal of the anti-CD137 scFv is linked to the heavy chain carboxy terminal of the anti-CLDN4 antibody via a linker;

(h) an anti-CLDN4/anti-CD137 bispecific antibody and/or a post-translationally modified product of the antibody containing a heavy chain of an anti-CLDN4 antibody containing a heavy chain variable region consisting of an amino acid sequence at amino acid positions 1-123 of SEQ ID NO: 6 and a light chain of an anti-CLDN4 antibody containing a light chain variable region consisting of an amino acid sequence at amino acid positions 1-109 of SEQ ID NO: 8, and an anti-CD137 scFv containing a light chain variable region consisting of an amino acid sequence at amino acid positions 1-111 of SEQ ID NO: 30 and a heavy chain variable region consisting of an amino acid sequence at amino acid positions 132-249 of SEQ ID NO: 30, in which the amino terminal of the anti-CD137 scFv is linked to the heavy chain carboxy terminal of the anti-CLDN4 antibody via a linker;

(i) an anti-CLDN4/anti-CD137 bispecific antibody and/or a post-translationally modified product of the antibody containing a heavy chain of an anti-CLDN4 antibody containing a heavy chain variable region consisting of an amino acid sequence at amino acid positions 1-123 of SEQ ID NO: 6 and a light chain of an anti-CLDN4 antibody containing a light chain variable region consisting of an amino acid sequence at amino acid positions 1-109 of SEQ ID NO: 8, and an anti-CD137 scFv containing a heavy chain variable region consisting of an amino acid sequence at amino acid positions 1-118 of SEQ ID NO: 32 and a light chain variable region consisting of an amino acid sequence at amino acid positions 134-244 of SEQ ID NO: 32, in which the amino terminal of the anti-CD137 scFv is linked to the heavy chain carboxy terminal of the anti-CLDN4 antibody via a linker; or (j) an anti-CLDN4/anti-CD137 bispecific antibodies and/or a post-translationally modified product of the antibodies containing a heavy chain of an anti-CLDN4 antibody containing a heavy chain variable region consisting of an amino acid sequence at amino acid positions 1-123 of SEQ ID NO: 6 and a light chain of an anti-CLDN4 antibody containing a light chain variable region consisting of an amino acid sequence at amino acid positions 1-109 of SEQ ID NO: 8, and an anti-CD137 scFv containing a heavy chain variable region consisting of an amino acid sequence at amino acid positions 1-121 of SEQ ID NO: 34 and a light chain variable region consisting of an amino acid sequence at amino acid positions 137-247 of SEQ ID NO: 34, in which the amino terminal of the anti-CD137 scFv is linked to the heavy chain carboxy terminal of the anti-CLDN4 antibody via a linker.

In one embodiment, the pharmaceutical composition of the present invention is a pharmaceutical composition containing the anti-CLDN4/anti-CD137 bispecific antibody of the present invention and/or a post-translationally modified product of the antibody described in the following (a) or (b):

(a) an anti-CLDN4/anti-CD137 bispecific antibody and/or a post-translationally modified product of the antibody containing a polypeptide consisting of an amino acid sequence at amino acid positions 1-705 of SEQ ID NO: 36 containing a heavy chain of an anti-CLDN4 antibody and an anti-CD137 scFv, and a light chain of an anti-CLDN4 antibody consisting of an amino acid sequence at amino acid positions 1-215 of SEQ ID NO: 40; or (b) an anti-CLDN4/anti-CD137 bispecific antibody and/or a post-translationally modified product of the antibody containing a polypeptide consisting of an amino acid sequence at amino acid positions 1-712 of SEQ ID NO: 38 containing a heavy chain of an anti-CLDN4 antibody and an anti-CD137 scFv, and a light chain of an anti-CLDN4 antibody consisting of an amino acid sequence at amino acid positions 1-215 of SEQ ID NO: 40.

The amounts of the anti-CLDN4/anti-CD137 bispecific antibody of the present invention and/or the post-translationally modified product of the antibody added in formulation are varied depending on the degree of symptom and the age of a patient, a dosage form of the formulation to be used, a binding titer of the antibody, or the like, and they can be used in an amount of, for example, about 0.001 mg/kg to 100 mg/kg.

<Pharmaceutical Use of Anti-CLDN4/Anti-CD137 Bispecific Antibody of Invention>

The anti-CLDN4/anti-CD137 bispecific antibody of the present invention and a pharmaceutical composition containing the same can be used for treating cancer of a subject. Besides, the present invention embraces a method for treating cancer including a step of administering a therapeutically effective amount of the anti-CLDN4/anti-CD137 bispecific antibody of the present invention to a subject. Furthermore, the present invention embraces the anti-CLDN4/anti-CD137 bispecific antibody of the present invention for use in treatment of cancer. In addition, the present invention embraces use, in production of a pharmaceutical composition for treating cancer, of the anti-CLDN4/anti-CD137 bispecific antibody of the present invention. Cancer to be treated by the present invention is not especially limited, and examples thereof include various peritoneal metastatic cancers, gastric cancer, lung cancer, blood cancers such as acute lymphoblastic leukemia, acute myelogenous leukemia, Hodgkin's lymphoma, non-Hodgkin's lymphoma, B cell lymphoma, multiple myeloma and T cell lymphoma, solid cancers such as myelodysplastic syndromes, adenocarcinoma, squamous cell carcinoma, adenosquamous carcinoma, undifferentiated carcinoma, large cell carcinoma, non-small cell lung cancer, small cell lung cancer, mesothelioma, skin cancer, skin T cell lymphoma, breast cancer, prostate cancer, bladder cancer, vaginal cancer, cervix cancer, head and neck cancer, uterine cancer, cervical cancer, liver cancer, gallbladder cancer, bile duct cancer, kidney cancer, pancreatic cancer, colon cancer, colorectal cancer, rectal cancer, small intestine cancer, gastric cancer, esophageal cancer, testicular cancer, ovarian cancer and brain tumor, cancers of bone tissues, cartilage tissues, adipose tissues, muscle tissues, vascular tissues and blood-forming tissues, sarcomas such as chondrosarcoma, Ewing's sarcoma, malignant hemangioendothelioma, malignant schwannoma, osteosarcoma and soft tissue sarcoma, and blastomas such as glioblastoma, glioblastoma multiforme, hepatoblastoma, medulloblastoma, nephroblastoma, neuroblastoma, pancreatoblastoma, pleuropulmonary blastoma and retinoblastoma. In one embodiment, cancer to be treated by the present invention is colorectal cancer, non-small cell lung cancer, small cell lung cancer, bladder cancer, ovarian cancer, breast cancer or prostate cancer. In one embodiment, cancer to be treated by the present invention is cancer in which CLDN4 is highly expressed as compared to a normal tissue. Cancer to be treated by the present invention is preferably cancer in which CLDN4 is highly expressed as compared to a normal tissue, or cancer selected from the group consisting of colorectal cancer, rectal cancer, lung cancer, non-small cell lung cancer, small cell lung cancer, bladder cancer, ovarian cancer, breast cancer and prostate cancer.

<Anti-CLDN4 Antibody of Invention>

The present invention also provides an anti-CLDN4 antibody or its antigen binding fragment described in any of the following (a) to (c):

(a) an anti-CLDN4 antibody or its antigen binding fragment containing a heavy chain variable region containing a CDR1 consisting of an amino acid sequence at amino acid positions 31-35 of SEQ ID NO: 2, a CDR2 consisting of an amino acid sequence at amino acid positions 50-66 of SEQ ID NO: 2, and a CDR3 consisting of an amino acid sequence at amino acid positions 99-114 of SEQ ID NO: 2, and a light chain variable region containing a CDR1 consisting of an amino acid sequence at amino acid positions 24-35 of SEQ ID NO: 4, a CDR2 consisting of an amino acid sequence at amino acid positions 51-57 of SEQ ID NO: 4, and a CDR3 consisting of an amino acid sequence at amino acid positions 90-98 of SEQ ID NO: 4;

(b) an anti-CLDN4 antibody or its antigen binding fragment containing a heavy chain variable region consisting of an amino acid sequence at amino acid positions 1-125 of SEQ ID NO: 2 and a light chain variable region consisting of an amino acid sequence at amino acid positions 1-109 of SEQ ID NO: 4; or (c) an anti-CLDN4 antibody or its antigen binding fragment containing a heavy chain variable region consisting of an amino acid sequence at amino acid positions 1-123 of SEQ ID NO: 6 and a light chain variable region consisting of an amino acid sequence at amino acid positions 1-109 of SEQ ID NO: 8.

In one embodiment, the anti-CLDN4 antibody of the present invention or its antigen binding fragment is an anti-CLDN4 antibody or its antigen binding fragment containing a heavy chain variable region consisting of an amino acid sequence at amino acid positions 1-125 of SEQ ID NO: 2 and a light chain variable region consisting of an amino acid sequence at amino acid positions 1-109 of SEQ ID NO: 4, or an anti-CLDN4 antibody or its antigen binding fragment containing a heavy chain variable region consisting of an amino acid sequence at amino acid positions 1-123 of SEQ ID NO: 6 and a light chain variable region consisting of an amino acid sequence at amino acid positions 1-109 of SEQ ID NO: 8. In one embodiment, the anti-CLDN4 antibody of the present invention or its antigen binding fragment is a heavy chain variable region consisting of an amino acid sequence at amino acid positions 1-125 of SEQ ID NO: 2. In one embodiment, the anti-CLDN4 antibody of the present invention or its antigen binding fragment is an anti-CLDN4 antibody or its antigen binding fragment containing a heavy chain variable region consisting of an amino acid sequence at amino acid positions 1-123 of SEQ ID NO: 6 and a light chain variable region consisting of an amino acid sequence at amino acid positions 1-109 of SEQ ID NO: 8.

As the heavy chain constant region of the anti-CLDN4 antibody, any of the constant regions Igγ, Igμ, Igα, Igδ and Igε can be selected. Igγ can be selected from, for example, Igγ1, Igγ2, Igγ3 and Igγ4. In one embodiment, the heavy chain constant region is an Igγ1 constant region, and for example, a human Igγ1 constant region. The heavy chain constant region of the anti-CLDN4 antibody of the present invention may contain an amino acid mutation such as LALA mutation, or P331G or P331S mutation in order to deteriorate ADCC and CDC. As the light chain constant region of the anti-CLDN4 antibody of the present invention, either of the constant regions Igλ and Igκ can be selected. In one embodiment, the light chain constant region is an Igκ constant region, and for example, a human Igκ constant region.

In one embodiment, the antigen binding fragment of the anti-CLDN4 antibody of the present invention is a scFv, a Fab, a Fab', or a F(ab')$_2$.

In one embodiment, the anti-CLDN4 antibody of the present invention is an anti-CLDN4 antibody containing a heavy chain containing a heavy chain variable region consisting of an amino acid sequence of SEQ ID NO: 2 and a light chain containing a light chain variable region consisting of an amino acid sequence of SEQ ID NO: 4, or an anti-CLDN4 antibody containing a heavy chain containing a heavy chain variable region consisting of an amino acid sequence of SEQ ID NO: 6 and a light chain containing a light chain variable region consisting of an amino acid sequence of SEQ ID NO: 8. In one embodiment, the anti-CLDN4 antibody of the present invention is an anti-CLDN4 antibody containing a heavy chain containing a heavy chain variable region consisting of an amino acid sequence of SEQ ID NO: 2 and a light chain containing a light chain variable region consisting of an amino acid sequence of SEQ ID NO: 4. In one embodiment, the anti-CLDN4 antibody of the present invention is an anti-CLDN4 antibody containing a heavy chain containing a heavy chain variable region consisting of an amino acid sequence of SEQ ID NO: 6 and a light chain containing a light chain variable region consisting of an amino acid sequence of SEQ ID NO: 8.

The present invention also provides an anti-CLDN4 antibody of the present invention or its antigen binding fragment to which a carbohydrate, a lipid, a metal (including a radioisotope), an organic compound (including a toxin, a near-infrared fluorescent dye, and a chelating agent) or the like (also referred to as a "modifier") is bound (also referred to as a "complex of the present invention"). Herein, the term "modifier" refers to a nonpeptide substance bound to an antibody or its antigen binding fragment directly or via a linker and the like. A modifier for use in the complex of the present invention is not especially limited, and examples thereof include polyethylene glycol, sugar chains, phospholipids, radioactive isotopes (for example, zirconium-89 ($^{89}$Zr), yttrium-90 ($^{90}$Y), indium-111 ($^{111}$In), astatine-211 ($^{211}$At), and actinium-225 ($^{225}$Ac)), organic compounds, toxins, near-infrared fluorescent dyes (for example, IRDye®), and chelating agents. The modifier for use in the complex may be directly bound to the anti-CLDN4 antibody of the present invention or its antigen binding fragment or may be bound thereto via any linker. In one embodiment, the complex of the present invention is an antibody drug conjugate (ADC) of the anti-CLDN4 antibody or its antigen binding fragment. A chemical drug and a linker for use in the ADC can be chosen from drugs and linkers generally used by those skilled in the art.

The present invention also provides a cell expressing the anti-CLDN4 antibody of the present invention or its antigen binding fragment on a cell surface thereof (for example, a chimeric antigen receptor-T cell; CAR-T cell). Such a cell can be produced by those skilled in the art using a polynucleotide encoding the anti-CLDN4 antibody of the present invention or its antigen binding fragment. As the cell expressing the anti-CLDN4 antibody of the present invention or its antigen binding fragment, various immune cells (such as a T cell, a NK cell, and a NKT cell) can be used.

In one embodiment, the anti-CLDN4 antibody of the present invention or its antigen binding fragment, the complex of the present invention, and an antibody or antigen binding fragment portion in the cell expressing the anti-CLDN4 antibody of the present invention or its antigen binding fragment on a cell surface thereof may be post-translationally modified. In one embodiment, the post-translational modification is pyroglutamylation at the N-terminal of the heavy chain variable region and/or lysine deletion at the heavy chain C-terminal.

The anti-CLDN4 antibody of the present invention or its antigen binding fragment, the complex of the present invention, and the cell expressing the anti-CLDN4 antibody of the present invention or its antigen binding fragment on a cell surface thereof can be produced by those skilled in the art based on sequence information of the VHs and the VLs of the anti-CLDN4 antibody of the present invention or its antigen binding fragment and information of the modifier for use in the complex of the present invention disclosed herein by employing a method known in this field. The anti-CLDN4 antibody of the present invention or its antigen binding fragment can be produced in accordance with, for example, a method described in a section of <Method for Producing Bispecific Antibody of Invention>, although not especially limited thereto.

The present invention also provides a pharmaceutical composition containing the anti-CLDN4 antibody of the present invention or its antigen binding fragment, the complex of the present invention, and the cell expressing the anti-CLDN4 antibody of the present invention or its antigen binding fragment on a cell surface thereof (hereinafter collectively referred to as the "anti-CLDN4 antibody and the like of the present invention" in this section), and a pharmaceutically acceptable excipient. The pharmaceutical composition can be used for treating cancer. The present invention additionally provides a method for treating cancer including a step of administering a therapeutically effective amount of the anti-CLDN4 antibody and the like of the present invention to a subject, the anti-CLDN4 antibody and the like of the present invention for use in treating cancer, and use, in production of a pharmaceutical composition for treating cancer, of the anti-CLDN4 antibody and the like of the present invention. A pharmaceutical use of the anti-CLDN4 antibody and the like of the present invention can be carried out by those skilled in the art according to <Pharmaceutical Composition or the Like of Invention> described above. Examples of cancer to be treated by the pharmaceutical use of the anti-CLDN4 antibody and the like of the present invention include cancer described above in <Pharmaceutical Composition or the Like of Invention>.

<Anti-CD137 Antibody of Invention>

The present invention also provides an anti-CD137 antibody or its antigen binding fragment containing a heavy chain variable region and a light chain variable region of an anti-CD137 antibody described in any of the following (a) to (d):

(a) a heavy chain variable region containing a CDR1 consisting of an amino acid sequence at amino acid positions 31-35 of SEQ ID NO: 10, a CDR2 consisting of an amino acid sequence at amino acid positions 50-66 of SEQ ID NO: 10, and a CDR3 consisting of an amino acid sequence at amino acid positions 99-107 of SEQ ID NO: 10, and a light chain variable region containing a CDR1 consisting of an amino acid sequence at amino acid positions 24-34 of SEQ ID NO: 12, a CDR2 consisting of an amino acid sequence at amino acid positions 50-56 of SEQ ID NO: 12, and a CDR3 consisting of an amino acid sequence at amino acid positions 89-98 of SEQ ID NO: 12;

(b) a heavy chain variable region containing a CDR1 consisting of an amino acid sequence at amino acid positions 31-35 of SEQ ID NO: 14, a CDR2 consisting of an amino acid sequence at amino acid positions 50-65 of SEQ ID NO: 14, and a CDR3 consisting of an amino acid sequence at amino acid positions 98-107 of SEQ ID NO: 14, and a light chain variable region containing a CDR1 consisting of an amino acid sequence at amino acid positions 23-35 of SEQ ID NO: 16, a CDR2 consisting of an amino acid sequence at amino acid positions 51-57 of SEQ ID NO: 16, and a CDR3 consisting of an amino acid sequence at amino acid positions 90-100 of SEQ ID NO: 16;

(c) a heavy chain variable region containing a CDR1 consisting of an amino acid sequence at amino acid positions 31-35 of SEQ ID NO: 18, a CDR2 consisting of an amino acid sequence at amino acid positions 50-65 of SEQ ID NO: 18, and a CDR3 consisting of an amino acid sequence at amino acid positions 98-107 of SEQ ID NO: 18, and a light chain variable region containing a CDR1 consisting of an amino acid sequence at amino acid positions 23-35 of SEQ ID NO: 20, a CDR2 consisting of an amino acid sequence at amino acid positions 51-57 of SEQ ID NO: 20, and a CDR3 consisting of an amino acid sequence at amino acid positions 90-100 of SEQ ID NO: 20; or (d) a heavy chain variable region containing a CDR1 consisting of an amino acid sequence at amino acid positions 31-35 of SEQ ID NO: 22, a CDR2 consisting of an amino acid sequence at amino acid positions 50-65 of SEQ ID NO: 22, and a CDR3 consisting of an amino acid sequence at amino acid positions 98-110 of SEQ ID NO: 22, and a light chain variable region containing a CDR1 consisting of an amino acid sequence at amino acid positions 23-35 of SEQ ID NO: 24, a CDR2 consisting of an amino acid sequence at amino acid positions 51-57 of SEQ ID NO: 24, and a CDR3 consisting of an amino acid sequence at amino acid positions 90-100 of SEQ ID NO: 24.

In one embodiment, the anti-CD137 antibody of the present invention or its antigen binding fragment contains a heavy chain variable region and a light chain variable region of an anti-CD137 antibody described in any of the following (a) to (i):

(a) a heavy chain variable region consisting of an amino acid sequence at amino acid positions 1-118 of SEQ ID NO: 10 and a light chain variable region consisting of an amino acid sequence at amino acid positions 1-109 of SEQ ID NO: 12;

(b) a heavy chain variable region consisting of an amino acid sequence at amino acid positions 1-118 of SEQ ID NO: 14 and a light chain variable region consisting of an amino acid sequence at amino acid positions 1-111 of SEQ ID NO: 16;

(c) a heavy chain variable region consisting of an amino acid sequence at amino acid positions 1-118 of SEQ ID NO: 18 and a light chain variable region consisting of an amino acid sequence at amino acid positions 1-111 of SEQ ID NO: 20;

(d) a heavy chain variable region consisting of an amino acid sequence at amino acid positions 1-121 of SEQ ID NO: 22 and a light chain variable region consisting of an amino acid sequence at amino acid positions 1-111 of SEQ ID NO: 24;

(e) a heavy chain variable region consisting of an amino acid sequence at amino acid positions 1-118 of SEQ ID NO: 26 and a light chain variable region consisting of an amino acid sequence at amino acid positions 134-242 of SEQ ID NO: 26;

(f) a heavy chain variable region consisting of an amino acid sequence at amino acid positions 1-118 of SEQ ID NO: 28 and a light chain variable region consisting of an amino acid sequence at amino acid positions 134-244 of SEQ ID NO: 28;

(g) a light chain variable region consisting of an amino acid sequence at amino acid positions 1-111 of SEQ ID NO: 30 and a heavy chain variable region consisting of an amino acid sequence at amino acid positions 132-249 of SEQ ID NO: 30;

(h) a heavy chain variable region consisting of an amino acid sequence at amino acid positions 1-118 of SEQ ID NO: 32 and a light chain variable region consisting of an amino acid sequence at amino acid positions 134-244 of SEQ ID NO: 32; or (i) a heavy chain variable region consisting of an amino acid sequence at amino acid positions 1-121 of SEQ ID NO: 34 and a light chain variable region consisting of an amino acid sequence at amino acid positions 137-247 of SEQ ID NO: 34.

In one embodiment, the antigen binding fragment of the anti-CD137 antibody of the present invention is a scFv. In one embodiment, the antigen binding fragment of the anti-CD137 antibody of the present invention is any of the following (a) to (e):

(a) an anti-CD137 scFv consisting of an amino acid sequence at amino acid positions 1-242 of SEQ ID NO: 26;

(b) an anti-CD137 scFv consisting of an amino acid sequence at amino acid positions 1-244 of SEQ ID NO: 28;

(c) an anti-CD137 scFv consisting of an amino acid sequence at amino acid positions 1-249 of SEQ ID NO: 30;

(d) an anti-CD137 scFv consisting of an amino acid sequence at amino acid positions 1-244 of SEQ ID NO: 32; or (e) an anti-CD137 scFv consisting of an amino acid sequence at amino acid positions 1-247 of SEQ ID NO: 34.

The anti-CD137 antibody of the present invention or its antigen binding fragment can be produced by those skilled in the art with reference to <Anti-CLDN4/anti-CD137 Bispecific Antibody of Invention> and the like described herein. The anti-CD137 antibody of the present invention or its antigen binding fragment may be used in a bispecific antibody with an antibody to any TAA (anti-TAA antibody), for example, used in treatment of cancer. In other words, the present invention also provides a bispecific antibody containing the anti-CD137 antibody of the present invention or its antigen binding fragment and the anti-TAA antibody or its antigen binding fragment (also referred to as the "anti-TAA/anti-CD137 bispecific antibody of the present invention"). The TAA is not especially limited as long as it is expressed on a cell surface of a tumor, and for example, HER2, EGFR, EpCAM, CEA, BCMA, PSMA, CD19, CD20, CD22, CD33, CD37, CD38, CD123, CD276 (B7-H3), GPC2, GPC3, GPRC5D, WT-1, NY-ESO-1, CLDN4, CLDN6, CLDN18.2, and TSPAN8 can be used. In one embodiment, the anti-TAA/anti-CD137 bispecific antibody of the present invention contains a scFv of an anti-CD137 antibody, and in another embodiment, the anti-TAA/anti- CD137 bispecific antibody of the present invention contains a scFv of an anti-CD137 antibody described in any of the following (a) to (e):
  (a) an anti-CD137 scFv consisting of an amino acid sequence at amino acid positions 1-242 of SEQ ID NO: 26;
  (b) an anti-CD137 scFv consisting of an amino acid sequence at amino acid positions 1-244 of SEQ ID NO: 28;
  (c) an anti-CD137 scFv consisting of an amino acid sequence at amino acid positions 1-249 of SEQ ID NO: 30;
  (d) an anti-CD137 scFv consisting of an amino acid sequence at amino acid positions 1-244 of SEQ ID NO: 32; or
  (e) an anti-CD137 scFv consisting of an amino acid sequence at amino acid positions 1-247 of SEQ ID NO: 34.

In one embodiment, the anti-TAA/anti-CD137 bispecific antibody of the present invention contains an anti-CLDN4 antibody or its antigen binding fragment, and in another embodiment, the anti-TAA/anti-CD137 bispecific antibody of the present invention contains an IgG type anti-CLDN4 antibody.

Specific examples to be referred to for further understanding of the present invention will now be provided, and it is noted that these examples are merely illustrative and do not limit the present invention.

EXAMPLES

Examples 1: Acquisition of Antibody Binding Selectively to Antigen Expressed in Peritoneal Metastatic Cancer Cell

[1-1. Acquisition of Peritoneal Metastatic Cancer Cell Derived from Patient]

Peritoneal metastatic cancer cells from a patient were obtained according to a method described in the literature by Fumiko Chiwaki and Hiroki Sasaki "Fukumaku Teni Gan (I, Sui, Ranso Gan Nado) Saibo Kabu No Juritsu (in Japanese) (Establishment of Peritoneal Metastasis Cancer (such as Gastric, Pancreatic, and Ovarian Cancer) Cell Lines)" (*Practical Guide for Cancer Research using Patient-Derived Experimental Model*, edited by Hiroki Sasaki, Yodosha Company, Ltd., 2019, p. 28-37).

Ascites fluid taken from the patient was centrifuged at room temperature and 430×g for 3 minutes, a supernatant was removed, and a hemolysis buffer was added to a precipitate to cause hemolysis. After centrifugation, the supernatant was removed, Dulbecco's PBS(−) (Nissui Pharmaceutical Co., Ltd., 05913; hereinafter referred to as the "PBS(−)") was added in an amount of 50 mL to wash the cells. Thereafter, the resultant cells were collected by centrifugation at room temperature and 430×g for 3 minutes. The whole cells in the collected ascites fluid were suspended again in RPMI-1640 (containing L-glutamine) medium (FUJIFILM Wako Pure Chemical Corporation, 189-02025) containing 10% FBS (Thermo Fisher Scientific, 10270-106) and ×1 Antibiotic-Antimycotic (Thermo Fisher Scientific, 15240062) (wherein the medium after the addition of FBS and the like in Example 1 is hereinafter referred to as the "RPMI-1640 medium"). The suspension was diluted, and the cells were seeded at $5\times10^6$ to $1\times10^7$ cells/10 mL each in a 100 mm collagen coated dish (hereinafter referred to as the "dish") (IWAKI, 4020-010) to be cultured at 37° C. in a 5% $CO_2$ incubator.

In the ascites fluid, there are adhesive cells and floating cells, and the adhesive cells include not only cancer cells but also non-cancer cells (such as fibroblasts and peritoneal mesothelial cells). The non-cancer cells have properties of detaching in a shorter time than the cancer cells, and thus these cells were removed by separating them from the whole cells in the ascites fluid. After removing the non-cancer cells, the cancer cells grew to approximately 80% confluency of the dish area, and then a process of passaging ½ of the whole cells to a new dish was repeated, and cells that had been passaged 5 times or more were considered adhesive cancer cells. For the floating cells, 5 ml of the culture supernatant and 5 ml of the RPMI-1640 medium were seeded into a new 100 mm dish from the culture dish to passage the cells, and cells that had been passaged 5 times or more were considered floating cancer cells. When peritoneal metastatic cancer cells derived from a single patient grew with both adhesive cancer cells and floating cancer cells, they were considered mixed cancer cells.

Herein, adhesive cancer cells, floating cancer cells, or mixed cancer cells isolated by the above method are generically referred to as the "peritoneal metastatic cancer cells." The obtained six cells (NSC-9C, NSC-15CF, NSC-16C, NSC-20C, NSC-22C, and NSC-32C (hereinafter also referred to as the "six types of the peritoneal metastatic cancer cells")) were used in the following examination.

[1-2: Production of Anti-Gastric Cancer Antigen-Antibody Producing Hybridoma]

The peritoneal metastatic cancer cells were immunized to VelocImmune mice produced using human monoclonal antibody development technology ("VelocImmune"® antibody technology; Regeneron (U.S. Pat. No. 6,596,541)) to obtain antibodies against a cancer antigen expressed on an anti-peritoneal metastatic cancer cell.

Among the peritoneal metastatic cancer cells obtained in Example 1-1, three cells NSC-9C, NSC-15CF, and NSC-16C or three cells NSC-20C, NSC-22C, and NSC-32C were mixed, and the resultants were suspended in a TiterMax® Gold ADJUVANT (Merck, T2684) or PBS(−) to prepare a suspension of the peritoneal metastatic cancer cells. The VelocImmune mice were immunized by administering this suspension several times. Lymphocytes was collected from the lymph nodes of the immunized mice and were subjected to cellular fusion with mouse myeloma cells SP2/0 (ATCC, CRL-1581) to produce hybridomas by a conventional method. Single colonies of the hybridomas were isolated with an automatic picking device to obtain a monocloned hybridoma cell (hereinafter referred to as the "clone"). The isolated clone was cultured at 37° C. in an 8% $CO_2$ incubator, and a supernatant after about 14 days was collected in a 96 well plate to use the following experiment.

[1-3: Selection of Antibody Binding Selectively to Peritoneal Metastatic Cancer Cell]

(1) Check of Binding to Peritoneal Metastatic Cancer Cell and EpCAM Expressing Cell A cell supernatant of the clone obtained in Example 1-2 contains an antibody (hereinafter referred to as the "antibody contained in the clone supernatant").

First, binding of the antibody contained in the clone supernatant to the six types of the peritoneal metastatic cancer cells obtained in Example 1-1 was measured by flow cytometry to select a clone producing an antibody binding strongly to the peritoneal metastatic cancer cells. BV421 Goat Anti-Mouse Ig (Becton, Dickinson and Company, 563846) was used for flow cytometry.

Besides, the binding of the antibody contained in the clone supernatant to human EpCAM-Myc-DDK expressing CHO-K1 cells was measured for excluding clones providing an antibody binding to EpCAM that is a cancer antigen. The human EpCAM-Myc-DDK expressing CHO-K1 cells were produced by transfection of CHO-K1 cells (ATCC, CCL-61) with an EPCAM (Myc-DDK-tagged)-Human epithelial cell adhesion molecule (EPCAM) (ORIGENE, RC201989). The binding of the antibody contained in the clone supernatant to the cells was measured by flow cytometry. BV421 Goat Anti-Mouse Ig was used for flow cytometry. Clones binding to an EpCAM expressing cells were excluded for selecting clones providing a supernatant that did not exhibit binding activity to the cell. As a positive control, CD326 (EpCAM) Monoclonal Antibody (1B7) (eBioscience, 14-9326) was used.

Furthermore, clones binding to cultured human peritoneal mesothelial cells were excluded for selecting clones binding selectively to peritoneal metastatic cancer cells. As the cultured human peritoneal mesothelial cell, Human Mesothelial Cell (Zenbio, MES-F, Lot. MESM050311A) (hereinafter also referred to as the "cultured human peritoneal mesothelial cell") was used, and binding between the cultured human peritoneal mesothelial cells cultured in Mesothelial Cell Growth Medium (Zenbio, MSO-1) and a clone thereof was measured by flow cytometry. BV421 Goat Anti-Mouse Ig was used for flow cytometry. Only clones that did not bind to the cultured human peritoneal mesothelial cells were selected.

Through the above experiment, a 3D11 clone was obtained as a clone providing an antibody binding to 5 or more of the six peritoneal metastatic cancer cells but not to human EpCAM and cultured peritoneal mesothelial cells.
(2) Purification of Antibody from Hybridoma Supernatant The 3D11 clone was cultured in a CD hybridoma medium (Thermo Fisher Scientific, 11279023). From culture supernatants thus obtained, a 3D11 antibody (hereinafter referred to as "3D11") were purified with MabSelect SuRe (GE Healthcare, 17-5438-02). The antibody was purified by a conventional method.
[1-4: Identification of Antigen Molecule Recognized by 3D11]
(1) Identification of Candidate Antigen Molecule by LC-MS/MS Measurement A candidate antigen molecule for 3D11 was identified. As a control antibody in this experiment, 1D10 and 10B5 were used. These antibodies showed a different binding pattern to peritoneal metastatic cancer cells than 3D11 in the process of obtaining 3D11.

A cell homogenate of NSC-15CF was prepared. To the cell homogenate, 3D11 and one of the two control antibodies (1D10, 10B5) were added, and Dynabeads Protein G (Life Technologies, 10003D) was further added thereto for stirring and washing. A protein bound to Dynabeads Protein G was digested using Trypsin/LysC (Promega Corporation, V5072) to obtain a peptide mixture. A solution containing the peptide mixture was subjected to LC-MS/MS measurement with UltiMate 3000 RSLCnano (Thermo Fisher Scientific) and Orbitrap Fusion (Thermo Fisher Scientific). The thus obtained LC-MS/MS data were subjected to comparative quantitative analysis and peptide/protein identification with Progenesis QI for Proteomics (Waters) and Mascot (Matrix Science) software to identify binding proteins. The binding proteins of 3D11 and the control antibodies were compared, and CLDN4 was identified as a candidate antigen molecule for 3D11.
(2) Antigen Determination of 3D11

A binding experiment to human CLDN4-Myc-DDK expressing CHO-K1 cells was performed for determining whether the CLDN4 thus identified in (1) is an antigen of 3D11. Human CLDN4-Myc-DDK expressing CHO-K1 cells were produced by transfection of CHO-K1 cells with CLDN4 (Myc-DDK-tagged)-Human claudin 4 (CLDN4) (ORIGENE, RC200490). As a result, it was confirmed that 3D11 bound to the human CLDN4-Myc-DDK expressing CHO-K1 cells and thus recognized CLDN4 as an antigen.

Examples 2: Sequence Determination of 3D11 and Production of Human Antibody

A gene encoding a heavy chain and a light chain of 3D11 was cloned by a conventional method to determine a nucleotide sequence and an amino acid sequence of 3D11. An amino acid sequence of a heavy chain variable region of 3D11 is shown in SEQ ID NO: 2, and an amino acid sequence of a light chain variable region thereof is shown in SEQ ID NO: 4. An antibody produced by VelocImmune mice are an antibody in which endogenous immunoglobulin heavy chain and light chain variable regions have been substituted with corresponding human variable regions. In other words, an antibody obtained by employing a VelocImmune technique irs an antibody having a variable region of a human antibody and a constant region of a mouse antibody (also referred to as a "chimeric antibody").

Reference Example: Anti-CLDN4/Anti-CD3 Bispecific Antibody for Use in Treatment of Cancer Peritoneal Metastasis Various types of drugs such as an antibody, an antibody-drug conjugate (ADC) antibody, and chimeric antigen receptor T-cell therapy (CAR-T) are known as a therapeutic agent for a TAA expressing selectively on a cancer cell, Among them, a bispecific T cell recruiting antibody (T cell recruiting antibody) is known as an innovative method by which cancer cell-selective cytotoxic activity can be obtained at a low antibody concentration. Therefore, a bispecific T cell recruiting antibody using 3D11 was examined.
(1) Production of Humanized Anti-CLDN4 Antibody A human anti-CLDN4/anti-CD3 scFv bispecific antibody was produced by the following method.

The human anti-CLDN4 antibody portion was designed by linking an IgG1 constant region of a human heavy chain to the heavy chain variable region of 3D11, and a constant region of the human light chain k to the light chain variable region by a conventional method. Besides, LALA mutation (L234 and L235A) in which each of amino acids at amino acid positions 238 and 239 (EU index: 234 and 235) of the heavy chain is substituted from leucine (L) to alanine (A), Knobs-into-holes mutation in which amino acids at amino acid positions 370, 372 and 411 (EU index: 366, 368 and 407) are respectively substituted from threonine (T) to serine (S), L to A, and tyrosine (Y) to valine (V), and mutation in which an amino acid at an amino acid position 301 (EU index: 297) is substituted from asparagine (N) to A were introduced. The thus produced humanized anti-CLDN4 antibody is referred to as 3D11.1. A polynucleotide encoding an amino acid sequence of 3D11.1 was synthesized by a conventional method and inserted into a pcDNA3.4 TOPO vector (Thermo Fisher Scientific).
(2) Production of Anti-CD3 scFv An anti-CD3 scFv portion was produced based on the sequences of a heavy chain variable region and a light chain variable region of a mouse anti-CD3 antibody described in Japanese Patent No. 5686953. Humanization of the anti-CD3 scFv was performed according to a method described in the literature (Front Biosci., 2008, Vol. 13, p. 1619-1633). In this process, a back mutation was introduced. The three-dimensional structure information (PDB code: 5FCS) was analyzed by an integrated computational chemistry system MOE provided by MOLSIS Inc. to determine positions for introducing the back mutation in the framework region. An amino acid sequence of the humanized anti-CD3 scFv is shown in SEQ ID NO: 41. A polynucleotide encoding the amino acid sequence described in SEQ ID NO: 41 was synthesized by a conventional method and inserted into a pcDNA3.1 (+) vector (Thermo Fisher Scientific, V79020).
(3) Production of Anti-CLDN4 (3D11)/Anti-CD3 scFv Bispecific Antibody A vector encoding 3D11.1 and anti-CD3 scFv was used to produce a bispecific antibody composed of a Fab region of the anti-CLDN4 antibody and a scFv region and Fc region of the anti-CD3 antibody according to a method described in Example 7 of PCT/JP2021/41839. The thus produced bispecific antibody is referred to as the anti-CLDN4 (3D11)/anti-CD3 scFv bispecific antibody.
(4) Evaluation of Medical Effect of Anti-CLDN4 (3D11)/Anti-CD3 scFv Bispecific
Antibody The in vitro redirected T cell cytotoxicity (RTCC) activity of the anti-CLDN4 (3D11)/anti-CD3 scFv bispecific antibody was measured according to a method described in Example 9 of PCT/JP2021/41839. It was confirmed that the anti-CLDN4 (3D11)/anti-CD3 scFv bispecific antibody has RTCC activity. Besides, the in vivo antitumor activity of the anti-CLDN4 (3D11)/anti-CD3 scFv bispecific antibody was evaluated according to a method described in Example 11 of PCT/JP2021/41839. The anti-CLDN4 (3D11)/anti-CD3 scFv bispecific antibody exhibited an antitumor effect in an in vivo mouse model with gastric cancer peritoneal metastasis. From these results, it was suggested that the anti-CLDN4 (3D11)/anti-CD3 scFv bispecific antibody is effective for the treatment of cancer.

Furthermore, in order to examine safety of the anti-CLDN4 (3D11)/anti-CD3 scFv bispecific antibodies, the anti-CLDN4 (3D11)/anti-CD3 scFv bispecific antibody was administered in a single dose intravenously to cynomolgus monkeys. As a result, death and dying examples were observed in the monkeys administered with the anti-CLDN4 (3D11)/anti-CD3 scFv bispecific antibody. Blood levels of IL-6 were remarkably increased in the dead monkeys after 1 hour and 6 hours of the administration, and in dying monkeys after 1 hour, 6 hours, and 24 hours of the administration. From these results, while the anti-CLDN4 (3D11)/anti-CD3 scFv bispecific antibody exerts medical effects in vitro and in vivo, a concern for a serious adverse reaction, presumably due to increased cytokines, has arisen. Therefore, it was concluded that the anti-CLDN4 (3D11)/anti-CD3 scFv bispecific antibody was not qualified as an antibody for treatment of human cancer.

Examples 3: Production of Anti-CLDN4 (3D11)/Anti-CD137 scFv Bispecific Antibody

A bispecific antibody with an anti-CD137 scFv (hereinafter referred to as the "anti-CLDN4 (3D11)/anti-CD137 scFv bispecific antibody") was produced using 3D11 for examination.
[3-1. Acquisition of Anti-CD137 Antibody]
(1) Production of CD137-Fc Fusion Protein Polynucleotides encoding an extracellular region of human CD137 consisting of an amino acid sequence at amino acid positions 1-186 of SEQ ID NO: 42 or an extracellular region of monkey CD137 consisting of an amino acid sequence at amino acid positions 1-186 of SEQ ID NO: 43 were respectively inserted into pFUSE-hIgG1-Fc1 vectors (InvivoGen, pfuse-hg1fc1) to produce expression vectors encoding fusion proteins of the extracellular regions of CD137 and human Fc (hereinafter respectively referred to as the "human CD137-human Fc fusion protein" and the "monkey CD137-human Fc fusion protein"). Each of the thus produced vectors was introduced into Expi293F cells (Thermo Fisher Scientific, A14527) or ExpiCHO-S cells (Thermo Fisher Scientific, A29133) with an Expi293 Expression System Kit (Thermo Fisher Scientific, A14635) or an ExpiCHO Expression System Kit (Thermo Fisher Scientific, A29133) for culturing. Proteins secreted into culture supernatants were purified with MabSelect SuRe or HiTrap MabSelect SuRe (GE Healthcare, 11-0034-94) to obtain human CD137-human Fc fusion protein and monkey CD137-human Fc fusion protein.
(2) Production of Monkey CD137-His Tag-3×FLAG Tag Fusion Protein Polynucleotides encoding an extracellular region of monkey CD137 consisting of an amino acid sequence at amino acid positions 1-183 of SEQ ID NO: 43, a His tag of SEQ ID NO: 44, and a 3×FLAG tag of SEQ ID NO: 45 were inserted in tandem into a pcDNA3.4 TOPO vector to produce a vector. The thus produced vector was introduced into ExpiCHO-S cells with an ExpiFectamine CHO Transfection Kit (Thermo Fisher Scientific, A29129) for culture. A protein secreted into a culture supernatant was purified with HisTrap excel (GE Healthcare Bioscience, 17-3712-06). The thus obtained fusion protein is referred to as the "monkey CD137-His tag-3×FLAG tag fusion protein."
(3) Production and Screening of Anti-CD137 Antibody Producing Hybridoma Clone VelocImmune mice or AlivaMab mice (Ablexis, U.S. Pat. No. 9,346,873) were immunized by administering the human CD137-human Fc fusion protein or human CD137-His tag protein (R&D Systems, 9220-4B) and immunoadjuvants several times. Lymphocytes were collected from the lymph nodes of the immunized mice by a conventional method and were subjected to cellular fusion with mouse myeloma cells SP2/0 to produce hybridomas. Single colonies of the hybridomas were isolated with an automatic picking device to obtain monocloned hybridoma cells (hereinafter referred to as the "clone"). Each clone was cultured for several days to obtain a culture supernatant. Binding to CD137 of antibodies contained in the culture supernatant was checked by the following method.

The binding to CD137 was evaluated by ELISA. In the evaluation, a plate coated with any one of the human CD137-His tag protein, the human CD137-human Fc fusion protein, the monkey CD137-human Fc fusion protein, and human Fc protein was used, and Goat Anti-Mouse IgG, Human ads-HRP (SouthernBiotech, 1030-05) was used as a secondary antibody. By this method, a plurality of clones binding to both human CD137 and monkey CD137 were obtained.
(4) Acquisition of Anti-CD137 Antibody and Check of Agonistic Activity The clones obtained in (3) were cultured in Hybridoma-SFM (Thermo Fisher Scientific, 12045-076), and from a culture supernatant thus obtained, anti-CD137 antibodies were purified with MabSelect SuRe. The purified anti-CD137 antibodies were checked for binding to CD137 and CD137 agonistic activity.

The binding to CD137 of the anti-CD137 antibodies was checked by ELISA described in (3). Measurement of the CD137 agonistic activity of the anti-CD137 antibodies was performed with 4-1BB Bioassay Kit (Promega Corporation, JA2351) by the following method. FcγRIIb CHO-K1 Cells (Promega Corporation, JA2251) were seeded in a 384 well plate (Greiner Bio-One, 781080) to be cultured at 37° C. and 5% $CO_2$ overnight. A culture supernatant was removed, the purified antibodies of each clone described above and 4-1BB Effector Cells (Promega Corporation, JA2351) were added thereto, and the resultant was allowed to stand still at 37° C. and 5% $CO_2$ for 6 hours. To the resultant, Bio-Glo Reagent (Promega Corporation, JA2351) was added to measure chemiluminescence by luciferase expression induction in response to CD137 agonistic activity. The same experiment as above was performed under FcγRIIb CHO-K1 Cells-free conditions for evaluating the CD137 agonistic activity in the absence of FcγRIIb CHO-K1 Cells.

Among the anti-CD137 antibodies thus evaluated, 3-34 derived from VelocImmune mice, and A2-32, A2-48, and A2-73 derived from AlivaMab mice had strong binding activity to human and monkey CD137 and exhibited CD137 agonistic activity dependent on the presence of FcγRIIb CHO-K1 Cells.

(5) Identification of Gene Sequence of Anti-CD137 Antibody

From each of the clones providing the anti-CD137 antibodies (3-34, A2-32, A2-48, and A2-73), a cell lysate was prepared by a conventional method, a cDNA was synthesized, and an antibody nucleotide sequence was identified. SEQ ID NO of the nucleotide sequence thus identified is shown in Table 1.

TABLE 1

|  | Nucleotide sequence of heavy chain variable region | Nucleotide sequence of light chain variable region |
| --- | --- | --- |
| 3-34 | SEQ ID NO: 9 | SEQ ID NO: 11 |
| A2-32 | SEQ ID NO: 13 | SEQ ID NO: 15 |
| A2-48 | SEQ ID NO: 17 | SEQ ID NO: 19 |
| A2-73 | SEQ ID NO: 21 | SEQ ID NO: 23 |

[3-2. Production of Anti-CLDN4 (3D11)/Anti-CD137 (3-34) scFv Bispecific Antibody]

The anti-CLDN4 (3D11)/anti-CD137 (3-34) scFv bispecific antibody (hereinafter also referred to as "3D11_3-34-j6_S") was designed based on the sequences of the heavy chain variable region and the light chain variable region of 3D11 and 3-34. In 3D11_3-34-j6_S thus produced, a GS linker is linked to the heavy chain carboxy terminal (also referred to as the "C-terminal") of the anti-CLDN4(3D11) antibody of the human IgG1κ type, and the amino terminal of an anti-CD137 (3-34) scFv (SEQ ID NO: 26) containing the heavy chain variable region and the light chain variable region of the anti-CD137 antibody is bounded to the C-terminal of the GS linker. Besides, amino acid mutations L234A, L235A, and P331S were introduced into the human IgG1 constant region of 3D11. Polynucleotides encoding the designed antibody were produced and inserted into pcDNA3.4 TOPO vectors by a conventional method. The expression vectors were genetically introduced into ExpiCHO-S cells, and 3D11_3-34-j6_S was purified from the culture supernatant. It was confirmed that 3D11_3-34-j6_S thus produced had anti-CD137 binding activity and CD137 agonistic activity in vitro, thus suggesting that it can be expected to be effective as a cancer drug.

Examples 4: Production of Anti-CLDN4 (hKM3900)/Anti-CD137 scFv Bispecific Antibody

[4-1. Production of Humanized Anti-CLDN4 (hKM3900) Antibody]

It has been reported that KM3900 that is an anti-CLDN4 antibody binds selectively to CLDN4 as compared with other claudin family molecules such as CLDN6 (PTL 1). Therefore, a humanized antibody of KM3900 was produced based on this report. Specifically, based on a humanized amino acid sequence of a variable region of KM3900, a humanized antibody was designed from sequences of a human Igγ1 constant region and a human Igκ constant region. Into the human Igγ1 constant region, an amino acid mutation L234A, L235A and P331G, or amino acid mutations L234A, L235A, and P331S were introduced. A humanized anti-CLDN4 (hKM3900) antibody was produced by a conventional method to be used in the following examination. An antibody having the amino acid mutations L234A, L235A, and P331G is referred to as "hKM3900," and an antibody having amino acid mutations L234A, L235A and P331S is referred to as "hKM3900_S." An amino acid sequence of a heavy chain variable region of hKM3900 is described in SEQ ID NO: 6, and an amino acid sequence of a light chain variable region thereof is described in SEQ ID NO: 8.

[4-2. Production of Anti-CLDN4/Anti-CD137 scFv Bispecific Antibody]

Anti-CD137 scFvs were designed from the anti-CD137 antibodies obtained in Example 3 (3-34, A2-32, A2-48, and A2-73) to produce bispecific antibodies of hKM3900 and the anti-CD137 scFvs (Table 2). The thus produced antibody is generically referred to as the "anti-CLDN4 (hKM3900)/anti-CD137 scFv."

(1) Production of Vector Encoding Anti-CLDN4 (hKM3900)/Anti-CD137 scFv Bispecific Antibody The anti-CLDN4 (hKM3900)/anti-CD137 scFv bispecific antibody was designed based on the sequence of hKM3900 and the sequences of the heavy chain variable region and the light chain variable region of the anti-CD137 antibody. In the anti-CLDN4 (hKM3900)/anti-CD137 scFv bispecific antibody, a GS linker is linked to the heavy chain or light chain C-terminal of the anti-CLDN4 (hKM3900) of the IgG1 type, and the amino terminal of an anti-CD137 scFv containing the heavy chain variable region and the light chain variable region of the anti-CD137 antibody is bound to the C-terminal of the GS linker. Besides, amino acid mutations L234A, L235A, and P331G or P331S were introduced into the human IgG1 constant region of hKM3900. Information on the designed antibodies is described in Table 2. Each of the polynucleotides encoding the designed antibodies was produced and inserted into a pcDNA3.4 TOPO vector by a conventional method. The thus produced vector is generically referred to as the "anti-CLDN4 (hKM3900)/anti-CD137 scFv bispecific antibody expression vector."

TABLE 2

Anti-CLDN4 (hKM3900)/anti-CD137 scFv Bispecific Antibody

| Antibody name | Anti-CLDN4 antibody | Anti-CD137 antibody | Anti-CD137 scFv | scFv-linked position | Fc mutation |
|---|---|---|---|---|---|
| hKM3900_3-34-j6 | hKM3900 | 3-34 | SEQ ID NO: 26 3-34-j6 | Heavy chain C-terminal (*) | P331G |
| hKM3900_3-34-j6_S | | 3-34 | SEQ ID NO: 26 3-34-j6 | Heavy chain C-terminal | P331S |
| hKM3900_L-3-34-j6 | | 3-34 | SEQ ID NO: 26 3-34-j6 | Light chain C-terminal | P331G |
| hKM3900_tA2-32 | | A2-32 | SEQ ID NO: 28 tA2-32 | Heavy chain C-terminal | P331G |
| hKM3900_tA2-32LH | | A2-32 | SEQ ID NO: 30 tA2-32LH | Heavy chain C-terminal | P331G |
| hKM3900_tA2-48 | | A2-48 | SEQ ID NO: 32 tA2-48 | Heavy chain C-terminal | P331G |
| hKM3900_tA2-73 | | A2-73 | SEQ ID NO: 34 tA2-73 | Heavy chain C-terminal | P331G |
| hKM3900_tA2-32_S | | A2-32 | SEQ ID NO: 28 tA2-32 | Heavy chain C-terminal | P331S |
| hKM3900_tA2-32LH_S | | A2-32 | SEQ ID NO: 30 tA2-32LH | Heavy chain C-terminal | P331S |
| hKM3900_tA2-48_S | | A2-48 | SEQ ID NO: 32 tA2-48 | Heavy chain C-terminal | P331S |
| hKM3900_tA2-73_S | | A2-73 | SEQ ID NO: 34 tA2-73 | Heavy chain C-terminal | P331S |

(*) C-terminal in the table means the carboxy terminal.

(2) Production of Anti-CLDN4 (hKM3900)/Anti-CD137 scFv Bispecific Antibody

The anti-CLDN4 (hKM3900)/anti-CD137 scFv bispecific antibody expression vectors were used to produce eleven anti-CLDN4 (hKM3900)/anti-CD137 scFv bispecific antibodies described in Table 2. Specifically, the anti-CLDN4 (hKM3900)/anti-CD137 scFv bispecific antibody expression vectors were introduced into ExpiCHO-S cells with ExpiFectamine CHO Transfection Kit to cause the anti-CLDN4/anti-CD137 scFv bispecific antibodies to be secreted into a culture supernatant. From the culture supernatant thus obtained, the anti-CLDN4 (hKM3900)/anti-CD137 scFv bispecific antibodies were purified by affinity purification with MabSelect SuRe. Furthermore, some of the anti-CLDN4 (hKM3900)/anti-CD137 scFv bispecific antibodies were additionally purified by size exclusion chromatography purification with HiLoad 26/600 superdex 200 pg (GE Healthcare, 28-9893-36) or Superdex 200 Increase 10/300 GL (GE Healthcare, 28-9909-44).

Hereinafter, the anti-CLDN4 (3D11)/anti-CD137 (3-34) scFv bispecific antibody and the anti-CLDN4 (hKM3900)/anti-CD137 scFv bispecific antibody produced in Examples 3 and 4 are generically referred to as the "anti-CLDN4/anti-CD137 scFv bispecific antibody" in some cases.

Examples 5: Evaluation of Binding Activity and Agonistic Activity of Anti-CLDN4 (hKM3900)/anti-CD137 scFv Bispecific Antibody The anti-CLDN4 (hKM3900)/anti-CD137 scFv bispecific antibody was evaluated for the binding activity to CLDN4 and CD137, and the CD137 agonistic activity.

[5-1. Evaluation of Binding Activity to CLDN4 of Anti-CLDN4 (hKM3900)/Anti-CD137 scFv Bispecific Antibody by Flow Cytometry]

The binding activity to CLDN4 of the anti-CLDN4 (hKM3900)/anti-CD137 scFv bispecific antibody was evaluated by flow cytometry. A CLDN4 gene prepared from CLDN4 (Myc-DDK-tagged)-Human claudin 4 was inserted into pCMV6-AC-GFP Mammalian Expression Vector (ORI-GENE, PS100010) to produce an expression vector for human CLDN4. The expression vectors for human CLDN4 were introduced into CHO-K1 cells to obtain human CLDN4 expressing CHO-K1.

As a test antibody, hKM3900 and the two anti-CLDN4 (hKM3900)/anti-CD137 scFv bispecific antibodies (hKM3900_tA2-32LH and hKM3900_3-34-j6) were used. Each of the test antibodies was serially diluted with Stain Buffer (FBS) (BD Bioscience, 554656) from a maximum concentration of 100 g/mL to 5.08 ng/mL with a common ratio of 3, and the human CLDN4 expressing CHO-K1 was stained with each test antibody dilute solution. As a secondary antibody, Allophycocyanin (APC) AffiniPure F(ab')2 Fragment Goat Anti-Human IgG, Fcγ fragment specific (Jackson ImmunoResearch, 109-136-170) was used. Fluorescence intensity was measured with FACS Canto II (BD Bioscience). Measurement results were analyzed with GraphPad Prism to calculate an apparent dissociation constant (KD) between human CLDN4 and the anti-CLDN4 (hKM3900)/anti-CD137 scFv bispecific antibody. Values of the apparent KD thus obtained are shown in Table 3.

The two anti-CLDN4 (hKM3900)/anti-CD137 scFv bispecific antibodies exhibited the same binding activity to human CLDN4 as the humanized anti-CLDN4 (hKM3900) antibody. Other anti-CLDN4 (hKM3900)/anti-CD137 scFv bispecific antibodies are also expected to exhibit CLDN4 binding activity equivalent thereto.

TABLE 3

| | hKM3900 | hKM3900_tA2-32LH | hKM3900_3-34-j6 |
|---|---|---|---|
| KD (nM) | 10.8 | 10.8 | 11.2 |

[5-2. Evaluation of Binding Activity to CD137 of Anti-CLDN4 (hKM3900)/Anti-CD137 scFv Bispecific Antibody by ELISA]

The binding activity to CD137 of the anti-CLDN4 (hKM3900)/anti-CD137 scFv bispecific antibody was detected by ELISA. The ELISA was performed by a conventional method. A 20 ng/20 µL/well human CD137-His tag protein (R&D SYSTEMS, 9220-4B) was immobilized on a 384 well plate (Thermo Fisher Scientific, 464718). As a test antibody, 11 anti-CLDN4 (hKM3900)/anti-CD137 scFv bispecific antibodies and a ctrl IgG_L-3-34-j6 antibody shown in Table 2 were used. The ctrl IgG_L-3-34-j6 antibody is an antibody in which an anti-CD137 scFv (3-34-j6) antibody is linked to a light chain carboxy terminal of an isotype control antibody. The test antibodies were serially diluted with TBS-T (Nippon Gene Co., Ltd., 310-07375) containing 5% Blocking One (Nacalai Tesque, Inc., 03953-95), and added in an amount of 20 µL/well. The antibody has a final concentration as illustrated in FIGS. 1-1 to 1-4. As a secondary antibody, Goat Anti-Human IgG Fc, Multi-Species SP ads-HRP (SouthernBiotech, 2014-05) was used. As a control antibody, hKM3900 was used. Infinite M200 PRO (TECAN) was used to measure absorbances at 450 nm and 570 nm. Results are illustrated in FIGS. 1-1 to 1-4. The anti-CLDN4 (hKM3900)/anti-CD137 scFv bispecific antibodies all bound to the human CD137-His tag protein in a concentration dependent manner. From this result, it was revealed that a linked position of the anti-CD137 scFv did not affect the binding activity to human CD137.

[5-3. Evaluation of Binding Activity to CD137 of Anti-CLDN4 (hKM3900)/Anti-CD137 scFv Bispecific Antibody by Surface Plasmon Resonance]

The binding activity to CD137 of the anti-CLDN4 (hKM3900)/anti-CD137 scFv bispecific antibody was detected by surface plasmon resonance (SPR). For SPR analysis, Biacore T200 (GE Healthcare Japan) was used. As a ligand, one obtained by fixing two anti-CLDN4 (hKM3900)/anti-CD137 scFv bispecific antibodies (hKM3900-3-34-j6, hKM3900_tA2-32LH) to Series S Sensor Chip Protein A (GE Healthcare, 29-1275-56) was used. As an analyte, one obtained by serially diluting human CD137-His tag or the monkey CD137-His tag-3×FLAG tag fusion protein produced in 3-1 (2) with HBS-EP+ from a maximum concentration of 200 nM to 0.0977 nM with a common ratio of 2 was used. The analytes were added to the channel having the ligand bound thereto at 50 µL/min for 2 minutes, then HBS-EP+ was added thereto at 50 µL/min for 10 minutes, and thus, binding and dissociation of the anti-CLDN4 (hKM3900)/anti-CD137 scFv bispecific antibody to and from CD137 were measured. Results obtained in this experiment were used to calculate, with data analysis software (BIA Evaluation), a binding rate constant (ka), a dissociation rate constant (kd), and a dissociation constant (KD) between human CD137 and the anti-CLDN4 (hKM3900)/anti-CD137 scFv bispecific antibody. Values of ka, kd, and KD are shown in Table 4.

As the result, it was revealed that the anti-CLDN4 (hKM3900)/anti-CD137 scFv bispecific antibody exhibited binding activity equivalent to both human CD137 and monkey CD137 antibodies.

[5-4. Evaluation of CD137 Agonistic Activity of Anti-CLDN4/Anti-CD137 scFv Bispecific Antibody in Coexistence of CLDN4 Expressing Cancer Cell]

Specific CD137 agonistic activity via CLDN4 expressing cancer cells of the anti-CLDN4/anti-CD137 scFv bispecific antibody was evaluated with 4-1BB Bioassay Kit.

Figures 1, 2:
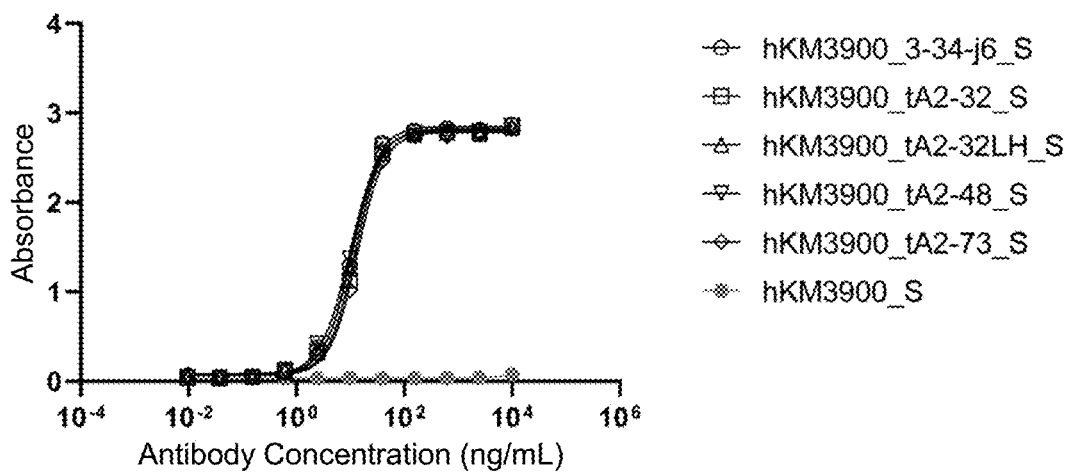
Figures 1, 2, 3:
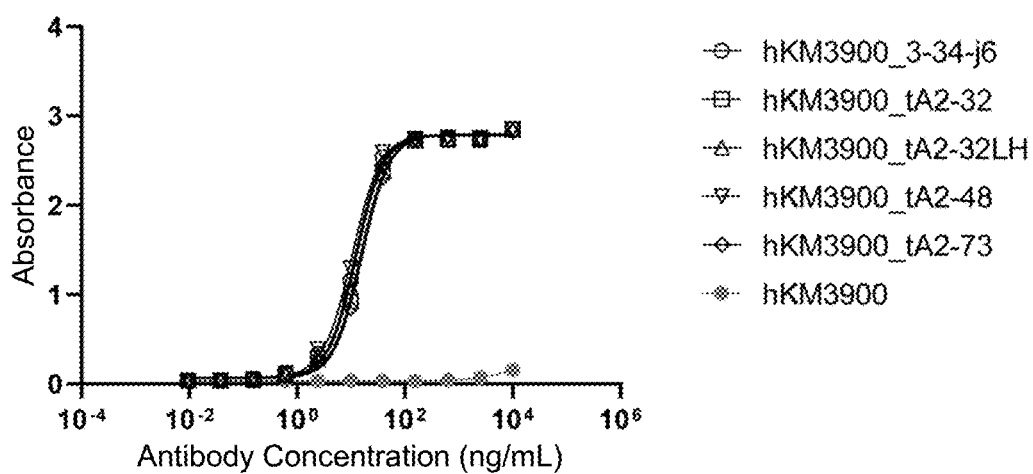

NCI-H322 cells (ECACC, 95111734) were suspended in RPMI-1640 medium (Thermo Fisher Scientific, 11875-093) containing 10% FBS (Cytiva, SH30070.03) to prepare a suspension. CLDN4 was expressed in NCI-H322. The suspension of NCI-H322 was added to a 384 well plate (Greiner Bio-One, 781080) at a density of 1× $10^4$ cells/well, and the resultant was cultured at 37° C. and 5% $CO_2$ overnight. On the next day, the medium was removed. A test antibody diluted with 1% FBS containing RPMI-1640 medium was added in an amount of 12.5 L/well each. The antibody has a final concentration as illustrated in FIG. 2-1 to FIG. 2-3. As the test antibody, 3D11_3-34-j6_S and the anti-CLDN4 (hKM3900)/anti-CD137 scFv bispecific antibody described in Table 2 were used. As a control antibody, hKM3900, a ctrl IgG_L-3-34-j6 antibody, and Urelumab (BMS, SEQ ID NO: 3 and SEQ ID NO: 6 described in International Publication No. WO2005/035584) were used.

A 4-1BB Effector Cells provided with the 4-1BB Bioassay Kits were suspended in 7 mL of 1% FBS-containing RPMI-1640 per vial, the resultant suspension was added in an amount of 12.5 µL to each well, and the resultant was allowed to stand still at 37° C. and 5% $CO_2$ for 6 hours. Bio-Glo Reagent was added to the plate in an amount of 25 µL/well, and chemiluminescence was measured with EnVision 2103 (Perkin Elmer). Results are illustrated in FIG. 2-1 to FIG. 2-3. The anti-CLDN4/anti-CD137 scFv bispecific antibody exhibited remarkable CD137 agonistic activity to the 4-1BB Effector Cells in the coexistence of the CLDN4 expressing cancer cells.

The same experiment as above was performed under NCI-H322-free conditions for evaluating the CD137 agonistic activity in the absence of the CLDN4 expressing cancer cells. As a result, it did not exhibit CD137 agonistic activity in the absence of the CLDN4 expressing cancer cells (FIG. 2-4 to FIG. 2-6). From this result, it was shown that the anti-CLDN4/anti-CD137 scFv bispecific antibody exerts CD137 agonistic activity only in the coexistence of the CLDN4 expressing cancer cells.

On the other hand, Urelumab exhibited CD137 agonistic activity in the coexistence of the CLDN4 expressing cancer cells, but the action was weak as compared with that of the anti-CLDN4/anti-CD137 bispecific antibody. Besides, Urelumab exhibited CD137 agonistic activity even in the absence of the CLDN4 expressing cancer cells.

From these results, the anti-CLDN4/anti-CD137 bispecific antibody can be expected to have a lower toxicity

TABLE 4

| Analyte | Ligand (only antibody listed) | ka (1/Ms) | kd (1/s) | KD (M) |
| --- | --- | --- | --- | --- |
| Human CD137-His Tag Protein | hKM3900_3-34-j6 | 2.32E+05 | 1.35E−03 | 5.81E−09 |
| | hKM3900_tA2-32LH | 3.74E+05 | 2.19E−03 | 5.84E−09 |
| Monkey CD137-His-3 × FLAG | hKM3900_3-34-j6 | 1.79E+05 | 1.91E−03 | 1.07E−08 |
| | hKM3900_tA2-32LH | 2.88E+05 | 1.92E−03 | 6.68E−09 | concern than Urelumab and exhibit specific and strong CD137 agonistic activity in a tumor tissue in which CLDN4 is highly expressed.

Example 6: Evaluation of In Vitro Effect of Anti-CLDN4/Anti-CD137 scFv Bispecific Antibody Evaluation of interferon-γ production promoting function and cancer cytotoxic activity of the anti-CLDN4/anti-CD137 scFv bispecific antibody were carried out.

[6-1. Production and Cryopreservation of Expanded Pan T Cell]

(1) Preparation of Expanded Pan T Cell

In Example 6, one obtained by adding FBS (Cytiva, SH30084.03) in a final concentration of 10% and penicillin streptomycin (Thermo Fisher Scientific, 15070-063) in a final concentration of 1% to RPMI-1640 (Sigma, R8758) is referred to as the "culture medium." Each of MEM Non-essential Amino Acid (Merck, M7145), Sodium pyruvate (Merck, S8636), GlutaMAX I (Thermo Fisher Scientific, 35050-061), and HEPES (Thermo Fisher Scientific, 15630-080) may be added to the culture medium in a final concentration of 1%. An anti-CD3 antibody (BioLegend, 317325) diluted to a final concentration of 1 to 3 µg/mL was added to a dish, and the anti-CD3 antibody was immobilized. Pan T Cell Isolation Kit, human (Miltenyi Biotec, 130-096-535) was used to isolate Pan T cells (including both CD4T cells and CD8T cells; hereinafter referred to as the "Pan T cells") from human peripheral blood mononuclear cells (LONZA, CC-2702) in accordance with a protocol recommended by the manufacturer. The isolated Pan T cells were centrifuged, a supernatant was removed, and the resultant was suspended in the culture medium. The whole Pan T cells suspended in the culture medium were seeded in the dish in which the anti-CD3 antibody had been immobilized. Besides, human IL-2 (PeproTech, 200-2) in a final concentration of 100 to 200 U/mL and an anti-CD28 antibody (BioLegend, 302923) in a final concentration of 1 to 4 µg/mL were added thereto, and the resultant was cultured at 37° C. in a 5% $CO_2$ incubator. After 3 days, the resultant cells were collected, the collected cell s were suspended in the culture medium, and seeded in a dish. Furthermore, human IL-2 in a final concentration of 100 to 200 U/mL was added thereto, and the resultant was cultured at 37° C. in a 5% $CO_2$ incubator. After 4 days, the whole cells were collected to be centrifuged, a supernatant was removed, the resultant was suspended again in a Cell Banker (Takara, CB011) or Bambanker (GC LYMPHOTEC Inc., CS-02-001), and the resultant was separated into tubes to be cryopreserved at −80° ° C. The cells thus cryopreserved are herein referred to as the "expanded Pan T cells."

[6-2. Production of 60As6-Luc/GFP Expressing Cell]

Preparation of a lentivirus solution containing Luc/GFP was carried out with L293T cells (Thermo Fisher Scientific, K4975-00) by a conventional method. For an introduction of pCDH-CMV-GL3-EF1a-GFP-T2A-puro based vector (donated by Associate Professor Ryouu Takahashi at Hiroshima University, Graduate School of Biomedical and Health Sciences, Department of Cellular and Molecular Biology (PLOS One, 2015, Vol. 10, e0123407)) into the L293T cells, Opti-MEM Reduced Serum Medium, GlutaMAX Supplement (Thermo Fisher Scientific, 51985-034), MISSION® Lentiviral Packaging Mix (SIGMA, SHP001), and Lipofectamin LTX (Thermo Fisher Scientific, 15338100) were used. For the collection of a GFP expressing lentivirus grown in L293T cells, a 45 µm Millex®-HV filter (Merck Millipore, SLHV033RS) was used. The virus solution was dispensed into a cryovial (Nalgene, 5000-0020) by 1 mL each to be cryopreserved at −80° C.

A CLDN4 expressing cancer cell line, 60As6 cells (received from Dr. Kazuyoshi Yanagihara at Institute of Biomaterials) was infected with a 60As6-Luc/GFP expressing lentivirus by a conventional method to produce 60As6-Luc/GFP expressing cells. Polybrene (SantaCruz, sc-134220) was used for increasing infection efficiency. As a medium, RPMI-1640 containing 10% FBS and 2 µg/mL Puromaycin (Thermo Fisher Scientific, A-11138-02) was used. The thus established cells will be herein referred to as the "60As6-Luc/GFP cells." It was confirmed through flow cytometry that CLDN4 was intrinsically highly expressed in the 60As6-Luc/GFP cells. The thus constructed cells were used in later experiments.

[6-3. Evaluation of Interferon-γ Production Promoting Function of Anti-CLDN4 (3D11)/Anti-CD137 scFv Bispecific Antibody in Coculture System of Cancer Cell and T Cell]

The interferon-γ production promoting function of the anti-CLDN4 (3D11)/anti-CD137 scFv bispecific antibody in a coculture system of the 60As6-Luc/GFP cells and the expanded Pan T cells was evaluated. A 0.1 µg/100 µL/well anti-CD3 antibody was added to a flat bottom 96 well plate (IWAKI, 3860-096) to immobilize the anti-CD3 antibody on the plate. The 60As6-Luc/GFP cells were seeded in the plate at $5×10^4$ cells/50 µL/well to be cultured at 37° C. in a 5% $CO_2$ incubator. On the next day, the expanded Pan T cells were seeded in the plate at $2×10^5$ cells/30 µL/well. The test antibodies and the isotype control were serially diluted with the culture medium from a maximum concentration of 50000 ng/ml with a common ratio of 5 and added in an amount of 20 µL each. As a test antibody, Urelumab and the anti-CLDN4 (3D11)/anti-CD137 scFv bispecific antibody (3D11_3-34-j6_S) were used, and as an isotype control, an IgG (lysozyme)-scFv (CD137) (prepared in house) was used. After 6 days, a production amount of interferon γ in a supernatant was measured with AlphaLISA Interferon-γ Measurement Kit (Perkin Elmer, AL217C) in accordance with a protocol recommended by the manufacturer. FIG. 3-1 illustrates a reaction curve of the production amount of interferon γ and the antibody concentration. The anti-CLDN4 (3D11)/anti-CD137 scFv bispecific antibody exhibited interferon-γ production promoting activity in a coculture system of the CLDN4 expressing cancer cell line, the 60As6-Luc/GFP cells, and the expanded Pan T cells. The interferon-γ production promoting function of the anti-CLDN4 (3D11)/anti-CD137 scFv bispecific antibodies was remarkably stronger than that of Urelumab.

[6-4. Evaluation of Interferon-γ Production Promoting Function of Anti-CLDN4 (hKM3900)/Anti-CD137 scFv Bispecific Antibody in Coculture System of Cancer Cell and T Cell]

The interferon-γ production promoting function of the anti-CLDN4 (hKM3900)/anti-CD137 scFv bispecific antibody in a coculture system of the 60As6-Luc/GFP cells and the expanded Pan T cells was evaluated by the same method as in 6-3. An anti-CD3 antibody was immobilized on a 96 well plate at 0.03 µg/100 µL/well. The 60As6-Luc/GFP cells were seeded at $2×10^4$ cells/50 µL/well. The expanded Pan T cells were seeded at $8×10^4$ cells/30 µL/well. As a test antibody, Urelumab serially diluted from a maximum concentration of 5000 ng/ml with a common ratio of 2 or the anti-CLDN4 (hKM3900)/anti-CD137 scFv bispecific antibody (hKM3900_3-34-j6 or hKM3900_tA2-32LH) was used. Each of the test antibody and an isotype control (lysozyme antibody) was added in an amount of 20 µL each. After 4 days, a production amount of interferon γ in a supernatant was measured. FIG. 3-2 illustrates a reaction curve of the production amount of interferon γ and the antibody concentration. The anti-CLDN4 (hKM3900)/anti-CD137 scFv bispecific antibody exhibited interferon-γ production promoting function in a coculture system of the 60As6-Luc/GFP cells and the expanded Pan T cells. The interferon-γ production promoting function of these bispecific antibodies was remarkably stronger than that of Urelumab.

[6-5. Evaluation of Interferon-γ Production Promoting Function of Anti-CLDN4 (3D11)/Anti-CD137 scFv Bispecific Antibody in Monoculture System of T Cell]

The interferon-γ production promoting function of the anti-CLDN4 (3D11)/anti-CD137 scFv bispecific antibody in a monoculture system of the expanded Pan T cells was evaluated. An anti-CD3 antibody was added to a flat bottom 96 well plate in an amount of 0.1 μg/100 μL/well to immobilize the anti-CD3 antibody on the plate. The expanded Pan T cells were seeded in the immobilized plate at $2 \times 10^5$ cells/80 μL/well. As a test antibody, Urelumab and the anti-CLDN4 (3D11)/anti-CD3 scFv bispecific antibody (3D11_3-34-j6_S) were used, and as an isotype control, an IgG (lysozyme)-scFv (CD137) (prepared in house) was used. The test antibodies and the isotype control were serially diluted with the culture medium from a maximum concentration of 50000 ng/ml with a common ratio of 5 and added in an amount of 20 μL each. After 6 days, a production amount of interferon γ in a supernatant was measured with AlphaLISA Interferon-γ Measurement Kit in the same method as in 6-3. FIG. 3-3 illustrates a reaction curve of the production amount of interferon γ and the antibody concentration. The anti-CLDN4 (3D11)/anti-CD137 scFv bispecific antibody did not exhibit interferon-γ production promoting function in a monoculture system of a T cell, but Urelumab exhibited interferon-γ production promoting activity. This result means that the anti-CLDN4 (3D11)/anti-CD137 scFv bispecific antibody does not exhibit T cell activity enhancing activity in an environment where there is no CLDN4 expressing cancer cell line.

[6-6. Evaluation of Interferon-γ Production Promoting Function of Anti-CLDN4 (hKM3900)/anti-CD137 scFv Bispecific Antibody in Monoculture System of T Cell]

Figures 1, 2, 3, 4:
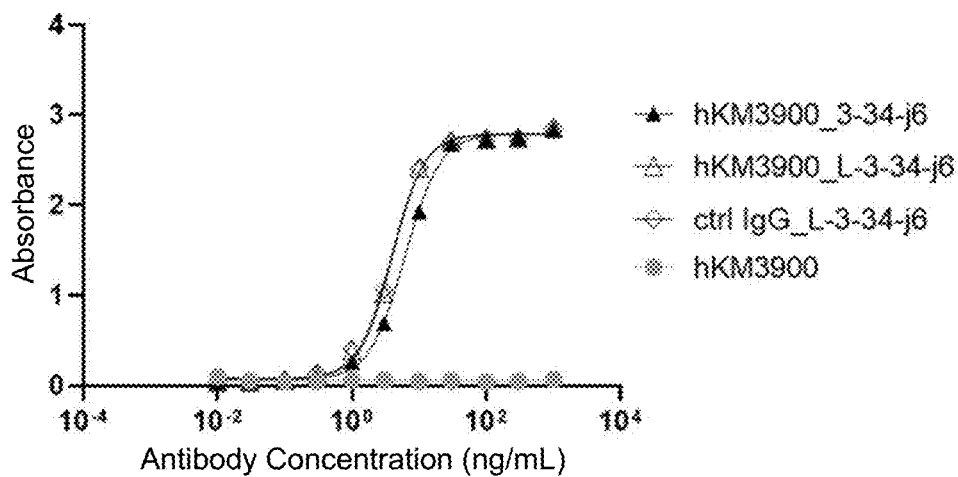

The interferon-γ production promoting function of the anti-CLDN4 (hKM3900)/anti-CD137 scFv bispecific antibody in a monoculture system of the expanded Pan T cells was evaluated in a method similar to that employed in 6-5. An anti-CD3 antibody was immobilized on a 96 well plate at 0.03 μg/100 μL/well. The expanded Pan T cells were seeded at $8 \times 10^4$ cells/80 μL/well. As a test antibody, Urelumab and the anti-CLDN4 (hKM3900)/anti-CD137 scFv bispecific antibody (hKM3900_3-34-j6 or hKM3900_tA2-32LH) were used. The test antibodies and an isotype control (lysozyme antibody) were serially diluted from a maximum concentration of 5000 ng/ml with a common ratio of 2 and added in an amount of 20 μL each. FIG. 3-4 illustrates a reaction curve of the interferon-γ production and the antibody concentration. The anti-CLDN4 (hKM3900)/anti-CD137 scFv bispecific antibody did not exhibit interferon-γ production promoting function in a monoculture system of a T cell, but Urelumab exhibited interferon-γ production promoting function.

The results in 6-5 and 6-6 mean that the anti-CLDN4/anti-CD137 scFv bispecific antibody does not exhibit T cell activity enhancing activity in an environment where there is no CLDN4 expressing cancer cell and suggest that systemic immunopotentiating activity reported as an adverse reaction of the anti-CD137 antibody is possibly reduced.

[6-7. Evaluation of Cancer Cytotoxic Activity of Anti-CLDN4 (3D11)/Anti-CD137 scFv Bispecific Antibody in Coculture System of Cancer Cell and T Cell]

The cancer cytotoxic activity (cancer cell growth inhibitory activity) of the anti-CLDN4 (3D11)/anti-CD137 scFv bispecific antibody was evaluated in a coculture system of the 60As6-Luc/GFP cells and the expanded Pan T cells. The 60As6-Luc/GFP cells were seeded in a flat bottom 96 well plate at $1 \times 10^4$ cells/50 μL/well each to be cultured at 37° C. in a 5% $CO_2$ incubator. After 2 hours, the expanded Pan T cells were seeded in the resultant 96 well plate at $1 \times 10^5$ cells/50 μL/well each. As a test antibody, Urelumab and the anti-CLDN4 (3D11)/anti-CD137 scFv bispecific antibody were used. These antibodies were serially diluted with the culture medium from a maximum concentration of 40000 ng/ml with a common ratio of 10 and added in an amount of 50 μL each. Besides, a 40 ng/ml anti-CD3 antibody was added thereto in an amount of 50 μL each, and measurement of fluorescence (GFP) area in each well was initiated with IncuCyte® ZOOM (Sartorius) at 37° C. in a 5% $CO_2$ incubator. The fluorescence area increased from 0 hours after the start of the measurement was used as an index of cell growth. FIG. 4 illustrates cancer cytotoxic activity (cancer cell growth rate) of a test antibody. The ordinate of FIG. 4 indicates a relative value obtained assuming that, in fluorescence area increased from 0 hours to 168 hours, a well where the test antibody was not added corresponds to 100%. As illustrated in FIG. 4, the anti-CLDN4 (3D11)/anti-CD137 scFv bispecific antibody exhibited the cytotoxic activity in a coculture system of the 60As6-Luc/GFP cells and the expanded Pan T cells. The cytotoxic activity of this bispecific antibody was remarkably stronger than that of Urelumab.

[6-8. Evaluation of Cancer Cell Cytotoxic Activity of Anti-CLDN4 (hKM3900)/Anti-CD137 scFv Bispecific Antibody in Coculture System of Cancer Cell and T Cell]

Figures 1, 2:
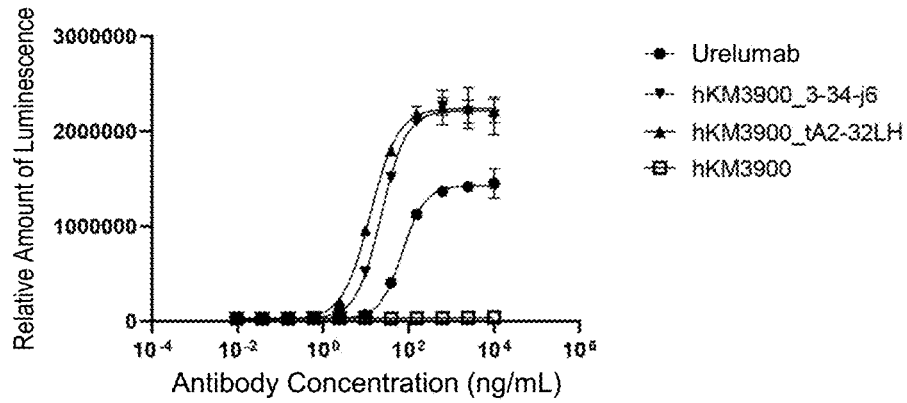
Figure 2:
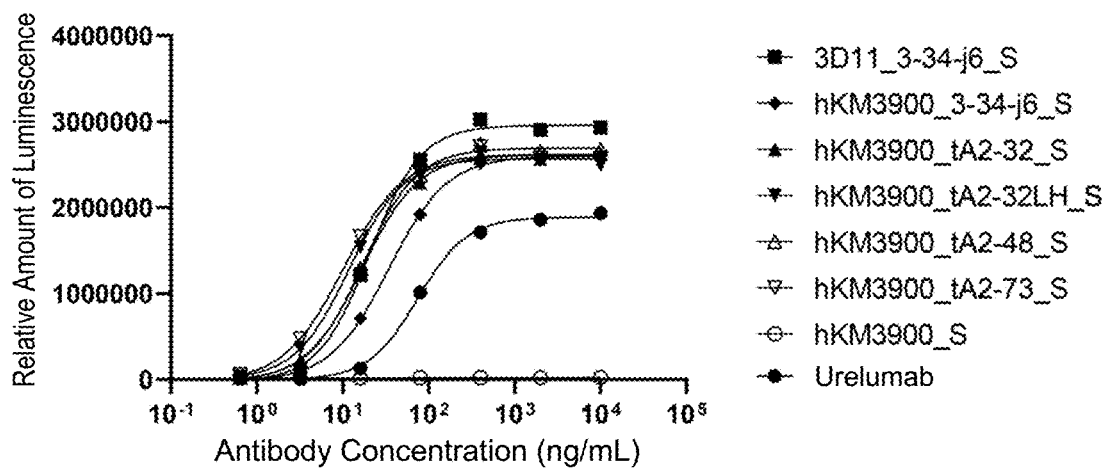
Figures 2, 3:
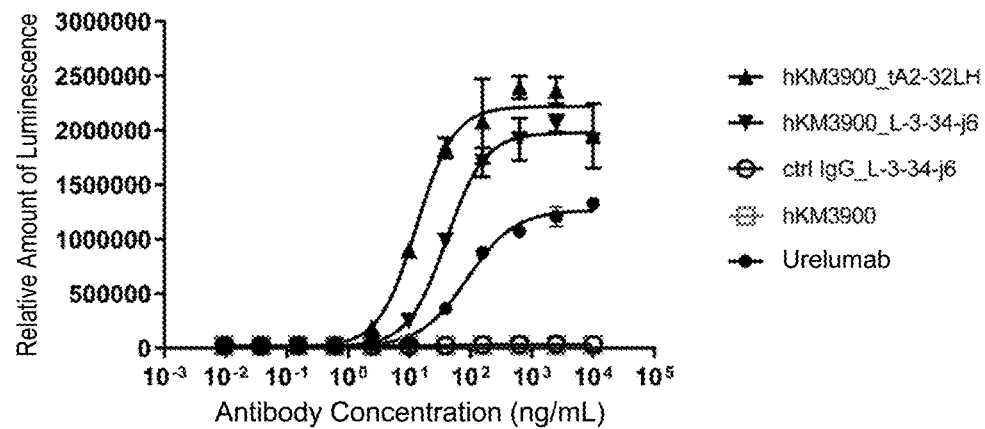
Figures 2, 3, 4:
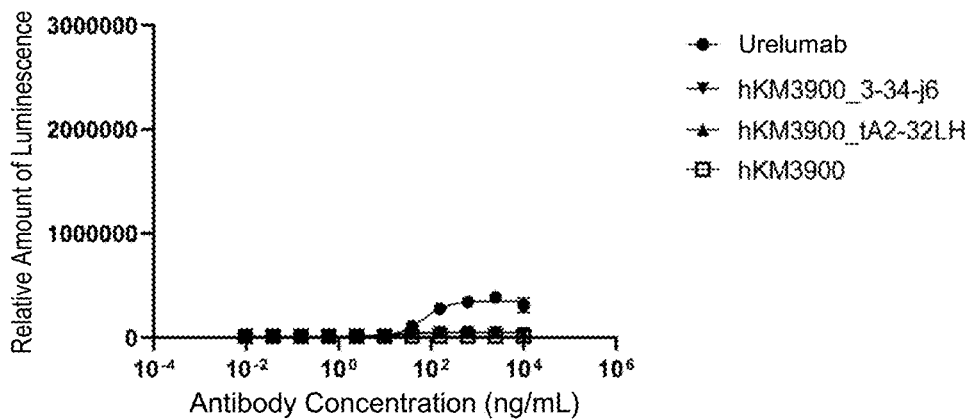
Figures 2, 3, 4, 5:
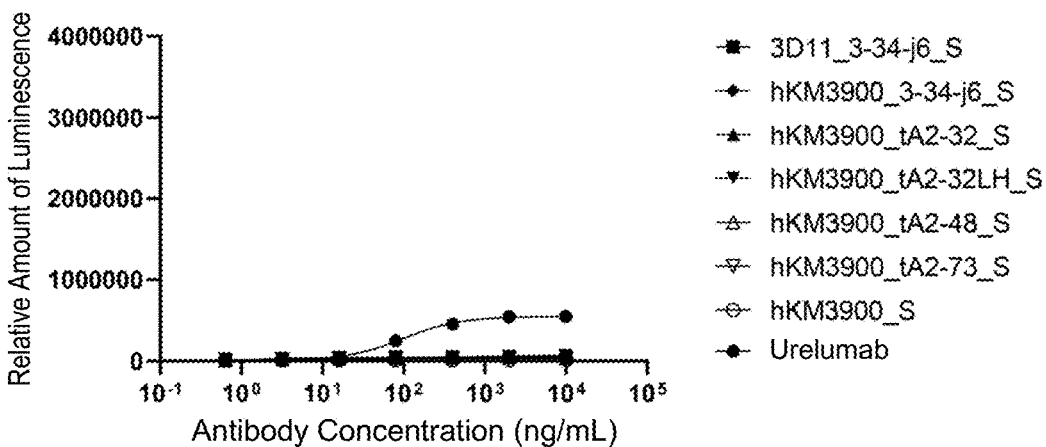

The cancer cell killing activity of the anti-CLDN4 (hKM3900)/anti-CD137 scFv bispecific antibody was evaluated in a coculture system of 60As6-Luc/GFP cells and the expanded Pan T cells. An anti-CD3 antibody was added to a flat bottom 96 well plate (Perkin Elmer, 6005680) at 1 ng/100 μL/well each to be fixed on the plate. The plate was washed with PBS (−) twice, the 60As6-Luc/GFP cells were seeded therein at $2 \times 10^4$ cells/50 μL/well, and the resultant was cultured at 37° C. in a 5% $CO_2$ incubator. On the next day, the expanded Pan T cells were seeded in the 96 well plate at $4.0 \times 10^4$ cells/30 μL/well. Besides, a test antibody and an isotype control at a concentration from 5000 ng/mL to 0.844 ng/mL were added in an amount of 20 L each. As the test antibody, Urelumab and the anti-CLDN4 (hKM3900)/anti-CD137 scFv bispecific antibody (hKM3900_3-34-j6 or hKM3900_tA2-32LH) were used. After 6 days, the measurement was performed. To some of the wells, 1% Triton-X100 (Sigma-Aldrich, T-9284) was added in an amount of 11 μL each for killing cells 30 minutes before the measurement. ONE-Glo Luciferase Measurement Kit (Promega Corporation, E6120) was used in accordance with a protocol recommended by the manufacturer to measure the luciferase activity of the 60As6-Luc/GFP cells in each well with ARVO X-3 (Perkin Elmer). A cancer death rate is indicated as a relative value assuming that an average of luciferase chemiluminescence in a well where the antibody was not added corresponds to 0% and that an average obtained in a well where Triton-X100 was added corresponds to 100%. As the isotype control, an anti-lysozyme antibody (prepared in house) was used. FIG. 5 illustrates a cell death rate curve of 60As6-Luc/GFP cells. In the coculture system of the 60As6-Luc/GFP cells and the expanded Pan T cells, the addition of the anti-CLDN4 (hKM3900)/ anti-CD137 scFv bispecific antibody remarkably increased the 60As6-Luc/GFP cell death rate. On the other hand, Urelumab, the anti-CD137 specific antibody, did not increase the cell death rate of the 60As6-Luc/GFP cell line.

Example 7: In Vivo Evaluation of Anti-CLDN4/Anti-CD137 scFv Bispecific Antibody

[7-1. In Vivo Antitumor Effect of Anti-CLDN4/Anti-CD137 scFv Bispecific Antibody]

A NCI-H322 cell was suspended in PBS (−) (WAKO, 045-29795), and a $5.0\times10^6$ cells/100 μL cell suspension was subcutaneously inoculated into 7-week-old female mice (NOG, In-Vivo Science Inc.). After 6 days of the inoculation, $3.4\times10^6$ cells/200 μL human peripheral blood mononuclear cells (Lonza, CC-2702) were injected through the tail vein. 15 days after the human peripheral blood mononuclear cell transplantation, the mice were divided into groups to start administration of the test antibody. Each group consisted of 10 mice, and the mice were distributed so that tumor volume between each group was almost equivalent to each other (day 0). As the test antibody, hKM3900_tA2-32LH was used. The test antibody and an isotype control (anti-lysozyme antibody) were mixed in PBS and intravenously administered. The administration was performed on days 0, 4, and 8, and tumor diameter and body weight were measured at the time of administration. For calculation of tumor volume, the following formula was used.

[Tumor volume (mm$^3$)]=[Major tumor diameter (mm)]×[Minor tumor diameter (mm)]$^2$×0.5

Figures 2, 3, 4, 5, 6:
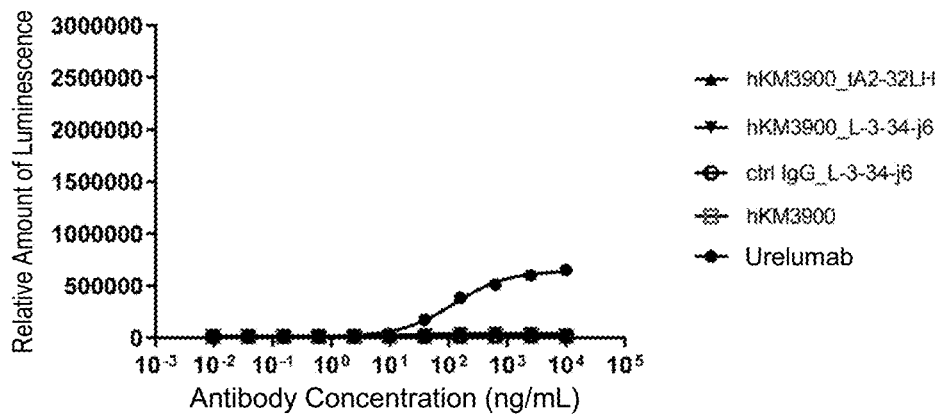
Figures 1, 3:
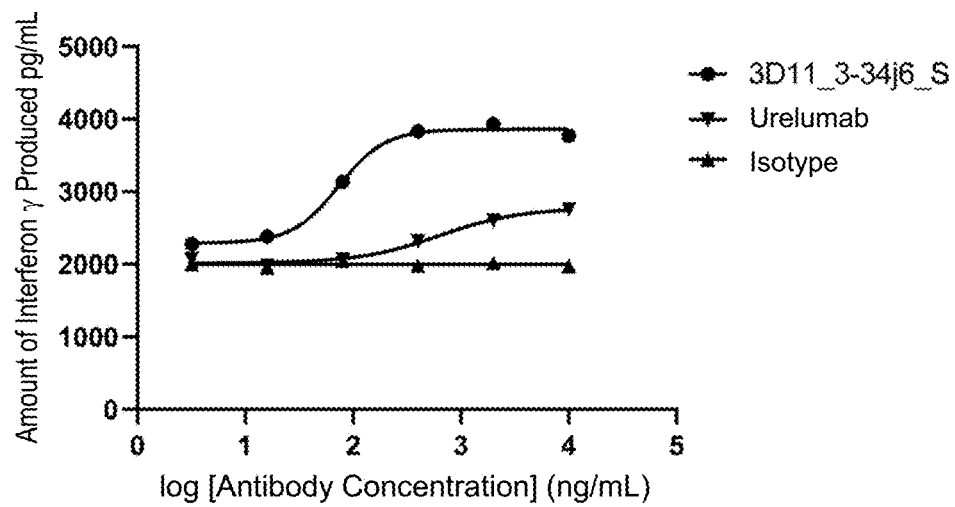
Figures 2, 3:
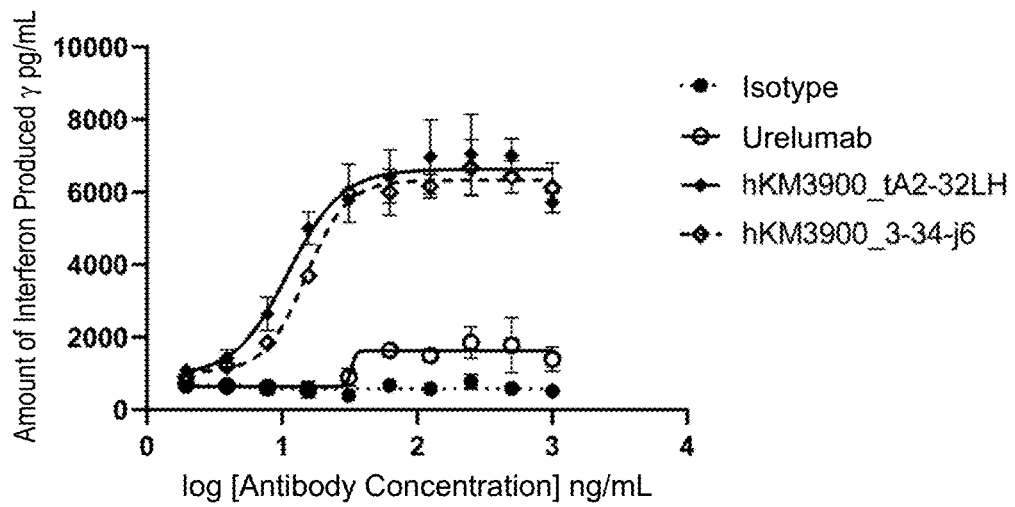
Figure 3:
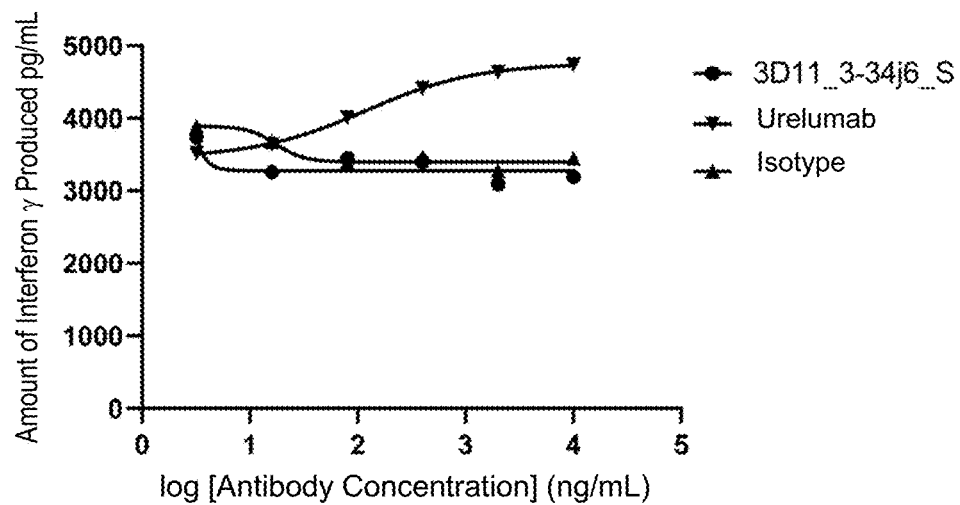
Figures 3, 4:
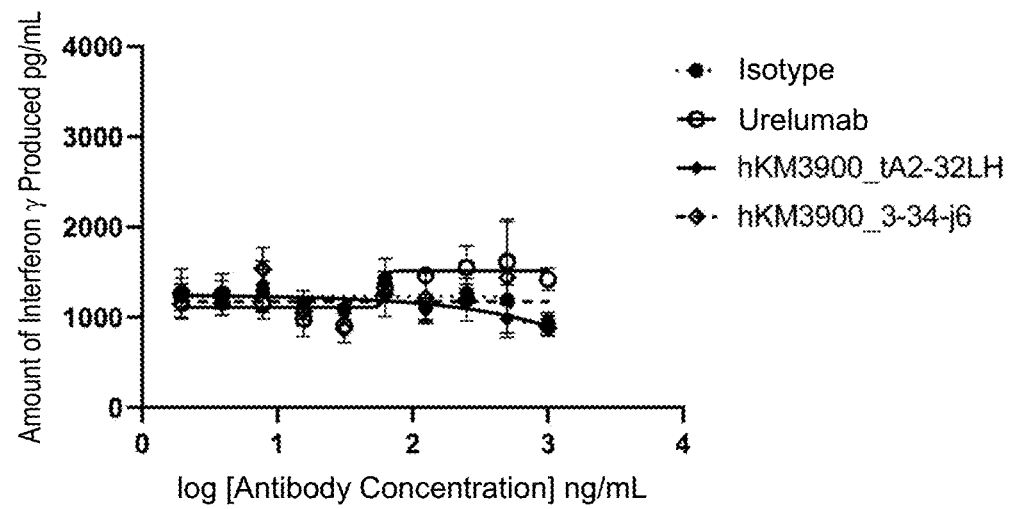
Figure 4:
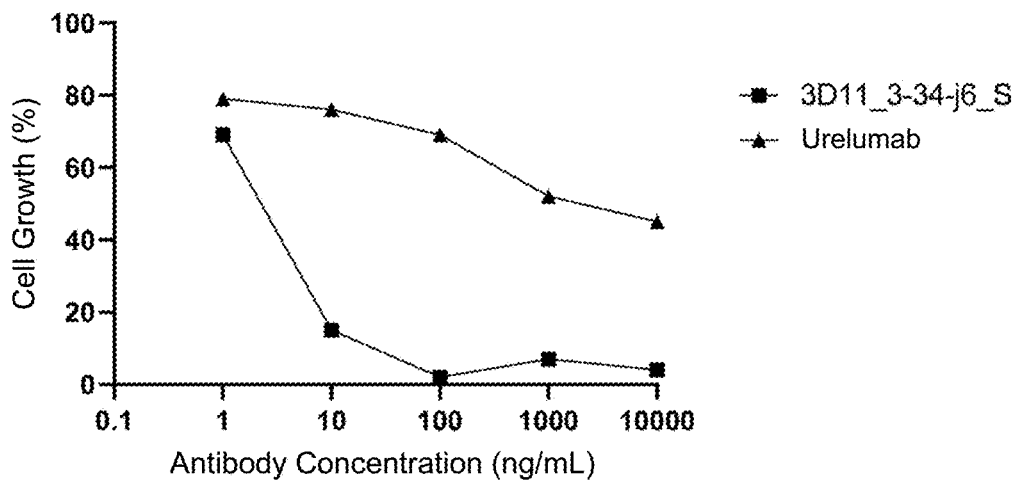
Figure 5:
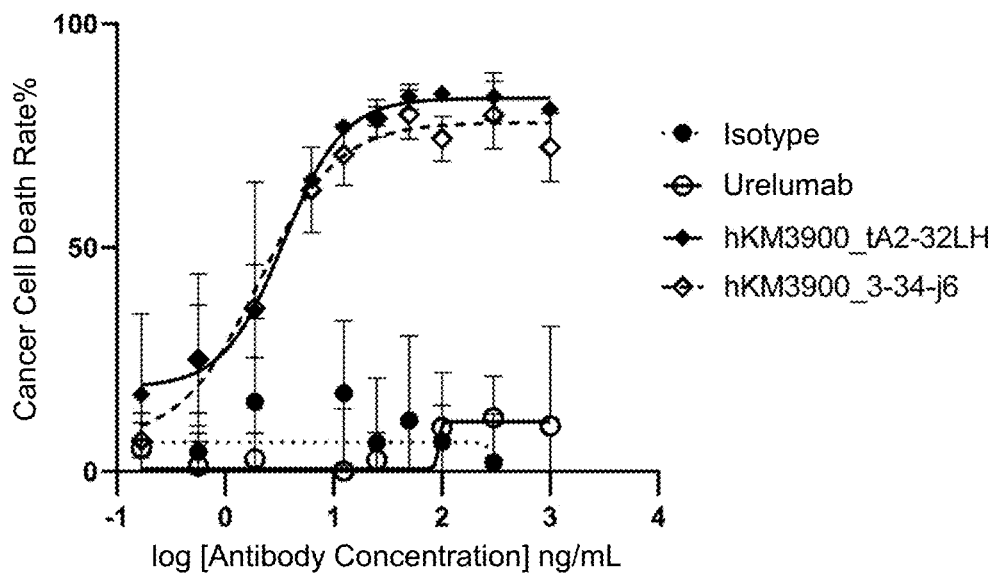
Figure 6:
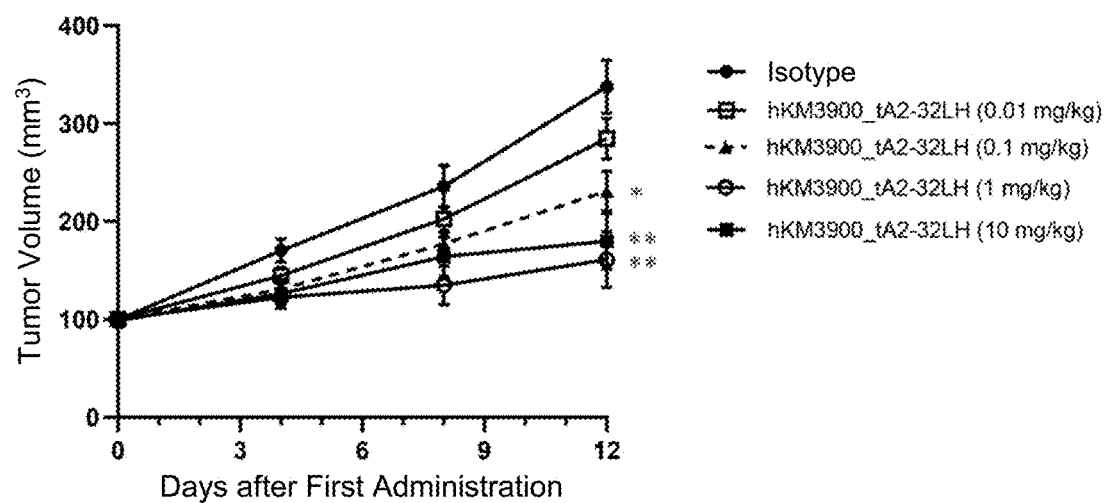

As illustrated in FIG. 6, a significant effect of reducing tumor volume was exhibited in the groups administered with 0.1, 1, or 10 mg/kg of hKM3900_tA2-32LH. The ordinate indicates the tumor volume, and the abscissa indicates days after the first administration. The solid and dashed lines indicate a shift in an average of the tumor volume for each group, and an error bar indicates the standard error of the average. Significance probability P-values (*: P<0.05 and **: P<0.01) were calculated by comparing the tumor volume on day 12 in the isotype control administration group and the hKM3900_tA2-32LH administration group through Dunnett's multiple comparison test. The number of cases in the 0.1 mg/kg hKM3900_tA2-32LH administration group on day 12 was 9.

[7-2. Safety Test of Anti-CLDN4 (hKM3900)/Anti-CD137 scFv Bispecific Antibody in Cynomolgus Monkey]

In order to examine safety of the anti-CLDN4 (hKM3900)/anti-CD137 scFv bispecific antibodies (hKM3900_3-34-j6 and hKM3900_tA2-32LH), each of the anti-CLDN4 (hKM3900)/anti-CD137 scFv bispecific antibodies was administered in a single dose intravenously to cynomolgus monkeys. As a result, no specific abnormalities were observed in levels of cytokines such as IL-6 and TNF-α in the serum of the monkeys administered with the anti-CLDN4 (hKM3900)/anti-CD137 scFv bispecific antibodies. Hence, it was concluded that the anti-CLDN4 (hKM3900)/anti-CD137 scFv bispecific antibodies are qualified as antibodies for treatment of cancer from the viewpoint of safety.

Examples 8: Treatment of Cancer by Anti-CLDN4/Anti-CD137 Bispecific Antibody

[8-1. Check of Expression Level of CLDN4]

In order to investigate how widely applicable CLDN4 is as a therapeutic target for cancer, the expression level of CLDN4 RNA in cancer tissues was investigated in The Cancer Genome Atlas (TCGA). As a result, it was confirmed that the expression of CLDN4 was elevated in cancer tissues of colorectal cancer, bladder cancer, lung cancer, and the like. Accordingly, it was suggested that CLDN4 is a possible therapeutic target not only for peritoneal metastatic cancer but also for other types of cancer. Besides, the expression level of CLDN4 RNA in normal tissues was investigated with the Genotype-Tissue Expression (GTEx). As a result, CLDN4 was found to be expressed in several normal tissues. However, the expression level of CLDN4 was lower in the normal tissues than in the cancer tissues. Therefore, it was suggested that a cancer drug therapeutically targeting CLDN4 is a possible therapeutic agent with a wide margin of safety ensured and a low concern for an adverse reaction.

INDUSTRIAL APPLICABILITY

An anti-CLDN4/anti-CD137 bispecific antibody of the present invention is expected to be useful for treatment of cancer. Besides, a polynucleotide, an expression vector, a transformed host cell, and a method for producing an antibody of the present invention are useful for producing the anti-CLDN4/anti-CD137 bispecific antibody.

SEQUENCE LISTING FREE TEXT

In number heading <223> of the following sequence listing, "Artificial Sequence" is described. Specifically, SEQ ID NO: 1 of the sequence listing shows a nucleotide sequence of a heavy chain variable region of 3D11, and SEQ ID NO: 2 shows an amino acid sequence of the heavy chain variable region of 3D11. SEQ ID NO: 3 shows a nucleotide sequence of a light chain variable region of 3D11, and SEQ ID NO: 4 shows an amino acid sequence of the light chain variable region of 3D11. SEQ ID NO: 5 shows a nucleotide sequence of a heavy chain variable region of hKM3900, and SEQ ID NO: 6 shows an amino acid sequence of the heavy chain variable region of hKM3900. SEQ ID NO: 7 shows a nucleotide sequence of a light chain variable region of hKM3900, and SEQ ID NO: 8 shows an amino acid sequence of the light chain variable region of hKM3900. SEQ ID NO: 9 shows a nucleotide sequence of a heavy chain variable region of 3-34, and SEQ ID NO: 10 shows an amino acid sequence of the heavy chain variable region of 3-34. SEQ ID NO: 11 shows a nucleotide sequence of a light chain variable region of 3-34, and SEQ ID NO: 12 shows an amino acid sequence of the light chain variable region of 3-34. SEQ ID NO: 13 shows a nucleotide sequence of a heavy chain variable region of A2-32, and SEQ ID NO: 14 shows an amino acid sequence of the heavy chain variable region of A2-32. SEQ ID NO: 15 shows a nucleotide sequence of a light chain variable region of A2-32, and SEQ ID NO: 16 shows an amino acid sequence of the light chain variable region of A2-32. SEQ ID NO: 17 shows a nucleotide sequence of a heavy chain variable region of A2-48, and SEQ ID NO: 18 shows an amino acid sequence of the heavy chain variable region of A2-48. SEQ ID NO: 19 shows a nucleotide sequence of a light chain variable region of A2-48, and SEQ ID NO: 20 shows an amino acid sequence of the light chain variable region of A2-48. SEQ ID NO: 21 shows a nucleotide sequence of a heavy chain variable region of A2-73, and SEQ ID NO: 22 shows an amino acid sequence of the heavy chain variable region of A2-73. SEQ ID NO: 23 shows a nucleotide sequence of a light chain variable region of A2-73, and SEQ ID NO: 24 shows an amino acid sequence of the light chain variable region of A2-73. SEQ ID NO: 25 shows a nucleotide sequence of a 3-34-j6 scFv, and SEQ ID NO: 26 shows an amino acid sequence of the 3-34-j6 scFv. SEQ ID NO: 27 shows a nucleotide sequence of a tA2-32 scFv, and SEQ ID NO: 28 shows an amino acid sequence of the tA2-32 scFv. SEQ ID NO: 29 shows a nucleotide sequence of a tA2-32LH scFv, and SEQ ID NO: 30 shows an amino acid sequence of the tA2-32LH scFv. SEQ ID NO: 31 shows a nucleotide sequence of a tA2-48 scFv, and SEQ ID NO: 32 shows an amino acid sequence of the tA2-48 scFv. SEQ ID NO: 33 shows a nucleotide sequence of a tA2-73 scFv, and SEQ ID NO: 34 shows an amino acid sequence of the tA2-73 scFv. SEQ ID NO: 35 shows a nucleotide sequence of a heavy chain of hKM3900_3-34-j6, and SEQ ID NO: 36 shows an amino acid sequence of the heavy chain of hKM3900_3-34-j6. SEQ ID NO: 37 shows a nucleotide sequence of a heavy chain of hKM3900_tA2-32LH, and SEQ ID NO: 38 shows an amino acid sequence of the heavy chain of hKM3900_tA2-32LH. SEQ ID NO: 39 shows a nucleotide sequence of a light chain of hKM3900, and SEQ ID NO: 40 shows an amino acid sequence of the light chain of hKM3900. SEQ ID NO: 41 shows an amino acid sequence of an anti-CD3 scFv-human Fc fusion protein. SEQ ID NO: 42 shows an amino acid sequence of human CD137. SEQ ID NO: 43 shows an amino acid sequence of monkey CD137. SEQ ID NO: 44 shows an amino acid sequence of a His tag protein. SEQ ID NO: 45 shows an amino acid sequence of a 3×FLAG tag. SEQ ID NOS: 46 to 54 show amino acid sequences of GS linkers. SEQ ID NO: 55 shows an amino acid sequence of a GKPGS linker.

The invention claimed is:

1. An anti-CLDN4/anti-CD137 bispecific antibody comprising a heavy chain variable region and a light chain variable region of an anti-CLDN4 antibody, and a heavy chain variable region and a light chain variable region of an anti-CD137 antibody, wherein the heavy chain variable region and the light chain variable region of the anti-CLDN4 antibody comprises:
- (a) a heavy chain variable region containing a CDR1 consisting of an amino acid sequence at amino acid positions 31-35 of SEQ ID NO: 6, a CDR2 consisting of an amino acid sequence at amino acid positions 50-66 of SEQ ID NO: 6, and a CDR3 consisting of an amino acid sequence at amino acid positions 99-112 of SEQ ID NO: 6, and
- (b) a light chain variable region containing a CDR1 consisting of an amino acid sequence at amino acid positions 24-35 of SEQ ID NO: 8, a CDR2 consisting of an amino acid sequence at amino acid positions 51-57 of SEQ ID NO: 8, and a CDR3 consisting of an amino acid sequence at amino acid positions 90-98 of SEQ ID NO: 8, wherein the heavy chain variable region and the light chain variable region of the anti-CD137 antibody comprises:
- (c) a heavy chain variable region containing a CDR1 consisting of an amino acid sequence at amino acid positions 31-35 of SEQ ID NO: 14, a CDR2 consisting of an amino acid sequence at amino acid positions 50-65 of SEQ ID NO: 14, and a CDR3 consisting of an amino acid sequence at amino acid positions 98-107 of SEQ ID NO: 14, and
- (d) a light chain variable region containing a CDR1 consisting of an amino acid sequence at amino acid positions 23-35 of SEQ ID NO: 16, a CDR2 consisting of an amino acid sequence at amino acid positions 51-57 of SEQ ID NO: 16, and a CDR3 consisting of an amino acid sequence at amino acid positions 90-100 of SEQ ID NO: 16, wherein the bispecific antibody comprises:
- (e) an IgG antibody consisting of a heavy chain containing the heavy chain variable region and a light chain containing the light chain variable region of the anti-CLDN4 antibody (anti-CLDN4 IgG antibody), and
- (f) an anti-CD137 single chain variable fragment (anti-CD137 scFv) containing the heavy chain variable region and the light chain variable region of the anti-CD137 antibody.

2. The bispecific antibody according to claim 1, wherein the heavy chain variable region and the light chain variable region of the anti-CLDN4 antibody comprises:
a heavy chain variable region consisting of an amino acid sequence at amino acid positions 1-123 of SEQ ID NO: 6 and a light chain variable region consisting of an amino acid sequence at amino acid positions 1-109 of SEQ ID NO: 8.

3. The bispecific antibody according to claim 2, wherein the heavy chain variable region and the light chain variable region of the anti-CD137 antibody are selected from:
- (a) a heavy chain variable region consisting of an amino acid sequence at amino acid positions 1-118 of SEQ ID NO: 14 and a light chain variable region consisting of an amino acid sequence at amino acid positions 1-111 of SEQ ID NO: 16; or
- (b) a light chain variable region consisting of an amino acid sequence at amino acid positions 1-111 of SEQ ID NO: 30 and a heavy chain variable region consisting of an amino acid sequence at amino acid positions 132-249 of SEQ ID NO: 30.

4. The bispecific antibody according to claim 1, comprising a LALA mutation of L234A and L235A in a Fc region of the anti-CLDN4 IgG antibody, wherein a position of the mutation is an amino acid position in human Igγ1 constant region according to EU index.

5. The bispecific antibody according to claim 1, comprising a P331G mutation in a Fc region of the anti-CLDN4 IgG antibody, wherein a position of the mutation is an amino acid position in human Igγ1 constant region according to EU index.

6. The bispecific antibody according to claim 1, comprising a LALA mutation and a P331G mutation in a Fc region of the anti-CLDN4 IgG antibody.

7. The bispecific antibody according to claim 1, wherein the anti-CD137 scFv
consisting of an amino acid positions 1-149 of SEQ ID NO: 30.

8. The bispecific antibody according to claim 1, wherein an amino terminal of the anti-CD137 scFv is linked to a heavy chain or light chain carboxy terminal of the anti-CLDN4 IgG antibody via a linker.

9. A pharmaceutical composition comprising the anti-CLDN4/anti-CD137 bispecific antibody according to claim 1, and a pharmaceutically acceptable excipient.

10. An anti-CLDN4/anti-CD137 bispecific antibody comprising: a heavy chain of an anti-CLDN4 antibody containing a heavy chain variable region consisting of an amino acid sequence at amino acid positions 1-123 of SEQ ID NO: 6 and a light chain of an anti-CLDN4 antibody containing a light chain variable region consisting of an amino acid sequence at amino acid positions 1-109 of SEQ ID NO: 8, and an anti-CD137 scFv containing a light chain variable region consisting of an amino acid sequence at amino acid positions 1-111 of SEQ ID NO: 30 and a heavy chain variable region consisting of an amino acid sequence at amino acid positions 132-249 of SEQ ID NO: 30, wherein an amino terminal of the anti-CD137 scFv is linked to a heavy chain carboxy terminal of the anti-CLDN4 antibody via a linker.

11. The anti-CLDN4/anti-CD137 bispecific antibody according to claim 10, wherein the linker is a GS linker.

12. The anti-CLDN4/anti-CD137 bispecific antibody according to claim 11, wherein the GS linker is a linker consisting of an amino acid sequence of SEQ ID NO: 54.

13. An anti-CLDN4/anti-CD137 bispecific antibody comprising a polypeptide consisting of an amino acid sequence at amino acid positions 1-712 of SEQ ID NO: 38 containing a heavy chain of an anti-CLDN4 antibody and an anti-CD137 scFv, and a light chain of an anti-CLDN4 antibody consisting of an amino acid sequence at amino acid positions 1-215 of SEQ ID NO: 40.

14. The anti-CLDN4/anti-CD137 bispecific antibody according to claim 13, which is post-translationally modified.

15. The anti-CLDN4/anti-CD137 bispecific antibody according to claim 14, wherein the post-translational modification is pyroglutamylation at an N-terminal of a heavy chain variable region and/or lysine deletion at a heavy chain C-terminal.

16. A polynucleotide for use in production of the anti-CLDN4/anti-CD137 bispecific antibody according to claim 13, which is selected from the group consisting of:
(a) a polynucleotide having a nucleotide sequence encoding a polypeptide consisting of an amino acid sequence at amino acid positions 1-712 of SEQ ID NO: 38 containing a heavy chain of an anti-CLDN4 antibody and an anti-CD137 scFv;
(b) a polynucleotide having a nucleotide sequence encoding a light chain of an anti-CLDN4 antibody consisting of an amino acid sequence at amino acid positions 1-215 of SEQ ID NO: 40; or
(c) a polynucleotide having a nucleotide sequence encoding a polypeptide consisting of an amino acid sequence at amino acid positions 1-712 of SEQ ID NO: 38 containing a heavy chain of an anti-CLDN4 antibody and an anti-CD137 scFv, and a polynucleotide having a nucleotide sequence encoding a light chain of an anti-CLDN4 antibody consisting of an amino acid sequence at amino acid positions 1-215 of SEQ ID NO: 40.

17. A polynucleotide having a nucleotide sequence encoding a heavy chain variable region or light chain variable region of an anti-CLDN4 antibody, wherein the
heavy chain variable region of an anti-CLDN4 antibody consisting of an amino acid sequence at amino acid positions 1-123 of SEQ ID NO: 6 and the
light chain variable region of an anti-CLDN4 antibody consisting of an amino acid sequence at amino acid positions 1-109 of SEQ ID NO: 8.

18. An expression vector, comprising the polynucleotide according to claim 17.

19. A host cell transformed with the expression vector according to claim 18.

20. A polynucleotide having a nucleotide sequence encoding a heavy chain variable region or light chain variable region of an anti-CD137 antibody, selected from the group consisting of:
(a) a polynucleotide having a nucleotide sequence encoding a heavy chain variable region of an anti-CD137 antibody consisting of an amino acid sequence at amino acid positions 1-118 of SEQ ID NO: 14;
(b) a polynucleotide having a nucleotide sequence encoding a light chain variable region of an anti-CD137 antibody consisting of an amino acid sequence at amino acid positions 1-111 of SEQ ID NO: 16;
(c) a polynucleotide having a nucleotide sequence encoding a light chain variable region of an anti-CD137 antibody consisting of an amino acid sequence at amino acid positions 1-111 of SEQ ID NO: 30;
(d) a polynucleotide having a nucleotide sequence encoding a heavy chain variable region of an anti-CD137 antibody consisting of an amino acid sequence at amino acid positions 132-249 of SEQ ID NO: 30.

21. A polynucleotide having a nucleotide sequence encoding an anti-CD137 scFv, comprising
a nucleotide sequence encoding an anti-CD137 scFv consisting of an amino acid sequence at amino acid positions 1-249 of SEQ ID NO: 30.

22. A host cell comprising a polynucleotide selected from the group consisting of:
(a) a polynucleotide having a nucleotide sequence encoding a heavy chain variable region of an anti-CLDN4 antibody consisting of an amino acid sequence at amino acid positions 1-123 of SEQ ID NO: 6;
(b) a polynucleotide having a nucleotide sequence encoding a light chain variable region of an anti-CLDN4 antibody consisting of an amino acid sequence at amino acid positions 1-109 of SEQ ID NO: 8;
(c) a polynucleotide having a nucleotide sequence encoding a heavy chain variable region of an anti-CD137 antibody consisting of an amino acid sequence at amino acid positions 1-118 of SEQ ID NO: 14;
(d) a polynucleotide having a nucleotide sequence encoding a light chain variable region of an anti-CD137 antibody consisting of an amino acid sequence at amino acid positions 1-111 of SEQ ID NO: 16;
(e) a polynucleotide having a nucleotide sequence encoding a light chain variable region of an anti-CD137 antibody consisting of an amino acid sequence at amino acid positions 1-111 of SEQ ID NO: 30;
(f) a polynucleotide having a nucleotide sequence encoding a heavy chain variable region of an anti-CD137 antibody consisting of an amino acid sequence at amino acid positions 132-249 of SEQ ID NO: 30;
(g) a polynucleotide having a nucleotide sequence encoding an anti-CD137 scFv consisting of an amino acid sequence at amino acid positions 1-249 of SEQ ID NO: 30;
(h) a polynucleotide having a nucleotide sequence encoding a polypeptide consisting of an amino acid sequence at amino acid positions 1-712 of SEQ ID NO: 38 containing a heavy chain of an anti-CLDN4 antibody and an anti-CD137 scFv; and
(i) a polynucleotide having a nucleotide sequence encoding a light chain of an anti-CLDN4 antibody consisting of an amino acid sequence at amino acid positions 1-215 of SEQ ID NO: 40.

23. A host cell comprising:
a polynucleotide having a nucleotide sequence encoding a polypeptide consisting of an amino acid sequence at amino acid positions 1-712 of SEQ ID NO: 38 containing a heavy chain of an anti-CLDN4 antibody and an anti-CD137 scFv, and a polynucleotide having a nucleotide sequence encoding a light chain of an anti-CLDN4 antibody consisting of an amino acid sequence at amino acid positions 1-215 of SEQ ID NO: 40.

24. A method for producing an anti-CLDN4/anti-CD137 bispecific antibody, comprising a step of culturing the host cell according to claim 23, wherein the anti-CLDN4/anti-CD137 bispecific antibody is encoded by the polynucleotide and the anti-CLDN4/anti-CD137 bispecific antibody is expressed in the host cell after culturing.

25. A method for treating cancer, comprising a step of administering a therapeutically effective amount of the anti-CLDN4/anti-CD137 bispecific antibody according to claim 1 to a subject, wherein the cancer is CLDN4 expressing cancer.

* * * * *

```
SEQUENCE LISTING

<160> NUMBER OF SEQ ID NOS: 60

<210> SEQ ID NO 1
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 3D11 VH
<220> FEATURE:
<221> NAME/KEY: CDS
<222> LOCATION: (1)..(375)

<400> SEQUENCE: 1 cag gtt cag ttg gga cag tct ggc ccc gaa gtg aag aaa cct ggc gcc       48
Gln Val Gln Leu Gly Gln Ser Gly Pro Glu Val Lys Lys Pro Gly Ala
1               5                   10                  15 tct gtg aag gtg tcc tgc aag gct tcc ggc tac tcc ttt atc tcc tac       96
Ser Val Lys Val Ser Cys Lys Ala Ser Gly Tyr Ser Phe Ile Ser Tyr
            20                  25                  30 ggc atc tcc tgg gtc cga cag gct cct gga caa ggc ttg gaa tgg atg      144
Gly Ile Ser Trp Val Arg Gln Ala Pro Gly Gln Gly Leu Glu Trp Met
        35                  40                  45 ggc tgg tcc tcc gtg tac aac ggc aac acc aac tac gtg cag aaa ttc      192
Gly Trp Ser Ser Val Tyr Asn Gly Asn Thr Asn Tyr Val Gln Lys Phe
    50                  55                  60 cag ggc aga gtg acc atg acc acc gac acc tct gcc tcc acc gcc tac      240
Gln Gly Arg Val Thr Met Thr Thr Asp Thr Ser Ala Ser Thr Ala Tyr
65                  70                  75                  80 atg gaa ctg cgg tcc ctg aga tct gat gac gcc gcc gtg tac tac tgc      288
Met Glu Leu Arg Ser Leu Arg Ser Asp Asp Ala Ala Val Tyr Tyr Cys
                85                  90                  95 gcc aga gac tct tac tcc tcc ggc tgg tct tac tac tcc ggc atg          336
Ala Arg Asp Ser Tyr Ser Ser Gly Trp Ser Tyr Tyr Ser Gly Met
            100                 105                 110 gat gtg tgg ggc cag ggc aca aca gtg acc gtg tcc tcc                   375
Asp Val Trp Gly Gln Gly Thr Thr Val Thr Val Ser Ser
        115                 120                 125

<210> SEQ ID NO 2
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<223> OTHER INFORMATION: Synthetic Construct

<400> SEQUENCE: 2

Gln Val Gln Leu Gly Gln Ser Gly Pro Glu Val Lys Lys Pro Gly Ala
1               5                   10                  15

Ser Val Lys Val Ser Cys Lys Ala Ser Gly Tyr Ser Phe Ile Ser Tyr
                20                  25                  30

Gly Ile Ser Trp Val Arg Gln Ala Pro Gly Gln Gly Leu Glu Trp Met
            35                  40                  45

Gly Trp Ser Ser Val Tyr Asn Gly Asn Thr Asn Tyr Val Gln Lys Phe
50                  55                  60

Gln Gly Arg Val Thr Met Thr Thr Asp Thr Ser Ala Ser Thr Ala Tyr
65                  70                  75                  80

Met Glu Leu Arg Ser Leu Arg Ser Asp Asp Ala Val Tyr Tyr Cys
                85                  90                  95

Ala Arg Asp Ser Tyr Ser Ser Gly Trp Ser Tyr Tyr Tyr Ser Gly Met
                100                 105                 110

Asp Val Trp Gly Gln Gly Thr Thr Val Thr Val Ser Ser
            115                 120                 125

<210> SEQ ID NO 3
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 3D11 VL
<220> FEATURE:
<221> NAME/KEY: CDS
<222> LOCATION: (1)..(327)

<400> SEQUENCE: 3 gag att gtg ctg acc cag tct cct ggc aca ctg tct ttg agc cct ggc      48
Glu Ile Val Leu Thr Gln Ser Pro Gly Thr Leu Ser Leu Ser Pro Gly
1               5                   10                  15 gag aga gct acc ctg tcc tgt aga gcc tct cag tcc gtg tcc tcc tct     96
Glu Arg Ala Thr Leu Ser Cys Arg Ala Ser Gln Ser Val Ser Ser Ser
                20                  25                  30 tac ctg gcc tgg tat cag cag aag cct gga cag gct ccc cgg ctg ttg    144
Tyr Leu Ala Trp Tyr Gln Gln Lys Pro Gly Gln Ala Pro Arg Leu Leu
            35                  40                  45 atc tac ggc gct tct tct aga gcc aca ggc atc cct gac cgg ttc tcc    192
Ile Tyr Gly Ala Ser Ser Arg Ala Thr Gly Ile Pro Asp Arg Phe Ser
50                  55                  60 gga tct ggc tct ggc acc gat ttc acc ctg acc atc aac cgg ctg gaa    240
Gly Ser Gly Ser Gly Thr Asp Phe Thr Leu Thr Ile Asn Arg Leu Glu
65                  70                  75                  80 ccc gag gat ttc gcc gtg tac tac tgc cag cag tac ggc tcc tct cct    288
Pro Glu Asp Phe Ala Val Tyr Tyr Cys Gln Gln Tyr Gly Ser Ser Pro
                85                  90                  95 tac tct ttt ggc cag ggc acc aag ctg gaa atc aag cgg                327
Tyr Ser Phe Gly Gln Gly Thr Lys Leu Glu Ile Lys Arg
                100                 105

<210> SEQ ID NO 4
<211> LENGTH: 109
<212> TYPE: PRT
<213> ORGANISM: Artificial Sequence
<220> FEATURE:
```

<223> OTHER INFORMATION: Description of Artificial Sequence: Synthetic
polypeptide
<220> FEATURE:
<223> OTHER INFORMATION: Synthetic Construct

<400> SEQUENCE: 4

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Asn Arg Leu Glu
65                  70                  75                  80

Pro Glu Asp Phe Ala Val Tyr Tyr Cys Gln Gln Tyr Gly Ser Ser Pro
                85                  90                  95

Tyr Ser Phe Gly Gln Gly Thr Lys Leu Glu Ile Lys Arg
            100                 105

<210> SEQ ID NO 5
<211> LENGTH: 369
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: hKM3900 VH
<220> FEATURE:
<221> NAME/KEY: CDS
<222> LOCATION: (1)..(369)

<400> SEQUENCE: 5 gaa gtg cag ctg gtt cag tct ggc gcc gaa gtg aag aaa cct ggc gcc      48
Glu Val Gln Leu Val Gln Ser Gly Ala Glu Val Lys Lys Pro Gly Ala
1               5                   10                  15 tcc gtg aag atc tcc tgc aag gct tct ggc tac acc ttc acc gac tac      96
Ser Val Lys Ile Ser Cys Lys Ala Ser Gly Tyr Thr Phe Thr Asp Tyr
            20                  25                  30 tac atg aac tgg gtc cga cag gct cct gga cag gga ctt gag tgg atg     144
Tyr Met Asn Trp Val Arg Gln Ala Pro Gly Gln Gly Leu Glu Trp Met
        35                  40                  45 gga gat gtg gtg ccc aac aac ggc gtg ccc acc tac aac cag aaa ttc     192
Gly Asp Val Val Pro Asn Asn Gly Val Pro Thr Tyr Asn Gln Lys Phe
    50                  55                  60 aag ggc aga gtg acc atc acc gcc gac aag tct acc tcc acc gcc tac     240
Lys Gly Arg Val Thr Ile Thr Ala Asp Lys Ser Thr Ser Thr Ala Tyr
65                  70                  75                  80 atg gaa ctg cgg agc ctg aga tct gag gac acc gcc gtg tac tac tgc     288
Met Glu Leu Arg Ser Leu Arg Ser Glu Asp Thr Ala Val Tyr Tyr Cys
                85                  90                  95 gcc aga cct cac tac tac tac gcc ggc aga tct ggc gcc atg gat tat     336
Ala Arg Pro His Tyr Tyr Tyr Ala Gly Arg Ser Gly Ala Met Asp Tyr
            100                 105                 110 tgg gga cag ggc acc ctg gtc acc gtg tcc tct                         369
Trp Gly Gln Gly Thr Leu Val Thr Val Ser Ser
        115                 120

<210> SEQ ID NO 6
<211> LENGTH: 123

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetic Construct

<400> SEQUENCE: 6

Glu Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Met
        35                  40                  45

Gly Asp Val Val Pro Asn Asn Gly Val Pro Thr Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Ala Arg Pro His Tyr Tyr Ala Gly Arg Ser Gly Ala Met Asp Tyr
            100                 105                 110

Trp Gly Gln Gly Thr Leu Val Thr Val Ser Ser
        115                 120

<210> SEQ ID NO 7
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: hKM3900 VL
<220> FEATURE:
<221> NAME/KEY: CDS
<222> LOCATION: (1)..(327)

<400> SEQUENCE: 7 gac atc cag ctg acc cag tct cca tcc tct ctg tct gcc tct gtg ggc    48
Asp Ile Gln Leu Thr Gln Ser Pro Ser Ser Leu Ser Ala Ser Val Gly
1               5                   10                  15 gac aga gtg aca att acc tgc acc gcc tcc tcc acc gtg tcc tct acc    96
Asp Arg Val Thr Ile Thr Cys Thr Ala Ser Ser Thr Val Ser Ser Thr
            20                  25                  30 tac ctg cac tgg tat cag cag aag ccc ggc aag gct ccc aag ctg ctg   144
Tyr Leu His Trp Tyr Gln Gln Lys Pro Gly Lys Ala Pro Lys Leu Leu
        35                  40                  45 atc tac tcc acc tcc aat ctg gcc tct ggc gtg ccc tct aga ttc tcc   192
Ile Tyr Ser Thr Ser Asn Leu Ala Ser Gly Val Pro Ser Arg Phe Ser
    50                  55                  60 gga tct ggc tct gga acc gac tat acc ctg aca atc tcc agc ctg cag   240
Gly Ser Gly Ser Gly Thr Asp Tyr Thr Leu Thr Ile Ser Ser Leu Gln
65                  70                  75                  80 cct gag gac ttc gcc acc tac tac tgc cac cag tac cac aga tcc cca   288
Pro Glu Asp Phe Ala Thr Tyr Tyr Cys His Gln Tyr His Arg Ser Pro
                85                  90                  95 cct acc ttt ggc cag ggc acc aag ctg gaa atc aag cgt               327
Pro Thr Phe Gly Gln Gly Thr Lys Leu Glu Ile Lys Arg
            100                 105
```

```
<210> SEQ ID NO 8
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetic Construct

<400> SEQUENCE: 8

Asp Ile Gln Leu Thr Gln Ser Pro Ser Ser Leu Ser Ala Ser Val Gly
1               5                   10                  15

Asp Arg Val Thr Ile Thr Cys Thr Ala Ser Ser Thr Val Ser Ser Thr
            20                  25                  30

Tyr Leu His Trp Tyr Gln Gln Lys Pro Gly Lys Ala Pro Lys Leu Leu
        35                  40                  45

Ile Tyr Ser Thr Ser Asn Leu Ala Ser Gly Val Pro Ser Arg Phe Ser
    50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys His Gln Tyr His Arg Ser Pro
                85                  90                  95

Pro Thr Phe Gly Gln Gly Thr Lys Leu Glu Ile Lys Arg
            100                 105

<210> SEQ ID NO 9
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 3-34 VH
<220> FEATURE:
<221> NAME/KEY: CDS
<222> LOCATION: (1)..(354)

<400> SEQUENCE: 9 cag gtc cag ctg cag cag tct gag gct gag ctg gtg agg cct ggg gcc       48
Gln Val Gln Leu Gln Gln Ser Glu Ala Glu Leu Val Arg Pro Gly Ala
1               5                   10                  15 tca gtg aag att tcc tgc aag gct ttt ggc tac acc ttc aca aac cat       96
Ser Val Lys Ile Ser Cys Lys Ala Phe Gly Tyr Thr Phe Thr Asn His
            20                  25                  30 cat ata aac tgg gtg aag cag agg cct gga cag ggc ctg gac tgg att      144
His Ile Asn Trp Val Lys Gln Arg Pro Gly Gln Gly Leu Asp Trp Ile
        35                  40                  45 gga tat att aat cct tat aat gat tat act acc ttc aac cgg aag ttc      192
Gly Tyr Ile Asn Pro Tyr Asn Asp Tyr Thr Thr Phe Asn Arg Lys Phe
    50                  55                  60 aag gac aag gcc aca ttg act gta cac aaa tcc tcc agc aca gcc tat      240
Lys Asp Lys Ala Thr Leu Thr Val His Lys Ser Ser Ser Thr Ala Tyr
65                  70                  75                  80 atg gag ctt agc ggc ctg aca tct gac gac tct gca gtc tat tac tgt      288
Met Glu Leu Ser Gly Leu Thr Ser Asp Asp Ser Ala Val Tyr Tyr Cys
                85                  90                  95 gca aga acc tgg ggt cac tgg tat ttc gat ctc tgg ggc cgt ggc acc      336
Ala Arg Thr Trp Gly His Trp Tyr Phe Asp Leu Trp Gly Arg Gly Thr
            100                 105                 110 gtg gtc act gtc tcc tca                                              354
Val Val Thr Val Ser Ser
```

```
                                       115

<210> SEQ ID NO 10
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetic Construct

<400> SEQUENCE: 10

Gln Val Gln Leu Gln Gln Ser Glu Ala Glu Leu Val Arg Pro Gly Ala
1               5                   10                  15

Ser Val Lys Ile Ser Cys Lys Ala Phe Gly Tyr Thr Phe Thr Asn His
            20                  25                  30

His Ile Asn Trp Val Lys Gln Arg Pro Gly Gln Gly Leu Asp Trp Ile
        35                  40                  45

Gly Tyr Ile Asn Pro Tyr Asn Asp Tyr Thr Thr Phe Asn Arg Lys Phe
    50                  55                  60

Lys Asp Lys Ala Thr Leu Thr Val His Lys Ser Ser Thr Ala Tyr
65                  70                  75                  80

Met Glu Leu Ser Gly Leu Thr Ser Asp Asp Ser Ala Val Tyr Tyr Cys
                85                  90                  95

Ala Arg Thr Trp Gly His Trp Tyr Phe Asp Leu Trp Gly Arg Gly Thr
            100                 105                 110

Val Val Thr Val Ser Ser
        115

<210> SEQ ID NO 11
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 3-34 VL
<220> FEATURE:
<221> NAME/KEY: CDS
<222> LOCATION: (1)..(327)

<400> SEQUENCE: 11 gaa ata gtg atg acg cag tct cca gcc acc ctg tct gtg tct cca ggg      48
Glu Ile Val Met Thr Gln Ser Pro Ala Thr Leu Ser Val Ser Pro Gly
1               5                   10                  15 gaa aga gcc acc ctc tcc tgt agg gcc agt cag agt gtt agc agc aac      96
Glu Arg Ala Thr Leu Ser Cys Arg Ala Ser Gln Ser Val Ser Ser Asn
            20                  25                  30 tta gcc tgg tac cag cag aaa cct ggc cag gct ccc agg ctc ctc atc     144
Leu Ala Trp Tyr Gln Gln Lys Pro Gly Gln Ala Pro Arg Leu Leu Ile
        35                  40                  45 tat gat tca tcc acc agg gcc act ggt atc cca gcc agg ttc agt ggc     192
Tyr Asp Ser Ser Thr Arg Ala Thr Gly Ile Pro Ala Arg Phe Ser Gly
    50                  55                  60 agt ggg tct ggg aca gac ttc act ctc acc atc agc agc ctg cag tct     240
Ser Gly Ser Gly Thr Asp Phe Thr Leu Thr Ile Ser Ser Leu Gln Ser
65                  70                  75                  80 gaa gat ttt gca gtt tat tac tgt cag cag tat aat aac tgg cct ccg     288
Glu Asp Phe Ala Val Tyr Tyr Cys Gln Gln Tyr Asn Asn Trp Pro Pro
                85                  90                  95
```

```
tgg acg ttc ggc caa ggg acc aag gtg gaa atc aaa cgg           327
Trp Thr Phe Gly Gln Gly Thr Lys Val Glu Ile Lys Arg
            100                 105
```

<210> SEQ ID NO 12
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetic Construct

<400> SEQUENCE: 12

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Asp Ser Ser Thr Arg Ala Thr Gly Ile Pro Ala Arg Phe Ser Gly
50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Trp Thr Phe Gly Gln Gly Thr Lys Val Glu Ile Lys Arg
            100                 105
```

<210> SEQ ID NO 13
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: A2-32 VH
<220> FEATURE:
<221> NAME/KEY: CDS
<222> LOCATION: (1)..(354)

<400> SEQUENCE: 13

```
cag gtg cag ctg cag gaa tcg ggc cca gga ctg gtg aag cct tcg gag           48
Gln Val Gln Leu Gln Glu Ser Gly Pro Gly Leu Val Lys Pro Ser Glu
1               5                   10                  15 acc ctg tcc ctc acc tgc act gtc tct ggc ggc tcc atc agt ggt tat           96
Thr Leu Ser Leu Thr Cys Thr Val Ser Gly Gly Ser Ile Ser Gly Tyr
            20                  25                  30 tac tgg agc tgg atc cgg cag ccc cca ggg aag ggc ctg gag tgg att          144
Tyr Trp Ser Trp Ile Arg Gln Pro Pro Gly Lys Gly Leu Glu Trp Ile
        35                  40                  45 gga tat atc tat tac agt gga ttc acc aac tac aac ccc tcc ctc aag          192
Gly Tyr Ile Tyr Tyr Ser Gly Phe Thr Asn Tyr Asn Pro Ser Leu Lys
    50                  55                  60 agt cga gtc acc ata tca gta gac acg tcc aag aac cag ttc tcc ctg          240
Ser Arg Val Thr Ile Ser Val Asp Thr Ser Lys Asn Gln Phe Ser Leu
65                  70                  75                  80 aaa ctg agc tct gtg acc gct gcg gac acg gcc gtg tat tat tgt acg          288
Lys Leu Ser Ser Val Thr Ala Ala Asp Thr Ala Val Tyr Tyr Cys Thr
                85                  90                  95 aga gat cac tcc cac tac tac tac atg gac gtc tgg ggc caa ggg acc          336
```

```
Arg Asp His Ser His Tyr Tyr Tyr Met Asp Val Trp Gly Gln Gly Thr
            100                 105                 110 acg gtc acc gtc tcc tca                                              354
Thr Val Thr Val Ser Ser
        115

<210> SEQ ID NO 14
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetic Construct

<400> SEQUENCE: 14

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Gly Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Phe Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Thr
                85                  90                  95

Arg Asp His Ser His Tyr Tyr Tyr Met Asp Val Trp Gly Gln Gly Thr
            100                 105                 110

Thr Val Thr Val Ser Ser
        115

<210> SEQ ID NO 15
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: A2-32 VL
<220> FEATURE:
<221> NAME/KEY: CDS
<222> LOCATION: (1)..(333)

<400> SEQUENCE: 15 cag tct gtg ctg act cag cca ccc tca gcg tct ggg acc ccc ggg cag    48
Gln Ser Val Leu Thr Gln Pro Pro Ser Ala Ser Gly Thr Pro Gly Gln
1               5                   10                  15 agg gtc acc atc tct tgt tct gga agc agc tcc aac atc gga agt aat    96
Arg Val Thr Ile Ser Cys Ser Gly Ser Ser Ser Asn Ile Gly Ser Asn
            20                  25                  30 act gta aac tgg tac cag cag ttc cca gga acg gcc ccc aaa ctc ctc   144
Thr Val Asn Trp Tyr Gln Gln Phe Pro Gly Thr Ala Pro Lys Leu Leu
        35                  40                  45 atc tat agt aat aat cag cgg ccc tca ggg gtc cct gac cga ttc tct   192
Ile Tyr Ser Asn Asn Gln Arg Pro Ser Gly Val Pro Asp Arg Phe Ser
    50                  55                  60 ggc tcc aag tct ggc acc tca gcc tcc ctg gcc atc agt ggg ctc cag   240
Gly Ser Lys Ser Gly Thr Ser Ala Ser Leu Ala Ile Ser Gly Leu Gln
65                  70                  75                  80
```

```
tct gag gat gag gct gat tat tac tgt gca gga tgg gat gac agc ctg      288
Ser Glu Asp Glu Ala Asp Tyr Tyr Cys Ala Gly Trp Asp Asp Ser Leu
            85                  90                  95 aat ggt ccg gta ttc ggc gga ggg acc aag ctg acc gtc cta ggt          333
Asn Gly Pro Val Phe Gly Gly Gly Thr Lys Leu Thr Val Leu Gly
        100                 105                 110

<210> SEQ ID NO 16
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetic Construct

<400> SEQUENCE: 16

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Phe Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Gly Trp Asp Asp Ser Leu
                85                  90                  95

Asn Gly Pro Val Phe Gly Gly Gly Thr Lys Leu Thr Val Leu Gly
            100                 105                 110

<210> SEQ ID NO 17
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: A2-48 VH
<220> FEATURE:
<221> NAME/KEY: CDS
<222> LOCATION: (1)..(354)

<400> SEQUENCE: 17 cag gtg cag ctg cag gag tcg ggc cca gga ctg gtg aag cct tcg gag     48
Gln Val Gln Leu Gln Glu Ser Gly Pro Gly Leu Val Lys Pro Ser Glu
1               5                   10                  15 acc ctg tcc ctc acc tgc act gtc tct ggt ggc tcc atc agt agt tac     96
Thr Leu Ser Leu Thr Cys Thr Val Ser Gly Gly Ser Ile Ser Ser Tyr
            20                  25                  30 tac tgg agc tgg atc cgg cag ccc ccc ggg aag gga ctg gaa tgg att    144
Tyr Trp Ser Trp Ile Arg Gln Pro Pro Gly Lys Gly Leu Glu Trp Ile
        35                  40                  45 ggg tat atc tat tac agt ggg tac acc aac tac aac ccc tcc ctc aag    192
Gly Tyr Ile Tyr Tyr Ser Gly Tyr Thr Asn Tyr Asn Pro Ser Leu Lys
    50                  55                  60 agt cga gtt aac ata tca gta gac acg tcc cag aac cag ttc tcc ctg    240
Ser Arg Val Asn Ile Ser Val Asp Thr Ser Gln Asn Gln Phe Ser Leu
65                  70                  75                  80
```

```
aag ctg aat tct ctg acc gct gcg gac acg gcc gtt tat tac tgt gcg    288
Lys Leu Asn Ser Leu Thr Ala Ala Asp Thr Ala Val Tyr Tyr Cys Ala
            85                  90                  95 aga aca cac tcc tat tac tac ggt atg gac gtc tgg ggc caa ggg acc    336
Arg Thr His Ser Tyr Tyr Tyr Gly Met Asp Val Trp Gly Gln Gly Thr
            100                 105                 110 acg gtc acc gtc tcc tca                                            354
Thr Val Thr Val Ser Ser
        115
```

<210> SEQ ID NO 18
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetic Construct

<400> SEQUENCE: 18

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Tyr Thr Asn Tyr Asn Pro Ser Leu Lys
    50                  55                  60

Ser Arg Val Asn Ile Ser Val Asp Thr Ser Gln Asn Gln Phe Ser Leu
65                  70                  75                  80

Lys Leu Asn Ser Leu Thr Ala Ala Asp Thr Ala Val Tyr Tyr Cys Ala
            85                  90                  95

Arg Thr His Ser Tyr Tyr Tyr Gly Met Asp Val Trp Gly Gln Gly Thr
            100                 105                 110

Thr Val Thr Val Ser Ser
        115
```

<210> SEQ ID NO 19
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: A2-48 VL
<220> FEATURE:
<221> NAME/KEY: CDS
<222> LOCATION: (1)..(333)

<400> SEQUENCE: 19

```
cag tct gtg ctg act cag cca ccc tca gcg tct ggg acc ccc ggg cag    48
Gln Ser Val Leu Thr Gln Pro Pro Ser Ala Ser Gly Thr Pro Gly Gln
1               5                   10                  15 agg gtc acc atc tct tgt tct gga agc agc tcc aac atc gga aat aat    96
Arg Val Thr Ile Ser Cys Ser Gly Ser Ser Ser Asn Ile Gly Asn Asn
            20                  25                  30 cct gta aac tgg tac cag cag ttc cca gga acg gcc ccc aaa ctc ctc    144
Pro Val Asn Trp Tyr Gln Gln Phe Pro Gly Thr Ala Pro Lys Leu Leu
        35                  40                  45 atc tat agt aat aat cag cgg ccc tca ggg gtc cct gac cga ttc tct    192
Ile Tyr Ser Asn Asn Gln Arg Pro Ser Gly Val Pro Asp Arg Phe Ser
```

```
ggc tcc aag tct ggc acc tca gcc tcc ctg gcc atc agt ggg ctc cag      240
Gly Ser Lys Ser Gly Thr Ser Ala Ser Leu Ala Ile Ser Gly Leu Gln
 65                  70                  75                  80 tct gag gat gag gct gat tat tac tgt gaa gca tgg gat gac agc ctg      288
Ser Glu Asp Glu Ala Asp Tyr Tyr Cys Glu Ala Trp Asp Asp Ser Leu
                 85                  90                  95 aat ggt ccg gta ttc ggc gga ggg acc aag ctg acc gtc cta ggt          333
Asn Gly Pro Val Phe Gly Gly Gly Thr Lys Leu Thr Val Leu Gly
            100                 105                 110

<210> SEQ ID NO 20
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetic Construct

<400> SEQUENCE: 20

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Asn Asn
                20                  25                  30

Pro Val Asn Trp Tyr Gln Gln Phe Pro Gly Thr Ala Pro Lys Leu Leu
            35                  40                  45

Ile Tyr Ser Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Glu Ala Trp Asp Asp Ser Leu
                 85                  90                  95

Asn Gly Pro Val Phe Gly Gly Gly Thr Lys Leu Thr Val Leu Gly
            100                 105                 110

<210> SEQ ID NO 21
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: A2-73 VH
<220> FEATURE:
<221> NAME/KEY: CDS
<222> LOCATION: (1)..(363)

<400> SEQUENCE: 21 cag gtg cag ctg cag gag tcg ggc cca gga ctg gtg aag cct tcg gag      48
Gln Val Gln Leu Gln Glu Ser Gly Pro Gly Leu Val Lys Pro Ser Glu
 1               5                  10                  15 acc ctg tcc ctc acc tgc act gtc tct ggt ggc tcc atc agt agt tac      96
Thr Leu Ser Leu Thr Cys Thr Val Ser Gly Gly Ser Ile Ser Ser Tyr
                20                  25                  30 tac tgg acc tgg atc cgg cag ccc cca ggg aag gga ctg gaa ttg gtt      144
Tyr Trp Thr Trp Ile Arg Gln Pro Pro Gly Lys Gly Leu Glu Leu Val
            35                  40                  45 gga tat atc tat tac agt ggt tac acc agc tac aac ccc tcc ctc aag      192
Gly Tyr Ile Tyr Tyr Ser Gly Tyr Thr Ser Tyr Asn Pro Ser Leu Lys
 50                  55                  60
```

```
agt cga gtc acc ata tca att gac acg tcc aag aac cag ttc tcc ctg      240
Ser Arg Val Thr Ile Ser Ile Asp Thr Ser Lys Asn Gln Phe Ser Leu
65                  70                  75                  80 cag ctg aac tct gtg acc gct gcg gac acg gcc gtg tat ttc tgt gcg      288
Gln Leu Asn Ser Val Thr Ala Ala Asp Thr Ala Val Tyr Phe Cys Ala
                85                  90                  95 cga gat gac tat ggt ggt aac ggc tac tac ggt gtg gac gtc tgg ggc      336
Arg Asp Asp Tyr Gly Gly Asn Gly Tyr Tyr Gly Val Asp Val Trp Gly
            100                 105                 110 caa ggg acc acg gtc acc gtc tcc tca                                  363
Gln Gly Thr Thr Val Thr Val Ser Ser
        115                 120

<210> SEQ ID NO 22
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetic Construct

<400> SEQUENCE: 22

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Thr Trp Ile Arg Gln Pro Pro Gly Lys Gly Leu Glu Leu Val
        35                  40                  45

Gly Tyr Ile Tyr Tyr Ser Gly Tyr Thr Ser Tyr Asn Pro Ser Leu Lys
    50                  55                  60

Ser Arg Val Thr Ile Ser Ile Asp Thr Ser Lys Asn Gln Phe Ser Leu
65                  70                  75                  80

Gln Leu Asn Ser Val Thr Ala Ala Asp Thr Ala Val Tyr Phe Cys Ala
                85                  90                  95

Arg Asp Asp Tyr Gly Gly Asn Gly Tyr Tyr Gly Val Asp Val Trp Gly
            100                 105                 110

Gln Gly Thr Thr Val Thr Val Ser Ser
        115                 120

<210> SEQ ID NO 23
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: A2-73 VL
<220> FEATURE:
<221> NAME/KEY: CDS
<222> LOCATION: (1)..(333)

<400> SEQUENCE: 23 cag tct gtg ctg act cag cca ccc tca gcg tct ggg acc ccc ggg cag      48
Gln Ser Val Leu Thr Gln Pro Pro Ser Ala Ser Gly Thr Pro Gly Gln
1               5                   10                  15 agg gtc acc atc tct tgt tct ggc agc agc tcc aac atc gga aat aat      96
Arg Val Thr Ile Ser Cys Ser Gly Ser Ser Ser Asn Ile Gly Asn Asn
            20                  25                  30 cct gta aac tgg tac cgg cag ctc cca gga acg gcc ccc aaa ctc ctc     144
```

```
Pro Val Asn Trp Tyr Arg Gln Leu Pro Gly Thr Ala Pro Lys Leu Leu
            35                  40                  45 atc tat agt aat aat cag cgg ccc tca ggg gtc cct gac cga ttc tct     192
Ile Tyr Ser Asn Asn Gln Arg Pro Ser Gly Val Pro Asp Arg Phe Ser
 50                      55                  60 ggc tcc aag tct ggc acc tca gcc tcc ctg gcc atc agt ggg ctc cag     240
Gly Ser Lys Ser Gly Thr Ser Ala Ser Leu Ala Ile Ser Gly Leu Gln
 65                  70                  75                  80 tct gag gat gag gct gat tat tac tgt gca gca tgg gat gac agc ctg     288
Ser Glu Asp Glu Ala Asp Tyr Tyr Cys Ala Ala Trp Asp Asp Ser Leu
                 85                  90                  95 aat ggt tgg gtg ttc ggc gga ggg acc aag ctg acc gtc cta ggt         333
Asn Gly Trp Val Phe Gly Gly Gly Thr Lys Leu Thr Val Leu Gly
            100                 105                 110

<210> SEQ ID NO 24
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetic Construct

<400> SEQUENCE: 24

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Asn Asn
             20                  25                  30

Pro Val Asn Trp Tyr Arg Gln Leu Pro Gly Thr Ala Pro Lys Leu Leu
         35                      40                  45

Ile Tyr Ser Asn Asn Gln Arg Pro Ser Gly Val Pro Asp Arg Phe Ser
 50                      55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly Trp Val Phe Gly Gly Gly Thr Lys Leu Thr Val Leu Gly
            100                 105                 110

<210> SEQ ID NO 25
<211> LENGTH: 726
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 3-34-j6 scFv
<220> FEATURE:
<221> NAME/KEY: CDS
<222> LOCATION: (1)..(726)

<400> SEQUENCE: 25 gaa gtt cag ctg ttg gaa agt ggt ggc gga ctg gtc cag cct ggc gaa      48
Glu Val Gln Leu Leu Glu Ser Gly Gly Gly Leu Val Gln Pro Gly Glu
 1               5                  10                  15 tct ctg aga ctg agc tgc aag gcc ttc ggg tat acc ttt acc aac cac      96
Ser Leu Arg Leu Ser Cys Lys Ala Phe Gly Tyr Thr Phe Thr Asn His
             20                  25                  30 cac atc aat tgg gtt cga caa gcc cct ggc aag tgc ctg gaa tgg gtc     144
His Ile Asn Trp Val Arg Gln Ala Pro Gly Lys Cys Leu Glu Trp Val
```

```
                    35                  40                  45
gga tat atc aac ccc tac aac gac tac acc acc ttc aac gac aag ttc        192
Gly Tyr Ile Asn Pro Tyr Asn Asp Tyr Thr Thr Phe Asn Asp Lys Phe
 50                  55                  60 aag gac cgg ttc acc ctg tcc gtg gat aag tcc aag agc acc gct tac        240
Lys Asp Arg Phe Thr Leu Ser Val Asp Lys Ser Lys Ser Thr Ala Tyr
 65                  70                  75                  80 ctg cag atg aac tcc ctg aga gcc gag gat aca gct gtg tat tac tgt        288
Leu Gln Met Asn Ser Leu Arg Ala Glu Asp Thr Ala Val Tyr Tyr Cys
                 85                  90                  95 gcc cgg acc tgg ggc cac tgg tac ttt gat ttg tgg ggc cag gga acc        336
Ala Arg Thr Trp Gly His Trp Tyr Phe Asp Leu Trp Gly Gln Gly Thr
            100                 105                 110 ctc gtg aca gtc tct tct ggc ggc gga agc gga ggc gga ggt tca            384
Leu Val Thr Val Ser Ser Gly Gly Gly Ser Gly Gly Gly Gly Ser
        115                 120                 125 ggc ggc ggt gga tct aac atc cag atg acc cag tct cca tcc agc ctg        432
Gly Gly Gly Gly Ser Asn Ile Gln Met Thr Gln Ser Pro Ser Ser Leu
130                 135                 140 tct gcc tct gtg ggc gac aga gtg aca att acc tgt cgg gcc tct cag        480
Ser Ala Ser Val Gly Asp Arg Val Thr Ile Thr Cys Arg Ala Ser Gln
145                 150                 155                 160 tcc gtg tcc agc aat ctg gct tgg tat cag cag aag ccc ggc aag gct        528
Ser Val Ser Ser Asn Leu Ala Trp Tyr Gln Gln Lys Pro Gly Lys Ala
                165                 170                 175 ccc aag ctg ctg atc tac gac tcc tcc acc aga gct acc ggc gtg cca        576
Pro Lys Leu Leu Ile Tyr Asp Ser Ser Thr Arg Ala Thr Gly Val Pro
            180                 185                 190 tct aga ttc tcc ggc tct ggc tct ggc acc gac ttt acc ctg aca att        624
Ser Arg Phe Ser Gly Ser Gly Ser Gly Thr Asp Phe Thr Leu Thr Ile
        195                 200                 205 tcc agc ctg cag cct gag gac ttc gcc acc tac tac tgc cag cag tac        672
Ser Ser Leu Gln Pro Glu Asp Phe Ala Thr Tyr Tyr Cys Gln Gln Tyr
210                 215                 220 aac aac tgg cct cct tgg acc ttc ggc tgc ggc acc aaa ctg gaa atc        720
Asn Asn Trp Pro Pro Trp Thr Phe Gly Cys Gly Thr Lys Leu Glu Ile
225                 230                 235                 240 aag cgc                                                                726
Lys Arg
```

<210> SEQ ID NO 26
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetic Construct

<400> SEQUENCE: 26

```
Glu Val Gln Leu Leu Glu Ser Gly Gly Gly Leu Val Gln Pro Gly Glu
  1               5                  10                  15

Ser Leu Arg Leu Ser Cys Lys Ala Phe Gly Tyr Thr Phe Thr Asn His
             20                  25                  30

His Ile Asn Trp Val Arg Gln Ala Pro Gly Lys Cys Leu Glu Trp Val
         35                  40                  45

Gly Tyr Ile Asn Pro Tyr Asn Asp Tyr Thr Thr Phe Asn Asp Lys Phe
     50                  55                  60

Lys Asp Arg Phe Thr Leu Ser Val Asp Lys Ser Lys Ser Thr Ala Tyr
```

```
                65                  70                  75                  80
Leu Gln Met Asn Ser Leu Arg Ala Glu Asp Thr Ala Val Tyr Tyr Cys
                    85                  90                  95

Ala Arg Thr Trp Gly His Trp Tyr Phe Asp Leu Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Asn Ile Gln Met Thr Gln Ser Pro Ser Ser Leu
130                 135                 140

Ser Ala Ser Val Gly Asp Arg Val Thr Ile Thr Cys Arg Ala Ser Gln
145                 150                 155                 160

Ser Val Ser Ser Asn Leu Ala Trp Tyr Gln Gln Lys Pro Gly Lys Ala
                165                 170                 175

Pro Lys Leu Leu Ile Tyr Asp Ser Ser Thr Arg Ala Thr Gly Val Pro
            180                 185                 190

Ser Arg Phe Ser Gly Ser Gly Ser Gly Thr Asp Phe Thr Leu Thr Ile
        195                 200                 205

Ser Ser Leu Gln Pro Glu Asp Phe Ala Thr Tyr Tyr Cys Gln Gln Tyr
210                 215                 220

Asn Asn Trp Pro Pro Trp Thr Phe Gly Cys Gly Thr Lys Leu Glu Ile
225                 230                 235                 240

Lys Arg

<210> SEQ ID NO 27
<211> LENGTH: 732
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: tA2-32 scFv
<220> FEATURE:
<221> NAME/KEY: CDS
<222> LOCATION: (1)..(732)

<400> SEQUENCE: 27 cag gtt cag ttg caa gaa tct ggc cca ggc ctc gtg aag ccc tcc gaa      48
Gln Val Gln Leu Gln Glu Ser Gly Pro Gly Leu Val Lys Pro Ser Glu
1               5                   10                  15 aca ctg tct ctg acc tgc aca gtg tcc ggc ggc tct atc tct ggc tac      96
Thr Leu Ser Leu Thr Cys Thr Val Ser Gly Gly Ser Ile Ser Gly Tyr
            20                  25                  30 tac tgg tcc tgg atc aga cag cct cct ggc aag tgc ctg gaa tgg atc     144
Tyr Trp Ser Trp Ile Arg Gln Pro Pro Gly Lys Cys Leu Glu Trp Ile
        35                  40                  45 ggc tac atc tac tac tct ggc ttc acc aac tac aac ccc agc ctg aag     192
Gly Tyr Ile Tyr Tyr Ser Gly Phe Thr Asn Tyr Asn Pro Ser Leu Lys
    50                  55                  60 tcc aga gtg acc atc agc gtg gac acc tct aag aac cag ttc tct ctg     240
Ser Arg Val Thr Ile Ser Val Asp Thr Ser Lys Asn Gln Phe Ser Leu
65                  70                  75                  80 aag ctg tcc tcc gtg acc gcc gct gat acc gct gtg tat tac tgc acc     288
Lys Leu Ser Ser Val Thr Ala Ala Asp Thr Ala Val Tyr Tyr Cys Thr
                85                  90                  95 cgg gac cac agc cac tac tac tac atg gac gtg tgg gga cag gga aca     336
Arg Asp His Ser His Tyr Tyr Tyr Met Asp Val Trp Gly Gln Gly Thr
            100                 105                 110 acc gtg aca gtc tct tca ggc ggt ggt gga tca ggc ggc gga gga agt     384
```

```
Thr Val Thr Val Ser Ser Gly Gly Gly Ser Gly Gly Gly Ser
        115                 120                 125 ggt ggc gga ggt tct cag tct gtg ctg acc caa cct cct tcc gct tct     432
Gly Gly Gly Gly Ser Gln Ser Val Leu Thr Gln Pro Pro Ser Ala Ser
130                 135                 140 ggc aca cct ggc cag aga gtg aca atc tct tgc tcc ggc tcc tcc tcc     480
Gly Thr Pro Gly Gln Arg Val Thr Ile Ser Cys Ser Gly Ser Ser Ser
145                 150                 155                 160 aac atc ggc tct aac acc gtg aac tgg tat cag cag ttc ccc ggc acc     528
Asn Ile Gly Ser Asn Thr Val Asn Trp Tyr Gln Gln Phe Pro Gly Thr
                165                 170                 175 gct cct aag ctg ctg atc tac tcc aac aac cag cgg cct tcc ggc gtg     576
Ala Pro Lys Leu Leu Ile Tyr Ser Asn Asn Gln Arg Pro Ser Gly Val
            180                 185                 190 ccc gat aga ttc tct ggc tct aag tcc ggc acc tct gcc agc ctg gct     624
Pro Asp Arg Phe Ser Gly Ser Lys Ser Gly Thr Ser Ala Ser Leu Ala
        195                 200                 205 att tct gga ctg cag agc gag gac gag gcc gac tat tat tgt gcc ggc     672
Ile Ser Gly Leu Gln Ser Glu Asp Glu Ala Asp Tyr Tyr Cys Ala Gly
    210                 215                 220 tgg gac gac tct ctg aac ggc cct gtt ttt ggc tgc ggc acc aaa ctg     720
Trp Asp Asp Ser Leu Asn Gly Pro Val Phe Gly Cys Gly Thr Lys Leu
225                 230                 235                 240 act gtg ctg ggc                                                      732
Thr Val Leu Gly <210> SEQ ID NO 28
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetic Construct

<400> SEQUENCE: 28

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Gly Tyr
            20                  25                  30

Tyr Trp Ser Trp Ile Arg Gln Pro Pro Gly Lys Cys Leu Glu Trp Ile
        35                  40                  45

Gly Tyr Ile Tyr Tyr Ser Gly Phe Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Thr
                85                  90                  95

Arg Asp His Ser His Tyr Tyr Met Asp Val Trp Gly Gln Gly Thr
            100                 105                 110

Thr Val Thr Val Ser Ser Gly Gly Gly Ser Gly Gly Gly Gly Ser
        115                 120                 125

Gly Gly Gly Gly Ser Gln Ser Val Leu Thr Gln Pro Pro Ser Ala Ser
130                 135                 140

Gly Thr Pro Gly Gln Arg Val Thr Ile Ser Cys Ser Gly Ser Ser Ser
145                 150                 155                 160

Asn Ile Gly Ser Asn Thr Val Asn Trp Tyr Gln Gln Phe Pro Gly Thr
                165                 170                 175
```

```
                      Ala Pro Lys Leu Leu Ile Tyr Ser Asn Asn Gln Arg Pro Ser Gly Val
                                  180                 185                 190

Pro Asp Arg Phe Ser Gly Ser Lys Ser Gly Thr Ser Ala Ser Leu Ala
                                  195                 200                 205

Ile Ser Gly Leu Gln Ser Glu Asp Glu Ala Asp Tyr Tyr Cys Ala Gly
                                  210                 215                 220

Trp Asp Ser Leu Asn Gly Pro Val Phe Gly Cys Gly Thr Lys Leu
                      225                 230                 235                 240

Thr Val Leu Gly

<210> SEQ ID NO 29
<211> LENGTH: 747
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: tA2-32LH scFv
<220> FEATURE:
<221> NAME/KEY: CDS
<222> LOCATION: (1)..(747)

<400> SEQUENCE: 29 caa tct gtt ctg acc caa cct cct tcc gcc tct ggc aca cct ggc cag        48
Gln Ser Val Leu Thr Gln Pro Pro Ser Ala Ser Gly Thr Pro Gly Gln
1               5                   10                  15 aga gtg acc atc tct tgc tcc ggc tcc tcc tcc aac atc ggc tct aac        96
Arg Val Thr Ile Ser Cys Ser Gly Ser Ser Ser Asn Ile Gly Ser Asn
            20                  25                  30 acc gtg aac tgg tat cag cag ttc ccc ggc acc gct cct aag ctg ctg       144
Thr Val Asn Trp Tyr Gln Gln Phe Pro Gly Thr Ala Pro Lys Leu Leu
        35                  40                  45 atc tac tcc aac aac cag cgg cct tcc ggc gtg ccc gat aga ttc tct       192
Ile Tyr Ser Asn Asn Gln Arg Pro Ser Gly Val Pro Asp Arg Phe Ser
    50                  55                  60 ggc tct aag tcc ggc acc tct gcc agc ctg gct att tct gga ctg cag       240
Gly Ser Lys Ser Gly Thr Ser Ala Ser Leu Ala Ile Ser Gly Leu Gln
65                  70                  75                  80 agc gag gac gag gcc gac tat tat tgt gcc ggc tgg gac gac tct ctg       288
Ser Glu Asp Glu Ala Asp Tyr Tyr Cys Ala Gly Trp Asp Asp Ser Leu
                85                  90                  95 aac ggc cct gtt ttt ggc ggt ggc acc aaa ctg aca gtg ctt gga ggc       336
Asn Gly Pro Val Phe Gly Gly Gly Thr Lys Leu Thr Val Leu Gly Gly
            100                 105                 110 ggt ggt gga tca ggc ggc ggt gga agt ggt ggt ggt ggt agc gga ggt       384
Gly Gly Gly Ser Gly Gly Gly Gly Ser Gly Gly Gly Gly Ser Gly Gly
        115                 120                 125 ggt gga tct cag gtg cag ctc caa gag tct gga cct ggc ctc gtg aag       432
Gly Gly Ser Gln Val Gln Leu Gln Glu Ser Gly Pro Gly Leu Val Lys
    130                 135                 140 cct tcc gag aca ctg tct ctg acc tgc aca gtg tcc ggc ggc tct atc       480
Pro Ser Glu Thr Leu Ser Leu Thr Cys Thr Val Ser Gly Gly Ser Ile
145                 150                 155                 160 tct ggc tac tac tgg tcc tgg atc aga cag cct cct ggc aag gga ctc       528
Ser Gly Tyr Tyr Trp Ser Trp Ile Arg Gln Pro Pro Gly Lys Gly Leu
                165                 170                 175 gag tgg atc ggc tac atc tac tac tct ggc ttc acc aac tac aac ccc       576
Glu Trp Ile Gly Tyr Ile Tyr Tyr Ser Gly Phe Thr Asn Tyr Asn Pro
            180                 185                 190
```

```
agc ctg aag tcc cgc gtg acc atc agc gtg gac acc tct aag aac cag    624
Ser Leu Lys Ser Arg Val Thr Ile Ser Val Asp Thr Ser Lys Asn Gln
    195                 200                 205 ttc tct ctg aag ctg tcc tcc gtg acc gcc gct gat acc gct gtg tat    672
Phe Ser Leu Lys Leu Ser Ser Val Thr Ala Ala Asp Thr Ala Val Tyr
210                 215                 220 tac tgc acc cgg gac cac agc cac tac tac tac atg gac gtg tgg gga    720
Tyr Cys Thr Arg Asp His Ser His Tyr Tyr Tyr Met Asp Val Trp Gly
225                 230                 235                 240 cag gga aca acc gtg aca gtg tcc tcc                                747
Gln Gly Thr Thr Val Thr Val Ser Ser
                245
```

<210> SEQ ID NO 30
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetic Construct

<400> SEQUENCE: 30

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Phe Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Gly Trp Asp Asp Ser Leu
                85                  90                  95

Asn Gly Pro Val Phe Gly Gly Gly Thr Lys Leu Thr Val Leu Gly Gly
            100                 105                 110

Gly Gly Ser Gly Gly Gly Gly Ser Gly Gly Gly Gly Ser Gly Gly
        115                 120                 125

Gly Gly Ser Gln Val Gln Leu Gln Glu Ser Gly Pro Gly Leu Val Lys
    130                 135                 140

Pro Ser Glu Thr Leu Ser Leu Thr Cys Thr Val Ser Gly Gly Ser Ile
145                 150                 155                 160

Ser Gly Tyr Tyr Trp Ser Trp Ile Arg Gln Pro Pro Gly Lys Gly Leu
                165                 170                 175

Glu Trp Ile Gly Tyr Ile Tyr Tyr Ser Gly Phe Thr Asn Tyr Asn Pro
            180                 185                 190

Ser Leu Lys Ser Arg Val Thr Ile Ser Val Asp Thr Ser Lys Asn Gln
        195                 200                 205

Phe Ser Leu Lys Leu Ser Ser Val Thr Ala Ala Asp Thr Ala Val Tyr
    210                 215                 220

Tyr Cys Thr Arg Asp His Ser His Tyr Tyr Tyr Met Asp Val Trp Gly
225                 230                 235                 240

Gln Gly Thr Thr Val Thr Val Ser Ser
                245
```

<210> SEQ ID NO 31

<211> LENGTH: 732
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: tA2-48 scFv
<220> FEATURE:
<221> NAME/KEY: CDS
<222> LOCATION: (1)..(732)

<400> SEQUENCE: 31

```
cag gtt cag ttg caa gaa tct ggc cca ggc ctc gtg aag ccc tcc gaa      48
Gln Val Gln Leu Gln Glu Ser Gly Pro Gly Leu Val Lys Pro Ser Glu
1               5                   10                  15 aca ctg tct ctg acc tgc aca gtg tcc ggc ggc tcc atc tct tcc tac      96
Thr Leu Ser Leu Thr Cys Thr Val Ser Gly Gly Ser Ile Ser Ser Tyr
            20                  25                  30 tac tgg tcc tgg atc aga cag cct cct ggc aag tgc ctg gaa tgg atc     144
Tyr Trp Ser Trp Ile Arg Gln Pro Pro Gly Lys Cys Leu Glu Trp Ile
        35                  40                  45 ggc tac atc tac tac tcc ggc tac acc aac tac aac ccc agc ctg aag     192
Gly Tyr Ile Tyr Tyr Ser Gly Tyr Thr Asn Tyr Asn Pro Ser Leu Lys
    50                  55                  60 tcc aga gtg aac atc tcc gtg gac acc agc cag aac cag ttc tct ctg     240
Ser Arg Val Asn Ile Ser Val Asp Thr Ser Gln Asn Gln Phe Ser Leu
65                  70                  75                  80 aag ctg aac tcc ctg acc gcc gct gat acc gct gtg tat tac tgc gct     288
Lys Leu Asn Ser Leu Thr Ala Ala Asp Thr Ala Val Tyr Tyr Cys Ala
                85                  90                  95 cgg acc cac agc tac tac tat ggc atg gac gtg tgg gga caa ggg aca     336
Arg Thr His Ser Tyr Tyr Tyr Gly Met Asp Val Trp Gly Gln Gly Thr
            100                 105                 110 acc gtg aca gtc tct tca ggc ggt ggt gga tca ggc ggc gga gga agt     384
Thr Val Thr Val Ser Ser Gly Gly Gly Ser Gly Gly Gly Gly Ser
        115                 120                 125 ggt ggc gga ggt tct cag tct gtg ctg acc caa cct cct tcc gct tct     432
Gly Gly Gly Gly Ser Gln Ser Val Leu Thr Gln Pro Pro Ser Ala Ser
    130                 135                 140 ggc aca cct ggc cag aga gtg acc atc agc tgt agc ggc tcc tcc tcc     480
Gly Thr Pro Gly Gln Arg Val Thr Ile Ser Cys Ser Gly Ser Ser Ser
145                 150                 155                 160 aac atc ggc aac aac ccc gtg aac tgg tat cag cag ttc ccc ggc aca     528
Asn Ile Gly Asn Asn Pro Val Asn Trp Tyr Gln Gln Phe Pro Gly Thr
                165                 170                 175 gcc cct aag ctg ctg atc tac tcc aac aac cag cgg cct tcc ggc gtg     576
Ala Pro Lys Leu Leu Ile Tyr Ser Asn Asn Gln Arg Pro Ser Gly Val
            180                 185                 190 ccc gat aga ttc tct ggc tct aag tcc ggc acc tct gcc agc ctg gct     624
Pro Asp Arg Phe Ser Gly Ser Lys Ser Gly Thr Ser Ala Ser Leu Ala
        195                 200                 205 att tct gga ctg cag agc gag gac gag gcc gac tac tat tgc gag gct     672
Ile Ser Gly Leu Gln Ser Glu Asp Glu Ala Asp Tyr Tyr Cys Glu Ala
    210                 215                 220 tgg gac gac tct ctg aac ggc cct gtg ttt ggc tgt ggc acc aaa ctg     720
Trp Asp Asp Ser Leu Asn Gly Pro Val Phe Gly Cys Gly Thr Lys Leu
225                 230                 235                 240 act gtg ctg ggc                                                      732
Thr Val Leu Gly
```

<210> SEQ ID NO 32

<211> LENGTH: 244
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Synthetic Construct

<400> SEQUENCE: 32

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Cys Leu Glu Trp Ile
        35                  40                  45

Gly Tyr Ile Tyr Tyr Ser Gly Tyr Thr Asn Tyr Asn Pro Ser Leu Lys
    50                  55                  60

Ser Arg Val Asn Ile Ser Val Asp Thr Ser Gln Asn Gln Phe Ser Leu
65                  70                  75                  80

Lys Leu Asn Ser Leu Thr Ala Ala Asp Thr Ala Val Tyr Tyr Cys Ala
                85                  90                  95

Arg Thr His Ser Tyr Tyr Tyr Gly Met Asp Val Trp Gly Gln Gly Thr
            100                 105                 110

Thr Val Thr Val Ser Ser Gly Gly Gly Ser Gly Gly Gly Gly Ser
        115                 120                 125

Gly Gly Gly Gly Ser Gln Ser Val Leu Thr Gln Pro Pro Ser Ala Ser
    130                 135                 140

Gly Thr Pro Gly Gln Arg Val Thr Ile Ser Cys Ser Gly Ser Ser Ser
145                 150                 155                 160

Asn Ile Gly Asn Asn Pro Val Asn Trp Tyr Gln Gln Phe Pro Gly Thr
                165                 170                 175

Ala Pro Lys Leu Leu Ile Tyr Ser Asn Asn Gln Arg Pro Ser Gly Val
            180                 185                 190

Pro Asp Arg Phe Ser Gly Ser Lys Ser Gly Thr Ser Ala Ser Leu Ala
        195                 200                 205

Ile Ser Gly Leu Gln Ser Glu Asp Glu Ala Asp Tyr Tyr Cys Glu Ala
    210                 215                 220

Trp Asp Asp Ser Leu Asn Gly Pro Val Phe Gly Cys Gly Thr Lys Leu
225                 230                 235                 240

Thr Val Leu Gly
```

<210> SEQ ID NO 33
<211> LENGTH: 741
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: tA2-73 scFv
<220> FEATURE:
<221> NAME/KEY: CDS
<222> LOCATION: (1)..(741)

<400> SEQUENCE: 33

```
cag gtt cag ttg caa gaa tct ggc cca ggc ctc gtg aag ccc tcc gaa      48
Gln Val Gln Leu Gln Glu Ser Gly Pro Gly Leu Val Lys Pro Ser Glu
1               5                   10                  15 aca ctg tct ctg acc tgc aca gtg tcc ggc ggc tcc atc tct tcc tac      96
```

```
                                                                               144
tac tgg acc tgg atc aga cag cct cct ggc aag tgc ttg gaa ctc gtg
Tyr Trp Thr Trp Ile Arg Gln Pro Pro Gly Lys Cys Leu Glu Leu Val
             35                  40                  45

192
ggc tac atc tac tac tcc ggc tac acc agc tac aac ccc agc ctg aag
Gly Tyr Ile Tyr Tyr Ser Gly Tyr Thr Ser Tyr Asn Pro Ser Leu Lys
 50                  55                  60

240
tcc aga gtg acc atc agc atc gac acc tct aag aac cag ttc agc ctg
Ser Arg Val Thr Ile Ser Ile Asp Thr Ser Lys Asn Gln Phe Ser Leu
 65                  70                  75                  80

288
cag ctc aac tcc gtg acc gct gct gat acc gct gtg tac ttc tgc gcc
Gln Leu Asn Ser Val Thr Ala Ala Asp Thr Ala Val Tyr Phe Cys Ala
                 85                  90                  95

336
aga gat gac tac ggc ggc aac ggc tat tat ggc gtg gac gtt tgg gga
Arg Asp Asp Tyr Gly Gly Asn Gly Tyr Tyr Gly Val Asp Val Trp Gly
             100                 105                 110

384
caa ggg aca acc gtg aca gtg tct agc gga ggt ggt gga tca ggc ggc
Gln Gly Thr Thr Val Thr Val Ser Ser Gly Gly Gly Gly Ser Gly Gly
         115                 120                 125

432
ggt gga agt ggt ggt ggt ggc tct cag tct gtg ctg acc caa cct cct
Gly Gly Ser Gly Gly Gly Gly Ser Gln Ser Val Leu Thr Gln Pro Pro
130                 135                 140

480
tct gcc tct ggc aca cct ggc cag aga gtg aca atc tct tgc tcc ggc
Ser Ala Ser Gly Thr Pro Gly Gln Arg Val Thr Ile Ser Cys Ser Gly
145                 150                 155                 160

528
tcc tcc tcc aac atc ggc aac aac ccc gtg aac tgg tac aga cag ctg
Ser Ser Ser Asn Ile Gly Asn Asn Pro Val Asn Trp Tyr Arg Gln Leu
                 165                 170                 175

576
cca ggc aca gcc cct aag ctg ctg atc tac tcc aac aac cag cgg cct
Pro Gly Thr Ala Pro Lys Leu Leu Ile Tyr Ser Asn Asn Gln Arg Pro
             180                 185                 190

624
tcc ggc gtg ccc gat aga ttc tct gga tct aag tcc ggc acc agc gcc
Ser Gly Val Pro Asp Arg Phe Ser Gly Ser Lys Ser Gly Thr Ser Ala
         195                 200                 205

672
agc ctg gct att tct gga ctg cag agc gag gac gag gcc gac tac tac
Ser Leu Ala Ile Ser Gly Leu Gln Ser Glu Asp Glu Ala Asp Tyr Tyr
210                 215                 220

720
tgt gcc gct tgg gac gat tct ctg aac gga tgg gtg ttc ggc tgc ggc
Cys Ala Ala Trp Asp Asp Ser Leu Asn Gly Trp Val Phe Gly Cys Gly
225                 230                 235                 240

741
acc aaa ctg act gtg ctg gga
Thr Lys Leu Thr Val Leu Gly
                 245

<210> SEQ ID NO 34
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetic Construct

<400> SEQUENCE: 34

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Tyr
             20                  25                  30

Tyr Trp Thr Trp Ile Arg Gln Pro Pro Gly Lys Cys Leu Glu Leu Val
```

```
                35                  40                  45
Gly Tyr Ile Tyr Tyr Ser Gly Tyr Thr Ser Tyr Asn Pro Ser Leu Lys
 50                  55                  60

Ser Arg Val Thr Ile Ser Ile Asp Thr Ser Lys Asn Gln Phe Ser Leu
 65                  70                  75                  80

Gln Leu Asn Ser Val Thr Ala Ala Asp Thr Ala Val Tyr Phe Cys Ala
                 85                  90                  95

Arg Asp Asp Tyr Gly Gly Asn Gly Tyr Tyr Gly Val Asp Val Trp Gly
                100                 105                 110

Gln Gly Thr Thr Val Thr Val Ser Ser Gly Gly Gly Ser Gly Gly
            115                 120                 125

Gly Gly Ser Gly Gly Gly Ser Gln Ser Val Leu Thr Gln Pro Pro
        130                 135                 140

Ser Ala Ser Gly Thr Pro Gly Gln Arg Val Thr Ile Ser Cys Ser Gly
145                 150                 155                 160

Ser Ser Ser Asn Ile Gly Asn Asn Pro Val Asn Trp Tyr Arg Gln Leu
                165                 170                 175

Pro Gly Thr Ala Pro Lys Leu Leu Ile Tyr Ser Asn Asn Gln Arg Pro
                180                 185                 190

Ser Gly Val Pro Asp Arg Phe Ser Gly Ser Lys Ser Gly Thr Ser Ala
            195                 200                 205

Ser Leu Ala Ile Ser Gly Leu Gln Ser Glu Asp Glu Ala Asp Tyr Tyr
210                 215                 220

Cys Ala Ala Trp Asp Asp Ser Leu Asn Gly Trp Val Phe Gly Cys Gly
225                 230                 235                 240

Thr Lys Leu Thr Val Leu Gly
                245

<210> SEQ ID NO 35
<211> LENGTH: 2115
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: hKM3900_3-34-j6  HC
<220> FEATURE:
<221> NAME/KEY: CDS
<222> LOCATION: (1)..(2115)

<400> SEQUENCE: 35 gaa gtg cag ctg gtt cag tct ggc gcc gaa gtg aag aaa cct ggc gcc    48
Glu Val Gln Leu Val Gln Ser Gly Ala Glu Val Lys Lys Pro Gly Ala
 1               5                  10                  15 tcc gtg aag atc tcc tgc aag gct tct ggc tac acc ttc acc gac tac    96
Ser Val Lys Ile Ser Cys Lys Ala Ser Gly Tyr Thr Phe Thr Asp Tyr
                20                  25                  30 tac atg aac tgg gtc cga cag gct cct gga cag gga ctt gag tgg atg   144
Tyr Met Asn Trp Val Arg Gln Ala Pro Gly Gln Gly Leu Glu Trp Met
            35                  40                  45 gga gat gtg gtg ccc aac aac ggc gtg ccc acc tac aac cag aaa ttc   192
Gly Asp Val Val Pro Asn Asn Gly Val Pro Thr Tyr Asn Gln Lys Phe
 50                  55                  60 aag ggc aga gtg acc atc acc gcc gac aag tct acc tcc acc gcc tac   240
Lys Gly Arg Val Thr Ile Thr Ala Asp Lys Ser Thr Ser Thr Ala Tyr
 65                  70                  75                  80 atg gaa ctg cgg agc ctg aga tct gag gac acc gcc gtg tac tac tgc   288
Met Glu Leu Arg Ser Leu Arg Ser Glu Asp Thr Ala Val Tyr Tyr Cys
```

-continued

| | | |
|---|---|---|
| gcc aga cct cac tac tac tac gcc ggc aga tct ggc gcc atg gat tat<br>Ala Arg Pro His Tyr Tyr Tyr Ala Gly Arg Ser Gly Ala Met Asp Tyr<br>           100                      105                     110 | 336 |
| tgg gga cag ggc acc ctg gtc acc gtg tcc tct gct agc aca aag ggc<br>Trp Gly Gln Gly Thr Leu Val Thr Val Ser Ser Ala Ser Thr Lys Gly<br>         115                      120                     125 | 384 |
| ccc tct gtg ttc cct ctg gct cct agc tct aag tcc acc tct ggc gga<br>Pro Ser Val Phe Pro Leu Ala Pro Ser Ser Lys Ser Thr Ser Gly Gly<br>130                      135                     140 | 432 |
| aca gct gct ctg ggc tgt ctg gtc aag gac tac ttc cct gag cct gtg<br>Thr Ala Ala Leu Gly Cys Leu Val Lys Asp Tyr Phe Pro Glu Pro Val<br>145                      150                     155                     160 | 480 |
| acc gtg tct tgg aac tct ggc gct ctg aca tcc ggc gtg cac aca ttt<br>Thr Val Ser Trp Asn Ser Gly Ala Leu Thr Ser Gly Val His Thr Phe<br>                   165                     170                     175 | 528 |
| cca gct gtg ctg cag tcc tcc ggc ctg tac tct ctg tcc tct gtc gtg<br>Pro Ala Val Leu Gln Ser Ser Gly Leu Tyr Ser Leu Ser Ser Val Val<br>         180                      185                     190 | 576 |
| acc gtg cct tcc agc tct ctg gga acc cag acc tac atc tgc aat gtg<br>Thr Val Pro Ser Ser Ser Leu Gly Thr Gln Thr Tyr Ile Cys Asn Val<br>                   195                     200                     205 | 624 |
| aac cac aag cct tcc aac acc aag gtg gac aag aag gtg gaa ccc aag<br>Asn His Lys Pro Ser Asn Thr Lys Val Asp Lys Lys Val Glu Pro Lys<br>         210                      215                     220 | 672 |
| tcc tgc gac aag acc cac acc tgt cct cca tgt cct gct cca gaa gct<br>Ser Cys Asp Lys Thr His Thr Cys Pro Pro Cys Pro Ala Pro Glu Ala<br>225                      230                     235                     240 | 720 |
| gct ggc gga cct tcc gtg ttc ctg ttt cct cca aag cct aag gac acc<br>Ala Gly Gly Pro Ser Val Phe Leu Phe Pro Pro Lys Pro Lys Asp Thr<br>                   245                     250                     255 | 768 |
| ctg atg atc tct cgg acc cct gaa gtg acc tgc gtg gtg gtg gat gtg<br>Leu Met Ile Ser Arg Thr Pro Glu Val Thr Cys Val Val Val Asp Val<br>         260                      265                     270 | 816 |
| tct cac gag gac cca gaa gtg aag ttc aat tgg tac gtg gac ggc gtg<br>Ser His Glu Asp Pro Glu Val Lys Phe Asn Trp Tyr Val Asp Gly Val<br>                   275                     280                     285 | 864 |
| gaa gtg cac aac gcc aag acc aag cct aga gag gaa cag tac aac tcc<br>Glu Val His Asn Ala Lys Thr Lys Pro Arg Glu Glu Gln Tyr Asn Ser<br>         290                      295                     300 | 912 |
| acc tac aga gtg gtg tcc gtg ctg acc gtg ctg cac cag gat tgg ctg<br>Thr Tyr Arg Val Val Ser Val Leu Thr Val Leu His Gln Asp Trp Leu<br>305                      310                     315                     320 | 960 |
| aac ggc aaa gag tac aag tgc aag gtg tcc aac aag gcc ctg cct gcc<br>Asn Gly Lys Glu Tyr Lys Cys Lys Val Ser Asn Lys Ala Leu Pro Ala<br>                   325                     330                     335 | 1008 |
| ggc atc gaa aag acc atc tcc aag gcc aag ggc cag cct agg gaa ccc<br>Gly Ile Glu Lys Thr Ile Ser Lys Ala Lys Gly Gln Pro Arg Glu Pro<br>         340                      345                     350 | 1056 |
| cag gtt tac acc ttg cca cct tct cgg gac gag ctg acc aag aac cag<br>Gln Val Tyr Thr Leu Pro Pro Ser Arg Asp Glu Leu Thr Lys Asn Gln<br>                   355                     360                     365 | 1104 |
| gtg tcc ctg acc tgt ctc gtg aag ggc ttc tac ccc tcc gat atc gcc<br>Val Ser Leu Thr Cys Leu Val Lys Gly Phe Tyr Pro Ser Asp Ile Ala<br>         370                      375                     380 | 1152 |
| gtg gaa tgg gag tct aat ggc cag cct gag aac aac tac aag aca acc<br>Val Glu Trp Glu Ser Asn Gly Gln Pro Glu Asn Asn Tyr Lys Thr Thr<br>385                      390                     395                     400 | 1200 |
| cct cct gtg ctg gac tcc gac ggc tca ttc ttc ctg tac tcc aag ctg | 1248 |

```
                Pro Pro Val Leu Asp Ser Asp Gly Ser Phe Leu Tyr Ser Lys Leu
                                405                 410                 415 aca gtg gac aag tcc aga tgg cag cag ggc aac gtg ttc tcc tgc agc             1296
Thr Val Asp Lys Ser Arg Trp Gln Gln Gly Asn Val Phe Ser Cys Ser
            420                 425                 430 gtg atg cac gag gcc ctg cac aat cac tac aca cag aag tct ctg tct             1344
Val Met His Glu Ala Leu His Asn His Tyr Thr Gln Lys Ser Leu Ser
        435                 440                 445 ctg agc ccc ggc aaa ggt ggc gga gga tct ggc gga ggc gga tcc gaa             1392
Leu Ser Pro Gly Lys Gly Gly Gly Gly Ser Gly Gly Gly Gly Ser Glu
    450                 455                 460 gtt cag ctg ttg gaa agt ggt ggc gga ctg gtc cag cct ggc gaa tct             1440
Val Gln Leu Leu Glu Ser Gly Gly Gly Leu Val Gln Pro Gly Glu Ser
465                 470                 475                 480 ctg aga ctg agc tgc aag gcc ttc ggg tat acc ttt acc aac cac cac             1488
Leu Arg Leu Ser Cys Lys Ala Phe Gly Tyr Thr Phe Thr Asn His His
                485                 490                 495 atc aat tgg gtt cga caa gcc cct ggc aag tgc ctg gaa tgg gtc gga             1536
Ile Asn Trp Val Arg Gln Ala Pro Gly Lys Cys Leu Glu Trp Val Gly
            500                 505                 510 tat atc aac ccc tac aac gac tac acc acc ttc aac gac aag ttc aag             1584
Tyr Ile Asn Pro Tyr Asn Asp Tyr Thr Thr Phe Asn Asp Lys Phe Lys
        515                 520                 525 gac cgg ttc acc ctg tcc gtg gat aag tcc aag agc acc gct tac ctg             1632
Asp Arg Phe Thr Leu Ser Val Asp Lys Ser Lys Ser Thr Ala Tyr Leu
    530                 535                 540 cag atg aac tcc ctg aga gcc gag gat aca gct gtg tat tac tgt gcc             1680
Gln Met Asn Ser Leu Arg Ala Glu Asp Thr Ala Val Tyr Tyr Cys Ala
545                 550                 555                 560 cgg acc tgg ggc cac tgg tac ttt gat ttg tgg ggc cag gga acc ctc             1728
Arg Thr Trp Gly His Trp Tyr Phe Asp Leu Trp Gly Gln Gly Thr Leu
                565                 570                 575 gtg aca gtc tct tct ggc ggc gga gga agc gga ggc gga ggt tca ggc             1776
Val Thr Val Ser Ser Gly Gly Gly Gly Ser Gly Gly Gly Gly Ser Gly
            580                 585                 590 ggc ggt gga tct aac atc cag atg acc cag tct cca tcc agc ctg tct             1824
Gly Gly Gly Ser Asn Ile Gln Met Thr Gln Ser Pro Ser Ser Leu Ser
        595                 600                 605 gcc tct gtg ggc gac aga gtg aca att acc tgt cgg gcc tct cag tcc             1872
Ala Ser Val Gly Asp Arg Val Thr Ile Thr Cys Arg Ala Ser Gln Ser
    610                 615                 620 gtg tcc agc aat ctg gct tgg tat cag cag aag ccc ggc aag gct ccc             1920
Val Ser Ser Asn Leu Ala Trp Tyr Gln Gln Lys Pro Gly Lys Ala Pro
625                 630                 635                 640 aag ctg ctg atc tac gac tcc tcc acc aga gct acc ggc gtg cca tct             1968
Lys Leu Leu Ile Tyr Asp Ser Ser Thr Arg Ala Thr Gly Val Pro Ser
                645                 650                 655 aga ttc tcc ggc tct ggc tct ggc acc gac ttt acc ctg aca att tcc             2016
Arg Phe Ser Gly Ser Gly Ser Gly Thr Asp Phe Thr Leu Thr Ile Ser
            660                 665                 670 agc ctg cag cct gag gac ttc gcc acc tac tac tgc cag cag tac aac             2064
Ser Leu Gln Pro Glu Asp Phe Ala Thr Tyr Tyr Cys Gln Gln Tyr Asn
        675                 680                 685 aac tgg cct cct tgg acc ttc ggc tgc ggc acc aaa ctg gaa atc aag             2112
Asn Trp Pro Pro Trp Thr Phe Gly Cys Gly Thr Lys Leu Glu Ile Lys
    690                 695                 700 cgc                                                                          2115
Arg
705
```

<210> SEQ ID NO 36
<211> LENGTH: 705
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Synthetic Construct

<400> SEQUENCE: 36

```
Glu Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Met
        35                  40                  45

Gly Asp Val Val Pro Asn Asn Gly Val Pro Thr Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Ala Arg Pro His Tyr Tyr Tyr Ala Gly Arg Ser Gly Ala Met Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Gly Ile Glu Lys Thr Ile Ser Lys Ala Lys Gly Gln Pro Arg Glu Pro
            340                 345                 350
```

```
Gln Val Tyr Thr Leu Pro Pro Ser Arg Asp Glu Leu Thr Lys Asn Gln
            355                 360                 365
Val Ser Leu Thr Cys Leu Val Lys Gly Phe Tyr Pro Ser Asp Ile Ala
370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
            420                 425                 430
Val Met His Glu Ala Leu His Asn His Tyr Thr Gln Lys Ser Leu Ser
            435                 440                 445
Leu Ser Pro Gly Lys Gly Gly Gly Gly Ser Gly Gly Gly Gly Ser Glu
        450                 455                 460
Val Gln Leu Leu Glu Ser Gly Gly Gly Leu Val Gln Pro Gly Glu Ser
465                 470                 475                 480
Leu Arg Leu Ser Cys Lys Ala Phe Gly Tyr Thr Phe Thr Asn His His
                485                 490                 495
Ile Asn Trp Val Arg Gln Ala Pro Gly Lys Cys Leu Glu Trp Val Gly
            500                 505                 510
Tyr Ile Asn Pro Tyr Asn Asp Tyr Thr Thr Phe Asn Asp Lys Phe Lys
            515                 520                 525
Asp Arg Phe Thr Leu Ser Val Asp Lys Ser Lys Ser Thr Ala Tyr Leu
            530                 535                 540
Gln Met Asn Ser Leu Arg Ala Glu Asp Thr Ala Val Tyr Tyr Cys Ala
545                 550                 555                 560
Arg Thr Trp Gly His Trp Tyr Phe Asp Leu Trp Gly Gln Gly Thr Leu
                565                 570                 575
Val Thr Val Ser Ser Gly Gly Gly Gly Ser Gly Gly Gly Gly Ser Gly
            580                 585                 590
Gly Gly Gly Ser Asn Ile Gln Met Thr Gln Ser Pro Ser Ser Leu Ser
        595                 600                 605
Ala Ser Val Gly Asp Arg Val Thr Ile Thr Cys Arg Ala Ser Gln Ser
610                 615                 620
Val Ser Ser Asn Leu Ala Trp Tyr Gln Gln Lys Pro Gly Lys Ala Pro
625                 630                 635                 640
Lys Leu Leu Ile Tyr Asp Ser Ser Thr Arg Ala Thr Gly Val Pro Ser
                645                 650                 655
Arg Phe Ser Gly Ser Gly Ser Gly Thr Asp Phe Thr Leu Thr Ile Ser
                660                 665                 670
Ser Leu Gln Pro Glu Asp Phe Ala Thr Tyr Tyr Cys Gln Gln Tyr Asn
            675                 680                 685
Asn Trp Pro Pro Trp Thr Phe Gly Cys Gly Thr Lys Leu Glu Ile Lys
            690                 695                 700
Arg
705

<210> SEQ ID NO 37
<211> LENGTH: 2136
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: hKM3900_tA2-32LH HC
```

```
<220> FEATURE:
<221> NAME/KEY: CDS
<222> LOCATION: (1)..(2136)

<400> SEQUENCE: 37 gaa gtg cag ctg gtt cag tct ggc gcc gaa gtg aag aaa cct ggc gcc      48
Glu Val Gln Leu Val Gln Ser Gly Ala Glu Val Lys Lys Pro Gly Ala
1               5                  10                 15 tcc gtg aag atc tcc tgc aag gct tct ggc tac acc ttc acc gac tac      96
Ser Val Lys Ile Ser Cys Lys Ala Ser Gly Tyr Thr Phe Thr Asp Tyr
            20                  25                  30 tac atg aac tgg gtc cga cag gct cct gga cag gga ctt gag tgg atg     144
Tyr Met Asn Trp Val Arg Gln Ala Pro Gly Gln Gly Leu Glu Trp Met
        35                  40                  45 gga gat gtg gtg ccc aac aac ggc gtg ccc acc tac aac cag aaa ttc     192
Gly Asp Val Val Pro Asn Asn Gly Val Pro Thr Tyr Asn Gln Lys Phe
    50                  55                  60 aag ggc aga gtg acc atc acc gcc gac aag tct acc tcc acc gcc tac     240
Lys Gly Arg Val Thr Ile Thr Ala Asp Lys Ser Thr Ser Thr Ala Tyr
65                  70                  75                  80 atg gaa ctg cgg agc ctg aga tct gag gac acc gcc gtg tac tac tgc     288
Met Glu Leu Arg Ser Leu Arg Ser Glu Asp Thr Ala Val Tyr Tyr Cys
                85                  90                  95 gcc aga cct cac tac tac tac gcc ggc aga tct ggc gcc atg gat tat     336
Ala Arg Pro His Tyr Tyr Tyr Ala Gly Arg Ser Gly Ala Met Asp Tyr
            100                 105                 110 tgg gga cag ggc acc ctg gtc acc gtg tcc tct gct agc aca aag ggc     384
Trp Gly Gln Gly Thr Leu Val Thr Val Ser Ser Ala Ser Thr Lys Gly
        115                 120                 125 ccc tct gtg ttc cct ctg gct cct agc tct aag tcc acc tct ggc gga     432
Pro Ser Val Phe Pro Leu Ala Pro Ser Ser Lys Ser Thr Ser Gly Gly
    130                 135                 140 aca gct gct ctg ggc tgt ctg gtc aag gac tac ttc cct gag cct gtg     480
Thr Ala Ala Leu Gly Cys Leu Val Lys Asp Tyr Phe Pro Glu Pro Val
145                 150                 155                 160 acc gtg tct tgg aac tct ggc gct ctg aca tcc ggc gtg cac aca ttt     528
Thr Val Ser Trp Asn Ser Gly Ala Leu Thr Ser Gly Val His Thr Phe
                165                 170                 175 cca gct gtg ctg cag tcc tcc ggc ctg tac tct ctg tcc tct gtc gtg     576
Pro Ala Val Leu Gln Ser Ser Gly Leu Tyr Ser Leu Ser Ser Val Val
            180                 185                 190 acc gtg cct tcc agc tct ctg gga acc cag acc tac atc tgc aat gtg     624
Thr Val Pro Ser Ser Ser Leu Gly Thr Gln Thr Tyr Ile Cys Asn Val
        195                 200                 205 aac cac aag cct tcc aac acc aag gtg gac aag aag gtg gaa ccc aag     672
Asn His Lys Pro Ser Asn Thr Lys Val Asp Lys Lys Val Glu Pro Lys
    210                 215                 220 tcc tgc gac aag acc cac acc tgt cct cca tgt cct gct cca gaa gct     720
Ser Cys Asp Lys Thr His Thr Cys Pro Pro Cys Pro Ala Pro Glu Ala
225                 230                 235                 240 gct ggc gga cct tcc gtg ttc ctg ttt cct cca aag cct aag gac acc     768
Ala Gly Gly Pro Ser Val Phe Leu Phe Pro Pro Lys Pro Lys Asp Thr
                245                 250                 255 ctg atg atc tct cgg acc cct gaa gtg acc tgc gtg gtg gtg gat gtg     816
Leu Met Ile Ser Arg Thr Pro Glu Val Thr Cys Val Val Val Asp Val
            260                 265                 270 tct cac gag gac cca gaa gtg aag ttc aat tgg tac gtg gac ggc gtg     864
Ser His Glu Asp Pro Glu Val Lys Phe Asn Trp Tyr Val Asp Gly Val
        275                 280                 285 gaa gtg cac aac gcc aag acc aag cct aga gag gaa cag tac aac tcc     912
Glu Val His Asn Ala Lys Thr Lys Pro Arg Glu Glu Gln Tyr Asn Ser
```

|  |  |  |  |  |  |  |  |  |  |  |  |  |
|---|---|---|---|---|---|---|---|---|---|---|---|---|
| Glu | Val | His | Asn | Ala | Lys | Thr | Lys | Pro | Arg | Glu | Gln | Tyr | Asn | Ser |
|  | 290 |  |  |  | 295 |  |  |  | 300 |  |  |  |  |  |

```
acc tac aga gtg gtg tcc gtg ctg acc gtg ctg cac cag gat tgg ctg      960
Thr Tyr Arg Val Val Ser Val Leu Thr Val Leu His Gln Asp Trp Leu
305                 310                 315                 320 aac ggc aaa gag tac aag tgc aag gtg tcc aac aag gcc ctg cct gcc     1008
Asn Gly Lys Glu Tyr Lys Cys Lys Val Ser Asn Lys Ala Leu Pro Ala
            325                 330                 335 ggc atc gaa aag acc atc tcc aag gcc aag ggc cag cct agg gaa ccc     1056
Gly Ile Glu Lys Thr Ile Ser Lys Ala Lys Gly Gln Pro Arg Glu Pro
        340                 345                 350 cag gtt tac acc ttg cca cct tct cgg gac gag ctg acc aag aac cag     1104
Gln Val Tyr Thr Leu Pro Pro Ser Arg Asp Glu Leu Thr Lys Asn Gln
    355                 360                 365 gtg tcc ctg acc tgt ctc gtg aag ggc ttc tac ccc tcc gat atc gcc     1152
Val Ser Leu Thr Cys Leu Val Lys Gly Phe Tyr Pro Ser Asp Ile Ala
370                 375                 380 gtg gaa tgg gag tct aat ggc cag cct gag aac aac tac aag aca acc     1200
Val Glu Trp Glu Ser Asn Gly Gln Pro Glu Asn Asn Tyr Lys Thr Thr
385                 390                 395                 400 cct cct gtg ctg gac tcc gac ggc tca ttc ttc ctg tac tcc aag ctg     1248
Pro Pro Val Leu Asp Ser Asp Gly Ser Phe Phe Leu Tyr Ser Lys Leu
            405                 410                 415 aca gtg gac aag tcc aga tgg cag cag ggc aac gtg ttc tcc tgc agc     1296
Thr Val Asp Lys Ser Arg Trp Gln Gln Gly Asn Val Phe Ser Cys Ser
        420                 425                 430 gtg atg cac gag gcc ctg cac aat cac tac aca cag aag tct ctg tct     1344
Val Met His Glu Ala Leu His Asn His Tyr Thr Gln Lys Ser Leu Ser
    435                 440                 445 ctg agc ccc ggc aaa ggt ggc gga gga tct ggc gga ggc gga tcc caa     1392
Leu Ser Pro Gly Lys Gly Gly Gly Gly Ser Gly Gly Gly Gly Ser Gln
450                 455                 460 tct gtt ctg acc caa cct cct tcc gcc tct ggc aca cct ggc cag aga     1440
Ser Val Leu Thr Gln Pro Pro Ser Ala Ser Gly Thr Pro Gly Gln Arg
465                 470                 475                 480 gtg acc atc tct tgc tcc ggc tcc tcc aac atc ggc tct aac acc         1488
Val Thr Ile Ser Cys Ser Gly Ser Ser Asn Ile Gly Ser Asn Thr
            485                 490                 495 gtg aac tgg tat cag cag ttc ccc ggc acc gct cct aag ctg ctg atc     1536
Val Asn Trp Tyr Gln Gln Phe Pro Gly Thr Ala Pro Lys Leu Leu Ile
        500                 505                 510 tac tcc aac aac cag cgg cct tcc ggc gtg ccc gat aga ttc tct ggc     1584
Tyr Ser Asn Asn Gln Arg Pro Ser Gly Val Pro Asp Arg Phe Ser Gly
    515                 520                 525 tct aag tcc ggc acc tct gcc agc ctg gct att tct gga ctg cag agc     1632
Ser Lys Ser Gly Thr Ser Ala Ser Leu Ala Ile Ser Gly Leu Gln Ser
530                 535                 540 gag gac gag gcc gac tat tat tgt gcc ggc tgg gac gac tct ctg aac     1680
Glu Asp Glu Ala Asp Tyr Tyr Cys Ala Gly Trp Asp Asp Ser Leu Asn
545                 550                 555                 560 ggc cct gtt ttt ggc ggt ggc acc aaa ctg aca gtg ctt gga ggc ggt     1728
Gly Pro Val Phe Gly Gly Gly Thr Lys Leu Thr Val Leu Gly Gly Gly
            565                 570                 575 ggt gga tca ggc ggc ggt gga agt ggt ggt ggt agc gga ggt ggt         1776
Gly Gly Ser Gly Gly Gly Gly Ser Gly Gly Gly Ser Gly Gly Gly
        580                 585                 590 gga tct cag gtg cag ctc caa gag tct gga cct ggc ctc gtg aag cct     1824
Gly Ser Gln Val Gln Leu Gln Glu Ser Gly Pro Gly Leu Val Lys Pro
    595                 600                 605
```

```
tcc gag aca ctg tct ctg acc tgc aca gtg tcc ggc ggc tct atc tct    1872
Ser Glu Thr Leu Ser Leu Thr Cys Thr Val Ser Gly Gly Ser Ile Ser
    610             615                 620 ggc tac tac tgg tcc tgg atc aga cag cct cct ggc aag gga ctc gag    1920
Gly Tyr Tyr Trp Ser Trp Ile Arg Gln Pro Pro Gly Lys Gly Leu Glu
625             630                 635                 640 tgg atc ggc tac atc tac tac tct ggc ttc acc aac tac aac ccc agc    1968
Trp Ile Gly Tyr Ile Tyr Tyr Ser Gly Phe Thr Asn Tyr Asn Pro Ser
            645                 650                 655 ctg aag tcc cgc gtg acc atc agc gtg gac acc tct aag aac cag ttc    2016
Leu Lys Ser Arg Val Thr Ile Ser Val Asp Thr Ser Lys Asn Gln Phe
    660                 665                 670 tct ctg aag ctg tcc tcc gtg acc gcc gct gat acc gct gtg tat tac    2064
Ser Leu Lys Leu Ser Ser Val Thr Ala Ala Asp Thr Ala Val Tyr Tyr
675                 680                 685 tgc acc cgg gac cac agc cac tac tac tac atg gac gtg tgg gga cag    2112
Cys Thr Arg Asp His Ser His Tyr Tyr Tyr Met Asp Val Trp Gly Gln
        690                 695                 700 gga aca acc gtg aca gtg tcc tcc                                    2136
Gly Thr Thr Val Thr Val Ser Ser
705             710

<210> SEQ ID NO 38
<211> LENGTH: 712
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetic Construct

<400> SEQUENCE: 38

Glu Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Met
        35                  40                  45

Gly Asp Val Val Pro Asn Asn Gly Val Pro Thr Tyr Asn Gln Lys Phe
    50                  55                  60

Lys Gly Arg Val Thr Ile Thr Ala Asp Lys Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Ala Arg Pro His Tyr Tyr Ala Gly Arg Ser Gly Ala Met Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205
```

```
Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Gly Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys Gly Gly Gly Ser Gly Gly Gly Gly Ser Gln
450                 455                 460

Ser Val Leu Thr Gln Pro Pro Ser Ala Ser Gly Thr Pro Gly Gln Arg
465                 470                 475                 480

Val Thr Ile Ser Cys Ser Gly Ser Ser Ser Asn Ile Gly Ser Asn Thr
                485                 490                 495

Val Asn Trp Tyr Gln Gln Phe Pro Gly Thr Ala Pro Lys Leu Leu Ile
            500                 505                 510

Tyr Ser Asn Asn Gln Arg Pro Ser Gly Val Pro Asp Arg Phe Ser Gly
        515                 520                 525

Ser Lys Ser Gly Thr Ser Ala Ser Leu Ala Ile Ser Gly Leu Gln Ser
530                 535                 540

Glu Asp Glu Ala Asp Tyr Tyr Cys Ala Gly Trp Asp Asp Ser Leu Asn
545                 550                 555                 560

Gly Pro Val Phe Gly Gly Gly Thr Lys Leu Thr Val Leu Gly Gly Gly
                565                 570                 575

Gly Gly Ser Gly Gly Gly Gly Ser Gly Gly Gly Gly Ser Gly Gly Gly
            580                 585                 590

Gly Ser Gln Val Gln Leu Gln Glu Ser Gly Pro Gly Leu Val Lys Pro
        595                 600                 605

Ser Glu Thr Leu Ser Leu Thr Cys Thr Val Ser Gly Gly Ser Ile Ser
610                 615                 620
```

```
Gly Tyr Tyr Trp Ser Trp Ile Arg Gln Pro Gly Lys Gly Leu Glu
625                 630                 635                 640

Trp Ile Gly Tyr Ile Tyr Tyr Ser Gly Phe Thr Asn Tyr Asn Pro Ser
            645                 650                 655

Leu Lys Ser Arg Val Thr Ile Ser Val Asp Thr Ser Lys Asn Gln Phe
                660                 665                 670

Ser Leu Lys Leu Ser Ser Val Thr Ala Ala Asp Thr Ala Val Tyr Tyr
            675                 680                 685

Cys Thr Arg Asp His Ser His Tyr Tyr Tyr Met Asp Val Trp Gly Gln
        690                 695                 700

Gly Thr Thr Val Thr Val Ser Ser
705                 710

<210> SEQ ID NO 39
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: hKM3900 LC
<220> FEATURE:
<221> NAME/KEY: CDS
<222> LOCATION: (1)..(645)

<400> SEQUENCE: 39 gac atc cag ctg acc cag tct cca tcc tct ctg tct gcc tct gtg ggc     48
Asp Ile Gln Leu Thr Gln Ser Pro Ser Ser Leu Ser Ala Ser Val Gly
1               5                   10                  15 gac aga gtg aca att acc tgc acc gcc tcc tcc acc gtg tcc tct acc     96
Asp Arg Val Thr Ile Thr Cys Thr Ala Ser Ser Thr Val Ser Ser Thr
            20                  25                  30 tac ctg cac tgg tat cag cag aag ccc ggc aag gct ccc aag ctg ctg    144
Tyr Leu His Trp Tyr Gln Gln Lys Pro Gly Lys Ala Pro Lys Leu Leu
        35                  40                  45 atc tac tcc acc tcc aat ctg gcc tct ggc gtg ccc tct aga ttc tcc    192
Ile Tyr Ser Thr Ser Asn Leu Ala Ser Gly Val Pro Ser Arg Phe Ser
    50                  55                  60 gga tct ggc tct gga acc gac tat acc ctg aca atc tcc agc ctg cag    240
Gly Ser Gly Ser Gly Thr Asp Tyr Thr Leu Thr Ile Ser Ser Leu Gln
65                  70                  75                  80 cct gag gac ttc gcc acc tac tac tgc cac cag tac cac aga tcc cca    288
Pro Glu Asp Phe Ala Thr Tyr Tyr Cys His Gln Tyr His Arg Ser Pro
                85                  90                  95 cct acc ttt ggc cag ggc acc aag ctg gaa atc aag cgt acg gtg gcc    336
Pro Thr Phe Gly Gln Gly Thr Lys Leu Glu Ile Lys Arg Thr Val Ala
            100                 105                 110 gct cct tcc gtg ttc atc ttc cca cct tcc gac gag cag ctg aag tcc    384
Ala Pro Ser Val Phe Ile Phe Pro Pro Ser Asp Glu Gln Leu Lys Ser
        115                 120                 125 ggc aca gct tct gtc gtg tgc ctg ctg aac aac ttc tac cct cgg gaa    432
Gly Thr Ala Ser Val Val Cys Leu Leu Asn Asn Phe Tyr Pro Arg Glu
    130                 135                 140 gcc aag gtg cag tgg aag gtg gac aat gcc ctg cag tcc ggc aac tcc    480
Ala Lys Val Gln Trp Lys Val Asp Asn Ala Leu Gln Ser Gly Asn Ser
145                 150                 155                 160 caa gag tct gtg acc gag cag gac tcc aag gac agc acc tac agc ctg    528
Gln Glu Ser Val Thr Glu Gln Asp Ser Lys Asp Ser Thr Tyr Ser Leu
                165                 170                 175 tcc tcc aca ctg acc ctg tcc aag gcc gac tac gag aag cac aag gtg    576
```

```
Ser Ser Thr Leu Thr Leu Ser Lys Ala Asp Tyr Glu Lys His Lys Val
            180                 185                 190 tac gcc tgc gaa gtg acc cat cag ggc ctg tct agc cct gtg acc aag      624
Tyr Ala Cys Glu Val Thr His Gln Gly Leu Ser Ser Pro Val Thr Lys
        195                 200                 205 tct ttc aac cgg ggc gag tgc                                          645
Ser Phe Asn Arg Gly Glu Cys
    210                 215
```

<210> SEQ ID NO 40
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetic Construct

<400> SEQUENCE: 40

```
Asp Ile Gln Leu Thr Gln Ser Pro Ser Ser Leu Ser Ala Ser Val Gly
1               5                   10                  15

Asp Arg Val Thr Ile Thr Cys Thr Ala Ser Ser Thr Val Ser Ser Thr
            20                  25                  30

Tyr Leu His Trp Tyr Gln Gln Lys Pro Gly Lys Ala Pro Lys Leu Leu
        35                  40                  45

Ile Tyr Ser Thr Ser Asn Leu Ala Ser Gly Val Pro Ser Arg Phe Ser
    50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys His Gln Tyr His Arg Ser Pro
                85                  90                  95

Pro Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 41
<211> LENGTH: 486
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: anti-CD3 scFv-human Fc fusion protein

<400> SEQUENCE: 41

```
Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
50                  55                  60

Ser Val Lys Asp Arg Phe Thr Ile Ser Arg Asp Asp Ser Lys Ser Thr
65                  70                  75                  80

Leu Tyr Leu Gln Met Asn Asn Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Gly Lys Pro
            115                 120                 125

Gly Ser Gly Lys Pro Gly Ser Gly Lys Pro Gly Ser Gly Lys Pro Gly
            130                 135                 140

Ser Gln Ala Val Val Thr Gln Glu Pro Ser Leu Thr Val Ser Pro Gly
145                 150                 155                 160

Gly Thr Val Thr Leu Thr Cys Arg Ser Ser Thr Gly Ala Val Thr Thr
                165                 170                 175

Ser Asn Tyr Ala Asn Trp Val Gln Gln Lys Pro Gly Gln Ala Pro Arg
            180                 185                 190

Gly Leu Ile Gly Gly Thr Asn Lys Arg Ala Pro Gly Thr Pro Ala Arg
            195                 200                 205

Phe Ser Gly Ser Leu Leu Gly Asp Lys Ala Ala Leu Thr Leu Ser Gly
210                 215                 220

Ala Gln Pro Glu Asp Glu Ala Glu Tyr Tyr Cys Ala Leu Trp Tyr Ser
225                 230                 235                 240

Asn Leu Trp Val Phe Gly Ser Gly Thr Lys Val Thr Val Leu Glu Pro
            245                 250                 255

Lys Ser Ser Asp Lys Thr His Thr Cys Pro Pro Cys Pro Ala Pro Glu
            260                 265                 270

Ala Ala Gly Gly Pro Ser Val Phe Leu Phe Pro Pro Lys Pro Lys Asp
            275                 280                 285

Thr Leu Met Ile Ser Arg Thr Pro Glu Val Thr Cys Val Val Val Asp
        290                 295                 300

Val Ser His Glu Asp Pro Glu Val Lys Phe Asn Trp Tyr Val Asp Gly
305                 310                 315                 320

Val Glu Val His Asn Ala Lys Thr Lys Pro Arg Glu Glu Gln Tyr Ala
                325                 330                 335

Ser Thr Tyr Arg Val Val Ser Val Leu Thr Val Leu His Gln Asp Trp
            340                 345                 350

Leu Asn Gly Lys Glu Tyr Lys Cys Lys Val Ser Asn Lys Ala Leu Pro
            355                 360                 365

Ala Pro Ile Glu Lys Thr Ile Ser Lys Ala Lys Gly Gln Pro Arg Glu
            370                 375                 380

Pro Gln Val Tyr Thr Leu Pro Pro Ser Arg Asp Glu Leu Thr Lys Asn
385                 390                 395                 400

Gln Val Ser Leu Trp Cys Leu Val Lys Gly Phe Tyr Pro Ser Asp Ile
                405                 410                 415

Ala Val Glu Trp Glu Ser Asn Gly Gln Pro Glu Asn Asn Tyr Lys Thr
```

```
                    420             425             430
Thr Pro Pro Val Leu Asp Ser Asp Gly Ser Phe Phe Leu Tyr Ser Lys
            435                 440                 445

Leu Thr Val Asp Lys Ser Arg Trp Gln Gln Gly Asn Val Phe Ser Cys
        450                 455                 460

Ser Val Met His Glu Ala Leu His Asn His Tyr Thr Gln Lys Ser Leu
465                 470                 475                 480

Ser Leu Ser Pro Gly Lys
                485

<210> SEQ ID NO 42
<211> LENGTH: 255
<212> TYPE: PRT
<213> ORGANISM: Homo sapiens

<400> SEQUENCE: 42

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 43
<211> LENGTH: 254
<212> TYPE: PRT
<213> ORGANISM: Macaca fascicularis

<400> SEQUENCE: 43

Met Gly Asn Ser Cys Tyr Asn Ile Val Ala Thr Leu Leu Leu Val Leu
```

```
            1               5                  10                 15
Asn Phe Glu Arg Thr Arg Ser Leu Gln Asp Leu Cys Ser Asn Cys Pro
                20                  25                  30
Ala Gly Thr Phe Cys Asp Asn Asn Arg Ser Gln Ile Cys Ser Pro Cys
            35                  40                  45
Pro Pro Asn Ser Phe Ser Ser Ala Gly Gly Gln Arg Thr Cys Asp Ile
        50                  55                  60
Cys Arg Gln Cys Lys Gly Val Phe Lys Thr Arg Lys Glu Cys Ser Ser
65                  70                  75                  80
Thr Ser Asn Ala Glu Cys Asp Cys Ile Ser Gly Tyr His Cys Leu Gly
                85                  90                  95
Ala Glu Cys Ser Met Cys Glu Gln Asp Cys Lys Gln Gly Gln Glu Leu
            100                 105                 110
Thr Lys Lys Gly Cys Lys Asp Cys Cys Phe Gly Thr Phe Asn Asp Gln
            115                 120                 125
Lys Arg Gly Ile Cys Arg Pro Trp Thr Asn Cys Ser Leu Asp Gly Lys
        130                 135                 140
Ser Val Leu Val Asn Gly Thr Lys Glu Arg Asp Val Val Cys Gly Pro
145                 150                 155                 160
Ser Pro Ala Asp Leu Ser Pro Gly Ala Ser Ser Ala Thr Pro Pro Ala
                165                 170                 175
Pro Ala Arg Glu Pro Gly His Ser Pro Gln Ile Ile Phe Phe Leu Ala
            180                 185                 190
Leu Thr Ser Thr Val Val Leu Phe Leu Phe Phe Leu Val Leu Arg
                195                 200                 205
Phe Ser Val Val Lys Arg Ser Arg Lys Lys Leu Leu Tyr Ile Phe Lys
210                 215                 220
Gln Pro Phe Met Arg Pro Val Gln Thr Thr Gln Glu Glu Asp Gly Cys
225                 230                 235                 240
Ser Cys Arg Phe Pro Glu Glu Glu Gly Gly Cys Glu Leu
                245                 250

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: His tag protein

<400> SEQUENCE: 44

His His His His His His
1               5

<210> SEQ ID NO 45
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 3xFLAG tag proteinE

<400> SEQUENCE: 45

Asp Tyr Lys Asp Asp Asp Asp Lys Gly Asp Tyr Lys Asp Asp Asp
1               5                   10                  15
```

Lys Ile Asp Tyr Lys Asp Asp Asp Asp Lys
          20                  25

<210> SEQ ID NO 46
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: GS linker

<400> SEQUENCE: 46

Gly Gly Gly Ser
1

<210> SEQ ID NO 47
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: GS linker

<400> SEQUENCE: 47

Ser Gly Gly Gly
1

<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: GS linker

<400> SEQUENCE: 48

Gly Gly Gly Gly Ser
1               5

<210> SEQ ID NO 49
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: GS linker

<400> SEQUENCE: 49

Ser Gly Gly Gly Gly
1               5

<210> SEQ ID NO 50
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: GS linker

<400> SEQUENCE: 50

```
Gly Gly Gly Gly Gly Ser
1               5

<210> SEQ ID NO 51
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: GS linker

<400> SEQUENCE: 51

Ser Gly Gly Gly Gly Gly
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: GS linker

<400> SEQUENCE: 52

Gly Gly Gly Gly Gly Gly Ser
1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: GS linker

<400> SEQUENCE: 53

Ser Gly Gly Gly Gly Gly Gly
1               5

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: GS linker

<400> SEQUENCE: 54

Gly Gly Gly Gly Ser Gly Gly Gly Gly Ser
1               5                   10

<210> SEQ ID NO 55
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: GKPGS linker
```

```
<400> SEQUENCE: 55

Gly Lys Pro Gly Ser
1               5

<210> SEQ ID NO 56
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 56

Gly Gly Gly Gly Ser
1               5

<210> SEQ ID NO 57
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 57

Ser Gly Gly Gly Gly
1               5

<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 58

Gly Lys Pro Gly Ser
1               5

<210> SEQ ID NO 59
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gly Gly Gly Gly Ser Gly Gly Gly Ser Gly Gly Gly Gly Ser
1               5                   10                  15

<210> SEQ ID NO 60
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 60

Gly Gly Gly Gly Ser Gly Gly Gly Gly Ser Gly Gly Gly Gly Ser Gly
1               5                   10                  15

Gly Gly Gly Ser
            20
```